US010595756B2

(12) United States Patent
Taub et al.

(10) Patent No.: US 10,595,756 B2
(45) Date of Patent: Mar. 24, 2020

(54) MULTI-FUNCTION ANALYTE MONITOR DEVICE AND METHODS OF USE

(71) Applicant: Abbott Diabetes Care Inc., Alameda, CA (US)

(72) Inventors: Marc B. Taub, Mountain View, CA (US); Nathan C. Crouther, San Francisco, CA (US); Jai Karan, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 15/989,650

(22) Filed: May 25, 2018

(65) Prior Publication Data

US 2018/0303389 A1 Oct. 25, 2018

Related U.S. Application Data

(63) Continuation of application No. 13/416,934, filed on Mar. 9, 2012, now Pat. No. 10,010,273.

(60) Provisional application No. 61/585,553, filed on Jan. 11, 2012, provisional application No. 61/451,488, filed on Mar. 10, 2011.

(51) Int. Cl.
*A61B 5/145* (2006.01)
*G01N 33/487* (2006.01)
*G06F 19/00* (2018.01)
*A61M 5/315* (2006.01)
*A61M 5/142* (2006.01)
*G16H 40/63* (2018.01)

(52) U.S. Cl.
CPC ..... *A61B 5/14532* (2013.01); *G01N 33/48792* (2013.01); *G06F 19/00* (2013.01); *A61M 5/14244* (2013.01); *A61M 5/31533* (2013.01); *A61M 2005/14208* (2013.01); *A61M 2205/3553* (2013.01); *A61M 2205/3584* (2013.01); *A61M 2205/6054* (2013.01); *G16H 40/63* (2018.01)

(58) Field of Classification Search
CPC .......... A61M 5/31533; A61B 5/14532; A61B 5/4839; G16H 40/63; G01N 33/47892
See application file for complete search history.

(56) References Cited

U.S. PATENT DOCUMENTS

| | | | | |
|---|---|---|---|---|
| 2008/0262469 A1* | 10/2008 | Brister | ................ | A61B 5/0002 604/504 |
| 2009/0131861 A1* | 5/2009 | Braig | .................. | A61B 5/1427 604/66 |
| 2010/0198142 A1* | 8/2010 | Sloan | ................ | A61B 5/14532 604/66 |

* cited by examiner

*Primary Examiner* — Nilay J Shah
(74) *Attorney, Agent, or Firm* — Vorys, Sater, Seymour and Pease LLP

(57) ABSTRACT

Methods, systems and devices for detecting an analyte sample, determining an analyte concentration associated with the detected analyte sample, storing the determined analyte concentration and a time associated with the determined analyte concentration, retrieving two or more stored analyte concentrations, and determining an adjusted dose level based at least in part on a current dose level and data associated with the two or more retrieved analyte concentrations are provided. For example, adjustments to dosage levels of long-acting insulin may be provided to assist in the management of diabetes and related conditions.

20 Claims, 49 Drawing Sheets

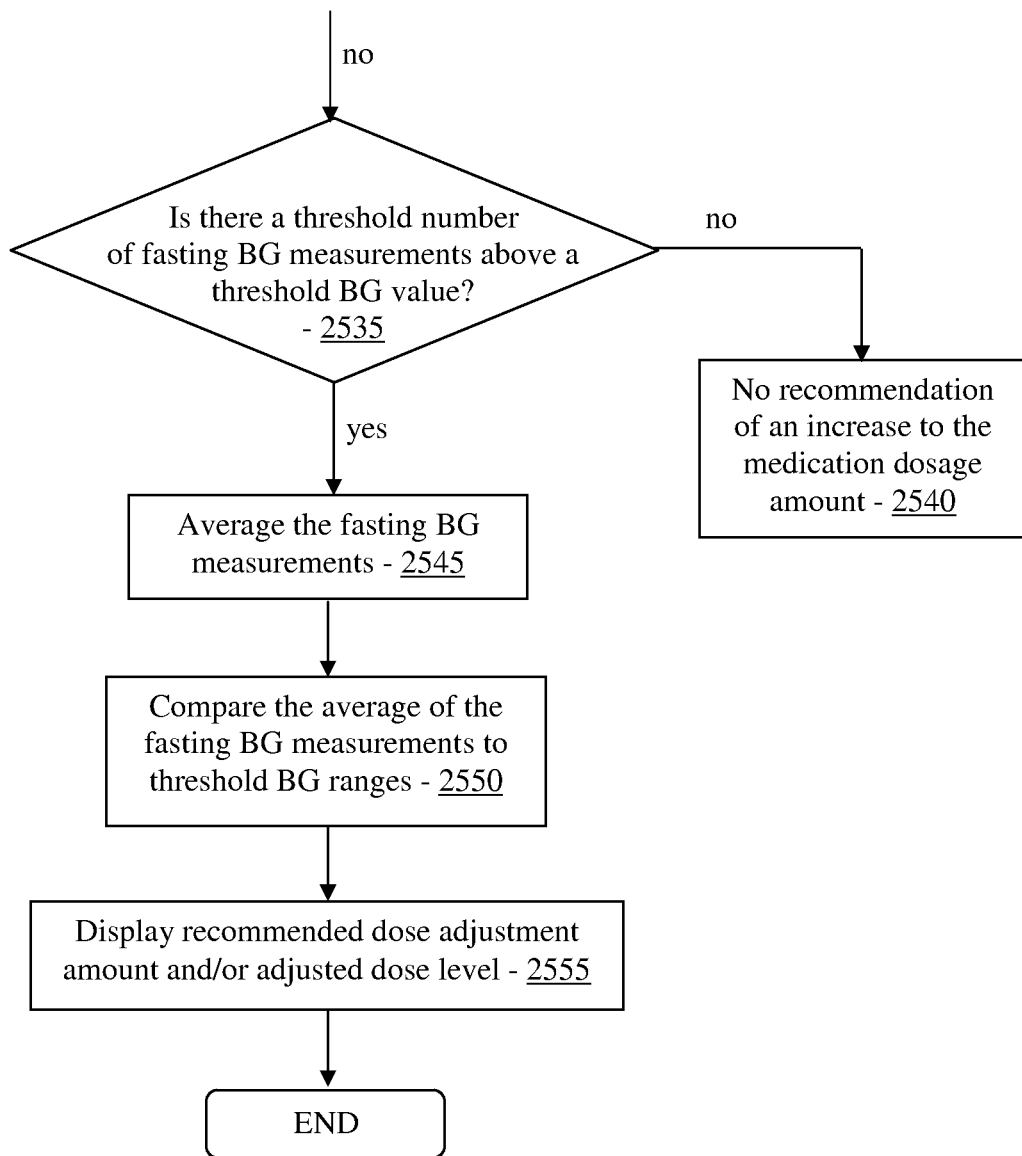
FIG. 25, continued

MULTI-FUNCTION ANALYTE MONITOR DEVICE AND METHODS OF USE

PRIORITY

This application is a continuation of U.S. patent application Ser. No. 13/416,934 filed Mar. 9, 2012, which claims benefit of priority under 35 U.S.C. § 119(e) to U.S. Provisional Application Nos. 61/451,488 filed Mar. 10, 2011, and 61/585,553 filed Jan. 11, 2012, the disclosures of which are each incorporated by reference herein in their entirety.

INTRODUCTION

In diabetes management, there exist devices which allow diabetic patients to measure their blood glucose levels. One such device is a hand-held electronic meter, for example a blood glucose meter such as the FREESTYLE® and PRECISION® blood glucose monitoring system available from Abbott Diabetes Care Inc., of Alameda, Calif., which receives blood samples via enzyme-based test strips. Typically, the patient inserts the test strip into a test strip opening or port in the meter housing, lances a finger or alternate body site to obtain a blood sample, applies the drawn blood sample to the test strip, and the meter provides for an analysis or determination of the corresponding blood glucose value, which is displayed or otherwise provided to the patient to show the level of glucose at the time of testing.

With the decreasing cost of electronic components and a corresponding increase in data processing capabilities of microprocessors, computational capability of electronic devices have been rapidly increasing. However, currently available glucose meters are generally configured with limited functionalities for use in connection with blood glucose testing and diabetes management.

SUMMARY

In view of the foregoing, in accordance with the various embodiments of the present disclosure, there are provided methods, devices and/or systems for providing a medication dosage calculation function into a health monitor device, such as a blood glucose meter, configured to perform data analysis and management based on, for example, the glucose level detected using the health monitor device. More specifically, in accordance with the various aspects of the present disclosure, provided are methods, systems and devices for detecting an analyte sample, determining an analyte concentration associated with the detected analyte sample, storing the determined analyte concentration and a time associated with the determined analyte concentration, retrieving two or more stored analyte concentrations, and determining an adjusted dose level based at least in part on a current dose level and data associated with the two or more retrieved analyte concentrations.

It should be noted that two or more of the embodiments described herein, including those described above, may be combined to produce one or more additional embodiments which include the combined features of the individual embodiments.

These and other aspects of the present disclosure are disclosed in the following detailed description of the embodiments, the appended claims and the accompanying figures.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference in their entirety.

DETAILED DESCRIPTION

As described in further detail below, in accordance with the various embodiments of the present disclosure, there are provided health monitor devices, such as blood glucose meter devices, that include therapy management including for example, medication dosage calculation functions, such as a single-dose calculation functions for administration of rapid acting insulin and/or long acting insulin, and/or related data analysis capabilities incorporated in the health monitor devices. In certain aspects of the present disclosure, method, device or system are provided to determine medication dose information based on, for example, fast or rapid acting and/or long acting insulin, to treat physiological conditions associated with diabetes or other appropriate conditions. In the manner described, in aspects of the present disclosure, patients with Type-1 or Type-2 diabetic conditions may improve their diabetes management, and further, the patients, users or health care professionals may be provided with tools to improve the treatment of such conditions.

Health Monitor Devices

Although in the disclosure herein, reference may be made to specific figures to aid in the description of certain embodiments, any and all aspects of the embodiment or embodiments described in conjunction with a specific figure may be found in any of the embodiments described herein. Aspects of an embodiment or embodiments described in connection with a specific figure are not limited to that figure and may be found in any embodiment described herein.

Figure 1:
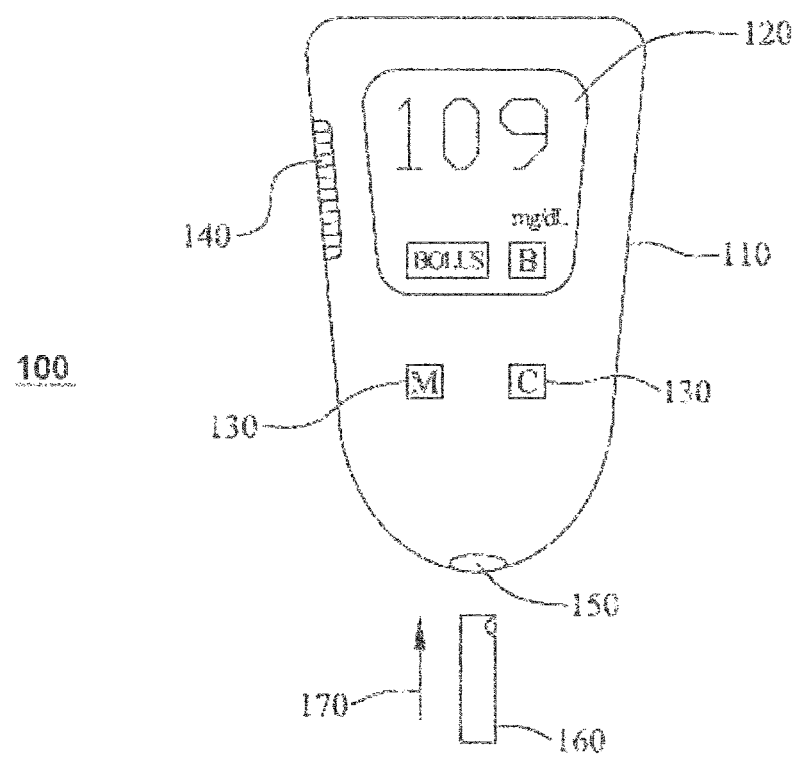
FIG. 1 is a health monitor device with a medication dose calculation function in accordance with embodiments of the present disclosure.

FIG. 1 shows a health monitor device with a medication dose calculation function in accordance with one embodiment of the present disclosure. Health monitor device with a medication dose calculation function 100 includes a housing 110 with a display unit 120 provided thereon. Also shown in FIG. 1 is a plurality of input buttons 130, each configured to allow the user of the health monitor device with a medication dose calculation function 100 to input or enter data or relevant information associated with the operation of the health monitor device with a medication dose calculation function 100. For example, the user of the health monitor device with a medication dose calculation function may operate the one or more input buttons 130 to enter a calibration code associated with a test strip 160, or other fluid sample reception means, for use in conjunction with the health monitor device with a medication dose calculation function 100.

In one embodiment, the health monitor device with a medication dose calculation function 100 may include a blood glucose meter with bolus calculation function configured to calculate a single bolus dosage of a medication such as insulin such as long acting, fast acting or rapid acting insulin. The test strip 160 for use in conjunction with the health monitor device with a medication dose calculation function 100 may be a blood glucose test strip configured to receive a blood sample thereon, in order to determine a blood glucose level of the received blood sample. Additionally, the user may operate the one or more input buttons 130 to adjust time and/or date information, as well as other features or settings associated with the operation of the health monitor device with a medication dose calculation function 100.

In aspects of the present disclosure, the strip port for receiving the test strip 160 may be integrated with the housing of the health monitor device 100, or alternatively, may be provided in a separate housing or as a separate component that may be physically or electrically coupled to the health monitoring device 100. In one aspect, a component including the strip port may be provided in a separate snap-on type housing which physically snaps onto the housing of the health monitor device 100. Additional information is provided in U.S. Pat. No. 7,041,468 issued on May 9, 2006 titled "Blood Glucose Tracking Apparatus and Method" and in U.S. Patent Application Publication No. 2004/0254434 published Dec. 16, 2004 titled "Glucose Measuring Module and Insulin Pump Combination", the disclosure of each of which is incorporated herein by reference for all purposes.

Referring back to FIG. 1, also shown is input unit 140 which, in one embodiment, may be configured as a jog dial, or the like, and provided on the housing 110 of the health monitor device with a medication dose calculation function 100. In one embodiment, as discussed in further detail below, the user or the patient may operate the input unit 140 to perform calculations and determinations associated with one or more medication dose estimation functions, such as a bolus dose estimation function, of the health monitor device with a medication dose calculation function 100. Also shown in FIG. 1 is a strip port 150 which is configured to receive the test strip 160 (with fluid sample provided thereon) substantially in the direction as shown by the directional arrow 170.

In operation, when the test strip 160 with the patient's fluid sample such as a blood sample is inserted into the strip port 150 of the health monitor device with a medication dose calculation function 100, a microprocessor or a control unit 210 (FIG. 2) of the health monitor device with a medication dose calculation function 100 may be configured to determine the associated analyte level in the fluid sample, and display the determined analyte level on the display unit 120.

In addition, in accordance with the various embodiments of the present disclosure, the health monitor device with a medication dose calculation function 100 may be configured to automatically enter into a medication dosage calculation mode to, for example, estimate a medication dosage amount based on information stored in the health monitor device with a medication dose calculation function 100 (such as the patient's insulin sensitivity, for example), and/or prompt the patient to provide additional information, such as the amount of carbohydrate to be ingested by the patient for determination of, for example, a carbohydrate bolus dosage determination. The patient may operate the input unit 140 in conjunction with the user interface menu provided on the display unit 120 to provide the appropriate information.

In another embodiment, the health monitor device with a medication dose calculation function 100 may be configured to prompt the patient to select whether to retrieve a predetermined or preprogrammed medication dosage amount such as, for example, a correction bolus or a carbohydrate bolus, following the display of the determined analyte level from the test strip 160. In this manner, in one embodiment of the present disclosure, the health monitor device with a medication dose calculation function 100 may be configured to automatically prompt the user or patient to select whether a medication dosage determination is desired following an analyte testing using the test strip 160.

Figure 2:
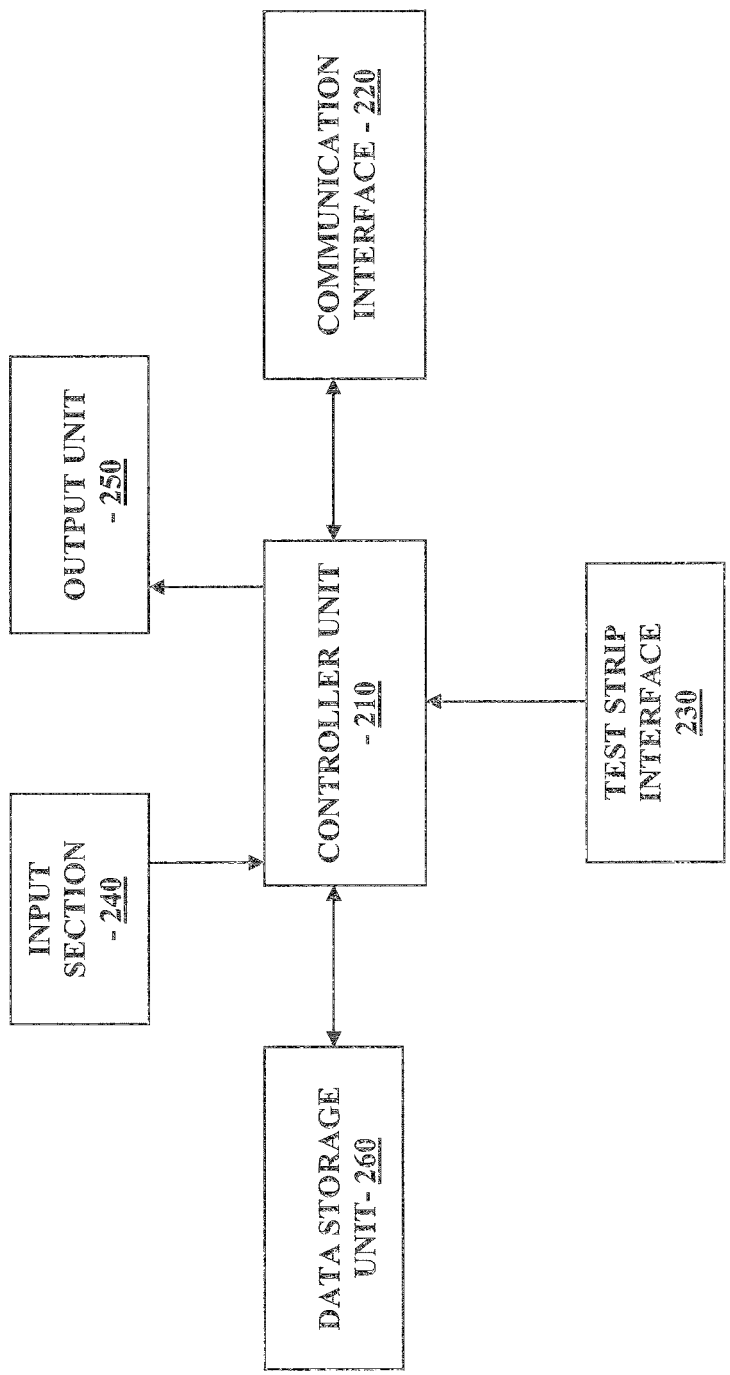
FIG. 2 is a block diagram of the health monitor device with a medication dose calculation function of FIG. 1 in embodiments of the present disclosure.

FIG. 2 is a block diagram of the health monitor device with a medication dose calculation function of FIG. 1 in one embodiment of the present disclosure. Referring to FIG. 2, the health monitor device with a medication dose calculation function 100 (FIG. 1) includes a controller unit 210 operatively coupled to a communication interface 220 and configured for bidirectional communication. The controller unit 210 is further operatively coupled to a test strip interface 230, an input section 240 (which, for example, may include the input unit 140 and the plurality of input buttons 130 as shown in FIG. 1), an output unit 250, and a data storage unit 260.

Referring to FIG. 2, in one embodiment of the present disclosure, the test strip interface 230 is configured for signal communication with the inserted test strip 160 (FIG. 1) for determination of the fluid sample on the test strip 160. In addition, the test strip interface 230 may include an illumination segment which may be configured to illuminate the strip port 150 (FIG. 1) using a light emitting diode (LED), for example, during the test strip 160 insertion process to assist the user in properly and accurately inserting the test strip 160 into the strip port 150. Additional information regarding illuminated strip ports and methods of powering the same can be found in U.S. Patent Application Publication No. 2005/0009126 published Jan. 13, 2005 titled "Method and Apparatus for Providing Power Management in Data Communication Systems", the disclosure of which is incorporated by reference herein.

Moreover, in a further aspect of the present disclosure, the test strip interface 230 may be additionally configured with a physical latch or securement mechanism internally provided within the housing 110 of the health monitor device with a medication dose calculation function 100 (FIG. 1) such that when the test strip 160 is inserted into the strip port 150, the test strip 160 is retained in the received position within the strip port 150 until the sample analysis is completed. Examples of such physical latch or securement mechanism may include a uni-directionally biased anchor mechanism, or a pressure application mechanism to retain the test strip 160 in place by applying pressure on one or more surfaces of the test strip 160 within the strip port 150. Additional information related to physical latch or securement mechanisms is provided in U.S. Pat. No. 7,740,580 issued Jun. 22, 2010 titled "Analyte Monitoring", the disclosure of which is incorporated by reference herein.

Referring back to FIG. 1, the output unit 250 may be configured to output display data or information including the determined analyte level on the display unit 120 (FIG. 1) of the health monitor device with a medication dose calculation function 100. In addition, in still a further aspect of the present disclosure, the output unit 250 and the input section 240 may be integrated, for example, in the case where the display unit 120 is configured as a touch sensitive display (e.g., a touch screen display) where the patient may enter information or commands via the display area using, for example, a finger or stylus, or any other suitable input device, and where, the touch sensitive display is configured as the user interface in an icon or motion driven environment, for example.

Referring yet again to FIG. 2, the communication interface 220 in one embodiment of the present disclosure includes a wireless communication section configured for bi-directional radio frequency (RF) communication with other devices to transmit and/or receive data to and from the health monitor device with a medication dose calculation function 100. In addition, the communication interface 220 may also be configured to include physical ports or interfaces such as a USB port, an RS-232 port, or any other suitable electrical connection port to allow data communication between the health monitor device with a medication dose calculation function 100 and other external devices such as a computer terminal (for example, at a physician's office or in hospital environment), an external medical device, such as an infusion device or including an insulin delivery device, or other devices that are configured for similar complementary data communication.

In one embodiment, the wireless communication section of the communication interface 220 may be configured for infrared communication, Bluetooth communication, or any other suitable wireless communication mechanism to enable the health monitor device with a medication dose calculation function for communication with other devices such as infusion devices, analyte monitoring devices, computer terminals, communication enabled mobile telephones, personal digital assistants (PDAs), or any other communication devices which the patient or user of the health monitor device with a medication dose calculation function 100 may use in conjunction therewith, in managing the treatment of a health condition, such as diabetes.

Figure 3:
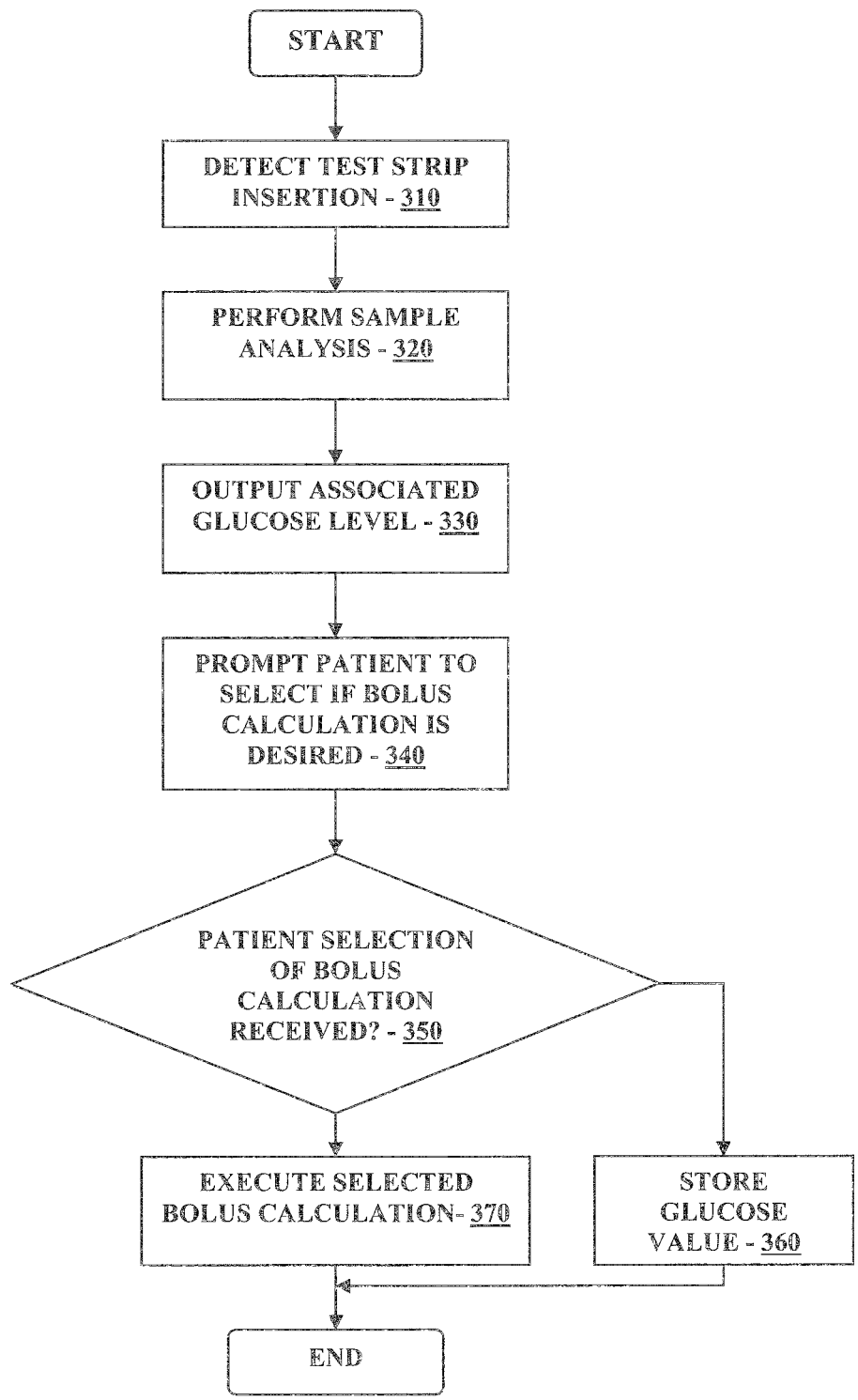
FIG. 3 is a flowchart illustrating the analyte level determination and medication dose calculation procedure in accordance with embodiments of the present disclosure.

FIG. 3 is a flowchart illustrating the analyte level determination and medication dose calculation procedure in accordance with one embodiment of the present disclosure. Referring to FIG. 3, a test strip is detected by the controller unit 210 (or the test strip interface 230) (310) of the health monitor device with a medication dose calculation function 100 (FIG. 1). Thereafter, the fluid sample, such as a blood sample, received from the inserted test strip 160 is analyzed (320) to determine the corresponding analyte level, such as a glucose level, and the determined analyte level is output (330) on the display unit 120 (FIG. 1) for example, in units of mg/dL.

Referring back to FIG. 3, after determining the analyte level and displaying the measured analyte level to the patient (330), a prompt command is generated and output to the patient to select if the medication dosage calculation is desired (340). More specifically, in one embodiment of the present disclosure, the controller unit 210 (FIG. 2) is configured to generate a command and display in the display unit 120 to query the user as to whether a medication dosage calculation determination is desired by the patient. Thereafter, a determination of whether or not the patient has selected to have the medication dosage calculation performed by the controller unit 210 is made (350). In one embodiment, the patient may operate one or more of the input buttons 130 or the input unit 140 to select whether or not to have the medication dosage calculation performed.

Referring again to FIG. 3, if it is determined that the patient has selected not to have the medication dosage determination performed, then the determined analyte value is displayed and/or stored (360), e.g., in memory of the health monitor device, and the routine terminates. For example, in one embodiment, the controller unit 210 (FIG. 2) may be configured to store the determined analyte value in the data storage unit 260 with associated time and/or date information of when the analyte value determination is performed. In an alternate embodiment, the measured analyte value may be stored substantially concurrently with the display of the analyte value.

On the other hand, if it is determined that the patient has selected to have the medication dosage calculation performed, the health monitor device with a medication dose calculation function 100 is configured to enter the medication dosage determination mode (370), described in further detail below in conjunction with FIG. 4, where the desired type of medication dosage is determined and provided to the patient. In another embodiment, the health monitor device with a medication dose calculation function 100 may be configured to store the glucose data even in the event the user selects to perform the medication dose calculation.

Figure 4:
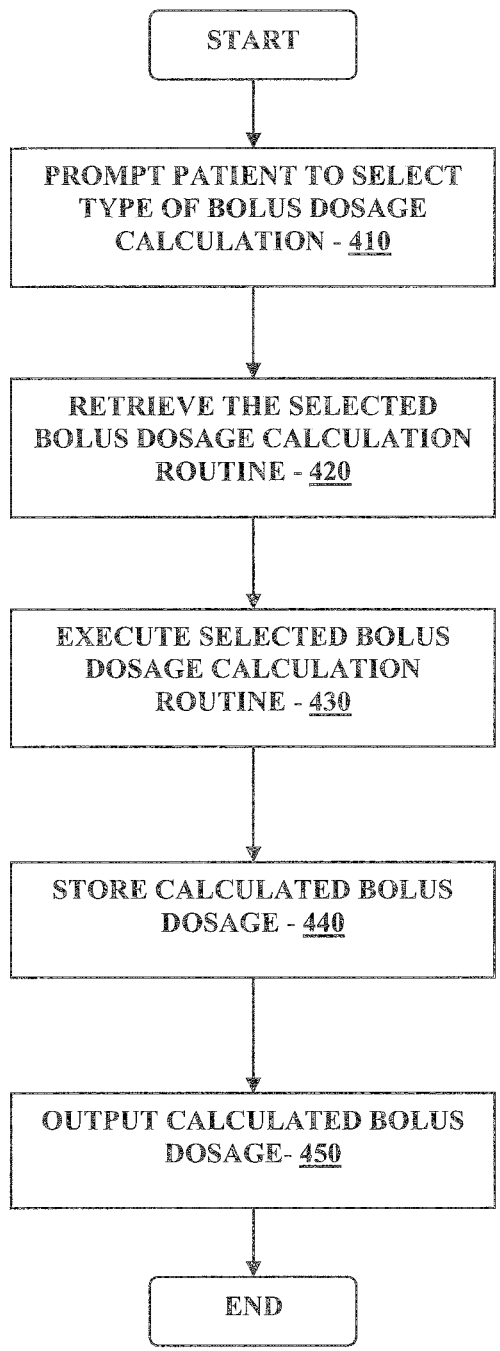
FIG. 4 is a flowchart illustrating the medication dose calculation procedure of FIG. 3 in accordance with embodiments of the present disclosure.

FIG. 4 is a flowchart illustrating the medication dose calculation procedure of FIG. 3 in accordance with one embodiment of the present disclosure. Referring to FIG. 4, when the health monitor device with a medication dose calculation function 100 (FIG. 1) enters the medication dosage determination mode as described above, the controller unit 210 (FIG. 2) is configured to prompt the patient (for example, by displaying the options to the patient on the display unit 120 (FIG. 1)) to select the type of desired medication dosage calculation 410. For example, the controller unit 210 may be configured to output a list of available medication dosage calculation options including, for example, bolus calculation options such as a carbohydrate bolus, a correction bolus, a dual or extended bolus, a square wave bolus, or any other suitable medication calculation function which may be programmed into the health monitor device with a medication dose calculation function 100 (and for example, stored in the data storage unit 260).

Referring back to FIG. 4, after the patient selects the desired medication dosage calculation in response to the prompt for medication type selection (410), the selected medication dosage calculation routine is retrieved (420) from the data storage unit 260, and thereafter executed (430). In one embodiment, the execution of the selected medication dosage calculation (430) may include one or more input prompts to the patient to enter additional information as may be required to perform the selected medication dosage calculation.

For example, in the case of calculating a carbohydrate bolus, the patient may be prompted to provide or enter an estimate of the carbohydrate amount that the patient is planning on ingesting. In this regard, a food database may be stored in the data storage unit 260 or elsewhere for easy access (e.g., a personal computer (PC), personal digital assistant (PDA), mobile telephone, or the like and to which the health monitor device may be coupled (e.g., wirelessly or by physical connection) to easily retrieve such information) to conveniently determine the corresponding carbohydrate amount associated with the type of food which the patient will be ingesting. Alternatively, the patient may provide the actual estimated carbohydrate count if such information is readily available by the patient. In addition to carbohydrate information, a food database may include additional information, e.g., calorie information, which may be selected by a patient for entry.

Alternatively, in the case of calculating a dual bolus of insulin, the patient is prompted to provide, in addition to a dose amount, time duration information for the extended portion of the bolus dosage to be infused or otherwise delivered to the patient. Similarly, the patient may further be prompted to provide insulin sensitivity information, and any other information as may be necessary to determine the selected bolus dosage amount in conjunction with other relevant information such as insulin on board information, and the time of the most recently administered bolus (so as to provide a warning to the patient if a bolus dosage has been administered within a predetermined time period, and a subsequent administration of the additional bolus dosage may potentially be harmful).

Referring back to FIG. 4, after the execution of the selected medication dosage calculation routine (430), the calculated medication dosage amount is stored (440) in the data storage unit 260, and the calculated medication dosage amount is output displayed to the patient (450) on the display unit 120 of the health monitor device with a medication dose calculation function 100, or audibly if the health monitor device is so configured. In certain embodiments, storing and output displaying the calculated medication dosage amount may be substantially concurrently performed, rather than sequentially.

Figure 5:
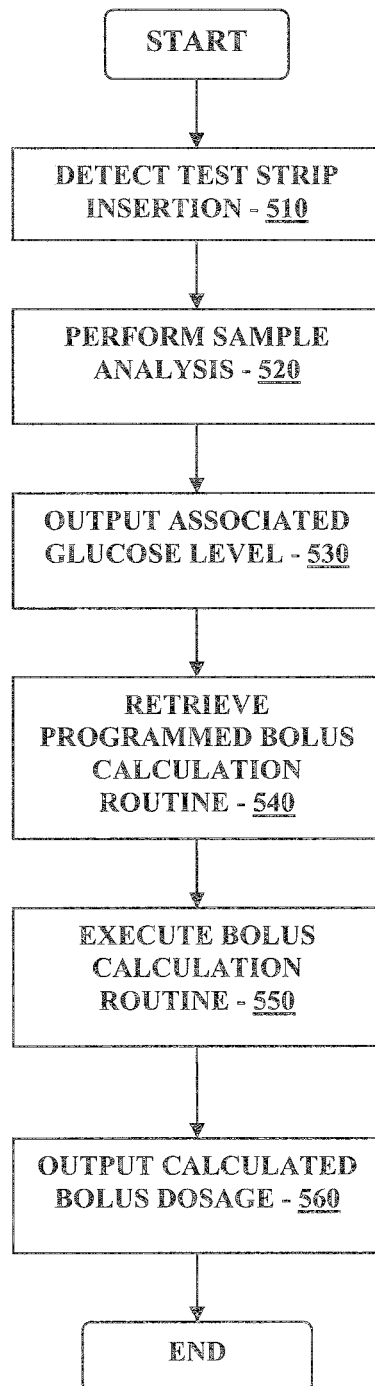
FIG. 5 is a flowchart illustrating the analyte level determination and medication dose calculation procedure in accordance with embodiments of the present disclosure.

FIG. 5 is a flowchart illustrating the analyte level determination and medication dose calculation procedure in accordance with another embodiment of the present disclosure. Referring to FIG. 5, a test strip 160 is inserted into the strip port 150 of the health monitor device with a medication dose calculation function 100 (510), the fluid sample on the test strip 160 is analyzed to determine the corresponding analyte level (520), and thereafter, output displayed (530).

Referring back to FIG. 5, an analyte level from the fluid sample received from the test strip 160 is determined (540). The controller unit 210 (FIG. 2) is configured to enter into the medication dosage determination mode, and to execute pre-programmed or predetermined medication calculation routine (550), and thereafter, output or display the calculated medication dosage amount (560). In this manner, in one embodiment of the present disclosure, the health monitor device with a medication dose calculation function 100 may be programmed or configured to automatically enter into the medication determination mode upon completion of the fluid sample analysis for analyte level determination.

In one embodiment of the present disclosure, the health monitor device with a medication dose calculation function 100 may be configured to execute different types of medication dosage calculation based on the patient specified parameters. For example, the health monitor device with a medication dose calculation function 100 may be configured to perform a carbohydrate bolus determination when the test strip sample analysis is performed within a predetermined time period of a meal event. For example, the health monitor device with a medication dose calculation function 100 may be programmed by the patient or a health care professional to automatically select the carbohydrate bolus determination if the test strip fluid sample analysis is performed within one hour prior to a meal time (which may be programmed into the health monitor device with a medication dose calculation function 100).

Figure 6A:
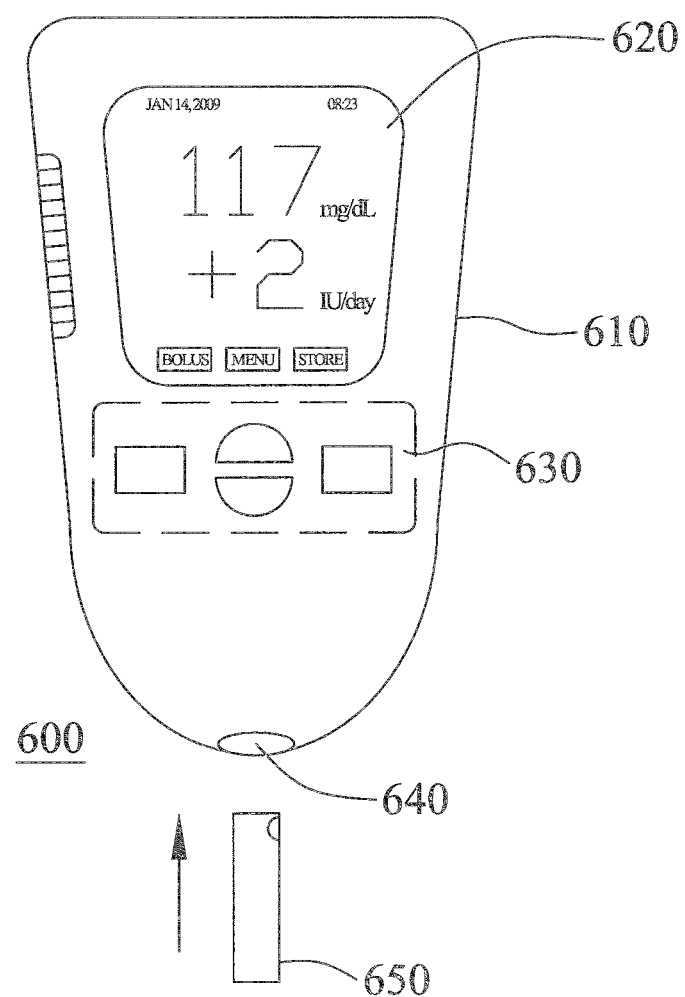
FIG. 6A shows a health monitor device with medication dose calculation function in accordance with embodiments of the present disclosure.

FIG. 6A shows a health monitor device with medication dose calculation function in accordance with another embodiment of the present disclosure. A health monitor device 600 in accordance with one or more embodiments may be used for determining a concentration of an analyte in blood or interstitial fluid. In one embodiment, the health monitor device 600 may be an analyte test meter, such as a glucose test meter that may be used for determining an analyte concentration, such as a blood glucose concentration, of a sample for determination of a blood glucose level of a patient, such as a patient with Type-1 or Type-2 diabetes.

Referring to FIG. 6A, in one embodiment, the health monitor device 600 may be a small portable device designed to be palm-sized and/or adapted to fit into, for example, a pocket or purse of a patient. The portable health monitor device 600 may have the appearance of a personal electronic device, such as a mobile phone or personal digital assistant (PDA), so that the user may not be identified as a person using a medical device. Additional information is provided in U.S. Pat. No. 7,041,468 issued on May 9, 2006 titled "Blood Glucose Tracking Apparatus and Method" and in U.S. Patent Application Publication No. 2004/0254434 published Dec. 16, 2004 titled "Glucose Measuring Module and Insulin Pump Combination", the disclosure of each of which is incorporated herein by reference for all purposes.

In another embodiment, the health monitor device 600 may be a larger unit for home use and designed to sit on a shelf or nightstand. In yet another embodiment, the health monitor device 600 may be designed for use in a hospital or doctor's office. The larger health monitor device units 600 may have the same functionality as the portable health monitor device 600 as described in further detail below.

Figure 6B:
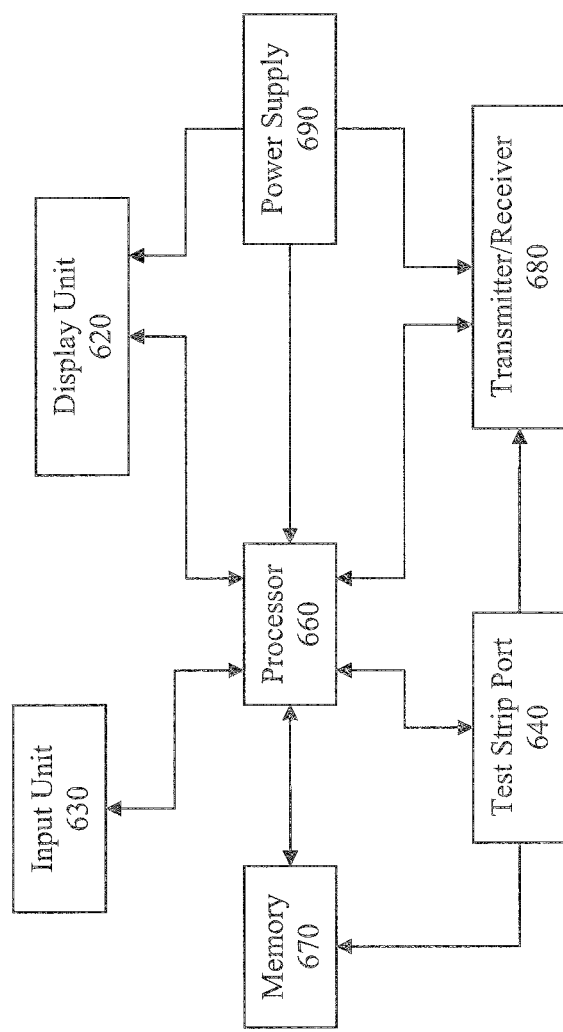
FIG. 6B is a block diagram of a configuration of the health monitor device shown in FIG. 6A in accordance with embodiments of the present disclosure.

Referring to FIGS. 6A and 6B, a health monitor device 600 includes a housing 610 and a display unit 620 provided thereon. In one embodiment, the display unit 620 may be a dot-matrix display. In other embodiments, other display types, such as liquid-crystal displays (LCD), plasma displays, light-emitting diode (LED) displays, or seven-segment displays, among others, may alternatively be used. The display unit 620 may display, in numerical or graphical form, for example, information related to, among others, a patient's current analyte concentration. Also incorporated within the housing 610 of the health monitor device 600 may be a processor 660 (FIG. 6B) and a memory device 670 (FIG. 6B). The memory device 670 (FIG. 6B) may store raw and/or analyzed data as well as store instructions which, when executed by the processor 660 (FIG. 6B), may provide, among others, instructions to the display unit 620, and may be used for analysis functions, such as analyte concentration analysis and medication dosage calculations.

In embodiments of the present disclosure, the memory device 670 (FIG. 6B) may include a readable and/or writable memory device such as, for example, but not limited to a read only memory (ROM), random access memory (RAM), flash memory device, or static random access memory (SRAM). In another embodiment, an optional transmitter/receiver unit 680 (FIG. 6B) may be incorporated into the housing 610 of the health monitor device 600. The transmitter/receiver unit 680 (FIG. 6B) may be used to transmit and/or receive analyzed or raw data or instructions to/from, for example, optional peripheral devices, such as a data analysis unit or a medication administration unit in a data network.

In another embodiment, the transmitter/receiver unit 680 (FIG. 6B) is a transceiver capable of both transmitting and receiving data. The transmitter/receiver unit 680 (FIG. 6B) may be configured for wired or wireless transmission, including, but not limited to, radio frequency (RF) communication, RFID (radio frequency identification) communication, WiFi or Bluetooth communication protocols, and cellular communication, such as code division multiple access (CDMA) or Global System for Mobile communications (GSM). In another embodiment, the health monitor device 600 may include a power supply 690 (FIG. 6B), such as a rechargeable power supply, e.g., a rechargeable battery.

Referring back to FIG. 6A, in one embodiment, the health monitor device 600 may also include a plurality of input buttons 630. Each of the plurality of input buttons 630 may be designated for a specific task, or alternatively, each of the plurality of input buttons 630 may be 'soft buttons'. In the case that the plurality of input buttons are 'soft buttons', each of the plurality of buttons may be used for a variety of functions. The variety of functions may be determined based on the current mode of the health monitor device 600, and may be distinguishable to a user by the use of button instructions shown on the display unit 620. Other input methods may also be incorporated including, but not limited to, a touch-pad, jog-wheel, or capacitive sensing slider inputs. Yet another input method may be a touch-sensitive display unit, as described further below and shown in FIG. 7.

Referring back to FIG. 6A, the health monitor device 600 may also include a strip port 640 which may be configured for receiving a test strip 650. The test strip 650 is configured to receive a fluid sample, such as a blood sample, from a patient. The test strip 650 may then be inserted into the strip port 640, whereby the health monitor device 600 may analyze the sample and determine the concentration of an analyte, such as glucose, in the sample. The analyte concentration of the sample may then be displayed on the display unit 620 as the analyte level of the patient. In another aspect, the health monitor device 600 may use a conversion function to convert a measured analyte concentration of a sample to a blood analyte concentration of a host. In another embodiment, the analyte concentration of the analyzed sample may be stored in the memory 670 (FIG. 6B) of the health monitor device 600. The stored analyte concentration data may additionally be tagged with date and/or time data related to the date and/or time the fluid sample was taken and analyzed. In another embodiment, the analyte concentration data may be transmitted via the transmitter/receiver unit 680 (FIG. 6B) to one or more peripheral devices for storage and/or further analysis.

As discussed above, in certain embodiments, a strip port to receive the test strip may be provided as a separate component that is configured to physically or electrically couple to the health monitoring device 600. Additional information is provided in U.S. Pat. No. 7,041,468 issued on May 9, 2006 titled "Blood Glucose Tracking Apparatus and Method" and in U.S. Patent Application Publication No. 2004/0254434 published Dec. 16, 2004 titled "Glucose Measuring Module and Insulin Pump Combination" the disclosures of each of which are incorporated herein by reference for all purposes.

In another embodiment, the health monitor device 600 may include instructions for calculating a medication dosage. The medication dosage may be, for example, a dosage of insulin in response to a blood glucose concentration data determined from the fluid sample on the test strip 650 received at the strip port 640. In one aspect, the medication dosage calculation may be based, at least in part, on a current patient analyte concentration data averaged with stored values of previous analyte concentration data.

In another aspect, the instructions for calculating a medication dosage may include instructions for calculating a dosage for a variety of types of medication, such as a variety of types of insulin. Insulin types may include, but are not limited to: long-acting insulin types such as LEVEMIR® insulin, available from Novo Nordisk, and LANTUS® insulin (insulin glargine), available from Sanofi-Aventis; intermediate-acting insulin types such as Neutral Protamine Hagedom (NPH), and lente insulin; fast-acting insulin types including NOVALIN® insulin, available from Novo Nordisk, recombinant human insulin such as HUMULIN® insulin, available from Eli Lilly and Company, and bovine insulin, and porcine insulin; rapid-acting insulin types such as NOVOLOG® insulin (aspart insulin), available from Novo Nordisk, HUMALOG® insulin (Lysine-Proline insulin), available from Eli Lilly and Company, and APIDRA® insulin (glulisine insulin), available from Sanofi-Aventis, and very-rapid-acting insulin types such as VIAJEC™ insulin, available from Biodel, Inc.

In another embodiment, the instructions for calculating a medication dosage may be instructions for calculating a recommended update to an existing medication dosage regimen. Data related to a current medication dosage regimen may be stored in the memory 670 of the health monitor device 600, including current prescribed medication types and dosages and an algorithm for calculating recommended medication dosage changes. Calculated medication dosage recommendations may be displayed to the patient on the display unit 620 of the health monitor device 600 for patient intervention, or further may be transmitted directly to a medication administration device, such as an insulin pump, for a medication dosage regimen update.

In another embodiment, the health monitor device 600 may include programming for alarm functions. Alarms may be used to inform patients when current analyte concentrations are outside threshold levels, when medication dosage regimens need to be updated, or when an error is detected. Alarms may be in the form of a visual, auditory, or vibratory alarm.

In yet another embodiment, the health monitor device 600 may include an integrated medication delivery system (not shown). Additional information is provided in U.S. Patent Publication No. 2006/0224141 published on Oct. 5, 2006, titled "Method and System for Providing Integrated Medication Infusion and Analyte Monitoring System", the disclosure of which is incorporated by reference for all purposes.

The integrated medication delivery system may be in the form of a drug delivery injection pen such as a pen-type injection device incorporated within the housing 610 of the health monitor device 600. Additional information is provided in U.S. Pat. Nos. 5,536,249 and 5,925,021, the disclosure of each of which is incorporated herein by reference for all purposes.

The integrated medication delivery system may be used for injecting a dose of medication, such as insulin, into a patient based on a prescribed medication dosage, and may be automatically updated with dosage information received from the medication dosage calculator described above. In another embodiment, the medication dosage of the medication delivery system may include manual entry of dosage changes made through, for example, the input buttons 630 of the health monitor device 600. Medication dosage information associated with the medication delivery system may be displayed on the display unit 620 of the health monitor device 600.

Figure 6C:
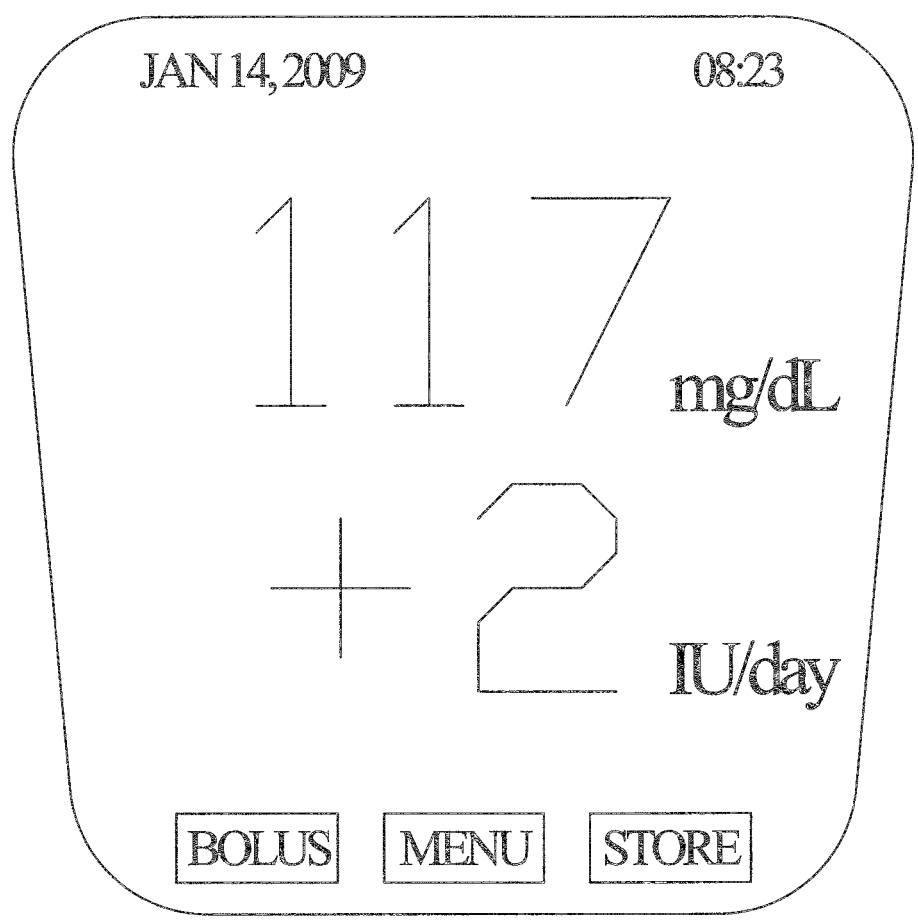
FIG. 6C is an illustration of a display of the health monitor device shown in FIG. 6A in accordance with embodiments of the present disclosure.

FIG. 6C is an illustration of a display of the health monitor device shown in FIG. 6A in one embodiment. Referring to FIG. 6C, the display unit 620 of the health monitor device 600 (FIG. 6A) may display a variety of data values to a patient. In one embodiment, the display unit 620 may display a current analyte concentration, such as the current blood glucose concentration of a patient, a recommended update to the patient's medication dosage regimen, such as insulin dosage updates, and the date and/or time of the current or most recent analyte test. Further, if the health monitor device 600 includes 'soft buttons', the display unit 620 may show the current function of said 'soft buttons' for the particular current operational mode of the health monitor device 600. Other information that may be displayed on the display unit 620 may include, but is not limited to, current medication dosage regimen data, recommended medication type, and historical patient analyte concentration data.

Information on the display unit 620 may be displayed in a variety of manners or format including, for example, numerical data, graphical data, symbols, pictures, and/or animations. In one aspect, the user may be able to choose the display style, for example, by pushing one of the input buttons 630. The display unit 620 may be a black and white display unit, or may alternatively be a color display unit, whereby, information may be displayed in a variety of colors. Colors may be used as indicators to a patient of changes in the current displayed information, or may be used for aesthetic purposes to allow for easier navigation of the data and/or menus. In another aspect, the brightness, contrast, tint, and/or color settings of the display unit 620 may be adjustable.

Figure 7:
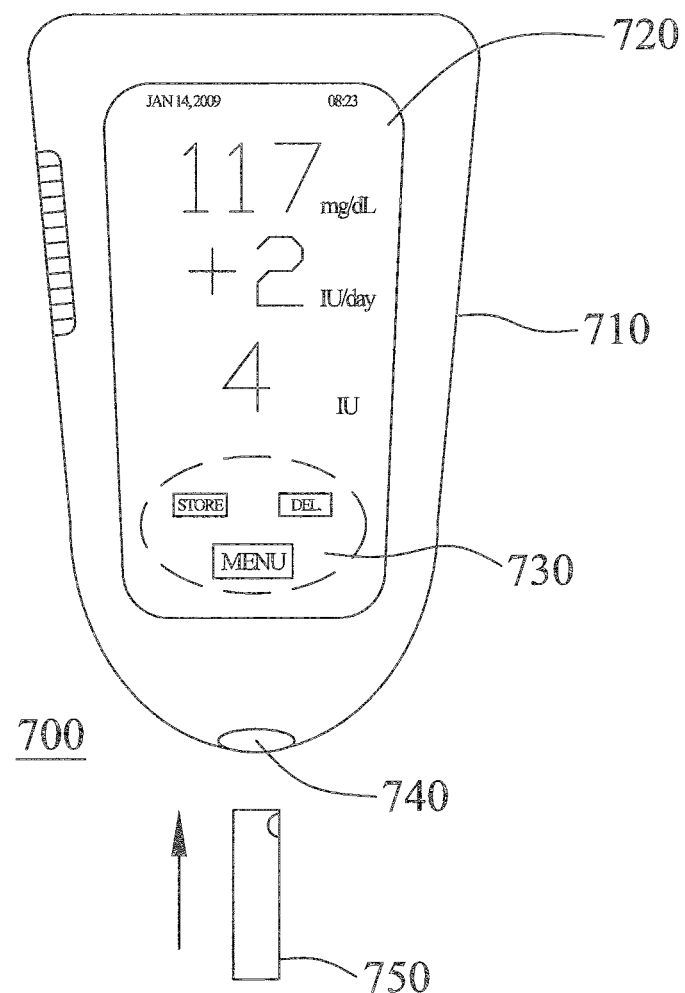
FIG. 7 shows a touch-screen health monitor device in accordance with embodiments of the present disclosure.

FIG. 7 shows a touch-screen health monitor device in accordance with one embodiment of the present disclosure. Referring to FIGS. 7 and 6A, a touch-screen health monitor device 700 may include the same functions and basic design as a health monitor device 600 without a touch-screen. A touch-screen health monitor device 700 may include a larger display unit 720 compared to the display unit 620 of a health monitor device 600 without a touch-screen in order to accommodate the extra area required for any touch-screen buttons 730 that may be used. Similar to a health monitor device 600 without a touch-screen, a touch-screen health monitor device 700 includes a housing 710, which has a touch-screen display unit 720 positioned thereon. The touch-screen health monitor device 700 may also include a strip port 740 for receiving a test strip 750, which may include a fluid sample for analysis, such as a blood sample for a blood glucose concentration analysis.

Continuous Analyte Monitoring Devices

In another embodiment, the health monitor device 600 (FIG. 6) may incorporate a continuous analyte monitoring device, where a transcutaneously implanted sensor may continually or substantially continually measure an analyte concentration of a bodily fluid. Examples of such sensors and continuous analyte monitoring devices include systems and devices described in U.S. Pat. Nos. 6,175,752, 6,560, 471, 5,262,305, 5,356,786, U.S. Patent Application Publication No. 2010/0198034 published Aug. 5, 2010 titled "Compact On-Body Physiological Monitoring Devices and Methods Thereof", and U.S. Patent Application Publication No. 2010/0324392 published Dec. 23, 2010 titled "Analyte Sensor and Apparatus for Insertion of the Sensor", the disclosures of each of which are incorporated herein by reference for all purposes.

Accordingly, in certain embodiments, the health monitor device 600 may be configured to operate or function as a data receiver or controller to receive analyte related data from a transcutaneously positioned in vivo analyte sensor such as an implantable glucose sensor. The analyte monitoring system may include a sensor, for example an in vivo analyte sensor configured for continuous or substantially continuous measurement of an analyte level of a body fluid, a data processing unit (e.g., sensor electronics) connectable to the sensor, and the health monitor device 600 configured to communicate with the data processing unit via a communication link. In aspects of the present disclosure, the sensor and the data processing unit (sensor electronics) may be configured as a single integrated assembly. In certain embodiments, the integrated sensor and sensor electronics assembly may be configured as a compact, low profile on-body patch device assembled in a single integrated housing and positioned on a skin surface of the user or the patient with a portion of the analyte sensor maintained in fluid contact with a bodily fluid such as an interstitial fluid during the sensor life time period (for example, sensor life time period including about 5 days or more, or about 7 days or more, or about 14 days or more, or in certain embodiments, about 30 days or more). In such embodiments, the on-body patch device may be configured for, for example, RFID or RF communication with the health monitor device 600 to wirelessly provide monitored or detected analyte related data to the health monitor device 600 based on a predetermined transmission schedule or when requested from the health monitor device 600. Predetermined transmission schedule may be programmed or configured to coincide with the analyte sample detection by the analyte sensor (for example, but not limited to including once every minute, once every 5 minutes, once every 15 minutes). Alternatively, the health monitor device 600 may be programmed or programmable to acquire the sampled analyte data (real time information and/or stored historical data) in response to one or more requests transmitted from the health monitor device 600 to the on-body patch device.

As discussed, embodiments include the on-body patch device including the data processing unit coupleable to the analyte sensor so that both devices are positioned in or on the user's body, with at least a portion of the analyte sensor positioned transcutaneously. The data processing unit in certain embodiments may include a portion of the sensor (proximal section of the sensor in electrical communication with the data processing unit) which is encapsulated within or on the printed circuit board of the data processing unit with, for example, potting material or other protective material. The data processing unit performs data processing functions, where such functions may include but are not limited to, filtering and encoding of analyte related signals, for transmission to the health monitor device 600. In certain embodiments, the sensor or the data processing unit or a combined sensor/data processing unit may be wholly implantable under the skin layer of the user.

In certain embodiments, transmitter/receiver section 680 of the health monitor device 600 includes an RF receiver and an antenna that is configured to communicate with the data processing unit, and the processor 660 of the health monitor device 600 is configured for processing the received data from the data processing unit such as data decoding, error detection and correction, data clock generation, and/or data bit recovery.

In operation, the health monitor device 600 in certain embodiments is configured to synchronize with the data processing unit to uniquely identify the data processing unit, based on, for example, identification information of the data processing unit, and thereafter, to periodically receive signals transmitted from the data processing unit associated with the monitored analyte levels detected by the sensor.

As described, in aspects of the present disclosure, the analyte monitoring system may include an on-body patch device with a thin profile that may be comfortably worn on the arm or other locations on the body (under clothing worn by the user or the patient, for example), the on-body patch device including an analyte sensor and circuitry and components for operating the sensor and processing and storing signals received from the sensor as well as for communication with the health monitor device 600. For example, one aspect of the on-body patch device may include electronics to sample the voltage signal received from the analyte sensor in fluid contact with the body fluid, and to process the sampled voltage signals into the corresponding glucose values and/or store the sampled voltage signal as raw data.

The on-body patch device in one aspect may further include an antenna such as a loop antenna to receive RF power from the an external device such as the health monitor device 600 described above, electronics to convert the RF power received via the antenna into DC (direct current) power for the on-body patch device circuitry, communication module or electronics to detect commands received from the health monitor device 600, and communication component such as an RF transmitter to transmit data to the health monitor device 600, a low capacity battery for providing power to sensor sampling circuitry (for example, the analog front end circuitry of the on-body patch device in signal communication with the analyte sensor), one or more non-volatile memory or storage device to store data including raw signals from the sensor or processed data based on the raw sensor signals.

In certain embodiments, the health monitor device 600 is also configured to operate as a data logger, interacting or communicating with the on-body patch device by, for example, periodically transmitting requests for analyte level information from the on-body patch device, and storing the received analyte level information from the on-body patch device in one or more memory components 670.

The various processes described above including the processes operating in the software application execution environment in the analyte monitoring system including the on-body patch device and/or the health monitor device 600 performing one or more routines described above may be embodied as computer programs developed using an object oriented language that allows the modeling of complex systems with modular objects to create abstractions that are representative of real world, physical objects and their interrelationships. The software required to carry out the inventive process, which may be stored in a memory or storage device of the storage unit of the various components of the analyte monitoring system described above in conjunction to the Figures including the on-body patch device or the health monitor device 600 may be developed by a person of ordinary skill in the art and may include one or more computer program products.

In one embodiment, an apparatus for bi-directional communication with an analyte monitoring system includes a storage device having stored therein one or more routines, a processing unit operatively coupled to the storage device and configured to retrieve the stored one or more routines for execution, a data transmission component operatively coupled to the processing unit and configured to transmit data based at least in part on the one or more routines executed by the processing unit, and a data reception component operatively coupled to the processing unit and configured to receive analyte related data from a remote location and to store the received analyte related data in the storage device for retransmission, where the data transmission component is programmed to transmit a query to a remote location, and further where the data reception component receives the analyte related data from the remote location in response to the transmitted query when one or more electronics in the remote location transitions from an inactive state to an active state upon detection of the query from the data transmission component.

Embodiments also include the on-body patch device including sensor electronics coupled to an analyte sensor positioned on a skin surface of a patient or a user. In one aspect, an introducer mechanism may be provided for the transcutaneous placement of the analyte sensor such that when the on-body patch device is positioned on the skin surface, a portion of the sensor is inserted through the skin surface and in fluid contact with a body fluid of the patient or the user under the skin layer.

In certain embodiments, when the health monitor device 600 is positioned or placed in close proximity or within a predetermined range of the on-body patch device, the RF power supply in the health monitor device 600 may be configured to provide the necessary power to operate the electronics in the on-body patch device, and accordingly, the on-body patch device may be configured to, upon detection of the RF power from the health monitor device 600, perform preprogrammed routines including, for example, transmitting one or more signals to the health monitor device 600 indicative of the sampled analyte level measured by the analyte sensor. In one embodiment, communication and/or RF power transfer between the health monitor device 600 and the on-body patch device may be automatically initiated when the health monitor device 600 is placed in close proximity to the on-body patch device. Alternatively, the health monitor device 600 may be configured such that user intervention, such as a confirmation request and subsequent confirmation by the user using, for example, the display 620 and/or input components 630 of the health monitor device 600, may be required prior to the initiation of communication and/or RF power transfer between the health monitor device 600 and the on-body patch device. In a further embodiment, the health monitor device 600 is user configurable between multiple modes, such that the user may choose whether the communication between the health monitor device 600 and on-body patch device is performed automatically or requires a user confirmation.

As discussed, some or all of the electronics in the on-body patch device in one embodiment may be configured to rely on the RF power received from the health monitor device 600 to perform analyte data processing and/or transmission of the processed analyte information to the health monitor device 600. That is, the on-body patch device may be discreetly worn on the body of the user or the patient, and under clothing, for example, and when desired, by positioning the health monitor device 600 within a predetermined distance from the on-body patch device, real time glucose level information may be received by the health monitor device 600. This routine may be repeated as desired by the patient (or on-demand or upon request, for example) to acquire monitored real time glucose levels at any time during the time period that the on-body patch device is worn by the user or the patient.

In another embodiment, the health monitor device 600 includes an integrated analyte test meter and lancing device for lancing a bodily fluid sample, such as a blood sample, and measuring an analyte concentration, such as a blood glucose concentration. Examples of such integrated devices include systems and devices described in U.S. Application Publication Nos. 2007/0149897 and 2008/0167578, the disclosures of each of which are incorporated herein by reference for all purposes.

In another embodiment, a health monitor device as described herein, e.g., a health monitor device 600, includes an integrated analyte test meter and lancing device for providing a bodily fluid sample, such as a blood sample, and measuring an analyte concentration, such as a blood glucose concentration. Examples of such integrated devices include systems and devices described in U.S. Application Publication Nos. 2007/0149897 and 2008/0167578, the disclosures of each of which are incorporated herein by reference for all purposes.

Health Monitor Device Designs

Figure 21:
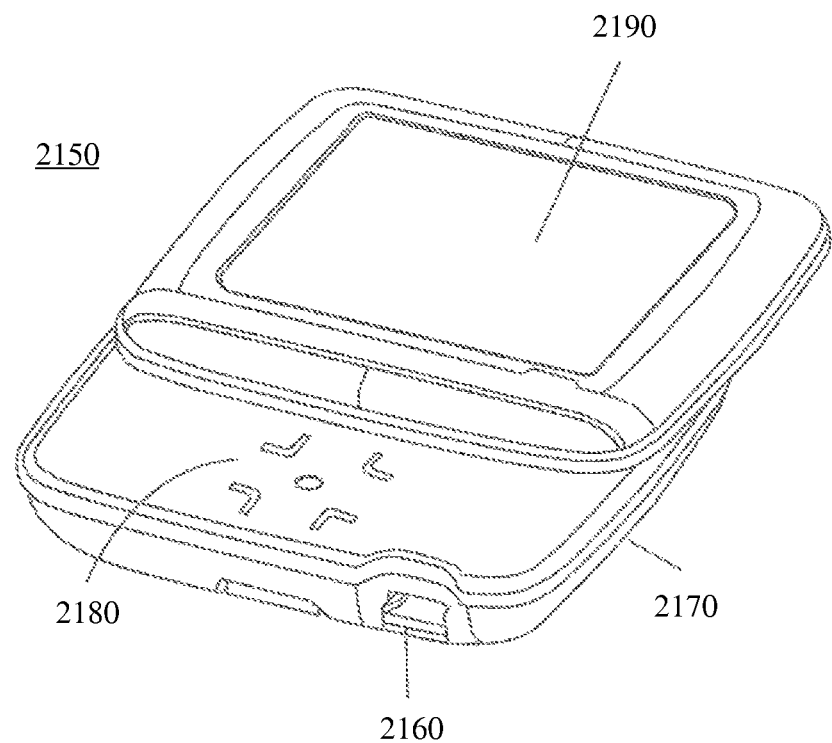
FIG. 21 shows a perspective view of a health monitor device according to embodiments of the present disclosure. The health monitor device is depicted in a "slider" configuration in which a portion of the meter housing including a display can be slid to an open or closed position to respectively expose or cover a portion of the meter housing including an input unit.

FIG. 21 shows a health monitor device with medication dose calculation function in accordance with another embodiment of the present disclosure. A health monitor device 2150 is provided which includes a test-strip port 2160, a housing 2170, an input unit 2180 and a display unit 2190. The health monitor device 2150 is depicted in a "slider" configuration in which a portion of the health monitor housing 2170 including display unit 2190 can be slid to an open or closed position to respectively expose or cover a portion of the health monitor housing 2170 including input unit 2180.

Figure 22:
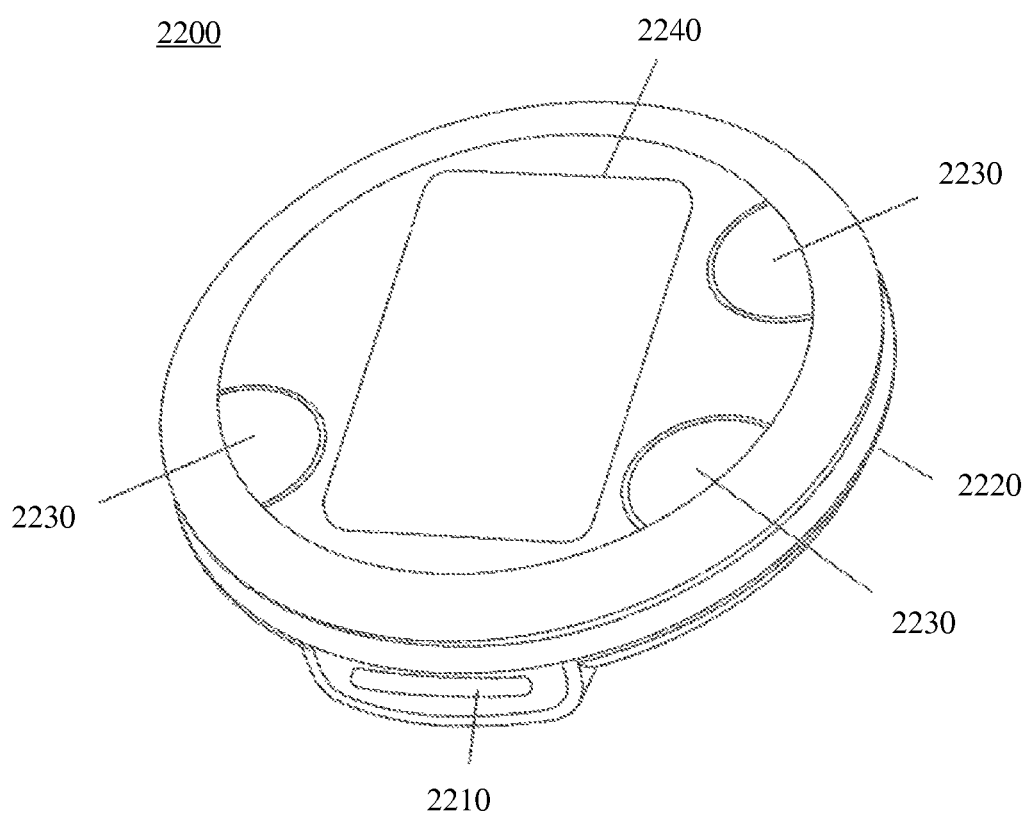
FIG. 22 shows a perspective view of a health monitor device according to embodiments of the present disclosure. The health monitor device is depicted in a substantially disk-shaped configuration with input units positioned peripherally to a display unit on the meter housing.

FIG. 22 shows a health monitor device with medication dose calculation function in accordance with another embodiment of the present disclosure. A health monitor device 2200 is provided which includes a test-strip port 2210, a housing 2220, an input unit 2230 and a display unit 2240. The health monitor device 2200 is depicted in a substantially disk-shaped configuration with input units 2230 positioned peripherally to display unit 2240 on the health monitor device housing 2220.

Figure 23:
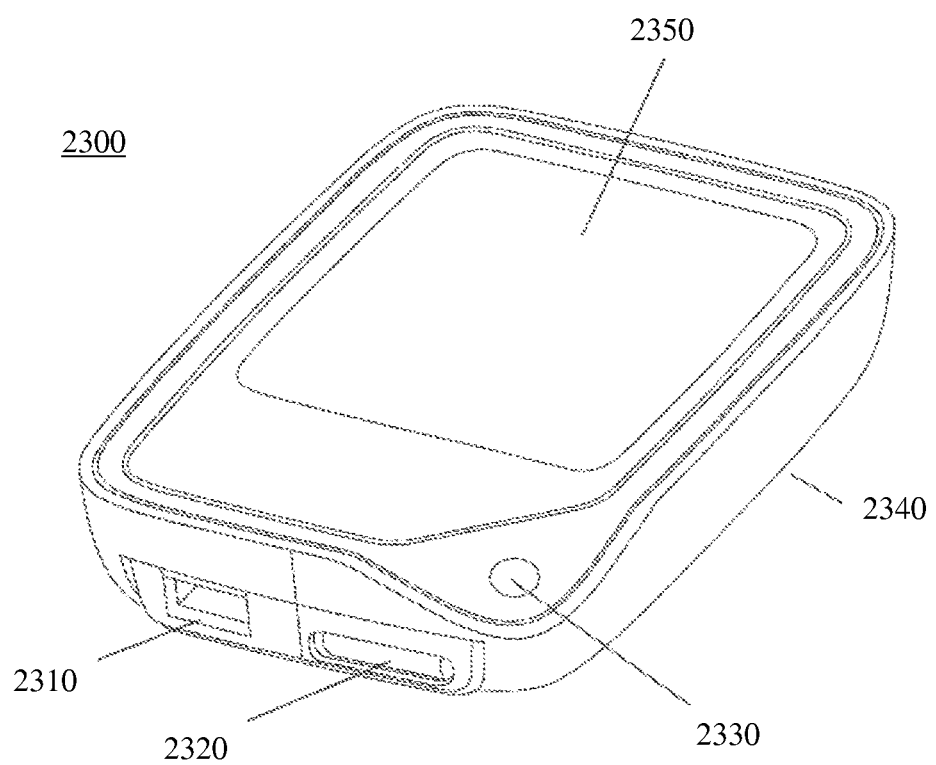
FIG. 23 shows a perspective view of a health monitor device according to embodiments of the present disclosure. The health monitor device is depicted in a configuration including a touch screen, an input unit and a communication port.

FIG. 23 shows a health monitor device with medication dose calculation function in accordance with another embodiment of the present disclosure. A health monitor device 2300 is provided which includes a test-strip port 2310, a communication port 2320, an input unit 2330, a housing 2340, and a touch-screen display unit 2350.

Medication Dosage Calculation

Figure 8:
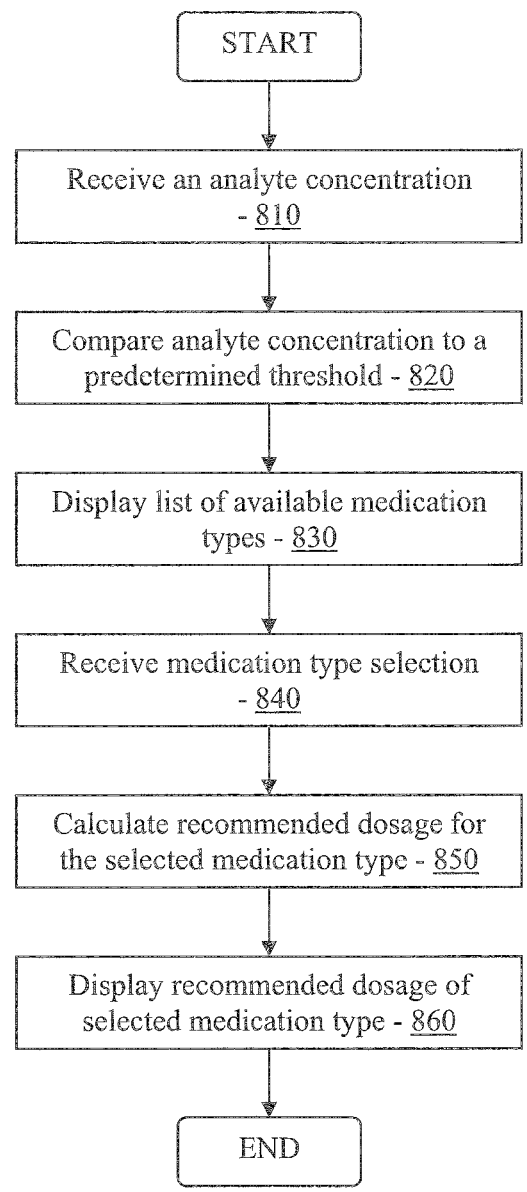
FIG. 8 is a flow chart illustrating a medication dosage calculation procedure for use in one or more embodiments of the present disclosure.

FIG. 8 is a flow chart illustrating a medication dosage calculation procedure for use in one or more embodiments of the present disclosure. Referring to FIG. 8, a device, such as a health monitor device 600 (FIG. 6A), receives an analyte concentration (810) for the current analyte level of a patient. The analyte level is compared to a predetermined threshold analyte level (820). For example, if the analyte is glucose and the analyte level is a blood glucose level of a patient, the threshold blood glucose level may be between 80 mg/dL and 120 mg/dL, or a tailored threshold determined by the patient or a healthcare professional. If the current analyte concentration level is above the predetermined threshold, a list of available medication types may be displayed (830) on the display unit 620 of a health monitor device 600. For example, if the analyte concentration level is a blood glucose concentration level for a patient suffering from, for example, diabetes, the list of available medication types may be a list of available insulin types. From the list of available medication types, a medication type is selected (840) and a recommended dosage for the selected medication type based upon the current analyte concentration level is calculated (850) and displayed (860).

Figure 9:
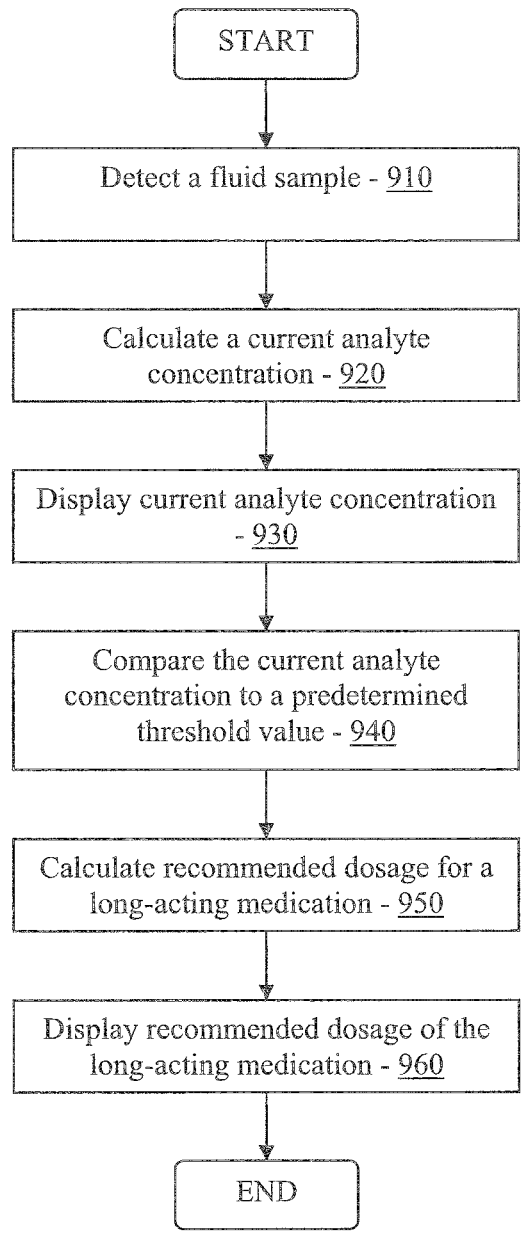
FIG. 9 is a flow chart illustrating an analyte concentration determination and medication dosage calculation in accordance with embodiments of the present disclosure.

FIG. 9 is a flow chart illustrating an analyte concentration determination and medication dosage calculation in one embodiment of the present disclosure. Referring to FIGS. 9 and 6A, a fluid sample is detected (910), for example, by applying the fluid sample to a test strip 650 and inserting the test strip 650 into a strip port 640 of the health monitor device 600. Upon detection of the fluid sample, a current analyte concentration is calculated (920) based on analysis of the fluid sample. In one embodiment, the health monitor device 600 may include a display unit 620, such as a dot-matrix display, and the current analyte concentration is displayed (930) on the display unit 620.

Still referring to FIGS. 9 and 6A, in one embodiment, the health monitor device 600 may include instructions or routines to perform a long-acting medication dosage calculation function. A long-acting medication may be a medication wherein a single dose may last for up to 12 hours, 24 hours, or longer. The instructions for a long-acting medication dosage calculation function may be in the form of software stored on the memory device 670 (FIG. 6B) and executed by the processor 660 (FIG. 6B) of the health monitor device 600. In one aspect, the long-acting medication dosage calculation function is an algorithm based on the current concentration of an analyte of a patient, wherein the long-acting medication dosage calculation function compares the current analyte concentration value to a predetermined threshold (940), which may be based on clinically determined threshold levels for a particular analyte, or may be tailored for individual patients by a doctor or other treating professional. If the current analyte concentration is above the predetermined threshold, the long-acting medication dosage calculation function may use the current analyte concentration value to calculate a recommended dosage of a long-acting medication (950). Once calculated, the recommended medication dosage may be displayed (960) on the display unit 620 of the health monitor device 600.

In one embodiment, the health monitor device 600 is configured to measure the blood glucose concentration of a patient and include instructions for a long-acting insulin dosage calculation function. Periodic injection or administration of long-acting insulin may be used to maintain a baseline blood glucose concentration in a patient with Type-1 or Type-2 diabetes. In one aspect, the long-acting medication dosage calculation function includes an algorithm or routine based on the current blood glucose concentration of a diabetic patient, to compare the current measured blood glucose concentration value to a predetermined threshold or an individually tailored threshold as determined by a doctor or other treating professional to determine the appropriate dosage level for maintaining the baseline glucose level.

In one embodiment, the long-acting insulin dosage calculation function may be based upon LEVEMIR® insulin, available from Novo Nordisk. LEVEMIR® insulin is a long-acting insulin indicated for once- or twice-daily subcutaneous administration for the treatment of adult and pediatric patients with type 1 diabetes mellitus or adult patients with type 2 diabetes mellitus who require basal (long-acting) insulin for the control of hyperglycemia (further information is available at the website located by placing "www" immediately in front of ".levemir-us.com"). Other types of long-acting insulin include LANTUS® insulin, available from Sanofi-Aventis, also known as insulin glargine. LANTUS® insulin is a long-acting insulin that has up to a 24 hour duration of action. Further information on LANTUS® insulin is available at the website located by placing "www" immediately in front of ".lantus.com".

Figure 10:
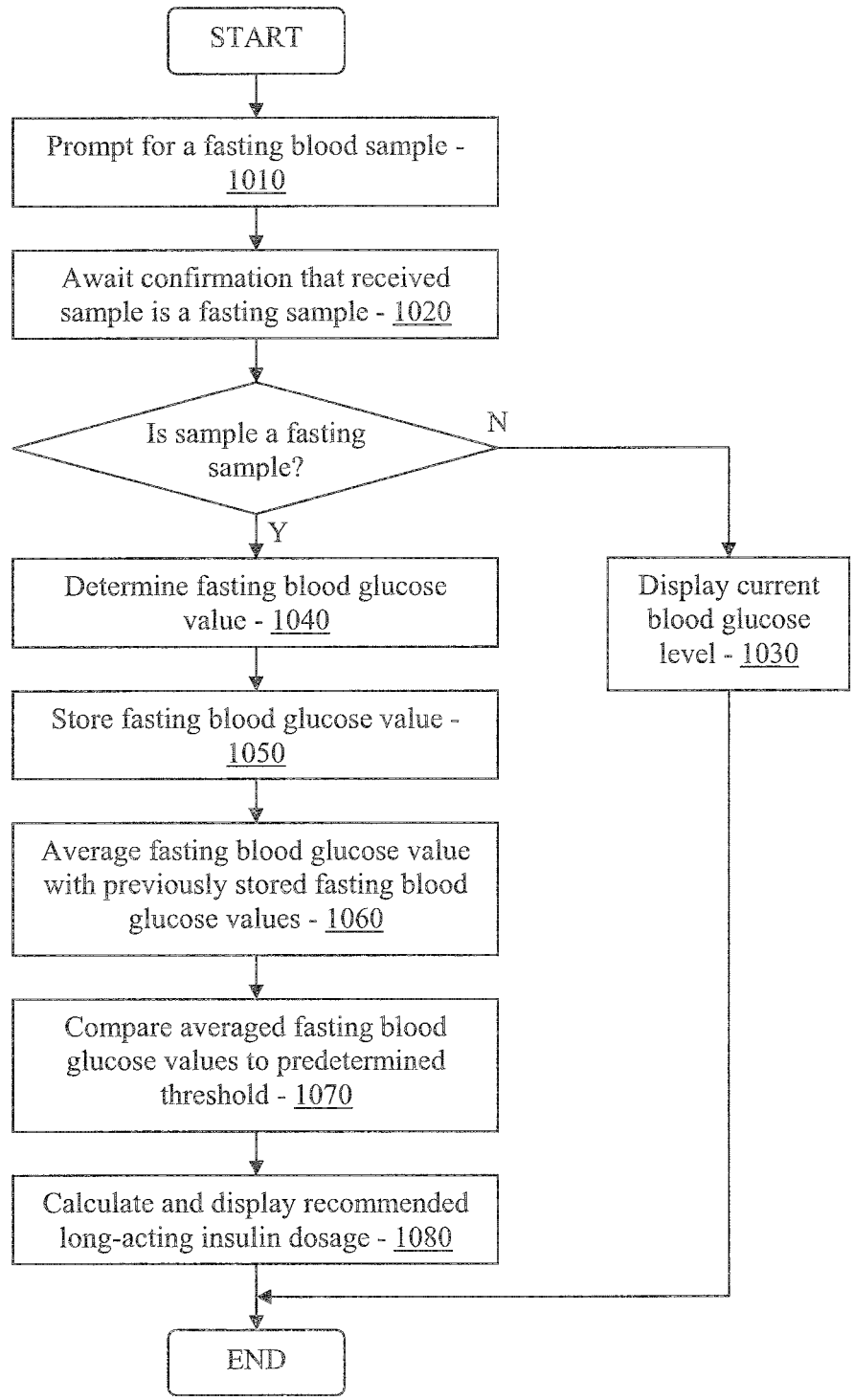
FIG. 10 is a flow chart illustrating a procedure for determining a recommended update to a long-acting insulin dosage regimen in accordance with embodiments of the present disclosure.

FIG. 10 is a flow chart illustrating a procedure for determining a recommended update to a long-acting insulin dosage regimen in one embodiment. Some patients with diabetes, including patients with type-1 diabetes and patients with type-2 diabetes, may require or be recommended to take insulin as a method for maintaining a safe blood glucose level. In some cases, a medical professional may determine that a dosage regimen of long-acting insulin, such as LEVEMIR® insulin, may be beneficial to a patient for maintaining a safe baseline blood glucose level. Long-acting insulin may be taken as, for example, a daily bolus dosage, and may have up to a 24-hour duration of action. Long-acting insulin may be used as an alternative for patients who may not wish to use an insulin pump, which provides a patient with a steady basal glucose level throughout the day. In some cases, a patient may require only the long-acting insulin dose to maintain a safe baseline blood glucose level, and may not require periodic doses of a fast or rapid acting insulin to correct for spikes in blood glucose levels resulting from, for example, carbohydrate intake. In one embodiment, among others, long-acting insulin may be taken as an injection by, for example, a syringe or injection pen, as an oral stimulant from, for example, an inhaler, or as a transdermal patch delivery system.

Patients using long-acting insulin may have different sensitivity to insulin. As such, it may be desirable for patients to periodically adjust their daily bolus dosage of long-acting insulin. Referring to FIG. 10, a glucose measuring device, such as the health monitor device 600 described above in conjunction with FIG. 6A, may prompt for a fasting blood sample (1010) to measure a fasting blood glucose level. A fasting blood sample may be a blood sample of a patient taken after a predetermined period of time without food, such as 8 hours without food typically obtained in the morning after a period of sleep. The fasting blood sample may be received on a test strip 650, which may be inserted into a strip port 640 of the health monitor device 600 for analysis.

Referring back to FIG. 10, in one embodiment, to ensure an accurate blood glucose reading, the health monitor device 600 may request and await confirmation that the provided blood sample is a fasting sample (1020). The confirmation that the provided blood sample is a fasting sample may be provided by the patient to the health monitor device 600 through, for example, the input buttons 630 of the health monitor device 600. Alternatively, the health monitor device 600 may determine whether the provided blood sample is a fasting sample by determining if the current time is in the morning following what would typically be a predetermined period of sleep, or comparing the current time to stored past data and basing whether the sample is a fasting sample or not based upon trends of what time during the day that previous provided fasting samples were obtained. In the event that the provided blood sample is not a fasting sample, the health monitor device 600 may calculate and display the current blood glucose level of the provided sample with a warning that the displayed value is not a fasting blood glucose level (1030). In one aspect, if the provided blood sample is not a fasting sample, no recommended long-acting insulin dosage regimen update is calculated or displayed.

Still referring to FIG. 10, if the received blood sample is confirmed to be a fasting blood sample, a fasting blood glucose level may be determined by analyzing the blood glucose level of the received blood sample (1040). Once the fasting blood glucose level is determined, the value may be stored (1050) in a memory 670 of the health monitor device 600, or alternatively, the value may be transmitted for storage in a memory of a secondary device or computer. In one embodiment, the stored fasting blood glucose level data is time and/or date stamped. For example, a time and/or date associated with the determined analyte concentration (e.g., the determined fasting blood glucose level) may be stored in a memory 670 of the health monitoring device 600, or alternatively, the time and/or date associated with the determined analyte concentration may be transmitted for storage in a memory of a secondary device or computer. Once the fasting blood glucose level data is stored in the memory 670, the data may be compared to a predetermined threshold value. In another embodiment, the current fasting blood glucose level may be averaged with stored fasting blood glucose level data from preceding days (1060), for example, the preceding, one, two, three, or four days, for comparison to the predetermined threshold value (1070).

If the current fasting blood glucose level or the averaged fasting blood glucose level is above the predetermined threshold, a dosage recommendation algorithm may be implemented based on the fasting blood glucose level. The dosage recommendation algorithm may be stored in the memory 670 in the health monitor device 600 and executed by the processor 660 in the health monitor device 600, to calculate and display on a display unit 620 a recommended long-acting insulin dosage (1080). Alternatively, the dosage recommendation algorithm may be stored in a peripheral device containing a memory, and data may be transmitted to one or more peripheral devices over a data network for analysis and the results transmitted back to the health monitor device 600 for display.

Patients using long acting insulin (e.g., basal insulin), for example patients that are starting a long-acting insulin regimen or patients that currently use long-acting insulin but who would like to improve their diabetes management, may need to adjust their dose level of long-acting insulin over time. In some instances, a patient adjusts the dose level of long-acting insulin over time until their fasting blood glucose level is within a threshold range. For example, a health care professional may determine a current dose level for a medication, such as long-acting insulin, for a patient. The patient may then titrate the current dose level over time until a target threshold range is achieved. By "titrate" is meant that the current dose level for a medication is adjusted over time until a target parameter (e.g., blood glucose level) is within a target threshold range. The target threshold range may be determined by a health care professional. In certain embodiments, the patient may use the health monitor device 600 to facilitate the determination of an adjusted dose level for a medication, such as long-acting insulin.

Figure 24:
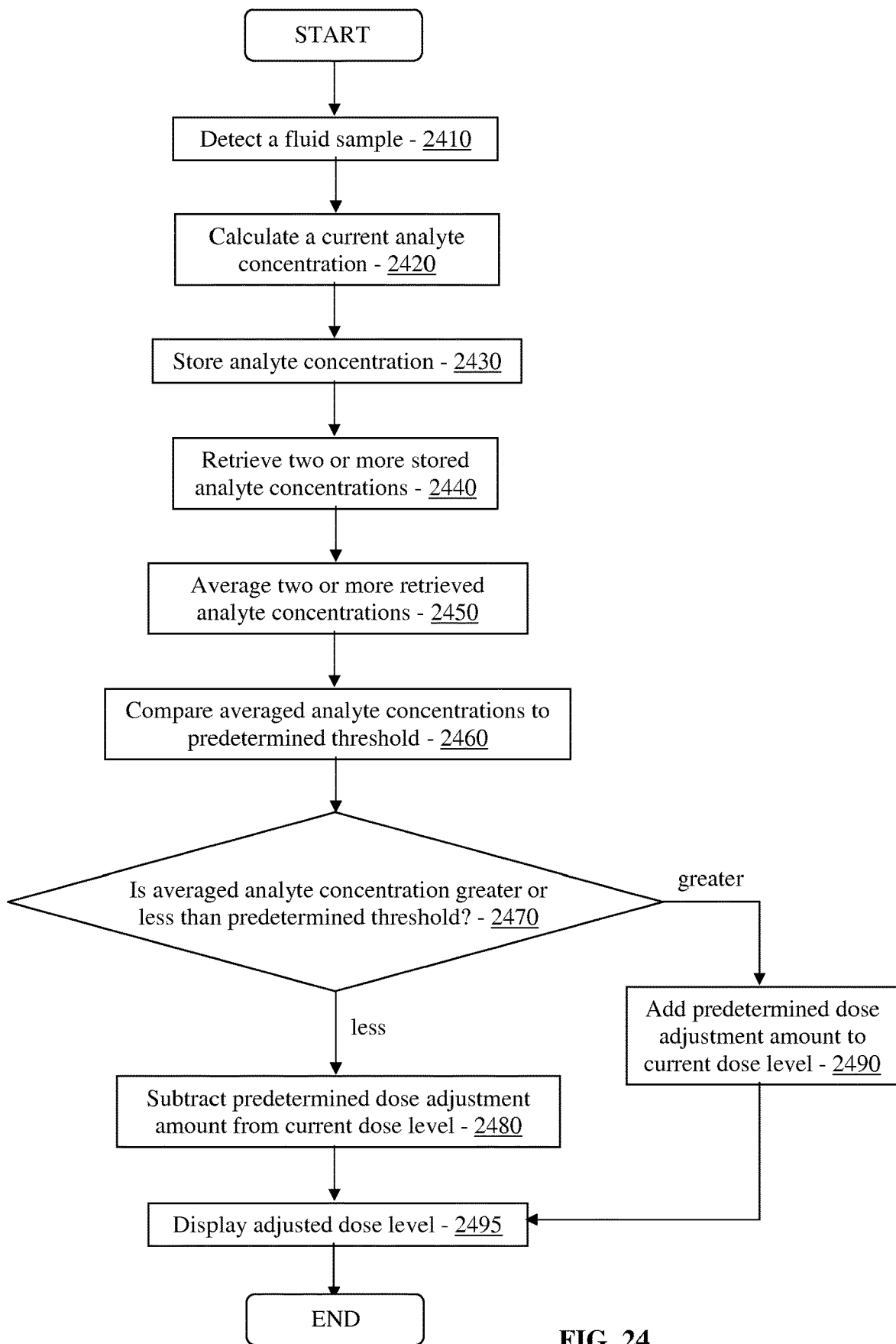
FIG. 24 is a flow chart illustrating a procedure for determining an adjusted dose level to a medication dosage regimen according to embodiments of the present disclosure.

FIG. 24 is a flow chart illustrating a procedure for determining an adjusted dose level to a medication dosage regimen in one embodiment of the present disclosure. Referring to FIGS. 24 and 6A, a fluid sample is detected (2410), for example, by applying the fluid sample to a test strip 650 and inserting the test strip 650 into a strip port 640 of the health monitor device 600. Upon detection of the fluid sample, a current analyte concentration is calculated (2420) based on analysis of the fluid sample. The current analyte concentration may be a current fasting blood glucose level. Once the analyte concentration is determined, the value may be stored (2430) in a memory 670 of the health monitor device 600. Alternatively, the value may be transmitted for storage in a memory of a secondary device or computer. In some embodiments, the stored analyte concentration data is time and/or date stamped. For example, a time and/or date associated with the determined analyte concentration (e.g., the determined fasting blood glucose level) may be stored in a memory 670 of the health monitoring device 600, or alternatively, may be transmitted for storage in a memory of a secondary device or computer.

In certain embodiments, the health monitor device is configured to titrate a medication dosage level only if a certain number of analyte measurements have been stored in the memory. For example, the health monitor device may titrate a medication dosage level if the number of analyte measurements stored in the memory is above a threshold amount, such as 2 or more, or 3 or more, or 4 or more, or 5 or more, or 6 or more, or 7 or more, etc. In some cases, the health monitor device may titrate a medication dosage level if the number of analyte measurements stored in the memory is above the threshold amount over a preceding time period, such as the preceding 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more, 16 days or more, 17 days or more, 18 days or more, 19 days or more, 20 days or more, 21 days or more, etc. In certain embodiments, the health monitor device may titrate a medication dosage level if the number of analyte measurements stored in the memory is 4 or more over the preceding 16 days. Other combinations of the number of analyte measurements and the number of preceding days are possible, as set forth above. In some cases, if the number of analyte measurements stored in the memory is not greater than the threshold amount over the preceding time period, then the health monitor device will not titrate the medication dosage level until the number of stored analyte measurements is greater than the threshold amount.

After the analyte concentration data is stored in the memory 670, two or more stored analyte concentrations may be retrieved from the memory (2440). In certain instances, the two or more retrieved analyte concentrations are analyzed and may be processed to determine one or more statistical parameters associated with the two or more retrieved analyte concentrations. For example, the two or more retrieved analyte concentrations may be averaged (2450) and compared to a predetermined threshold range (2460). In some cases, the most recent analyte concentrations (e.g., fasting blood glucose levels) are averaged, such as the 2, 3, 4, 5, 6, 7, 8, 9, 10, etc. most recent analyte concentrations. In some cases, the analyte concentrations (e.g., fasting blood glucose levels) from the preceding time period, as described above, may be averaged for comparison to the predetermined threshold range (2460). As described above, the predetermined threshold range may be determined by a health care professional and stored in the memory 670 of the health monitor device 600. In some cases, the threshold range may be modified by the patient and/or the health care professional.

If the average of the analyte concentrations (e.g., fasting blood glucose levels) is less than the threshold range, then this is an indication that the current dose level of medication (e.g., long-acting insulin) is too high. In this case, a predetermined dose adjustment amount is subtracted from the current dose level to give an adjusted dose level (2480) that is less than the current dose level.

If the average of the analyte concentrations (e.g., fasting blood glucose levels) is greater than the threshold range, then this is an indication that the current dose level of medication (e.g., long-acting insulin) is too low. In this case, a predetermined dose adjustment amount may be added to the current dose level to give an adjusted dose level (2490) that is greater than the current dose level. In certain embodiments, the health monitor device may be configured such that a certain number of analyte concentrations must be above the threshold range before the health monitor device will recommend an increase in the medication dosage level. For example, the health monitor device may be configured such that 20% or more, 25% or more, 30% or more, 40% or more, 50% or more, 60% or more, 75% or more, etc. analyte concentrations must be above the threshold range before the health monitor device will recommend an increase in the medication dosage level.

If the average of the analyte concentrations (e.g., fasting blood glucose levels) is within or equal to the threshold range, then the algorithm may recommend no change to the current medication dose level (e.g., long-acting insulin dosage regimen). For example, a recommended change to the current medication dose level may not be displayed and the current dose level may be displayed instead.

The predetermined dose adjustment amount may be determined by a health care professional and stored in the memory 670 of the health monitor device 600. For instance, the predetermined dose adjustment amount may be one or more units of insulin (e.g., long-acting insulin), such as two or more units, three or more units, four or more units, six or more units, or eight or more units of insulin, or ten or more units of insulin. The predetermined dose adjustment amount may include whole units or partial units, for example half units of insulin. In some instances, the predetermined dose adjustment amount may be a percentage of the current dose level. For instance, the predetermined dose adjustment amount may be 2% or more, or 3% or more, or 4% or more, or 5% or more, or 6% or more, or 7% or more, or 8% or more, or 9% or more, or 10% or more, or 12% or more, or 15% or more, etc. of the current dose level.

In certain embodiments, the dose level of medication has a maximum dose level. If the adjusted dose level (e.g., the current dose level plus the predetermined dose adjustment amount) would be greater than the maximum dose level, then health monitor device 600 may display information and/or a message to the user. For example, the health monitor device 600 may display the maximum dose level, an alert and/or a message notifying the user that the maximum dose level has been reached. The health monitor device 600 may also display a message suggesting that the user contact a health care professional. In some cases, the maximum dose level is the maximum daily insulin dose level for a patient, which may include both basal insulin and mealtime bolus insulin doses. In certain instances, the health monitor device is configured to not display a recommended dose adjustment amount if the dose adjustment amount would cause the medication dosage level to be greater than the maximum dose level.

Other warning messages may be displayed upon the occurrence of certain events, such as, but not limited to, if an analyte concentration is below a threshold level, if an analyte concentration is above a threshold level, if an analyte concentration is greater than a predetermined amount below a threshold level, if an analyte concentration is greater than a predetermined amount above a threshold level, if a post-meal analyte concentration is above a threshold level, if a post-meal analyte concentration is above a threshold level more than a predetermined number of times, if a pre-meal analyte concentration is above a threshold level, or if a pre-meal analyte concentration is above a threshold level more than a predetermined number of times. These warning messages may be displayed to the user and may be associated with an alert and/or a message suggesting that the user contact a health care professional.

In certain embodiments, the adjusted dose level may be determined according to a predetermined schedule. For instance, a patient may determine an adjusted dose level every 3 days, or every 4 days, or every 5 days, or every 6 days, or once a week, or every ten days, or every 14 days, or every 16 days, or every two weeks, or every three weeks, or every month, and the like. In some instances, the predetermined schedule is determined by a health care professional and/or a patient and stored in a memory 670 of the health monitor device 600. The health monitor device 600 may then prompt the patient according to the predetermined schedule to determine the patient's adjusted dose level. For instance, if the predetermined schedule is every 4 days, then every 4 days, the health monitor device 600 may display a request confirming whether the patient wants to determine an adjusted dose level. If the patient inputs a positive confirmation, then the health monitor device 600 may proceed with determining the adjusted dose level, as described herein.

In some cases, an adjusted dose level is determined as described herein and the health monitor device 600 may request to confirm the adjusted dose level. The health monitor device may request an input command from the user, where the input command is either an acknowledgment confirming the adjusted dose level or a rejection of the adjusted dose level. In certain cases, if the input command is an acknowledgment confirming the adjusted dose level, then the adjusted dose level may replace the current dose level and may be stored in the memory 670 of the health monitor device 600 as a new current dose level. Subsequent determinations of an adjusted dose level may use the new current dose level to determine a subsequent adjusted dose level based on subsequently obtained analyte concentrations, as described above.

In certain embodiments, two or more threshold ranges and two or more predetermined dose adjustment amounts may be used to determine the adjusted dose level. For example, a first threshold range may be associated with a first predetermined dose adjustment amount, and a second threshold range may be associated with a second predetermined dose adjustment amount. In some cases, the predetermined dose adjustment amounts are different. For instance, if the average of the analyte concentrations is within the first threshold range, then the processor 660 may use the first predetermined dose adjustment amount to determine the adjusted dose level. If the average of the analyte concentrations is within the second threshold range, then the processor 660 may use the second predetermined dose adjustment amount to determine the adjusted dose level.

An example of a table of threshold ranges and their corresponding dose adjustment amounts is shown in Table I-A below. The values in Table I-A are representative values. The actual values used may vary from patient to patient and may be determined by a health care professional. The target threshold ranges for fasting blood glucose concentration and insulin dose adjustment amounts may be set by the user or may be customized target threshold ranges and dose adjustment amounts as determined by a health care professional. For example, for certain patients, the target fasting blood glucose range may be from 70-130 mg/dL, and the corresponding threshold ranges and dose adjustment amounts may be customized as desired and the patient and/or the health care professional.

TABLE I-A

| Threshold Range | Dose Adjustment Amount (% of current dosage level) |
|---|---|
| >180 mg/dL | Increase 10% |
| 140-180 mg/dL | Increase 7% |
| 100-139 mg/dL | Increase 4% |
| <95 mg/dL | Decrease 4% |

Referring to Table I-A above, the health monitor device 600 determines the average of the analyte concentrations and compares the average to the threshold ranges in the table. The threshold range that encompasses the average of the analyte concentrations is determined. The dose adjustment amount corresponding to that threshold range in the table may be used to determine the adjusted dose level. For example, if the average of the analyte concentrations is 140 mg/dL, then, according to Table I-A, the dose adjustment amount would be an increase of 7% in the dose of insulin. In some cases, the dose adjustment amount is added directly to the current dose level to give the adjusted dose level. The dose adjustment amount may be corrected or adjusted before being added to the current dose level. For example, the dose adjustment amount may be increased or decreased based on other information, such as, but not limited to, insulin sensitivity, whether a hypoglycemic event occurred within a previous time period, whether a hyperglycemic event occurred within a previous time period, level of physical activity, time of day, amount of stress, illness, amount of other medication, food intake (e.g., alcohol and/or fat consumption), combinations thereof, and the like.

If the average of the analyte concentrations is less than a threshold amount (e.g., less than 95 mg/dL), then this is an indication that the current dose level of medication (e.g., long-acting insulin) is too high, and a dose adjustment amount may be subtracted from the current dose level to give the adjusted dose level. For example, if the average of the analyte concentrations is less than 95 mg/dL, then, according to Table I-A, the dose adjustment amount is 4% of the current dose level and is subtracted from the current dose level to give the adjusted dose level.

In some cases, the dose adjustment amount may be a predetermined dose adjustment amount determined by the patient and/or a health care professional (e.g., in units or half units of insulin). For instance, an example of a table of threshold ranges and their corresponding dose adjustment amounts is shown in Table I-B below.

TABLE I-B

| Threshold Range | Dose Adjustment Amount (units of insulin) |
|---|---|
| >180 mg/dL | Increase 8 units |
| 140-180 mg/dL | Increase 6 units |
| 120-139 mg/dL | Increase 4 units |
| 95-119 mg/dL | Increase 2 units |
| 70-94 mg/dL | No change |
| <70 mg/dL | Decrease by a dose adjustment amount |

In some instances, if the average of the analyte concentrations is less than a threshold amount (e.g., less than 70 mg/dL in Table I-B above), then this is an indication that the current dose level of medication (e.g., long-acting insulin) is too high, and a dose adjustment amount may be subtracted from the current dose level to give the adjusted dose level. In some cases, the dose adjustment amount that is subtracted from the current dose level depends on the current dose level. For example, the dose adjustment amount may be a percentage of the current dose level, such as 2%, 3%, 4%, 5%, 6%, 7%, 8%, 9%, 10%, 12%, 15%, 20%, or 25% of the current dose level. In some cases, the dose adjustment amount may depend on additional data, such as a medication dose level of rapid-acting insulin. For example, the dose adjustment amount may be the amount the medication dose level of rapid-acting insulin increased over the past week. In certain instances, the dose adjustment amount is a percentage of the amount the medication dose level of rapid-acting insulin increased over the past week, such as 5%, 10%, 15%, 20%, or 25% of the amount the medication dose level of rapid-acting insulin increased over the past week.

In certain embodiments, the health monitor device is configured to recommend a decrease in the medication dosage amount if there is a hypoglycemic event in the preceding time period. Hypoglycemic events may include blood glucose measurements of 70 mg/dL or less, 65 mg/dL or less, 60 mg/dL or less, 55 mg/dL or less, or 50 mg/dL or less, etc. For example, the health monitor device may be configured to recommend a decrease in the medication dosage amount if 1 or more, or 2 or more, or 3 or more, or 4 or more, or 5 or more hypoglycemic events occurred within the preceding time period. In some instances, the health monitor device may be configured to recommend a decrease in the medication dosage amount if 2 or more blood glucose measurements were 70 mg/dL or less within the preceding time period. In some instances, the health monitor device may be configured to recommend a decrease in the medication dosage amount if 1 or more blood glucose measurement was 50 mg/dL or less within the preceding time period. The health monitor device may be configured to recommend a decrease in the medication dosage amount of 5%, 10%, 15%, 20%, 25% or more. In some cases, the health monitor device is configured to recommend a 10% decrease in the current dosage amount if a hypoglycemic event occurred within the preceding time period, as set forth above. In certain instances, if one or more hypoglycemic events occurred within the preceding time period, as described above, then the health monitor device may be configured to recommend a decrease in the medication dosage amount and not recommend any increases in the medication dosage amount.

Figure 25:
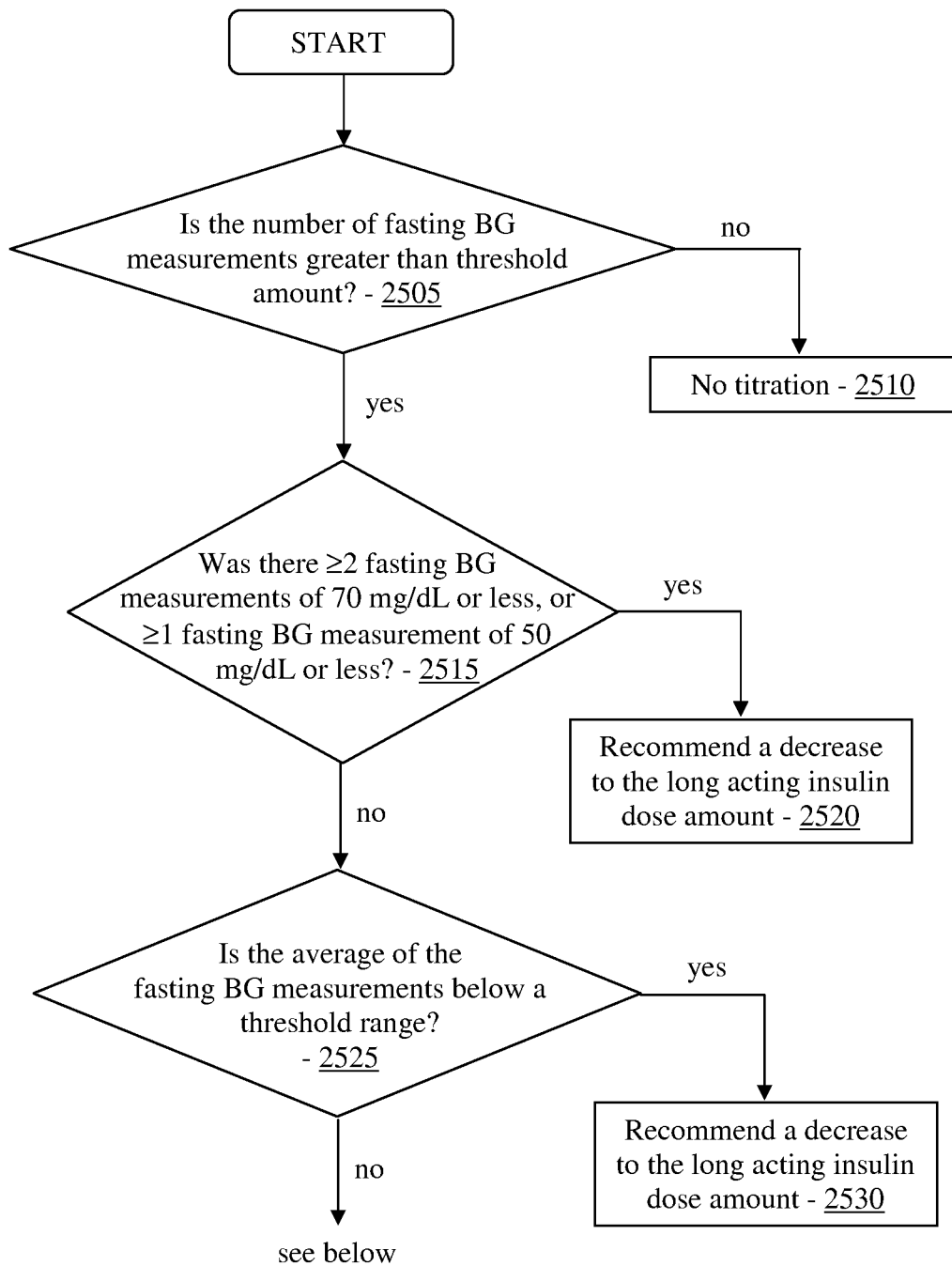
FIG. 25 is a flow chart illustrating a procedure for determining an adjusted dose level to a long-acting insulin dosage regimen according to embodiments of the present disclosure.

FIG. 25 is a flow chart illustrating a procedure for determining an adjusted dose level to a long-acting insulin dosage regimen. Referring to FIGS. 25, 6A and 6B, after measuring several fasting blood glucose measurements and storing those measurements in a memory 670 of the health monitor device 600, the health monitor device 600 may analyze the stored data to titrate the patient's long acting insulin dose level. The health monitor device 600 may first determine whether the number of fasting blood glucose measurements over a preceding time period is greater than a threshold amount (2505). For example, the health monitor device 600 may determine if there are 4 or more fasting blood glucose measurements over the preceding 16 days. If the number of fasting blood glucose measurements over the preceding time period is less than the threshold amount, then the health monitor device 600 will not titrate the medication dosage amount (2510). If the number of fasting blood glucose measurements over the preceding time period is the threshold amount or greater, then the health monitor device 600 may continue to the next step of the procedure. The health monitor device 600 may then determine if there was a hypoglycemic event within the preceding time period. For example, the health monitor device 600 may determine if there were one or more hypoglycemic events (e.g., 2 or more fasting blood glucose measurements of 70 mg/dL or less; or 1 or more fasting blood glucose measurements of 50 mg/dL or less) within the preceding time period (2515). If there were one or more hypoglycemic events, then the health monitor device 600 will recommend a decrease in the long acting insulin dose amount (2520). For example, if there were hypoglycemic events within the preceding time period, then the health monitor device 600 may recommend that the medication dosage amount be decreased by 10% of the current dosage amount. If there were no hypoglycemic events within the preceding time period, then the health monitor device 600 may continue to the next step of the procedure. The health monitor device 600 may then determine if the average of the fasting blood glucose measurements is below a threshold range (2525). If the average of the fasting blood glucose measurements is below the threshold range, then the health monitor device 600 may recommend a decrease to the long acting insulin dose amount (2530). For example, if the average of the fasting blood glucose measurements is below 95 mg/dL, then the health monitor device 600 may recommend that the long acting insulin dose amount be decreased by 4% of the current dose amount. If the average of the fasting blood glucose measurements is above the threshold range, then the health monitor device 600 may continue to the next step of the procedure. The health monitor device 600 may then determine if there is a threshold number or more of fasting blood glucose measurements that are above a threshold blood glucose value (2535). If the number of fasting blood glucose measurements that are above the threshold blood glucose value is not above the threshold number, then the health monitor device 600 will not recommend an increase to the medication dosage amount (2540). For example, if less than 3 out of 4 fasting blood glucose measurements were above the threshold blood glucose value, then the health monitor device 600 will not recommend an increase in the long acting insulin dosage amount. If there was a threshold number of fasting blood glucose measurements above the threshold blood glucose value, then the health monitor device 600 may recommend an increase in the medication dosage level. For instance, if 3 out of 4 (or more) fasting blood glucose measurements are above the threshold range, then the health monitor device 600 may recommend an increase in the long acting insulin dosage amount. The health monitor device 600 then determines the average of the fasting blood glucose measurements over the preceding time period (2545). The health monitor device 600 then compares the average of the fasting blood glucose measurements to a series of threshold ranges (2550), where each range corresponds to a recommended dose adjustment amount. The health monitor device 600 may then recommend (e.g., display) the appropriate corresponding dose adjustment amount and/or the adjusted dose level to the patient (2555). For instance, if the average is greater than 180 mg/dL, then the health monitor device 600 may recommend that the long acting insulin dosage amount be increased by 10% of the current dose amount. If the average is 140-180 mg/dL, then the health monitor device 600 may recommend that the long acting insulin dosage amount be increased by 7% of the current dose amount. If the average is 100-139 mg/dL, then the health monitor device 600 may recommend that the long acting insulin dosage amount be increased by 4% of the current dose amount. If the average is less than 95 mg/dL, then the health monitor device 600 may recommend that the long acting insulin dosage amount be decreased by 4% of the current dose amount.

Additional information regarding threshold ranges, titration of long acting and rapid acting insulin dosage amounts, and long acting and rapid acting insulin dose adjustment amounts to a patient's medication dosage regimen are described in Bergenstal, et al., *Diabetes Care*, vol. 31, no. 7 (July 2008) pp. 1305-10.

In certain embodiments, the health monitor device 600 includes a display unit 620, and the adjusted dose level is displayed (see FIG. 24, 2495) on the display unit 620. The display unit 620 of the health monitor device 600 (see FIG. 6A) may display a variety of data values to a patient. For example, the display unit 620 may display a current analyte concentration, such as the current analyte (e.g., blood glucose) concentration of a patient, two or more retrieved analyte concentrations, data associated with (e.g., an average of) the two or more retrieved analyte concentrations, a predetermined dose adjustment amount to the current dose level of medication, a recommended dose adjustment amount to the current dose level of medication, an adjusted dose level of the patient's medication dosage regimen, such as insulin dosage, and the date and/or time of the current or most recent analyte test and/or adjusted dose level.

In certain embodiments, the health monitor device 600 may output a request for predetermined information. For example, the health monitor device 600 may display a request for an acknowledgement confirming whether a hypoglycemic event occurred. In some instances, the request for an acknowledgement confirming whether a hypoglycemic event occurred is displayed after the health monitor device has displayed the average of the two or more retrieved analyte concentrations but before the adjusted dose level is displayed. If the patient inputs a confirmation that a hypoglycemic event occurred, then the health monitor device 600 may display a modified adjusted dose level that is less than the adjusted dose level. In some instances, if the patient inputs a confirmation that a hypoglycemic event occurred, then the health monitor device 600 does not display the adjusted dose level. For example, instead of displaying the adjusted dose level, the health monitor device 600 may display a message suggesting that the patient contact a health care professional.

In certain embodiments, the health monitor device is a blood glucose meter, and may be used to facilitate the determination of an adjusted dose level for a medication, such as long-acting insulin (e.g., basal insulin), as described herein.

The severity of the symptoms of diabetes for patients may vary from individual to individual. For some diabetic patients, it may be advantageous to use insulin to maintain a stable baseline blood glucose level, and additionally to use fast-acting insulin injections to compensate for periodic blood glucose level fluctuations resulting from, for example, carbohydrate intake. For such patients, it may be advantageous to have a method of calculating adjustments to daily insulin dosages to maintain a safe baseline blood glucose level, as well as on-the-spot dosage recommendations to correct for periodic blood glucose level fluctuations.

Insulin used to maintain a stable baseline blood glucose level may be administered through, among others, the use of an insulin pump in the form of a basal insulin infusion pump (small dosages of insulin injected into the body at periodic intervals throughout the day), or may be administered through the use of single daily injections of long-acting insulin, such as LEVEMIR® insulin. In other embodiments, long-acting insulin may be administered at various other intervals, such as twice a day, or every other day. Fast-acting and rapid-acting insulin, for example, are more often used as single dose bolus injections for immediate correction to periodic blood glucose level fluctuations, which may be used in conjunction with the long-acting insulin used to maintain the baseline blood glucose level. Accurate calculation and administration of insulin to a diabetic patient is used as a measure for maintaining safe blood glucose levels in order to avoid incidents of hyperglycemia.

Figure 11:
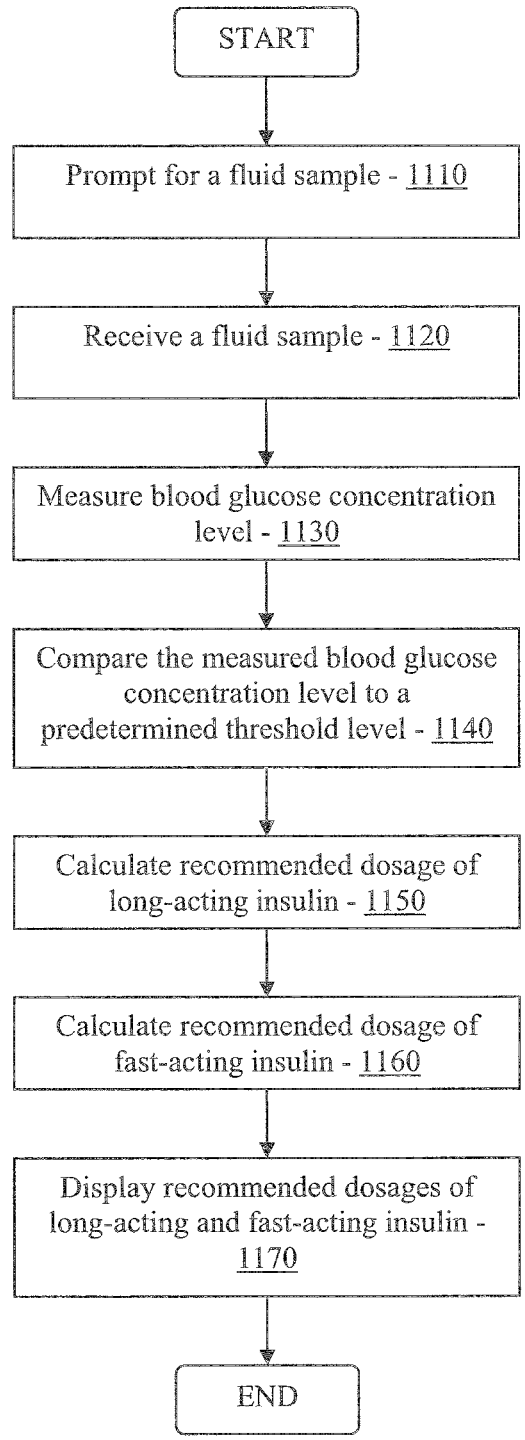
FIG. 11 is a flow chart illustrating a procedure for calculating a dosage recommendation for a long-acting insulin and a fast-acting insulin in accordance with embodiments of the present disclosure.

FIG. 11 is a flow chart illustrating a procedure for calculating a dosage recommendation for a long-acting insulin and a fast-acting insulin in one embodiment. Typically, long-acting insulin dosage regimens are calculated and adjusted based upon a patient's fasting blood glucose level, or the blood glucose level of a patient after predetermined length of time, such as 8 hours, without food (or after 8 hours of sleep). The fasting glucose level may be considered to be the baseline glucose level of a patient, and is further used for determining a long-acting insulin dosage calculation, which is typically used for controlling the baseline glucose level of a patient. On the other hand, fast-acting insulin bolus dosages are typically calculated based upon a current or future blood glucose level regardless of activities such as eating and exercise, as fast-acting insulin bolus dosages are typically used to correct for a current on-the-spot blood glucose level fluctuation.

Referring to FIG. 11, a glucose measuring device, such as the health monitor device 600 described above in conjunction with FIG. 6A, may prompt for a fluid sample (1110) to measure a blood glucose level. The fluid sample may be received (1120) at a strip port 640 of the health monitor device 600 in the form of a blood sample applied to a test strip 650. The received sample may then be analyzed in order to measure a blood glucose concentration level (1130). The measured blood glucose concentration level may then be compared to a predetermined threshold level (1140) for determination of whether an insulin dosage may be required in order to adjust the blood glucose concentration level to a safe or optimal level.

In the case that an insulin dosage is determined to be required or recommended, the health monitor device 600 may calculate a recommended dosage of a long-acting insulin (1150) as well as a recommended dosage of a fast-acting insulin (1160). The dosages may be calculated based upon one or more software algorithms stored within a memory unit of the health monitor device 600. Once calculated, the recommended dosages of long-acting and fast-acting may be displayed on a display unit 620 of the health monitor device 600 (1170).

In one embodiment, the health monitor device 600, may only recommend a long-acting insulin dosage when the received blood sample is a fasting blood sample. In another embodiment, the health monitor device 600 may determine whether to recommend a long-acting insulin dosage or a fast-acting insulin dosage or both, based upon the current time of day, whereby the time of day consideration may be determined by analyzing trends of previous data stored in the memory 670 of the health monitor device 600.

In certain embodiments, the health monitor device is a blood glucose meter, and may be configured to calculate a long-acting insulin dosage (e.g., basal insulin dosage) and a fast-acting insulin dosage (e.g., bolus insulin dosage), as described herein. For example, the health monitor device may recommend a long acting insulin dosage based on fasting blood glucose measurements, as described herein. In some instances, the health monitor device is configured to titrate a patient's long acting insulin dosage amount and recommend an adjustment dose amount to the patient's current long acting insulin dosage amount, as described herein. In addition, the health monitor device may be configured to recommend fast acting insulin dosage amounts based on non-fasting blood glucose measurements, such as mealtime (e.g., pre-meal) blood glucose measurements taken before breakfast, lunch and dinner, and blood glucose measurements taken before bedtime. In certain cases, the health monitor device is also configured to titrate a patient's fast acting insulin dosage amount and recommend an adjustment dose amount to the patient's current fast acting insulin dosage amount.

In certain embodiments, the health monitor device may be configured to assist a patient or a health care provider in determining a starting medication dosage amount. The health monitor device may be configured to calculate a starting medication dosage amount, such as a long acting insulin dosage amount and/or a fast acting insulin dosage amount, based on one or more patient parameters. For example, the patient parameters may include, but are not limited to the patient's weight, whether the titration algorithm is a normal, conservative or pediatric titration algorithm, which meal is typically the largest meal of the day for the patient, which meal is typically the smallest meal of the day for the patient, and the like. A conservative titration algorithm may include settings such as a fasting blood glucose target range of 100-120 mg/dL, a current long-acting insulin dose level of 15 units and a maximum long-acting insulin dose of 25 units. A normal (e.g., standard) titration algorithm may include settings such as a fasting blood glucose target range of 70-110 mg/dL, a current long-acting insulin dose level of 15 units and a maximum long-acting insulin dose of 30 units. A pediatric titration algorithm may include settings such as a fasting blood glucose target range of 70-110 mg/dL, a current long-acting insulin dose level of 5 units and a maximum long-acting insulin dose of 10 units. Other settings may be used as desired and may be customized by the patient and/or the health care professional depending on the individual needs of the patient.

In certain embodiments, the health monitor device may titrate the patient's fast acting dosage amount for each meal bolus dosage, such as fast acting insulin dosage amounts for breakfast, lunch and dinner. In some embodiments, the health monitor device is configured to titrate a patient's fast acting insulin dosage amount for a meal based on non-fasting blood glucose measurements for that meal. The non-fasting blood glucose measurements for a certain meal (e.g., breakfast, lunch, dinner or bedtime blood glucose measurements) may be obtained over a preceding time period, such as the preceding time period of 1 day, 2 days, 3 days, 4 days, 5 days, 6 days, 1 week (e.g., 7 days), 2 weeks (e.g., 14 days), 3 weeks (e.g., 21 days), 4 weeks (e.g., 28 days), 1 month, 2 months, 3 months, etc. In some cases, the non-fasting blood glucose measurements may be obtained over the preceding 28 days.

In some instances, the health monitor device is configured to titrate a meal bolus dosage level if the number of stored analyte measurements for that meal is above a threshold amount over the preceding time period. In certain embodiments, the health monitor device may titrate the meal bolus dosage level for a meal if the number of stored analyte measurements for that meal is greater than the threshold amount of 4 or more, 5 or more, 6 or more, 7 or more, 8 or more, 9 or more, or 10 or more, etc. over the preceding time period. For example, the health monitor device may be configured to titrate the meal bolus dosage level if the number of stored analyte measurements for that meal is 7 or more over the preceding time period. In some cases, if the number of stored analyte measurements for that meal is not greater than the threshold amount, the health monitor device will not titrate the medication dosage level for that meal until the number of stored analyte measurements for that meal is greater than the threshold amount.

In certain cases, if a certain percentage (e.g., 20% or more, 25% or more, 30% or more, 40% or more, 50% or more, 60% or more, 75% or more, etc.) of the mealtime blood glucose values for a certain meal over the preceding time period were below a threshold amount (e.g., below the patient's blood glucose target range for that meal), then the health monitor device may recommend that the fast acting insulin dosage amount for that meal be decreased by a predetermined dose adjustment amount. For instance, if more than one-half (e.g., more than 50%) of the mealtime blood glucose values for that meal over the preceding time period were below a threshold amount (e.g., below the patient's blood glucose target range for that meal), then the health monitor device may recommend that the fast acting insulin dosage amount for that meal be decreased by a predetermined dose adjustment amount.

In some cases, if a certain percentage (e.g., 20% or more, 25% or more, 30% or more, 40% or more, 50% or more, 60% or more, 75% or more, etc.) of the mealtime blood glucose values for a certain mean over the preceding time period were above a threshold amount (e.g., above the patient's blood glucose target range for that meal), then the health monitor device may recommend that the fast acting insulin dosage amount for that meal be increased by a predetermined dose adjustment amount. For example, if more than one-half (e.g., more than 50%) of the mealtime blood glucose values for that meal over the preceding time period were above a threshold amount (e.g., above the patient's blood glucose target range for that meal), then the health monitor device may recommend that the fast acting insulin dosage amount for that meal be increased by a predetermined dose adjustment amount.

In certain embodiments, if the average of the mealtime blood glucose values for a certain meal over the preceding time period is below a threshold amount (e.g., below the patient's blood glucose target range for that meal), then the health monitor device may recommend that the fast acting insulin dosage amount for that meal be decreased by a predetermined dose adjustment amount.

In certain embodiments, if the average of the mealtime blood glucose values for a certain meal over the preceding time period were above a threshold amount (e.g., above the patient's blood glucose target range for that meal), then the health monitor device may recommend that the fast acting insulin dosage amount for that meal be increased by a predetermined dose adjustment amount.

The predetermined dose adjustment amount may be a predetermined number of units of insulin, such as 1 unit, 2 units, 3 units, 4 units, 5 units, 6 units, 7 units, 8 units, 9 units, 10 units, etc. In some embodiments, the predetermined dose adjustment amount depends on the current mealtime dose amount. The health monitor device may be configured to recommend a greater dose adjustment amount the greater the current mealtime dose amount. For instance, if the current mealtime dose amount is less than or equal to a threshold amount (e.g., 10 units or less), then the health monitor device may recommend a dose adjustment amount (e.g., 1 unit). If the current mealtime dose amount is within a greater threshold range (e.g., 11 units 5 current mealtime dose amount ≤19 units), then the health monitor device may recommend a greater dose adjustment amount (e.g., 2 units). If the current mealtime dose amount is greater than or equal to an even greater threshold amount (e.g., 20 units or more), then the health monitor device may recommend an even greater dose adjustment amount (e.g., 3 units).

An example of a table of threshold ranges and their corresponding dose adjustment amounts is shown in Table II below. The values in Table II are representative values. The actual values used may vary from patient to patient and may be determined by a health care professional.

TABLE II

| Current Mealtime Dose Amount (units of insulin) | Pattern of mealtime blood glucose values below target | Pattern of mealtime blood glucose values above target |
| --- | --- | --- |
| ≤10 units | Decrease by 1 unit | Increase by 1 unit |
| ≥11-19 units | Decrease by 2 units | Increase by 2 units |
| ≥20 units | Decrease by 3 units | Increase by 3 units |

In certain embodiments, the predetermined dose adjustment amount depends on the current dose amount. In some cases, the predetermined dose adjustment amount is a percentage of the current dose amount, such as 5%, 10%, 15%, 20%, 25%, etc. of the current dose amount. For example, if the average of the mealtime blood glucose values for a certain meal over the preceding time period was below a threshold amount (e.g., below the patient's blood glucose target range for that meal), then the health monitor device may recommend that the fast acting insulin dosage amount for that meal be decreased by 10% of the current dose amount. Alternatively, if the average of the mealtime blood glucose values for a certain meal over the preceding time period was above a threshold amount (e.g., above the patient's blood glucose target range for that meal), then the health monitor device may recommend that the fast acting insulin dosage amount for that meal be increased by 10% of the current dose amount.

Figure 26:
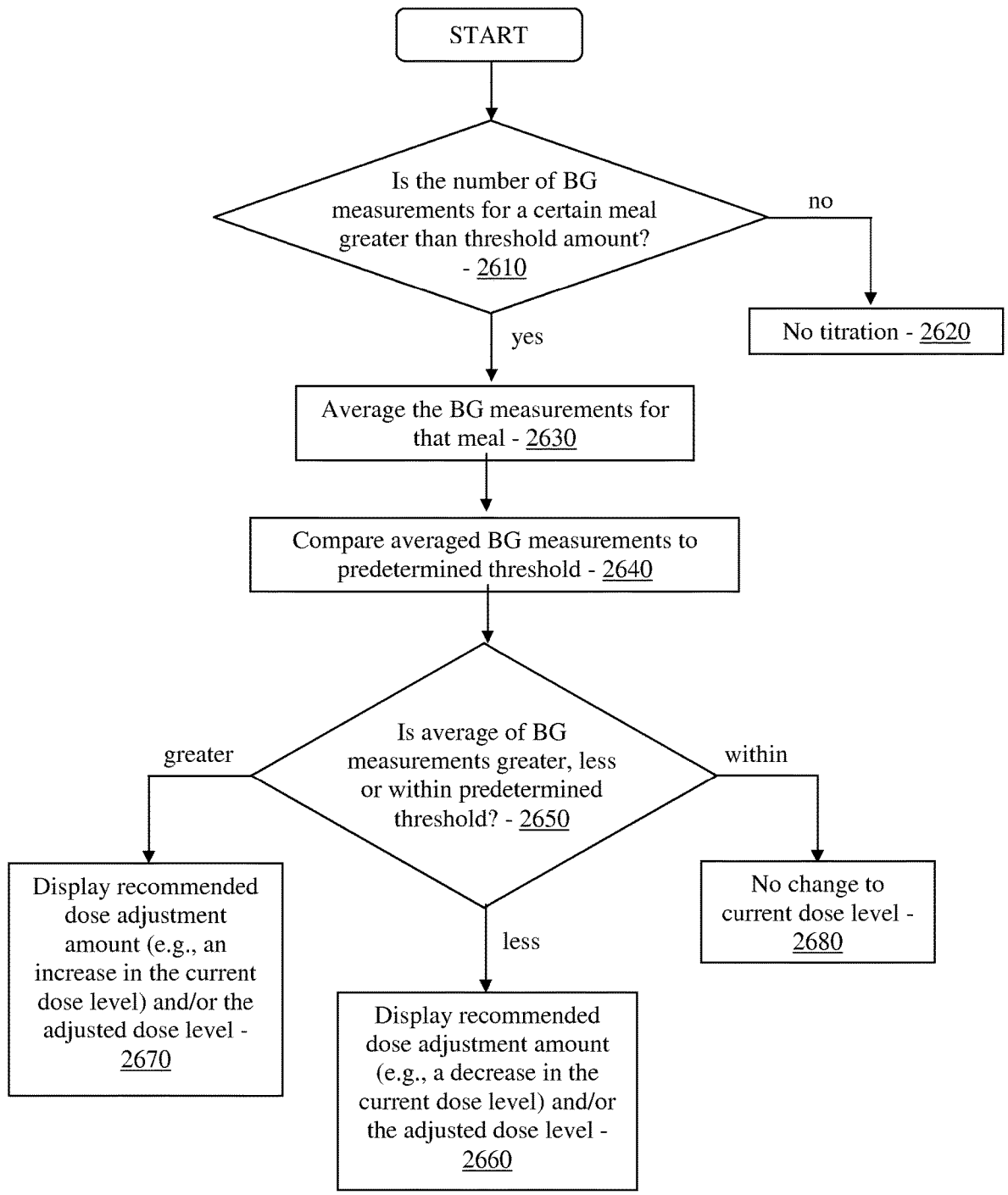
FIG. 26 is a flow chart illustrating a procedure for determining an adjusted dose level to a fast-acting insulin dosage regimen according to embodiments of the present disclosure.

FIG. 26 is a flow chart illustrating a procedure for determining an adjusted dose level to a fast acting insulin dosage regimen. Referring to FIGS. 26, 6A and 6B, after measuring several mealtime blood glucose measurements and storing those measurements in a memory 670 of the health monitor device 600, the health monitor device 600 may analyze the stored data to titrate the patient's fast acting insulin dose level. The health monitor device 600 may first determine whether the number of blood glucose measurements for a certain meal (e.g., breakfast, lunch or dinner) over the preceding time period is greater than a threshold amount (2610). For example, the health monitor device 600 may determine if there are 7 or more blood glucose measurements for a certain meal over the preceding 28 days. If the number of blood glucose measurements for that meal over the preceding time period is less than the threshold amount, then the health monitor device 600 will not titrate the medication dosage amount (2620). If the number of blood glucose measurements for that meal over the preceding time period is the threshold amount or greater, then the health monitor device 600 may titrate the medication dosage amount. For instance, if there were 7 or more blood glucose measurements for that meal over the preceding 28 days, then the health monitor device 600 may titrate the medication dosage amount. The health monitor device 600 may then determine the average of the blood glucose measurements for that meal over the preceding time period (2630). The health monitor device 600 may then compare the average of the blood glucose measurements for that meal to a predetermined threshold range (2640). The health monitor device 600 may determine if the average of the blood glucose measurements for that meal is greater than or less than the predetermined threshold range (2650). If the average of the blood glucose measurements for that meal is below the threshold range, then the health monitor device 600 may recommend (e.g., display) a predetermined dose adjustment amount (e.g., a decrease in the current dose level) and/or the adjusted dose level to the patient (2660). For instance, if the average of the blood glucose measurements for that meal is less than 100 mg/dL, then the health monitor device 600 may recommend that the fast acting insulin dosage amount be decreased by 10% of the current dose amount. If the average of the blood glucose measurements for that meal is above the threshold range, then the health monitor device 600 may recommend (e.g., display) a predetermined dose adjustment amount (e.g., an increase in the current dose level) and/or the adjusted dose level to the patient (2670). For instance, if the average of the blood glucose measurements for that meal is greater than 140 mg/dL, then the health monitor device 600 may recommend that the fast acting insulin dosage amount be increased by 10% of the current dose amount. If the average of the blood glucose measurements for that meal is within or equal to the threshold range, then the health monitor device 600 may recommend no change to the current medication dose level (e.g., long-acting insulin dosage regimen) (2680). For example, a recommended change to the current medication dose level may not be displayed and the current dose level may be displayed instead.

In certain embodiments, the health monitor device may be configured to recommend fast acting insulin dosage amounts based on non-fasting blood glucose measurements. Non-fasting blood glucose measurements may include pre-meal blood glucose measurements taken before breakfast, lunch and dinner, and blood glucose measurements taken before bedtime. In some cases, the health monitor device may be configured to recommend fast acting insulin dosage amount based on non-fasting blood glucose measurement s and also based on the amount of carbohydrates consumed. In certain cases, the health monitor device is also configured to titrate a patient's fast acting insulin dosage amount and recommend an adjusted dose amount based on the patient's current fast acting insulin dosage amount and also the amount of carbohydrates consumed. The health monitor device may titrate the patient's fast acting dosage amount for each meal bolus dosage, such as fast acting insulin dosage amounts for breakfast, lunch and dinner. In some embodiments, the health monitor device is configured to titrate a patient's fast acting insulin dosage amount based on non-fasting blood glucose measurements and the amount of carbohydrates consumed. The non-fasting blood glucose measurements may be obtained over a preceding time period, such as the preceding 1 day, 2 days, 3 days, 4 days, 5 days, 6 days, 1 week, 2 weeks, 3 weeks, 1 month, etc.

In certain cases, if a certain percentage (e.g., 20% or more, 30% or more, 40% or more, 50% or more, 60% or more, etc.) of the mealtime blood glucose values for the previous week were below a threshold amount (e.g., below the patient's blood glucose target range), then the health monitor device may recommend that the fast acting insulin dosage amount for that meal be decreased to an adjusted dose amount based on the amount of carbohydrates consumed. For instance, if more than one-half of the mealtime blood glucose values for the previous week were below a threshold amount (e.g., below the patient's blood glucose target range), then the health monitor device may recommend that the fast acting insulin dosage amount for that meal be decreased to an adjusted dose amount based on the amount of carbohydrates consumed.

In other cases, if a certain percentage (e.g., 20% or more, 30% or more, 40% or more, 50% or more, 60% or more, etc.) of the mealtime blood glucose values for the previous week were above a threshold amount (e.g., above the patient's blood glucose target range), then the health monitor device may recommend that the fast acting insulin dosage amount for that meal be increased to an adjusted dose amount based on the amount of carbohydrates consumed.

For example, if more than one-half of the mealtime blood glucose values for the previous week were above a threshold amount (e.g., above the patient's blood glucose target range), then the health monitor device may recommend that the fast acting insulin dosage amount for that meal be increased to an adjusted dose amount based on the amount of carbohydrates consumed.

The adjusted dose amount may be a predetermined number of units of insulin per amount of carbohydrates consumed, such as 1 unit/25 g, 1 unit/20 g, 1 unit/15 g, 1 unit/10 g, 2 units/15 g, 3 units/15 g, 4 units/15 g, 5 units/15 g, etc. In some embodiments, the adjusted dose amount depends on the current mealtime dose amount. The health monitor device may be configured to recommend a greater adjusted dose amount the greater the current mealtime dose amount.

An example of a table of current mealtime dose amounts and their corresponding adjusted dose amounts is shown in Tables III-A and III-B below. The values in Tables III-A and III-B are representative values. The actual values used may vary from patient to patient and may be determined by a health care professional.

TABLE III-A

| Current Mealtime Dose Amount (units of insulin/g carbohydrate) | Pattern of mealtime blood glucose values below target | Pattern of mealtime blood glucose values above target |
| --- | --- | --- |
| 1 unit/20 g | Decrease to 1 unit/25 g | Increase to 1 unit/15 g |
| 1 unit/15 g | Decrease to 1 unit/20 g | Increase to 1 unit/10 g |
| 1 unit/10 g | Decrease to 1 unit/15 g | Increase to 2 units/15 g |
| 2 units/15 g | Decrease to 1 unit/10 g | Increase to 3 units/15 g |
| 3 units/15 g | Decrease to 2 units/15 g | Increase to 4 units/15 g |

Other current mealtime dose amounts and their corresponding adjusted dose amounts may be used, for example as shown in Table III-B below. The actual values used may vary from patient to patient and may be determined by a health care professional.

TABLE III-B

| Current Mealtime Dose Amount (units of insulin/g carbohydrate) | Pattern of mealtime blood glucose values below target | Pattern of mealtime blood glucose values above target |
| --- | --- | --- |
| 1 unit/40 g | Decrease to 1 unit/50 g | Increase to 1 unit/30 g |
| 1 unit/30 g | Decrease to 1 unit/40 g | Increase to 1 unit/20 g |
| 1 unit/20 g | Decrease to 1 unit/30 g | Increase to 1 units/10 g |
| 1 units/10 g | Decrease to 1 unit/20 g | Increase to 1 units/5 g |

Additional information regarding titration of long acting and rapid acting insulin dosage amounts for a patient's medication dosage regimen are described in Bergenstal, et al., *Diabetes Care*, vol. 31, no. 7 (July 2008) pp. 1305-10.

In certain embodiments, the health monitor device may include additional titration parameters and/or safety features. In some cases, the health monitor device may be configured to use certain blood glucose measurements in the determination of an adjusted dose amount. For example, the health monitor device may be configured to log a blood glucose measurement if the patient manually adjusts the recommended dosage amount, but not use that blood glucose measurement in a titration calculation. In certain instances, the health monitor device is configured to log a blood glucose measurement, but not use that measurement in a titration calculation, if the blood glucose measurement was taken within a certain time period following the prior blood glucose measurement. For example, if a mealtime blood glucose measurement was taken within a certain time period after the prior blood glucose measurement, such as 5 hours or less, or 4 hours or less, or 3 hours or less, or 2 hours or less, or 1 hour or less, after the prior blood glucose measurement, then the health monitor device may log the blood glucose measurement, but not include that measurement into a titration calculation. In some cases, the health monitor device is configured to log a blood glucose measurement, but not use that measurement in a titration calculation if the measurement occurred 3 hours or less from the prior blood glucose measurement.

It is to be understood that the procedures described above in conjunction with FIG. 11 are not limited to only the calculation of a long-acting insulin and a fast-acting insulin, but may be applicable to any combination of one or more medications used to treat a number of physiological conditions, including, among others, various analyte concentrations, heart-rate, breathing rate, or blood pressure, whereby some or all of the medications may be configured for dosage updates based upon a variety of mitigating factors, such as carbohydrate intake or physical activity.

Figure 12:
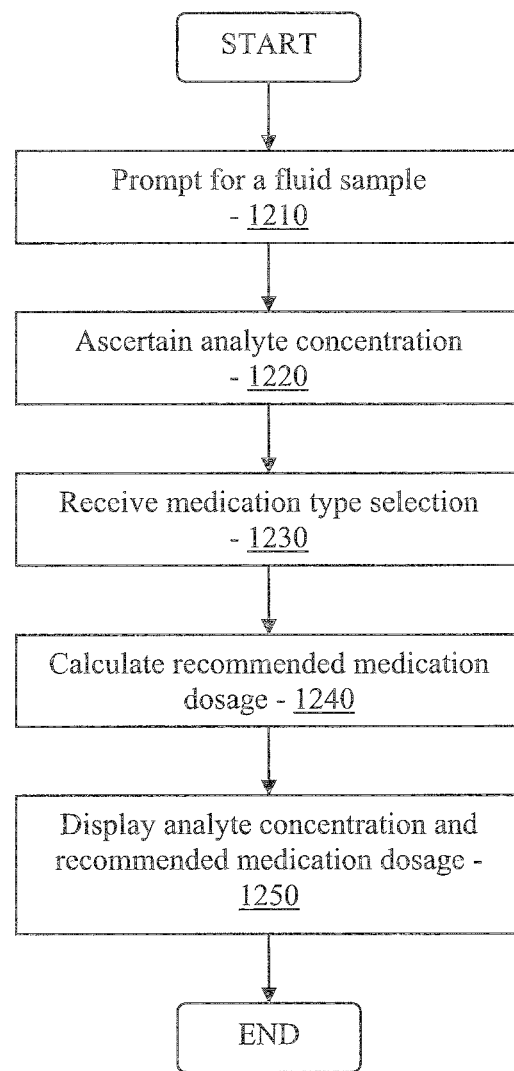
FIG. 12 is a flow chart illustrating a means for calculating a dosage recommendation for one or more selectable medication types in accordance with embodiments of the present disclosure.

In one embodiment, a health monitor device 600 (FIG. 6A) with a medication dosage calculator may include a medication type selector function. The medication type selector function may allow a patient to request a recommended dosage for a variety of medication types. FIG. 12 is a flow chart illustrating a means for calculating a dosage recommendation for one or more selectable medication types. Referring to FIG. 12, a health monitor device 600 may prompt for a fluid sample (1210) and subsequently analyze the fluid sample to ascertain an analyte concentration (1220). In one embodiment, the health monitor device 600 may be a blood glucose measuring device, and may receive a fluid sample in the form of a blood sample applied to a test strip 650 and inserted into a strip port 640 of the health monitor device 600. The blood sample may be analyzed to discern a blood glucose concentration, which may be used as an indicator for the blood glucose level of a patient from which the sample was obtained.

Once an analyte concentration is ascertained, a medication type selection is received (1230). The medication type selection may be established via a number of different methods, including providing a list of available medication types for which the health monitor device 600 is programmed to calculate dosage information. For example, if the health monitor device 600 is a glucose measuring device intended for the measurement of a patient's blood glucose level, the corresponding medication for dosage calculation may be insulin. In this case, the glucose measuring device may include programming or algorithms for calculating insulin dosage information for a variety of insulin types, including long-acting insulin, intermediate-acting insulin, fast-acting insulin, rapid-acting insulin, and very-rapid acting insulin. Further, programming or algorithms may be exclusive to specific insulin compositions, even amongst the general categories of insulin types. In another aspect, the medication type may be selected automatically by the health monitor device 600 based on, for example, a pre-programmed treatment regimen.

Referring back to FIG. 12, once a medication type is chosen, the program or algorithm associated with the selected medication type may be applied to the ascertained analyte concentration in order to calculate a recommended medication dosage (1240). The recommended medication dosage and the ascertained analyte concentration may then be displayed on a display unit 620 of the health monitor device 600 (1250). In another embodiment, the selected medication type may also be displayed on the display unit to allow for confirmation that the recommended medication dosage is meant for the correct medication type.

In another embodiment, a list of available medication types for display and for selection may be limited to a predetermined list of available medications as indicated by the user, or alternatively by a doctor or other health care professional. In this manner, in one aspect of the present disclosure, a list or subset of available medication types for selection (and subsequent dosage calculation, for example) may be limited to a predetermined list of available (or pre-stored) or permitted medication stored in the health monitor device 600. The list of available or permitted medication may be stored in the memory 670 of the health monitor device 600. Alternatively, the health monitor device 600 may include programming or software instructions which, when a particular medication is selected, other medication known or determined to be incompatible with the selected medication (for example, due to potential adverse reactions when mixed with the selected medication), may automatically be removed from the list of available medication types before providing the list to the user of the device 600.

In another embodiment, the memory 670 of the health monitor device 600 may store information related to a patient's medical history, for example, information related to medications the patient has been previously determined to cause allergic or undesirable reactions. Accordingly, the memory 670 may store, for example, a dynamic list of available medications that are appropriate for the medication dose determination in response to or based on a selection of a type of the medication selected for dosage calculation, or alternatively, based on one or more other characteristics based on the physiological condition of the user or the medication composition.

In some instances, it may be advantageous for a patient to make use of more than one medication to control a disease or health condition. For example, diabetic patients, including patients with Type-1 and severe Type-2 diabetes, may benefit from using more than one type of insulin to help control their blood glucose level. For example, it may be advantageous to use long-acting insulin to maintain a stable baseline blood glucose level, and additionally to use fast-acting insulin injections to compensate for periodic blood glucose level fluctuations resulting from, for example, carbohydrate intake. Accordingly, in one aspect there is provided techniques for calculating adjustments to daily insulin dosages to maintain a safe baseline blood glucose level, as well as on-the-spot dosage recommendations to correct for periodic blood glucose level fluctuations.

Figure 13:
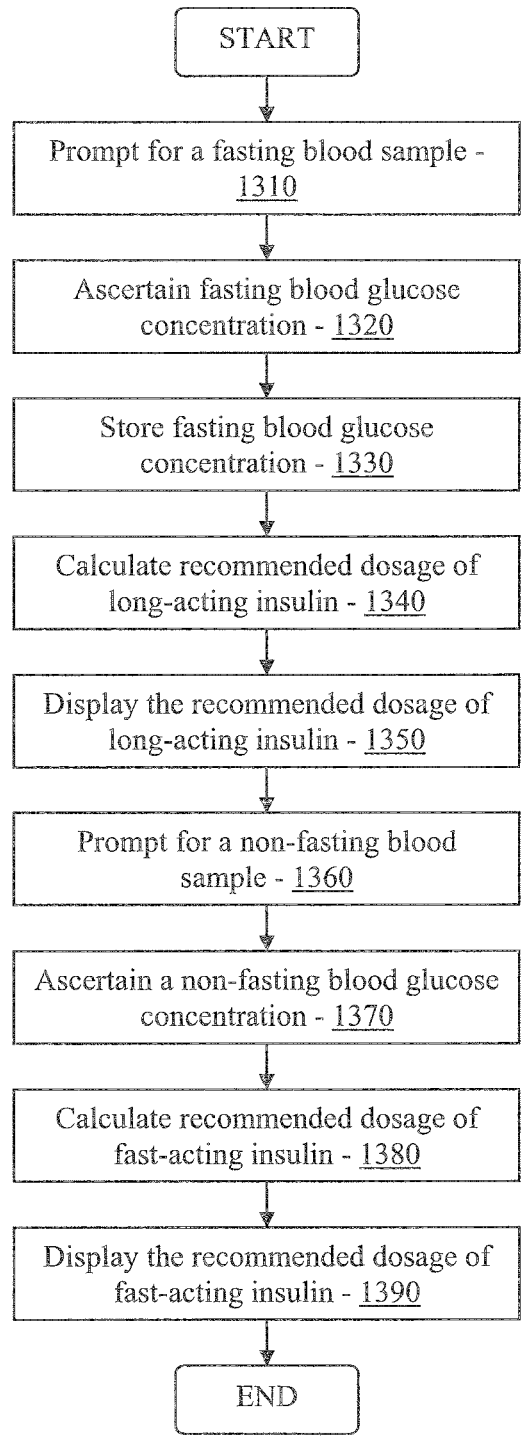
FIG. 13 is a flow chart illustrating a means for calculating insulin dosage information for more than one type of insulin in accordance with embodiments of the present disclosure.

FIG. 13 is a flow chart illustrating a means for calculating insulin dosage information for more than one type of insulin. In one embodiment, the more than one type of insulin may include a combination of a long-acting insulin and a rapid-acting insulin. In one aspect, dosages of the long-acting insulin may be calculated based upon a fasting blood glucose level of a patient. Referring to FIG. 13, a health monitor device 600 (FIG. 6A) may prompt for a fasting blood sample (1310). The fasting blood sample may be a blood sample taken from a patient after a predetermined length of time, such as at least 8 hours, without food and applied to a test strip 650 to be inserted into a strip port 640 of the health monitor device 600 for analysis. As a fasting blood sample is taken after at least 8 hours without food, often the blood sample is taken in the morning following 8 hours of sleep. In one aspect, in order to discern a consistent fasting blood glucose level, the health monitor device 600 may prompt for the fasting blood sample at the same time every morning. Once the fasting blood sample is received by the health monitor device 600, the sample may then be analyzed in order to ascertain a blood glucose concentration (1320) of the patient from which the sample was obtained. Once ascertained, the blood glucose concentration may be stored (1330) in a memory 670 of the health monitor device 600. In one aspect, the stored blood glucose concentration may be date and/or time stamped. An algorithm for calculating a long-acting insulin dosage recommendation may then be applied to the ascertained blood glucose concentration in order to calculate a recommended long-acting insulin dosage (1340) to be displayed on a display unit 620 of the health monitor device 600 (1350).

The algorithm or routine for determining a long-acting insulin dosage recommendation may be a dosage update algorithm based upon initial settings as determined by, for example, a health care professional or an insulin manufacturer specification. In one embodiment, an initial daily prescribed dosage of long-acting insulin, such as LEVEMIR® insulin (which has up to a 24 hour active time), may be 10 units of insulin per day. 10 units/day of LEVEMIR® insulin may be the starting dosage of a long-acting insulin regimen. The fasting blood glucose concentration may be measured on a daily basis, and each measurement stored in a memory. By taking a mean average of the stored fasting blood glucose concentrations, the fasting blood glucose concentration average may be compared to a predetermined target fasting blood glucose concentration threshold. In one aspect, a recommended update to the daily dosage of long acting insulin may be calculated weekly, based upon the average glucose concentration of the preceding two or more days, and follow the below dosage schedule:

| Average Glucose Concentration | Insulin Dose Adjustment Amount (units/day) |
| --- | --- |
| >180 mg/dL | +8 |
| 140-180 mg/dL | +6 |
| 120-139 mg/dL | +4 |
| 95-119 mg/dL | +2 |
| 70-94 mg/dL | 0 |
| <70 mg/dL | Decrease by a dose adjustment amount |

In another embodiment, the algorithm for calculating a long-acting insulin dosage recommendation may be a daily dosage update. The algorithm may compare a fasting blood glucose concentration to a predetermined threshold level, for example, a target threshold level as determined by a health care professional. If the fasting blood glucose concentration is greater than the target threshold level, the algorithm may recommend an increase of long-acting insulin. This may continue each day until the fasting blood glucose concentration is at or below the target threshold level. If the fasting blood glucose concentration is less than the target threshold level, the algorithm may recommend a decrease of long-acting insulin.

In other embodiments, the target threshold level of fasting blood glucose concentration may be set by the user or may be a customized target threshold as determined by a health care professional.

In another embodiment, the algorithm for calculating a long-acting insulin dosage recommendation may be based on both an upper and lower threshold value. For example, a health care professional may recommend a safe fasting blood glucose concentration of between a predefined range. In such a case, the algorithm may update the long-acting insulin dosage on a daily basis. In one aspect, if the fasting blood glucose concentration is greater than the upper threshold, the algorithm may recommend an increase to the current long-acting insulin dosage by 1 IU/day, while if the fasting blood glucose concentration is less than the lower threshold, the algorithm may recommend a decrease to the current long-acting insulin dosage by 1 IU/day. Furthermore, if the fasting blood glucose concentration is between the upper and lower threshold, the algorithm may recommend no change to the current long-acting insulin dosage regimen.

In another embodiment, the algorithm for calculating a long-acting insulin dosage recommendation may be based upon past and present fasting blood glucose concentration values. In one aspect, the algorithm may not recommend an update to a current glucose dosage unless the fasting blood glucose concentration is above or below a certain upper and lower threshold. In a further aspect, the algorithm may not recommend an update to a current glucose dosage unless the fasting blood glucose concentration is outside a certain threshold for a certain number of consecutive days, such as, for example, for two or more consecutive days. In certain embodiments, the algorithm may not recommend an update to a current glucose dosage unless the fasting blood glucose concentration is outside a certain threshold for a certain number of days within a time period, such as, for example, for two or more days within a week.

In another embodiment, if the difference between a current fasting blood glucose concentration and a preceding day's fasting blood glucose concentration is outside a predetermined threshold level, a software program for calculating the insulin dosage update may be programmed to not recommend an update to an insulin dosage regimen for safety measures in the case that the current fasting blood glucose concentration is in error or is not an acceptable value. Furthermore, the algorithm may be programmed to not recommend an update to an insulin dosage regimen if the insulin dosage regimen was recently updated, for example, if the insulin dosage regimen was updated within the preceding two days.

In another aspect, if it is determined that current measured values are found to be outside threshold values, such as if the difference between a current fasting blood glucose concentration and a preceding day's fasting blood glucose concentration is outside a predetermined threshold, an alarm system may activate. The alarm system may be in the form of an auditory, visual, and/or vibratory alarm, or may be an alarm notification transmitted over a data network to, for example, a health care professional. Other values that may activate the alarm system may include, an upper or lower threshold current blood glucose value, a threshold number of consecutive days wherein the fasting blood glucose value increased or decreased, a missed expected sample time, or if an error is detected.

Referring back to FIG. 13, the health monitor device 600 may also include programming to calculate a fast-acting insulin dosage. In one embodiment, while the dosage calculation for a long-acting insulin is used to maintain a stable safe baseline glucose concentration, a fast-acting insulin injection may be used to help stabilize blood glucose concentration fluctuations throughout the day due to, for example, carbohydrate intake. To that end, the health monitor device 600 may prompt for or the patient may initiate a non-fasting bodily fluid sample (1360), which may be in the form of a blood sample applied to a test strip 650 and received at the strip port 640 of the health monitor device 600.

Non-fasting blood samples may be taken periodically throughout the day at regular intervals or at irregular intervals depending upon a patient's physical state, such as when a patient determines that his/her blood glucose level is lower or higher than one or more predetermined threshold or desired level. Furthermore, events may also define when a patient takes a non-fasting blood sample, such as before or after meals, exercise, or after taking other medications. For instance, a patient may take a non-fasting blood sample before each meal, such as breakfast, lunch and dinner, and/or before bedtime.

Once the non-fasting blood sample is received at the strip port 640 of the health monitor device 600, the blood sample may then be analyzed and a blood glucose concentration is determined (1370). An algorithm for calculating a fast-acting insulin dosage recommendation may then be applied to the ascertained blood glucose concentration in order to calculate a recommended fast-acting insulin dosage (1380) to be displayed on a display unit 620 of the health monitor device 600 (1390). In other embodiments, the algorithm may be designed for calculating a dosage recommendation for an intermediate, rapid, or very-rapid acting insulin type or a combination thereof.

Integrated Medication Delivery System

In other embodiments, a health monitor device as described herein, e.g., a health monitor device 600, including programming for calculating a medication dosage or therapy profile recommendation may further include an integrated medication delivery system. In one embodiment the integrated medication delivery system may automatically deliver the medication dosage as recommended by the health monitor device 600. In one aspect, the health monitor device 600 may be preprogrammed with information related to the medication of the medication delivery system thus eliminating any possible errors resulting from a patient's accidental entry of a wrong medication in a medication selector function of the health monitor device 600. In another aspect, the medication delivery system may be detachable from the health monitor device 600.

In another embodiment, a health monitor device 600 including programming for calculating medication dosages for two or more medication types may further include an integrated medication delivery system. In one aspect, the medication delivery system may include two or more reservoirs, each designated for storing one the two or more medication types, and each with an individual delivery mechanism. In another aspect, the two or more reservoirs may share a single delivery mechanism. In one aspect, the medication delivery system may automatically deliver each medication in doses as recommended by the health monitor device 600.

In another embodiment, the health monitor device 600 may include a corresponding docking station or one or more other peripheral devices. The docking station may include, among others, a transmitter whereby when the health monitor device 600 is docked to the docking station, the health monitor device 600 and docking station may communicate over a data network with, for example, a health care professional, for the transfer of data or receipt of instructions or new dosage regimens. The docking station transmitter may be configured for transmission protocols including, but not limited to, cellular telephone transmission, such as code division multiple access (CDMA) or Global System for Mobile communications (GSM), internet communication, facsimile communications, and/or telephone communication. In another aspect, the docking station may also be configured to provide power for recharging a rechargeable battery of the health monitor device 600. In another aspect, the docking station may be configured for communication with a personal computer for additional storage, programming, and/or communication.

Replenishment Management System

In another embodiment, the health monitor device 600 may include software for monitoring and ordering replacements for consumable products associated with the health monitor device 600. Consumable products may include, among others, analyte test strips, lancing devices, types of medication, such as types of long-acting and fast-acting insulin, medication deliver devices, such as syringes or injection pens, integrated lancet and testing striplet devices, sensors for an implantable sensor glucose monitoring system, or batteries.

Figure 14:
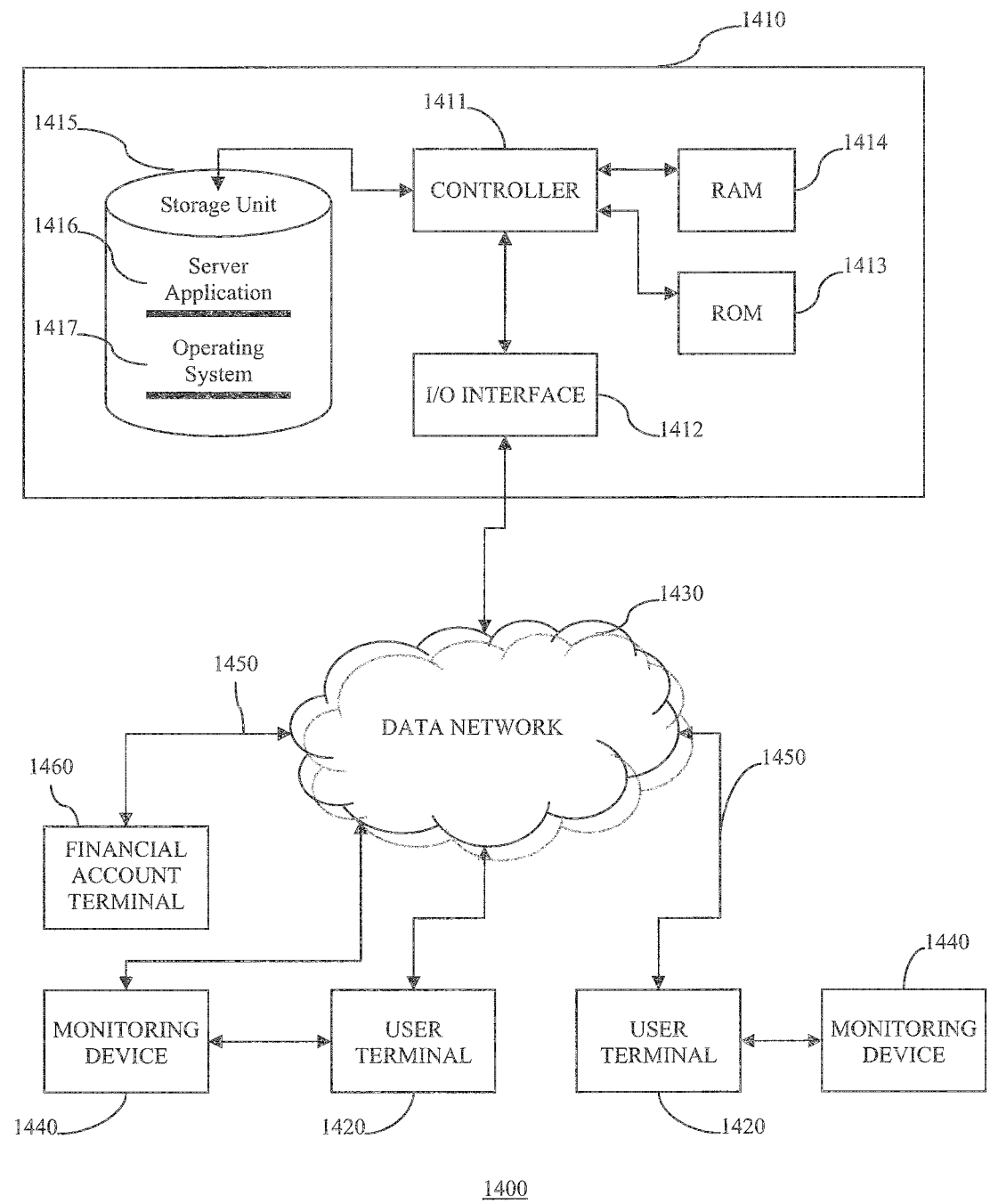
FIG. 14 illustrates a block diagram of a replenishment management system in accordance with embodiments of the present disclosure.

FIG. 14 illustrates a block diagram of a replenishment management system in accordance with one embodiment of the present disclosure. Referring to FIG. 14, the replenishment management system 1400 includes a server terminal 1410 operatively coupled to one or more user terminals 1420 via a data network 1430. As can be seen from the Figure, each of the user terminals 1420 are also configured to be operatively connected to a respective one or more testing or monitoring devices 1440. As will be discussed in further detail below, there is also provided a financial account terminal 1460 operatively coupled to the data network 1430 for communication with the server terminal 1410 and a corresponding one of the user terminals 1420.

In one embodiment, the testing or monitoring device 1440 may include a health monitor device as described above in conjunction with FIG. 6A, which may be configured to automatically and wirelessly transmit the measured analyte data to the server terminal 1410 at a predetermined frequency over the wireless connection 1451. In this case, the server terminal 1410 may be configured to detect and receive the measured analyte data from the health monitor device and to store the received data in a corresponding user account associated with the health monitor device. Furthermore, in another embodiment, the health monitor device is configured to transmit medication dosage information, such as insulin dosage information, to the server terminal 1410. The medication dosage information may be information related to periodic dosages of long-acting and/or fast-acting insulin.

Referring back to FIG. 14, it can be seen that each of the user terminals 1420, the financial account terminal 1460, and the server terminal 1410 are operatively coupled to the data network 1430 via a corresponding data communication link 1450. Within the scope of the present disclosure, the data communication link 1450 may include wired or wireless communication path which may be configured for secure, encrypted bi-directional data exchange over the data network 1430. In particular, the data communication link 1450 in one embodiment may include Wi-Fi data communication, infrared data communication (for example Infrared Data Association (IrDA) communication), BLUETOOTH® data communication, ZIGBEE® data communication, USB or FIREWIRE® cable based data communication, Ethernet cable based data communication, and dial up modem data communication.

For example, in one embodiment, the user terminals 1420 may include, among others, one of a personal computer (including a desk top or a laptop computer) or a handheld communication device such as an IPHONE® device, BLACKBERRY® device, Internet access enabled mobile telephones, a bi-directional communication enabled pager, and a communication enabled personal digital assistant (PDA). In one embodiment, the user terminals 1420 include an output unit such as a display and/or speakers, an input unit such as a keyboard or a touch-sensitive screen, as well as a controller such as a CPU for performing user instructed procedures at the user terminals 1420. Moreover, within the scope of the present disclosure, the user terminals 1420 may be configured to communicate with the data network 1430 using a wireless data communication protocol such as BLUETOOTH® data communication, 801.11x, and ZIGBEE® data communication. Additionally, the user terminal 1420 may be also configured to communicate with the testing or monitoring device 1440 via short range RF communication path, an IrDA communication path, or using BLUETOOTH® communication protocol. Additionally, the testing or monitoring device 1440 may also be configured to connect to the respective user terminals 1420 via a wired connection such as a USB connection, an RS-232 cable connection, an IEEE 1394 or FIREWIRE® connection, or an Ethernet cable connection.

Referring again to FIG. 14, the financial account terminal 1460 may be configured to communicate with the server terminal 1410 and the user terminals 1420 over the data network 1430 using either or a wired or wireless secure and encrypted connection. As is generally the case, because financial account related information is very sensitive, high level of security for data communication to and from the financial account terminal 1430 may be used such as encryption level exceeding 128-key encryption, and the like. Within the scope of the present disclosure, the financial account terminal 1460 may include one of a banking institution terminal, a credit card institution terminal, a brokerage institution terminal, and any other financial institution terminal which maintains a financial account of a user with which financial account transactions may be performed. This aspect of the present disclosure is discussed in further detail below.

Referring yet again to FIG. 14, the server terminal 1410 in one embodiment may include a controller 1411 operatively coupled to an input/output (I/O) interface unit 1412, a read-only memory (ROM) 1413, a random access memory (RAM) 1414, and a storage unit 1415. In one embodiment, the storage unit 1415 includes a server application 1416 and an operating system 1417. In this manner, the controller 1411 may in one embodiment be configured to communicate with the user terminals 1420 and the financial account terminal 1460 over the data network 1410 via the I/O interface unit 1412, under the control of the various processes and routines stored in the ROM 1413 and the storage unit 1415 as well as user transmitted requests and information.

In one embodiment, the server application 1416 and the operating system 1417 of the storage unit may be configured to provide a proprietary interface for the users, to execute secure and encrypted data communication over the data network 1400. More specifically, the server terminal 1410 may be configured to provide a proprietary internet-based user interface at a predetermined URL for the users to login from the user terminals 1420, for example, for communication with the server terminal 1410. Alternatively, within the scope of the present disclosure, the data network 1430 may include the internet, and wherein the server application 1416 and the operating system 1417 of the server terminal 1410 are configured to provide a dedicated website for allowing the users to securely and easily login to their respective accounts using the user terminals 1420 over the data network.

Referring still again to FIG. 14, the storage unit 1415 of the server terminal 1410 in one embodiment may be configured to store data and information related to the user accounts such as, but not limited to, user account login identification and password, user contact information such as telephone and/or facsimile numbers, email address, billing and shipping addresses, user account profile information such as replenishment level information, seasonality or periodicity of user use of the testing, monitoring, or dosing device, prescribed medication information, user financial account information (for example, a bank routing number and bank account number in the case of a banking institution), and user testing, monitoring, or medication dosing device data information such as the user strip order history, medication order history, health related monitoring data such as previously measured glucose levels, user specific basal profile information, bolus determination information, insulin sensitivity, trend information determined based on the measured glucose levels (and determined by the controller 1411), and health care professional information for the user such as contact information for the user's physician, hospital, and nursing facilities.

In addition, within the scope of the present disclosure, the storage unit 1415 may further be configured to store an expiration information and/or lot number associated with the consumable item, or to calculate expiration information from the lot number. For example, the server terminal 1410 may be configured to determine the expiration information of the consumable item prior to or at the time of replenishment transaction (discussed in detail below), based on one or more of several factors, and further configured to transmit the expiration information to the user terminal 1420 associated with the replenishment transaction. The one or more of the several factors determining the expiration information associated with the consumable item includes the lot number associated with the consumable item, where each lot number has a unique expiration date associated therewith, a shipment date of the consumable item from the manufacturer, and a date of manufacture of the consumable item.

In this manner, in one embodiment, the user requesting the replenishment transaction for the consumable item will be notified of the expiration information such as the expiration date associated with the consumable item, and will be alerted that the consumable item will not function as optimally beyond the expiration date. In the case of glucose test strips, to ensure the accuracy of the test results showing the measured glucose levels it is important that the user/patient be aware of such expiration date of the glucose test strips, so that the measured glucose levels are as accurate as possible. In the case of medication, such as insulin, the importance of a patient's awareness of the expiration date may be even more important than the expiration date of a consumable item, such as a glucose test strip. In the case of medication, expired medication may not only have a diminished effectiveness, it may in fact have a severely detrimental effect on the patient's health.

Moreover, in the case where there is a physician or treatment advised, or other guideline as to frequency or threshold of testing, monitoring, or dosing, a warning signal may be generated and communicated to a health care professional or to the user in the case where the consumption of the test materials, as determined by the server terminal 1410, is less or more than the consumption required to meet this frequency or threshold of testing, monitoring or dosing.

Referring back to FIG. 14, in one embodiment of the present disclosure, based on the measured glucose levels for a given patient from a respective user terminal 1420, the controller 1411 of the server terminal 1410 may be configured to determine trend information based on measured glucose levels so as to determine and correspondingly generate for the user terminal 1420 for display, a color coded indication of the user's glucose level projections including arrow indicators, color coded warning or notification indicators, and associated audible alerts. For example, based on the user's measured glucose level for a predetermined period of time contemporaneously received from the user terminal 1420, the server terminal 1410 may be configured to generate and transmit to the user terminal 1420 a color coded arrow indicator for display on the user terminal 1420 to visually and easily inform the user of the projected or anticipated trend in the glucose level based on the measured glucose levels.

In another embodiment, based on the insulin dosage information for a given patient from a respective user terminal 1420, the controller 1411 of the server terminal 1410 may be configured to determine trend information based on insulin dosage information so as to determine and correspondingly generate for the user terminal 1420 for display, a color coded indication of the user's projected future insulin dosage information, including projected increase or decrease in insulin dosage. In one aspect, the controller 1411 may be configured to alert the patient if the rate of change of the insulin dosage information over a period of time is above a certain threshold, possibly indicating an advancement in a user's health condition, such as a worsening of a diabetic condition. When the change of insulin dosage over a period of time is above a predetermined threshold, it may be an indication that the user should visit their primary care physician in order to ascertain information relating to the health condition of the patient, and possibly determine a change in treatment or medication.

Referring still again to FIG. 14, the server application 1416 stored in the storage unit 1415 of the server terminal 1410 may be configured to perform, under the control of the controller 1411, the various procedures and processes as discussed below in conjunction with FIGS. 15-19, as well as to store any information related to the user accounts and profiles within the scope of the present disclosure.

Figure 15:
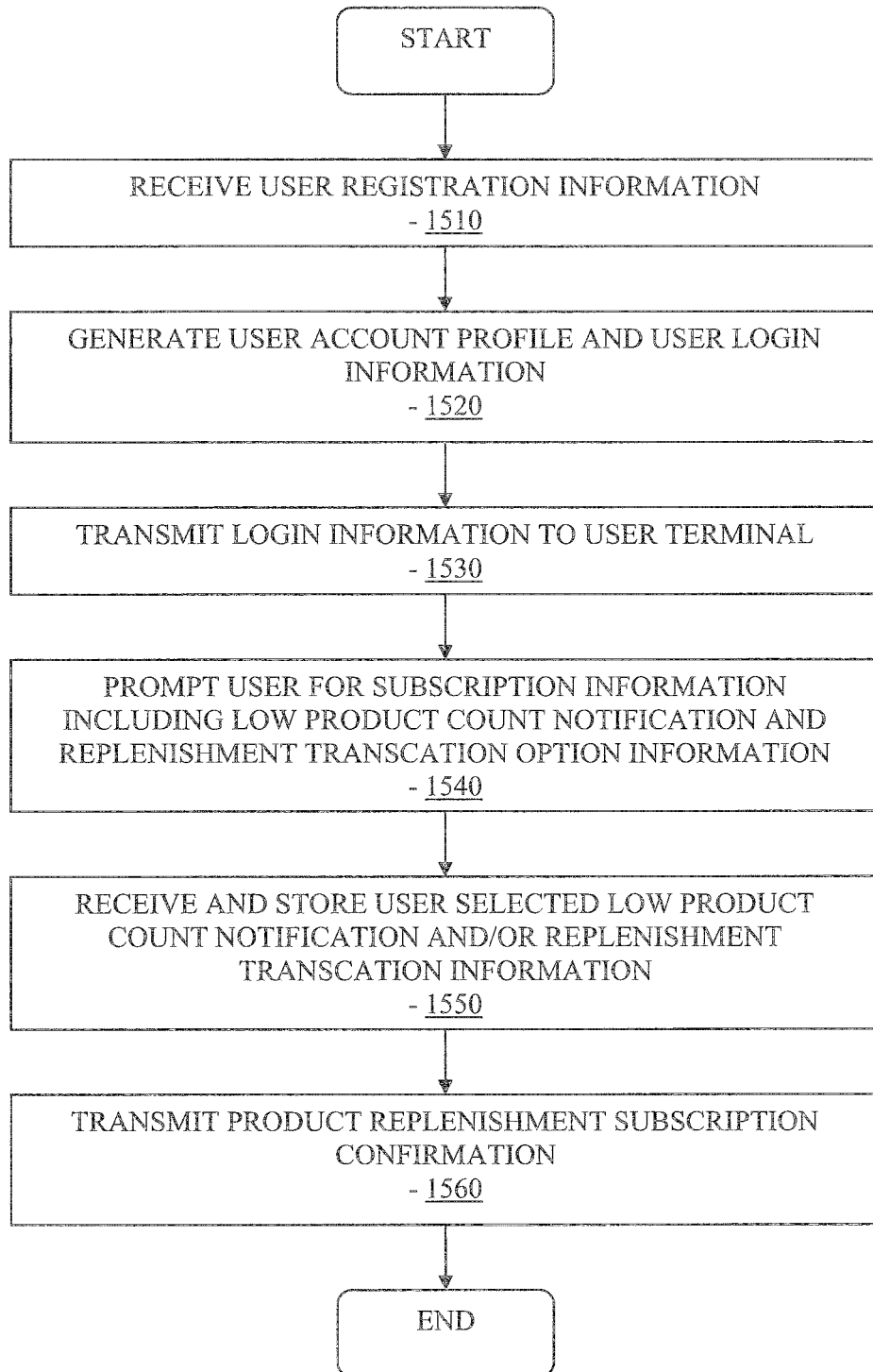
FIG. 15 is a flowchart illustrating user account registration setup and account subscription process in accordance with embodiments of the present disclosure.

FIG. 15 is a flowchart illustrating user account registration setup and account subscription process in accordance with one embodiment of the present disclosure. Referring to the Figure, at step 1510, the server terminal 1410 (FIG. 14) receives from a user terminal 1420 user account registration information. The received user account registration information may include, among others, the user name, user address, the user telephone number, the user testing, monitoring, or dosing device information such as model information of the testing, monitoring, or dosing device, and the user medication prescription information.

Thereafter at step 1520, the server terminal 1410 is configured to generate a user account profile and login information including password and login identification, all of which are stored in the storage unit 1415 of the server terminal 1410. Then at step 1530, the server terminal 1410 is configured to transmit the user login information including the generated login identification information and associated password to the user terminal 1420. After transmitting the user login information or alternatively, substantially contemporaneously to the login information transmission, the server terminal 1410 is configured to transmit a prompt or request to the user terminal for the user desired subscription information for the consumable product replenishment. In one embodiment, the user desired consumable product replenishment subscription information may include low product count threshold notification information and consumable product replenishment transaction option information. A low product count threshold information may be a low test strip count or a low medication, such as insulin, amount.

More specifically, at step 1540, the server terminal 1410 in one embodiment is configured to request from the user via the user terminal 1420 when the user wishes to be notified of a low consumable product count for performing a replenishment procedure, and also, the user's desired purchase transaction option such as establishing a link to the user's financial institution. For example, if the user wishes to be notified of a low test strip count level when the user has 150 or less strips for usage with the health monitor device, the user may specify 150 as the low strip count level at which point, the user desired notification by the server terminal 1410 that replenishment procedure would be necessary. Furthermore, in one embodiment, the replenishment transaction option information provided to the user terminal 1420 by the server terminal 1410 may include one of establishing a link to the user's financial account institution for processing the purchase transaction for the purchase of the replenishment consumable product, prompting the user to allow purchase transactions over the data network 1430, and a simple replenishment notification with option to perform the purchase transaction for the purchase of the replenishment product.

Referring again to FIG. 15, at step 1550, the server terminal 1410 is configured to receive the user selected low consumable product count notification and the replenishment transaction information for the user account from the user terminal 1420. The server terminal 1410 then stores the received information related to the user selected low consumable product count notification and the chosen replenishment transaction option in the storage unit 1415 associated with the user account information also stored therein.

Then, as can be seen from FIG. 15, the server terminal 1410 may be configured to transmit a notification to the user terminal 1420 a confirmation of the receipt and the information which the user selected for the low consumable product count notification level and the product replenishment transaction that the user selected. Thereafter, the user account registration setup and account subscription process shown in FIG. 15 ends.

Figure 16:
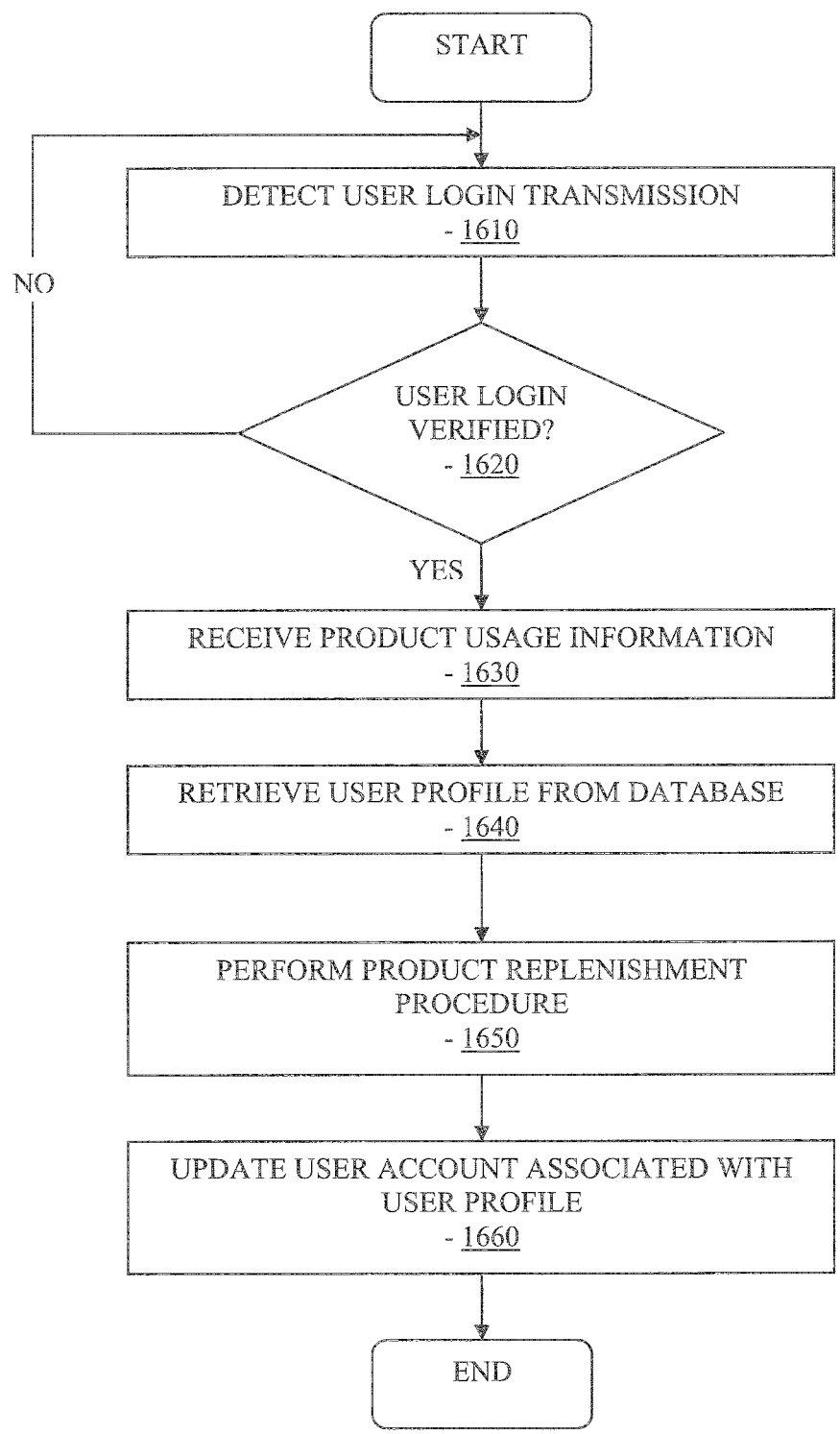
FIG. 16 is a flowchart illustrating an overall replenishment procedure for the user account in accordance with embodiments of the present disclosure.

FIG. 16 is a flowchart illustrating an overall replenishment procedure for the user account in accordance with one embodiment of the present disclosure. Referring to the Figure, at step 1610, the server terminal 1410 (FIG. 14) in one embodiment is configured to detect a user login transmission, including, for example, the detection of the user account login identification information and the corresponding password transmitted from the user terminal 1420 over the data network 1430. Thereafter at step 1620, the server terminal 1410 is configured to verify the received user account login identification information. That is, in one embodiment, the server terminal 1410 is configured to confirm the accuracy of the received account login identification information from the user terminal 1420, and to correspond the received account login identification information to a corresponding stored user account. In one embodiment, the server terminal 1410 may be configured to search the storage unit 1415 for a user account profile generated and which corresponds to the received user account login identification information.

Referring to FIG. 16, if at step 1620 the received user account login identification information verification fails, the procedure returns to step 1610 and waits for a subsequent transmission of the user account login identification information from the user terminal 1420. Optionally, the server terminal 1410 may be configured to generate and transmit a login fail notification corresponding to the failed verification of the user account login at step 1620 to the corresponding user terminal 1420. On the other hand, if at step 1620 it is determined that the received user account login identification is verified, and thus, a corresponding user account profile is recognized by the server terminal 1410, then at step 1630, the server terminal 1410 is configured to receive a consumable product usage information from the user terminal 1420 whose user is now logged into the corresponding user account profile. Consumable product usage information may include, among others, usage information for the number of test strips or dosage information for a medication, such as a long-acting and/or a fast-acting insulin.

Thereafter, the server terminal 1420 is configured in one embodiment to retrieve the corresponding user account profile from the storage unit 1415, for example, (such as in a database associated with the storage of the user account profiles in the storage unit 1415). Then, with the consumable product usage information received from the user terminal 1420, and the corresponding user account profile retrieved from the storage unit 1415, in one embodiment, the server terminal 1410 at step 1650 is configured to perform a consumable product replenishment procedure discussed in further detail below to replenish the consumable product supply associated with the user account profile.

While the present embodiment is mainly described in conjunction with glucose test strips to be used for the periodic glucose level testing and with insulin medication to be used for controlling a patient's blood glucose level, the present disclosure may be applied and would equally cover any procedure which is configured to replenish a given quantity of consumables (for example, medications to be consumed at a predetermined time interval). Referring back to the Figure, upon completing the consumable product replenishment procedure at step 1650, the server terminal 1410 may be configured to update the user account profile associated with the user by for example, updating the database stored in the storage unit 1415 of the server terminal 1410 associated with the user account profile for the user that is logged in.

Furthermore, within the scope of the present disclosure, the database stored in the storage unit 1415 may also be linked to systems that are configured to track user demand, so as to forecast and anticipate demand, and also to track overall consumption patterns, preference, seasonal demand, geographic demand, and other similar demographic data for use in managing supply side activities more effectively and efficiently. The individual user data in the database stored in the storage unit 1415 may also include insurance or other individual reimbursement coverage rates of the individual user. These data may be used to determine a user co-pay and the amount that the insurance or other individual reimbursement coverage allows to the individual user. The results of these calculations on the user data in the database stored in the storage unit 1415 may be used as a basis for purchase or charge transaction to user for the co-pay amount, to charge the insurance or other individual reimbursement coverage for the amount so covered, and also to provide an alert signal in the case that the individual user may exceed the limits of payment coverage, as stored in the database in the storage unit 1415, so that action may be taken based on the alert signal.

Figure 17:
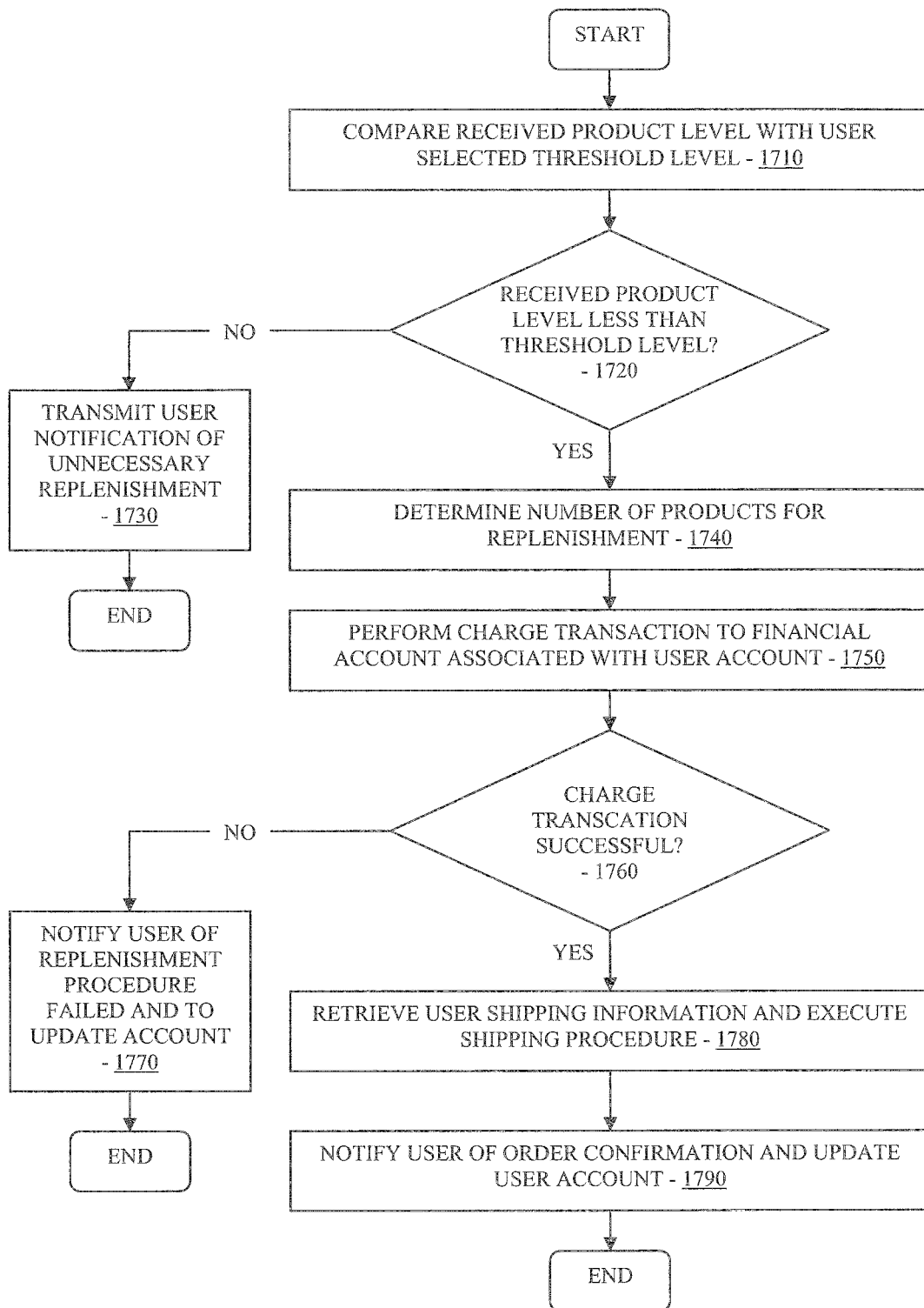
FIG. 17 is a flowchart illustrating the replenishment procedure shown in FIG. 16 in further detail in accordance with embodiments of the present disclosure.

FIG. 17 is a flowchart illustrating the replenishment procedure shown in FIG. 16 in further detail in accordance with one embodiment of the present disclosure. More specifically, the strip replenishment procedure of step 1650 (FIG. 16) in one embodiment begins at step 1710 where the server terminal 1410 (FIG. 14) in one embodiment is configured to compare the received consumable product usage level with a user selected threshold level. Referring back to FIG. 14, the user selected threshold level in one embodiment may correspond to the one or more of low consumable product count notification level which the user selected during the user account registration procedure as shown in FIG. 15. Moreover, the received consumable product usage level at step 1710 in one embodiment corresponds with the received consumable product usage information at step 1630 (FIG. 16) received from the user terminal 1420.

Referring back to FIG. 17, after the comparing step at step 1710 (or as a result of the comparison step of step 1710), the consumable product replenishment procedure at step 1720 determined whether the received consumable product usage level is below the user selected threshold level. If it is determined at step 1720 that the received consumable product usage level is above the user selected threshold level, then at step 1730, the server terminal 1410 transmits a user notification to the corresponding user terminal 1420 notifying that replenishment is unnecessary, and thereafter, the consumable product replenishment procedure terminates.

On the other hand, if at step 1720 it is determined that the received consumable product usage level is below the user selected threshold level, then at step 1740, the server terminal is configured to determine the amount of the consumable product needed for replenishment. More specifically, the server terminal 1410 in one embodiment may be configured to not only determine whether consumable product replenishment is necessary for the associated user account, but also, what the amount of necessary replenishment should be based on one or more predetermined factors such as the desired or optimal consumable product level or count selected by the user (and previously stored in the storage unit 1415, for example, of the server terminal 1410), and the time frame in which the consumable product replenishment procedure is triggered based upon the user account profile information (that is, based on the user's consumable product usage history profile, whether the triggered consumable product replenishment procedure is temporally closer to the most immediately preceding consumable product replenishment procedure).

Within the scope of the present disclosure, such usage historical information determined by the server terminal 1410, for example, may provide valuable information to the user as well as to the server terminal 1410 to maintain an efficient and reliable consumable product replenishment routine so as to not result in either over supply of products, or a supply of consumable products running dangerously low.

Referring back to FIG. 17, after determining the number of consumable products that are needed for replenishment at step 1740 associated with the user account profile, at step 1750, the server terminal 1410 (FIG. 14) in one embodiment is configured to perform a charge transaction to the financial account associated with the user account so as to charge the user's financial account for the purchase and shipping of the replenishment products to the user associated with the user account profile. In one embodiment, as discussed above, the server terminal 1410 is configured to retrieve the financial account information stored and associated with the user account and performs the charge transaction over the data network 1430 with the corresponding financial account terminal 1450. As discussed above, the financial account information in one embodiment may include one of a bank account, a credit card account a debit account, a pre-paid financial account, or any other cash or cash equivalent account (such as the redemption of airline miles or vendor points) which the server terminal 1410 is configured to recognize with monetary value.

Referring again to FIG. 17, at step 1760, it is determined whether the charge transaction performed at step 1750 is successful. More specifically, the server terminal 1410 in one embodiment is configured to interact with the financial account terminal 1460 over the data network 1430 in order to perform the charge or debit transaction for the amount associated with the amount of replacement product. If the associated financial account terminal 1460 returns a failed transaction notification to the server terminal 1410 based on the server terminal 1410 transmission of the charge transaction over the data network 1430, then at step 1770, the server terminal 1410 in one embodiment is configured to generate and transmit a notification to the user terminal 1420 notifying the user at the user terminal 1420 that the consumable product replenishment procedure has failed. Also, the server terminal 1410 is configured to notify the user that the reason for consumable product replenishment failure is due to inaccurate or outdated financial account information associated with the user account, and thus, is configured to prompt the user to update the user's financial account associated with the user's account profile stored in the server terminal 1410.

On the other hand, referring back to FIG. 17, if at step 1760, it is determined that the consumable product replenishment charge transaction is successful, then at step 1780, the server terminal 1410 is configured to retrieve the user shipping information associated with the user account profile, and executes the shipping procedure to ship the replenishment consumable products purchased by the user to the user's designated shipping location. In one embodiment, the server terminal 1410 may be configured to prompt the user to verify or update the desired shipping location (such as destination address and time frame for shipping to include expedited shipping or custom shipping options, for example).

Referring again to FIG. 17, upon executing the shipping procedure at step 1780, the server terminal at step 1790 is configured to generate and transmit a notification to the user terminal 1420 associated with the user account confirming the shipment of the ordered products as well as the shipping and the fulfilled order details. Also, the server terminal 1410 is configured to update the associated user account based on the charge transaction and the shipping transaction performed. In this manner, in accordance with one embodiment of the present disclosure, the users may conveniently place a shipment order of products in advance of running low on the product, and rather than relying upon the user's manual calculation or determination of the needed products based upon the user's usage, such determination is automatically performed for the user, and the user can easily make the purchase transactions for the replenishment consumable products quickly and easily.

Figure 18:
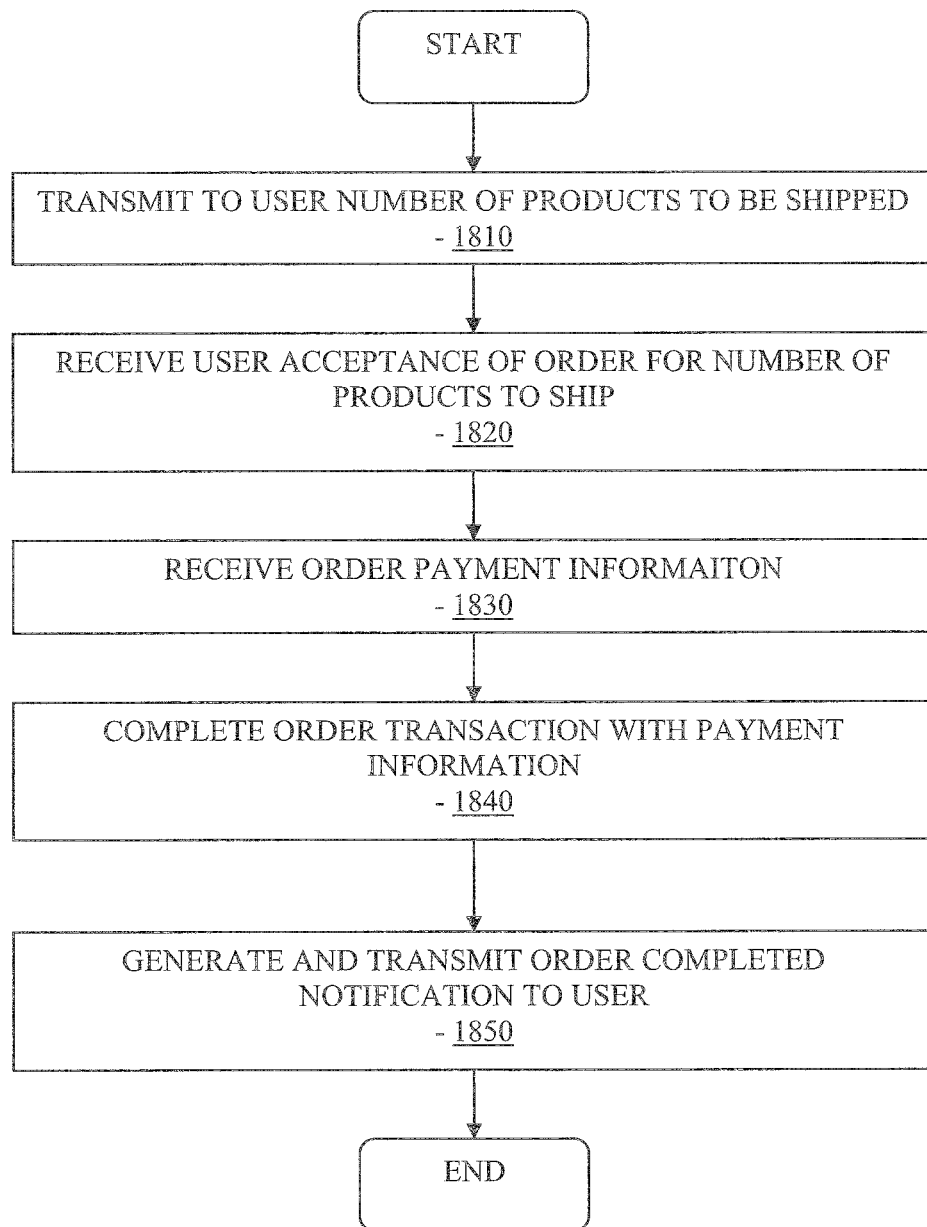
FIG. 18 is a flowchart illustrating the replenishment procedure shown in FIG. 16 in further detail in accordance with embodiments of the present disclosure.

FIG. 18 is a flowchart illustrating the replenishment procedure shown in FIG. 16 in further detail in accordance with another embodiment of the present disclosure. Referring to the Figure, in one embodiment of the present disclosure, the server terminal 1410 is configured to transmit to the user terminal 1420 a predetermined or calculated amount of consumable products to be shipped at step 1810. In one embodiment, the server terminal 1410 may be configured to determine the amount of consumable products to be shipped based one or more predetermined factors such as the user product usage level, the user selection of low consumable product notification information, the user's desired consumable product inventory, and the user's desired frequency of product replenishment.

Responsive to the amount of consumable products to be shipped notification received from the server terminal 1410, the user may confirm the received number of consumable products to be shipped as the number of products that the user wants to receive, and thus, may transmit an acceptance notification to the server terminal 1410 which, the server terminal 1410 at step 1820 is configured to receive, for example, as an acceptance of the order associated with the amount of consumable products to be shipped to the user. Thereafter at step 1830, the server terminal 1410 may be configured to receive order payment information for the purchase of the amount of consumable products that the user has accepted to be shipped to the user. In one embodiment, the user may transmit from the user terminal 1420 to the server terminal 1410 over the data network 1430, a user financial account information, such as a credit card information or a bank account information to be used to perform the purchase transaction.

Referring back to FIG. 18, thereafter at step 1840, the server terminal 1410, having received the financial account information from the user terminal 1420, performs and completes the order transaction for the purchase of the amount of consumable products accepted by the user and to be shipped to the user with the received payment information. Upon performing and successfully confirming the order transaction at step 1840, the server terminal 1410 is configured in one embodiment to generate an order confirmation notification and to transmit the notification to the user. In one embodiment, the order confirmation notification may include the amount of consumable products ordered, the shipping or mailing address where the ordered products are to be shipped, and the amount charged to the financial account associated with the payment information.

In this embodiment, it can be seen that the user is not required to provide the user's financial account information to have it stored, for example, in the user account profile at the server terminal 1410. This approach would be particularly desirable for users who do not wish to have their financial account information disseminated and stored in vendor sites such as the server terminal 1410 configured to perform consumable product replenishment procedures.

Figure 19:
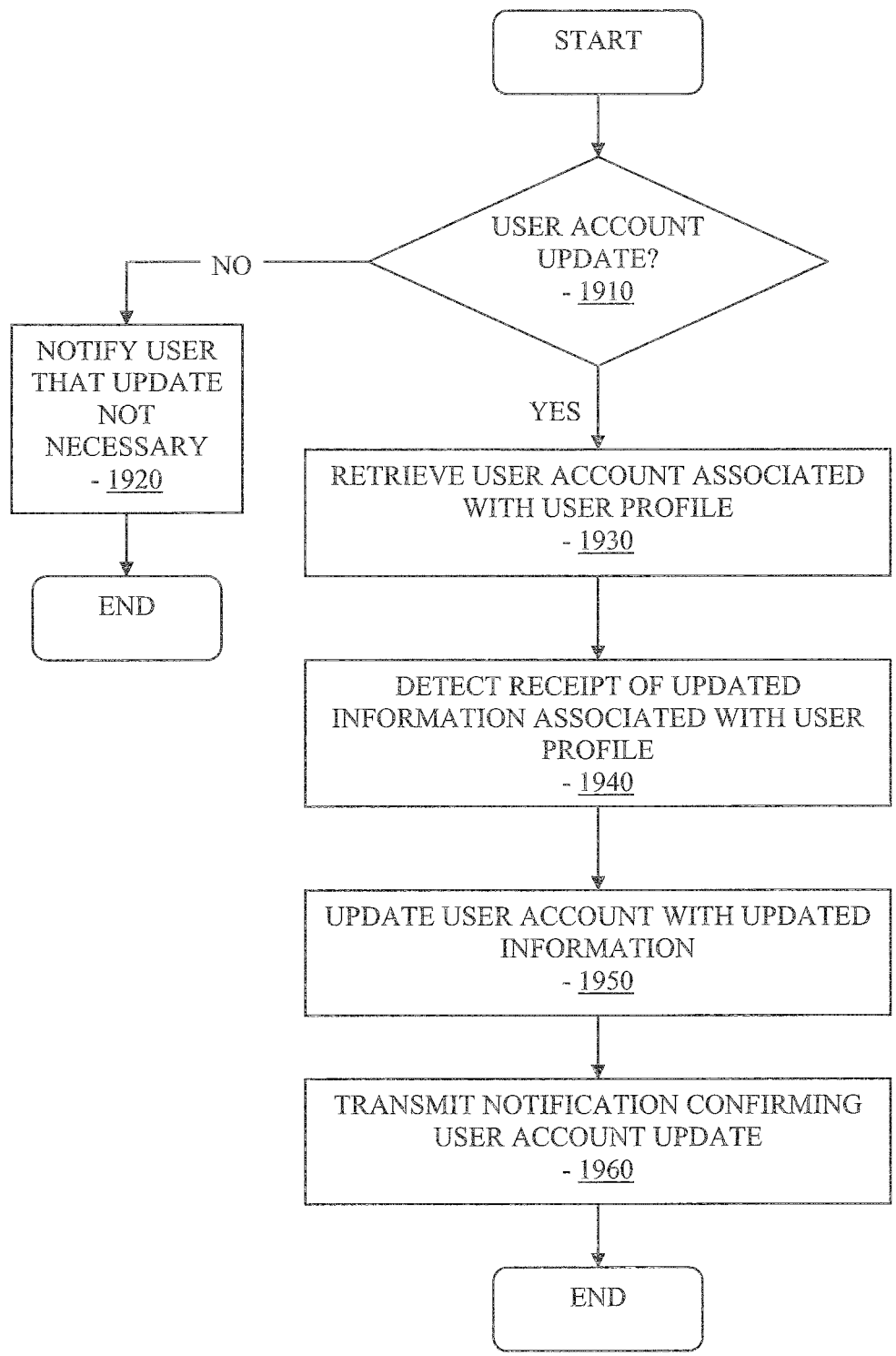
FIG. 19 is a flowchart illustrating a user account update and maintenance procedure in accordance with embodiments of the present disclosure.

FIG. 19 is a flowchart illustrating a user account update and maintenance procedure in accordance with one embodiment of the present disclosure. Referring to the Figure, at step 1910, a user account update procedure is prompted. This may be a server terminal 1410 (FIG. 14) triggered procedure (for example, when it is determined that the user financial account information stored in the server terminal 1410 is outdated or no longer accurate), or alternatively, the user at the user terminal 1420 may initiate the user account update procedure of step 1910 based on the user's desire to modify one or more settings or parameters associated with the user account profile.

Referring to the Figures, in the case where the server terminal 1410 determines that the user account update is not needed, then at step 1920, it is determined that the account update procedure is unnecessary and a corresponding notification is transmitted to the user terminal 1420. For example, in the case where the user prompts a parameter which the user wishes to modify (such as by modifying the shipping information), if the server terminal 1410 determines at step 1910 that the updated information with which the user wishes to update is the same at that which is stored in the server terminal 1410, then, rather than expending the processing power of the server terminal 1410 to perform the user account update procedure, the server terminal 1410 is configured to generate and transmit the notification to the user terminal that the user specified account update is not necessary.

On the other hand, if it is determined that the user account update is to be performed at step 1910, then at step 1930, the server terminal 1410 is configured to retrieve the stored user account associated with the user profile. Thereafter, at step 1940, the server terminal 1410 is configured to detect the receipt of updated information associated with the user profile received from the user terminal 1420. Thereafter, the server terminal 1410 at step 1950 is configured to update the user account with the updated information received from the user terminal 1420. In one embodiment, the server terminal 1410 may be configured to update the database stored in the storage unit 1415, and which is associated with the user account to be updated based on the account update information received from the user terminal 1420. Upon completing the user account update with the received updated information, the server terminal 1410 at step 1960 is configured to transmit a notification to the user terminal 1420 to notify and confirm the update to the user account.

In the manner described above, in accordance with the various embodiments of the present disclosure, there is provided method and system for providing subscription based transaction for consumable items such as glucose test strips or insulin, which diabetic patients may effectively use to easily replenish glucose test strips or insulin when the patient is running low on such items. In one embodiment, the user's use of the account or access to the subscription based account profile serves to compare the number of remaining test strips with the desired minimum number of strips which the patient may have specified or the amount of remaining insulin with the desired minimum amount of insulin which the patient may have specified, and to automatically initiate and execute the purchase transaction of the test strips, insulin, or other consumables for the user to order, and deliver the products to the patient on time such that the patient does not run low on the item.

In this manner, in accordance with the various embodiments of the present disclosure, an efficient system and method for the user to always maintain a minimum number of consumable items on order or to be ordered based on the user's rate of usage of the item are provided.

Furthermore, within the scope of the present disclosure, the server terminal 1410 (FIG. 14) may be configured to provide a loyalty based rewards program such that based a predetermined criteria, the users may be provided with a discounted price for the replenishment orders of the test strips or medication, such as insulin, and/or be offered a replacement health monitor device or medication delivery device based on the user's replenishment transaction history.

For example, the server terminal 1410 may be configured to flag a user account profile which has executed a threshold amount of replenishment transactions (whether based on the number of products ordered for replenishment, or based on the total value of the replenishment transactions sum), and to offer an incentive to continue to maintain the user account, and thus with the replenishment transactions. In one embodiment, the server terminal 1410 may be configured to automatically offer to send a replacement health monitor device and/or medication deliver system, such as a syringe or injection pen, at every calendar year (or at a predetermined frequency) so long as the user's frequency and volume of replenishment transaction satisfies a threshold level. Alternatively, the server terminal 1410 may be configured to apply a price discount for future replenishment transactions based on the user satisfying the threshold level discussed above. In this manner, within the scope of the present disclosure, the users or patients are provided with an incentive to continue to maintain the user account and to continue performing the replenishment transactions.

Additionally, in a further embodiment of the present disclosure, where there are existing contracts with a provider of insurance or other individual reimbursement, or with a government or authority which provides group discounts when certain conditions are met, such as group price discounts or other special commercial terms, the server terminal 1410 may be configured to automatically provide the special commercial terms to the provider of insurance or other individual reimbursement, or to the a government or authority.

In this manner, in aspects of the present disclosure, there are provided health monitor devices, such as a blood glucose meter, with improved or higher functionalities. In certain aspect, the health monitor devices may be configured to provide medication dosage calculation, such as single dose of rapid or fast acting insulin, long acting insulin, or combinations thereof, and further configured to incorporate additional features related to improving the management of the physiological condition.

In accordance with aspects of the present disclosure, the program instructions and/or associated application for execution by the one or more processor driven device such as, for example, the health monitor device 100 (FIG. 1) may be transferred over data network for installation and subsequent execution by the devices that are downloading the applications, for example, the health monitor device 100. For example, the application associated with the various program instructions for implementing the medication dose calculation function may be downloadable over the air (OTA) over a cellular network and installed in one or more devices in communication in the cellular network. In addition, the executable program or application may be installed for execution in the one or more components of devices in the various systems described above, over a data network such as the internet, a local area network, a wide area network and the like.

Moreover, in aspects of the present disclosure, the various components of the overall systems described above including, for example, the health monitor device, data processing terminal or remote computing device (such as a personal computer terminal or server terminal) as described above may each be configured for bi-directional or uni-directional communication over one or more data communication network to communicate with other devices and/or components, including, for example, infusion devices, analyte monitoring device such as continuous glucose monitoring system, computer terminals at a hospital or a health care professional's office, the patient or user's residence or office, or the device/component vendor/supplier or manufacturer (for example, the vendor or manufacturer of the test strips, insulin, and lancing device and the like) or any other location where the network component is capable of wired or wireless communication over a data network with other devices or components in data communication over the data network. Additionally, secure encrypted data communication may be provided, including encryption based on public/private key pair, password protection and the like to maintain a desired level of security of the data transferred.

The various processes described above including the processes operating in the software application execution environment overall systems described above performing the various functions including those routines described in conjunction with FIGS. 3-5, 8-13, and 15-19, may be embodied as computer programs developed using an object oriented language that allows the modeling of complex systems with modular objects to create abstractions that are representative of real world, physical objects and their interrelationships. The software required to carry out the inventive process, which may be stored in the storage unit of one or more components in the one or more overall system described above, may be developed by a person of ordinary skill in the art and may include one or more computer program products.

In addition, while one or more of the processes described in connection with FIGS. 3-5, 8-13, and 15-19 are described herein in connection with a particular embodiment of a health monitor device, e.g., a health monitor device 600, it should be noted that the one or more processes may also be performed as appropriate utilizing one or more additional embodiments of the health monitor devices described herein, e.g. a health monitor device 100 or a health monitor device 700 as described herein.

Strip Port Configured to Receive Test Strips Having Different Dimensions and/or Electrode Configurations In some embodiments, a health monitor device as described herein includes a strip port configured to receive test strips having different dimensions and/or electrode configurations, e.g., as described in the U.S. patent application Ser. No. 12/695,947 filed on Jan. 28, 2010, and entitled "Universal Test Strip Port", the disclosure of which is incorporated by reference herein.

Test-Strip Port Configured to Receive Analyte Test Strips Having Voltage-Driven Fill Indicator In some embodiments, a health monitor device as described herein includes a strip port configured to receive analyte test strips configured to include a voltage-driven fill indicator. An analyte test strip configured to include a voltage-driven fill indicator can include a fill-indicator which is visible at an end of the analyte test strip, e.g., an end of the analyte test strip other than an end which is inserted into the health monitor device during the analyte measurement process. In one embodiment, the inclusion of a voltage-driven fill indicator in an analyte test strip can be implemented using a film which darkens or changes color when sufficient voltage is applied to it. An electrode can be included in the analyte test strip which is configured to make electrical contact with the film. The film can be variously positioned on the analyte test strip including, e.g., at an end of the analyte test strip.

A health monitor device configured to receive an analyte test strip including a voltage-driven fill indicator can be configured to sense when the analyte test strip is sufficiently full of liquid (e.g., blood). This can be accomplished, for example, through the use of electrical contacts positioned in the test strip port and configured to contact one or more fill-indicator electrodes of the analyte test strip. The health monitor device can be configured such that when the health monitor device senses that the analyte test strip is sufficiently full of liquid, it applies a voltage to an electrochromic film positioned between the electrode contacting the film and a ground electrode. The film is selected such that the voltage applied by the health monitor device is sufficient to darken the film or effect a change in its color. A variety of films and other electrochromic materials capable of darkening and/or changing color in response to an applied voltage are known in the art, including, e.g., polyaniline, viologens, polyoxotungstates and tungsten oxide. Additional description of an electrochromic film is provided, for example, in U.S. Patent Application No. 2007/0153355, the disclosure of which is incorporated by reference herein. Accordingly, a visual indication of analyte test strip fill can be provided.

Visual Fill Indicator

In some embodiments, a health monitor device as described herein is configured to include a visual fill indicator. The visual fill indicator may be configured to produce a visual indication when the analyte test strip is sufficiently full of liquid (e.g., blood). This can be accomplished, for example, through the use of electrical contacts positioned in the test strip port and configured to contact one or more fill-indicator electrodes of the analyte test strip. The health monitor device can be configured such that when the health monitor device senses that the analyte test strip is sufficiently full of liquid, the health monitor device displays a visual indication to the user indicating that the analyte test strip is sufficiently full of liquid (e.g., blood). In certain instances, the visual fill indicator includes a visual indication on a display of the device. For instance, the visual indication may include text, graphics (e.g., one or more icons and/or animations), etc. displayed to a user on the display of the device.

In certain embodiments, the visual fill indicator includes a light source. For example, the light source can be, but is not limited to, a light, an LED, an OLED, etc. In some cases, the light source is positioned on the health monitor device in an area visible to the user while the user is using the device. For instance, the light source may be positioned on the front of the device, such as adjacent to or included in a display of the device, adjacent to or included in a test strip port of the device, adjacent to or included in a button of the device, and the like. In certain cases, the visual fill indicator may be included in an analyte test strip, for example at or near an end of an analyte test strip opposite the end inserted into the health monitor device during use.

Test Strip Ejector

In some embodiments, a health monitor device as described herein is configured to include an optional analyte test strip ejector configured to eject an analyte test strip from a test strip port of the health monitor device. An analyte test strip ejector may be useful, for example, where it is desirable to eject an analyte test strip containing a sample of bodily fluid, e.g., blood, following an analyte measurement conducted using the health monitor device. This allows a user of the health monitor device to dispose of the contaminated analyte test strip without touching the analyte test strip.

In some embodiments, the analyte test strip ejector slideably engages a portion of the housing of the health monitor device. The analyte test strip ejector may be configured such that upon insertion of an analyte test strip into the test strip port, the analyte test strip ejector is moved rearward with respect to the test strip port and in the direction of insertion. In order to eject the analyte test strip, a user physically moves the analyte test strip ejector forward with respect to the test strip port and in the opposite of the direction of insertion. This movement in-turn exerts force upon the analyte test strip expelling it from the test strip port. Alternatively, the analyte test strip ejector may be configured such that insertion of the analyte test strip into a strip port of the health monitor device positions the analyte test strip ejector in a "cocked" position, e.g., by engaging a spring mechanism. The health monitor device may include a button, switch, or other suitable mechanism for releasing the cocked ejector from the cocked position such that it ejects the analyte test strip from the strip port of the health monitor device. Additional information regarding analyte test strip ejectors is provided in the U.S. patent application Ser. No. 12/695,947, filed on Jan. 28, 2010, and entitled "Universal Test Strip Port", the disclosure of which is incorporated by reference herein.

Splash-Proof Test Strip Port

In some embodiments, a health monitor device as described herein is configured to include a contamination resistant test strip port and/or a splash-proof test strip port. In one such embodiment, the test strip port includes one or more sealing members positioned so as to limit and/or prevent internal contamination of the test strip port with fluids and/or particles present in the environment outside the test strip port. In another embodiment, the test strip port includes an internal beveled face which can limit and/or prevent ingress of one or more external contaminants into the internal area of the test strip port.

Additional disclosure and examples of contamination resistant test strip ports are provided in U.S. patent application Ser. No. 12/539,217, filed Aug. 11, 2009, and entitled "Analyte Sensor Ports," the disclosure of which is incorporated by reference herein.

In some embodiments, the test strip ports described herein can be configured to work with (e.g., engage with or operate in connection with) additional mechanisms and/or devices designed to limit and/or prevent contamination of the internal areas of the test strip ports themselves or the internal areas of the health monitor device into which the test strip ports can be integrated. For example, mechanisms, devices and methods of protecting test strip port openings are described in U.S. Pat. No. 7,820,105 issued Oct. 26, 2010 titled "Analyte Meter Protectors and Methods", and U.S. Pat. No. 7,740,580 issued Jun. 22, 2010 titled "Analyte Monitoring", the disclosure of each of which is incorporated by reference herein. Test strip ports according to the present disclosure can also be configured to be replaceable and/or disposable, and/or configured so as to limit and/or prevent contamination of the health monitor device in which the test strip port is integrated. Additional description is provided, for example, in U.S. Application Publication No. 2010/0064800, published Mar. 18, 2010, entitled "Strip Connectors for Measurement Devices;" the disclosure of which is incorporated by reference herein.

Fluid-Wicking Test-Strip Port Interface

In some embodiments, a test strip port as disclosed herein is optionally configured as a fluid-wicking test strip port interface. In some such embodiments, the test strip port is configured to include one or more hydrophilic and/or absorptive materials positioned in proximity to an opening in the test strip port, wherein the opening is configured to receive an analyte test strip. The hydrophilic and/or absorptive materials may be positioned, for example, surrounding or substantially surrounding the opening in the test strip port. In some embodiments, the one or more hydrophilic and/or absorptive materials are positioned above and/or below the test strip port opening. In other embodiments, the one or more hydrophilic and/or absorptive materials are positioned to the left and/or right of the test strip port opening. In some embodiments, the one or more hydrophilic and/or absorptive materials define at least a portion of the opening in the test strip port.

In certain embodiments, one or more, e.g., 2, rotating absorptive guards are positioned in relation to the test strip port opening (e.g., directly above and/or below the test strip port opening) such that during insertion of an analyte test strip, e.g., an analyte test strip, the absorptive guards each rotate while making contact with the analyte test strip. The rotating absorptive guards can be configured to engage the test strip port housing or the health monitor device housing, e.g., by engaging one or more shafts positioned on the test strip port housing or the health monitor device housing. The rotating action of the absorptive guards, e.g., about the one or more shafts, can mitigate added resistance which may be experienced by the user as a result of contact between the analyte test strip and the one or more absorptive guards as the user inserts the analyte test strip into the test strip port. In some embodiments, once the analyte test strip is inserted, the absorptive guards form a barrier at the point or points of contact with the analyte test strip such that unwanted or excess fluid is prevented or at least substantially inhibited from entering the test strip port opening. The one or more rotating absorptive guards may be disposable and/or replaceable. For example, the absorptive guards may be configured such that they can be easily removed from the test strip port for cleaning, disposal and/or replacement. In one embodiment, the rotating absorptive guards have a substantially cylindrical shape, however, an absorptive guard having any suitable shape may be utilized.

In some embodiments, a test strip port configured as a fluid-wicking test strip port interface includes one or more paths and/or channels sized for capillary action which are positioned relative to the opening in the test strip port such that they facilitate the wicking of fluid away from the opening in the test strip port. These one or more paths and/or channels may include a hydrophilic and/or absorptive material and/or coating. In some embodiments, the one or more paths and/or channels include a mechanism by which air, when displaced by fluid, can escape the one/or more paths and/or channels. For example, in one embodiment, the one/or more paths and/or channels connect to one/or more additional paths and/or channels which provide an opening to the external environment of a health monitor device which incorporates a test strip port as described herein. In some embodiments, the one or more paths and/or channels are positioned to facilitate flow of fluid in the general direction of a gravitational force applied during the insertion process. In some embodiments, the one or more paths and/or channels terminate in a reservoir positioned, for example, in the housing of the test strip port or the housing of a health monitor device configured to include the test strip port.

In some embodiments, a fluid-wicking test strip port interface is configured to provide one or more alternative paths for a fluid which are more energetically favorable than a path which would bring the fluid into the internal environment of the test strip port through the opening in the test strip port.

In some embodiments, the fluid-wicking portion of a fluid-wicking test strip port interface according to the present disclosure is separately disposable and/or replaceable. In other embodiments, the fluid-wicking portion is physically integrated with the test strip port housing and/or the housing of a health monitor device which includes a test strip port according to the present disclosure such that the fluid-wicking portion is not configured to be separately disposable and/or replaceable.

In additional embodiments, the hydrophilic and/or absorptive material and/or coating may include a material which changes color when contacted with a fluid. This may provide, for example, an indication that excess fluid was subject to wicking action by the hydrophilic and/or absorptive material and/or coating.

While the fluid-wicking test strip port interface has been described above with reference to the test strip ports disclosed herein, it should be noted that the features of the fluid-wicking test strip port interface may provide similar effects when used in connection with other openings in health monitor devices, or openings in other devices. For example, the features of the fluid-wicking test strip port interface may be used to prevent or inhibit fluid ingress into a battery compartment or communication port of a health monitor device.

Integration with Analyte Monitoring Systems

In some embodiments, a health monitor device as described herein may be integrated with an analyte monitoring system including an implanted or partially implanted analyte sensor, e.g., a system including an implanted or partially implanted glucose sensor (e.g., a continuous glucose sensor). A system including an implanted or partially implanted glucose sensor may include a health monitor device as described herein, which is configured to receive analyte data from the implanted or partially implanted glucose sensor either directly or through an intermediate device, e.g., an RF-powered measurement circuit coupled to an implanted or partially implanted analyte sensor. In some embodiments, where a health monitor device according to the present disclosure is integrated with an analyte monitoring system, the health monitor device does not include a strip port for receiving an analyte test strip. In other embodiments, where a health monitor device according to the present disclosure is integrated with an analyte monitoring system, the health monitor device includes a strip port for receiving an analyte test strip. In one embodiment, where the health monitor device includes a strip port, the health monitor device may be used to calibrate the analyte monitoring system, e.g., using one point calibration or other calibration protocol. For additional information, see U.S. Pat. No. 6,175,752, the disclosure of which is incorporated by reference herein. In some embodiments, the health monitor device may be configured to communicate with the implanted or partially implanted analyte sensor via Radio Frequency Identification (RFID) and provide for intermittent or periodic interrogation of the implanted analyte sensor.

Exemplary analyte monitoring systems that may be utilized in connection with the disclosed health monitor device include those described in U.S. Pat. Nos. 7,041,468; 5,356,786; 6,175,752; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,461,496; 6,503,381; 6,591,125; 6,616,819; 6,618,934; 6,676,816; 6,749,740; 6,893,545; 6,942,518; 6,514,718; 5,264,014; 5,262,305; 5,320,715; 5,593,852; 6,746,582; 6,284,478; 7,299,082; U.S. Patent Application Publication No. 2010/0198034 published Aug. 5, 2010 titled "Compact On-Body Physiological Monitoring Devices and Methods Thereof"; U.S. Patent Application Publication No. 2010/0324392 published Dec. 23, 2010 titled "Analyte Sensor and Apparatus for Insertion of the Sensor"; U.S. Pat. No. 7,866,026, issued Jan. 11, 2011, entitled "Method for Making Calibration-Adjusted Sensors"; U.S. Patent Application Publication No. 2010/0326842, published Dec. 30, 2010, entitled "Extruded Electrode Structures and Methods of Using Same"; U.S. Pat. No. 7,811,231 issued Oct. 12, 2010 titled "Continuous Glucose Monitoring System and Methods of Use"; U.S. Patent Application Publication No. 2007/0095661; U.S. Patent Application Publication No. 2006/0091006; U.S. Pat. No. 7,740,581 issued Jun. 22, 2010 titled "Methods of Determining Concentration of Glucose"; U.S. Patent Application Publication No. 2008/0267823; U.S. Patent Application Publication No. 2007/0108048; U.S. Pat. No. 7,822,557 issued Oct. 26, 2010 titled "Analyte Sensors and Methods"; U.S. Patent Application Publication No. 2008/0066305; U.S. Pat. No. 7,811,430 issued Oct. 12, 2010 titled "Biosensors and Methods of Making"; U.S. Pat. No. 7,802,467 issued Sep. 28, 2010 titled "Analyte Sensors and Methods of Use"; and U.S. Pat. No. 7,846,311 issued Dec. 7, 2010 titled "In Vitro Analyte Sensor and Methods of Use"; the disclosures of each which are incorporated by reference herein.

Integration with Medication Delivery Devices and/or Systems

In some embodiments, the health monitor devices disclosed herein may be included in and/or integrated with, a medication delivery device and/or system, e.g., an insulin pump module, such as an insulin pump or controller module thereof. In some embodiments the health monitor device is physically integrated into a medication delivery device. In other embodiments, a health monitor device as described herein may be configured to communicate with a medication delivery device or another component of a medication delivery system. Additional information regarding medication delivery devices and/or systems, such as, for example, integrated systems, is provided in U.S. Patent Application Publication No. 2006/0224141, published on Oct. 5, 2006, entitled "Method and System for Providing Integrated Medication Infusion and Analyte Monitoring System", and U.S. Patent Application Publication No. 2004/0254434, published on Dec. 16, 2004, entitled "Glucose Measuring Module and Insulin Pump Combination," the disclosure of each of which is incorporated by reference herein. Medication delivery devices which may be provided with health monitor device as described herein include, e.g., a needle, syringe, pump, catheter, inhaler, transdermal patch, or combination thereof. In some embodiments, the medication delivery device or system may be in the form of a drug delivery injection pen such as a pen-type injection device incorporated within the housing of a health monitor device. Additional information is provided in U.S. Pat. Nos. 5,536,249 and 5,925,021, the disclosure of each of which is incorporated by reference herein.

The medication delivery system may be used for injecting a dose of medication, such as insulin, into a patient based on a prescribed medication dosage, and may be automatically updated with dosage information received from the health monitor device. In another embodiment, the medication dosage of the medication delivery system may include manual entry of dosage changes made through, for example, an optional input unit coupled to the housing of the health monitor device. Medication dosage information associated with the medication delivery system may be displayed on an optional display unit disposed on the housing of the health monitor device.

Communication Interface

As discussed previously herein, a health monitor device according to the present disclosure can be configured to include a communication interface. In some embodiments, the communication interface includes a receiver and/or transmitter for communicating with a network and/or another device, e.g., a medication delivery device and/or a patient monitoring device, e.g., a continuous glucose monitoring device. In some embodiments, the communication interface is configured for communication with a health management system, such as the COPILOT™ system available from Abbott Diabetes Care Inc., Alameda, Calif.

The communication interface can be configured for wired or wireless communication, including, but not limited to, radio frequency (RF) communication (e.g., Radio-Frequency Identification (RFID), ZIGBEE® communication protocols, WIFI®, infrared, wireless Universal Serial Bus (USB), Ultra Wide Band (UWB), BLUETOOTH® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the health monitor device and other external devices such as a computer terminal (for example, at a physician's office or in hospital environment), an external medical device, such as an infusion device or including an insulin delivery device, or other devices that are configured for similar complementary data communication.

In one embodiment, the communication interface is configured for infrared communication, BLUETOOTH® communication, or any other suitable wireless communication protocol to enable the health monitor device to communicate with other devices such as infusion devices, analyte monitoring devices, computer terminals and/or networks, communication enabled mobile telephones, personal digital assistants, or any other communication devices which the patient or user of the health monitor device may use in conjunction therewith, in managing the treatment of a health condition, such as diabetes.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WIFI® connection to the internet at a WIFI® hotspot.

In one embodiment, the health monitor device is configured to wirelessly communicate with a server device via the communication interface, e.g., using a common standard such as 802.11 or BLUETOOTH® RF protocol, or an IrDA infrared protocol. The server device could be another portable device, such as a smart phone, Personal Digital Assistant (PDA) or notebook computer, or a larger device such as a desktop computer, appliance, etc. In some embodiments, the server device has a display, such as a liquid crystal display (LCD), as well as an input device, such as buttons, a keyboard, mouse or touch-screen. With such an arrangement, the user can control the health monitor device indirectly by interacting with the user interface(s) of the server device, which in turn interacts with the health monitor device across a wireless link.

In some embodiments, the communication interface is configured to automatically or semi-automatically communicate data stored in the health monitor device, e.g., in an optional data storage unit, with a network or server device using one or more of the communication protocols and/or mechanisms described above.

Figure 20:
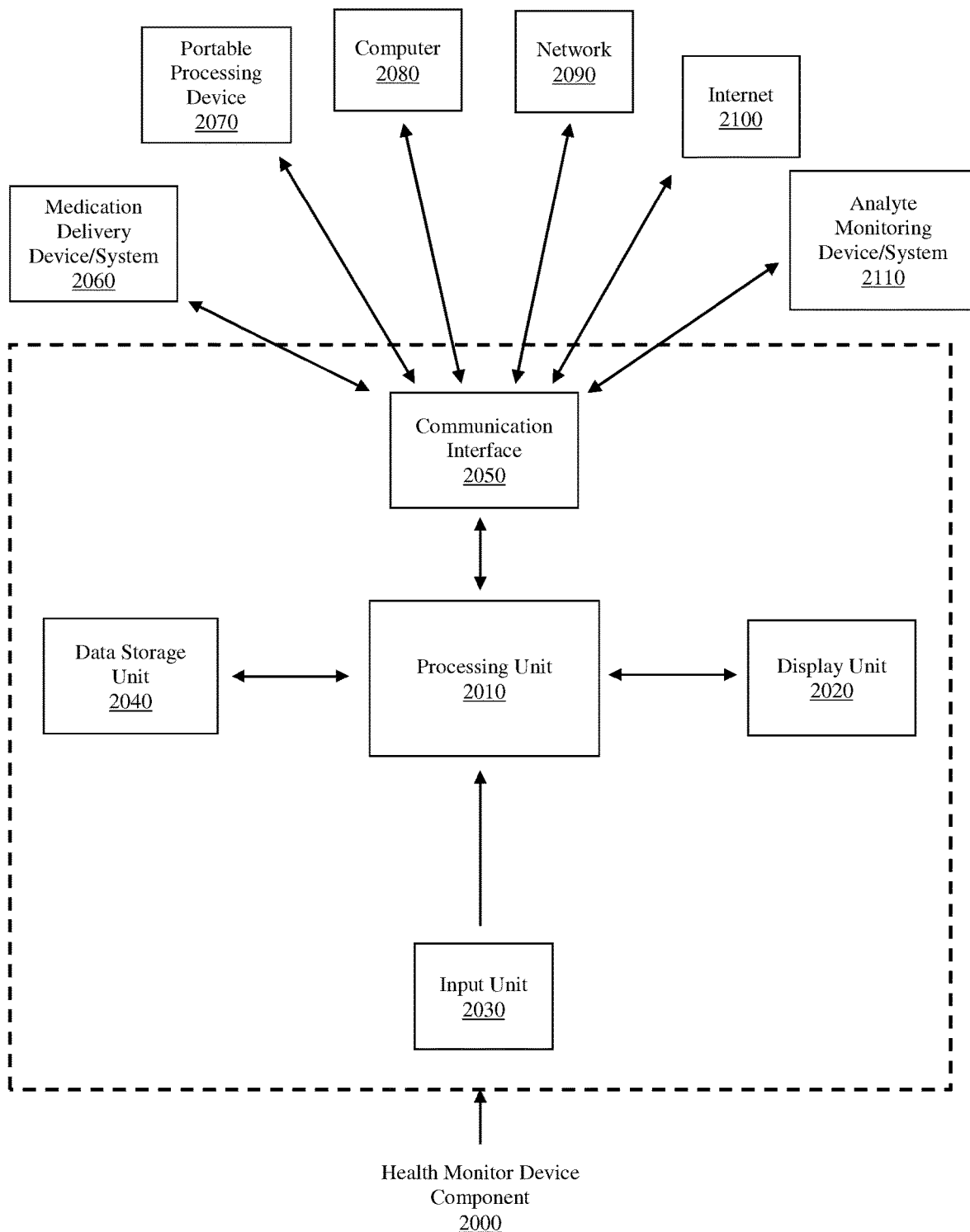
FIG. 20 is a block diagram showing data flow within a health management system, e.g., a diabetes management system, including an embodiment of a health monitor device according to embodiments of the present disclosure.

With reference to FIG. 20, in some embodiments, the present disclosure provides a system, e.g., a diabetes management system, of which a health monitor device according to the present disclosure is a component 2000 thereof. In some embodiments, each of Input Unit 2030, Display Unit 2020, Data Storage Unit 2040 and Communication Interface 2050 can be integrated into the housing of the health monitor device including a Processing Unit 2010. In some embodiments, one or more of Input Unit 2030, Display Unit 2020, Data Storage Unit 2040 and Communication Interface 2050 are provided as a separate modular hardware unit capable of releasably engaging with the housing of the health monitor device to form an integrated unit. In other embodiments, one or more of Input Unit 2030, Display Unit 2020, Data Storage Unit 2040 and Communication Interface 2050 are provided as a separate device or as a component of a separate device which is configured to communicate with the health monitor device and thus transfer data between the device or component and the processing unit of the health monitor device. In some embodiments, Display Unit 2020 and Input Unit 2030 are integrated into a single unit, e.g., a touch screen display.

FIG. 20 also depicts a variety of optional devices and/or systems one or more of which can be configured to communicate with the health monitor device. As shown in FIG. 20, the communication interface 2050, which is configured to communicate with the processing unit 2010, can be configured to communicate with one or more of a medication delivery device and/or system 2060, a portable processing device 2070, a computer 2080, a network 2090, an internet 2100 and an analyte monitoring device and/or system 2110 (e.g., a system including an implanted or partially implanted analyte sensor).

Input Unit

As discussed previously herein, a health monitor device according to the present disclosure can be configured to include an input unit and/or input buttons coupled to the housing of the health monitor device and in communication with a controller unit and/or processor. In some embodiments, the input unit includes one or more input buttons and/or keys, wherein each input button and/or key is designated for a specific task. Alternatively, or in addition, the input unit may include one or more input buttons and/or keys that can be 'soft buttons' or 'soft keys'. In the case where one or more of the input buttons and/or keys are 'soft buttons' or 'soft keys', these buttons and/or keys may be used for a variety of functions. The variety of functions may be determined based on the current mode of the health monitor device, and may be distinguishable to a user by the use of button instructions shown on an optional display unit of the health monitor device. Yet another input method may be a touch-sensitive display unit, as described in greater detail below.

In addition, in some embodiments, the input unit is configured such that a user can operate the input unit to adjust time and/or date information, as well as other features or settings associated with the operation of a health monitor device.

In certain embodiments, the input unit may include a rotation-based user interface. A rotation-based user interface may be rotated to positively indicate a selection (similar to how pressing a button positively indicates a selection). For example, a rotation-based user interface may be rotated in a first direction to indicate a first selection and rotated in a second direction to indicate a second selection. In some cases, the first and second directions may be opposite directions. A rotation-based user interface may be used to indicate a selection on a display unit of the health monitor device. For instance, the rotation-based user interface may be rotated in a first direction to indicate a "yes" or "ok" selection, or may be rotated in a second direction different (e.g., opposite) from the first direction to indicate a "no" or "cancel" selection. In some cases, the rotation-based user interface may be rotated to scroll forwards or backwards through a series of selections displayed on the display unit, or to highlight different selections displayed on the display unit.

Figure 41A:
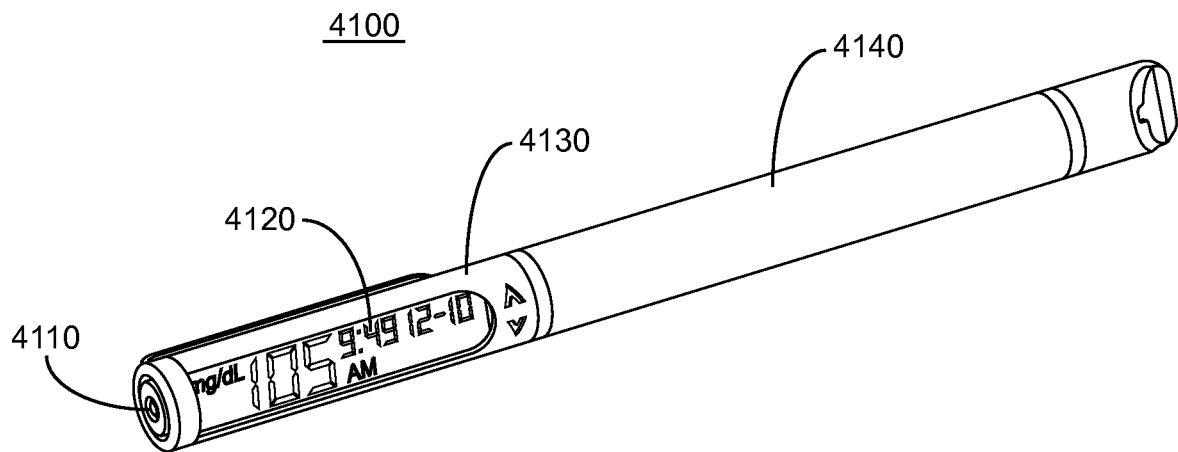
FIGS. 41A and 41B show a side perspective view and an enlarged view, respectively, of a health monitor device configured with a rotation-based input unit according to embodiments of the present disclosure.
Figure 41B:
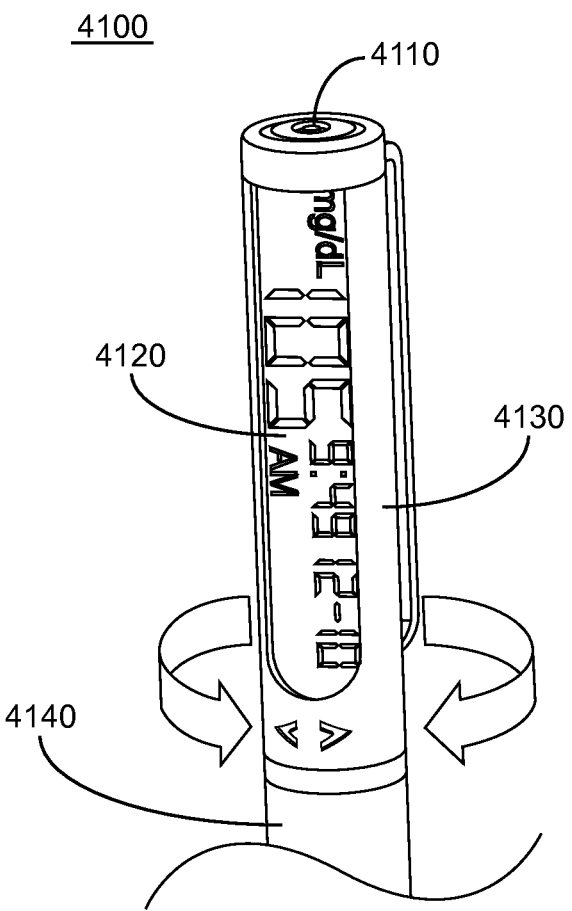

An embodiment of a health monitor device that includes a rotation-based user interface is shown in FIGS. 41A and 41B. FIG. 41A shows a perspective view of a health monitor device 4100 that includes a rotation-based user interface. The health monitor device 4100 includes a display 4120 that displays information to the user, such as analyte concentration, a date and a time. The health monitor device 4100 also includes a button 4110. In addition, the health monitor device 4100 includes a rotation-based user interface. As shown in FIGS. 41A and 41B, the health monitor device has an elongated cylindrical shape, similar to the shape of a pen. The rotation-based user interface may be used by rotating a first portion 4130 of the device relative to a second portion 4140 of the device. For example, the first portion 4130 may be rotated in a first direction or a second direction indicated by the arrows in FIG. 41B.

Voice Tagging

In some embodiments, the input unit includes a microphone. Such a microphone can be utilized in connection with a voice-tagging function of a health monitor device according to the present disclosure. For example, a health monitor device according to the present disclosure can be configured to include a digital voice recorder which receives input from the microphone and stores digital voice files, e.g., as MP3 or WAV files. These digital voice files can be correlated with particular analyte measurement events to provide additional information which can be later reviewed, e.g., by the end user or a health care professional. For example, a user of a health monitor device according to the present disclosure may choose to record a brief message regarding his/her state of health or food intake activity in proximity to (e.g., within a predetermined time period of) the time of a particular analyte measurement.

As discussed previously herein, in some embodiments, a health monitor device according to the present disclosure includes an optional display unit or a port for coupling an optional display unit to the health monitor device. The display unit is in communication with a control unit and/or processor and displays the analyte test strip signals and/or results determined from the analyte test strip signals including, for example, analyte concentration, rate of change of analyte concentration, and/or the exceeding of a threshold analyte concentration (indicating, for example, hypo- or hyperglycemia).

The display unit can be a dot-matrix display, e.g., a dot-matrix LCD display. In some embodiments, the display unit includes a liquid-crystal display (LCD), thin film transistor liquid crystal display (TFT-LCD), plasma display, light-emitting diode (LED) display, seven-segment display, E-ink (electronic paper) display or combination of two or more of the above. The display unit can be configured to provide, an alphanumeric display, a graphical display, a video display, an audio display, a vibratory output, or combinations thereof. The display can be a color display. In some embodiments, the display is a backlit display.

In certain embodiments, the display is an electronic paper display. In some cases, the electronic paper display is configured to have a high contrast ratio, which in some cases may facilitate an increase in legibility of the text, numbers, graphics, etc. displayed by the display. For example, the electronic paper display may have a contrast ratio of 5:1 or greater, such as 7:1 or greater, or 10:1 or greater, or 15:1 or greater, or 20:1 or greater. In certain instances, the display is a segmented display. By "segmented display" or "segment display" is meant a display that is divided into two or more areas with each area configured to be individually controlled. As such, different text, number, graphics, etc. may be displayed in each segment and may be refreshed and/or changed independently from the other segments of the display.

In certain instances, the display is flexible. For example, the display may be curved, such that one or more areas of the display are not co-planar with the other areas of the display. In some instances, a flexible display may facilitate an increase in impact resistance, such that the display can withstand impacts (such as being dropped, hit, etc.) without being significantly damaged. For example, a flexible display may be impact resistant, such that the display does not crack or chip from being dropped from a height of 3 feet or more, such as 4 feet or more, or 5 feet or more, or 6 feet or more, or 7 feet or more, or 8 feet or more, or 9 feet or more, or 10 feet or more. In some cases, the flexible display is a flexible electronic paper display.

The display unit can also be configured to provide, for example, information related to a patient's current analyte concentration as well as predictive analyte concentrations, such as trending information.

In some embodiments an input unit and a display unit are integrated into a single unit, for example, the display unit can be configured as a touch sensitive display, e.g., a touch-screen display, where the user may enter information or commands via the display area using, for example, the user's finger, a stylus or any other suitable implement, and where, the touch sensitive display is configured as the user interface in an icon driven environment, for example.

Alternative Displays and Communication Interfaces

In some embodiments, the display unit does not include a screen designed to display results visually. Instead of or in addition to a visual display as described above, in some embodiments the optional display unit of the health monitor device is configured to communicate results to the user through an alternative display or communication interface.

In some instances, the health monitor device is configured to communicate information audibly to a user of the health monitor device, e.g., via an integrated speaker, or via separate speakers through a headphone jack or BLUETOOTH® headset. For example, the health monitor device may be configured to communicate information audibly through a voice output. The voice output may be configured to provide an audible indication of information including, for example, analyte concentration, rate of change of analyte concentration, and/or the exceeding of a threshold analyte concentration (indicating, for example, hypo- or hyperglycemia). The voice output may be configured to communicate the information as spoken numbers and/or words. For instance, the voice output may audibly speak an analyte concentration to the user as a series of numbers and/or words. In certain instances, the health monitor device is configured to provide a voice output selection to the user, which may be configured to allow the user to select various aspects of the voice output, such as, but not limited to, volume of the voice output, gender of the spoken voice, language of the spoken voice, and the like.

In some embodiments, the health monitor device is configured to communicate information to a user audibly through the use of sound tones. For example, one or more sound tones may be used to communicate information (e.g., an analyte concentration) to the user. Sound tones may be used to communicate qualitative and/or quantitative information to the user. For instance, to communicate qualitative information, a low frequency sound tone may be used to indicate a low analyte concentration and a high frequency sound tone may be used to indicate a high analyte concentration. To communicate quantitative information, different sound tones may be used to communicate different numbers and/or letters to the user. Various aspects of the sound tones may be varied to distinguish different numbers and letters from each other, such as, but not limited to, the number of sound tones, the frequency or pitch of the sound tone, the length of the sound tone, the time between successive sound tones, combinations thereof, and the like. As an example, a three digit analyte concentration reading may be communicated to the user using sound tones as follows: the first digit (e.g., representing the hundred's position) may be communicated as a low frequency tone for zero or 1 to 5 high frequency tones representing the numbers 1 to 5; the second digit (e.g., representing the ten's position) may be communicated as 1 to 5 low frequency tones representing the numbers 0 to 4 or 1 to 5 high frequency tones representing the numbers 5 to 9; and the third digit (e.g., representing the one's position) may be communicated as 1 to 5 low frequency tones representing the numbers 0 to 4 or 1 to 5 high frequency tones representing the numbers 5 to 9. Other combinations of various sound tones may be used as desired.

In certain embodiments, the health monitor device is configured to communicate results visually, but through an alternative display or communication interface different from the display unit described above. For example, one or more lights may be used to communicate information (e.g., an analyte concentration) to the user. Lights may be used to communicate qualitative and/or quantitative information to the user. For instance, to communicate qualitative information, a light with a first color may be used to indicate a low analyte concentration, a light with a second color may be used to indicate a moderate analyte concentration and a light with a third color may be used to indicate a high analyte concentration. Alternatively, a light may illuminate once to indicate a low analyte concentration, the light may illuminate twice to indicate a moderate analyte concentration and the light may illuminate three times to indicate a high analyte concentration. To communicate quantitative information, different colors or sequences of lights may be used to communicate different numbers and/or letters to the user. Various aspects of the lights may be varied to distinguish different numbers and letters from each other, such as, but not limited to, the color of the lights, the number of lights, the frequency of illumination of the light, the length of the illumination, the time between successive illuminations of the light, combinations thereof, and the like. As an example, a three digit analyte concentration reading may be communicated to the user using two lights (e.g., a first light and a second light) as follows: the first digit (e.g., representing the hundred's position) may be communicated as 1 to 5 flashes of the first light representing the numbers 0, 100, 200, 300 or 400; the second digit (e.g., representing the ten's position) may be communicated as 1 to 5 flashes of the second light representing the numbers 0, 20, 40, 60 or 80. As another example, a three digit analyte concentration reading may be communicated to the user using three lights (e.g., a first light, a second light and a third light) as follows: the first digit (e.g., representing the hundred's position) may be communicated as 1 to 5 flashes of the first light representing the numbers 0, 100, 200, 300 or 400; the second digit (e.g., representing the ten's position) may be communicated as 1 to 5 flashes of the second light representing the numbers 0, 20, 40, 60 or 80; and the third digit (e.g., representing the one's and/or ten's position) may be communicated as 1 to 5 flashes of the third light representing the numbers 0, 5, 10, 15 or 20. Alternatively, different color lights may be used to represent different digits as described above. Other combinations of various lights may be used as desired.

Alternative display or communication interfaces herein may be used alone or in combination with each other or with a display unit as described above. For example, a health monitor device may be configured to include a display unit, a speaker (e.g., configured for audible communication) and one or more lights configured to communicate information visually. Embodiments of the health monitor device that include all three types of communication may be configured by the user as desired. In other embodiments, the health monitor device does not include a display unit as described above. For instance, the health monitor device may include a speaker (e.g., configured for audible communication) and one or more lights configured to communicate information visually, or only a speaker, or only one or more lights configured to communicate information visually. Embodiments of the health monitor device that do not include a display unit may facilitate production of a health monitor device suitable for use by a user with impaired vision. Health monitor devices that do not include a display unit may also facilitate production of a health monitor device with a small form factor, such as a health monitor device that is portable or that may be comfortably worn on a key chain, a wrist, etc.

Braille Display

In certain embodiments, the health monitor device includes a display unit adapted for use by a user with impaired vision. For example, the health monitor device may include a Braille display. The Braille display may be configured to communicate information to the user using one or more Braille cells that can each display a Braille character. For example, each Braille character, or Braille cell, may include six dot positions, arranged in a rectangle having two columns of three dots each. A dot may be raised at any of the six positions to form sixty-four ($2^6$) possible Braille characters, including the arrangement in which no dots are raised. Different letters, numbers and symbols may be represented by different combinations of raised and un-raised (e.g., flat) dots in each Braille cell. A Braille display may include one or more Braille cells arranged on a surface of the health monitor device. In certain instances, the Braille display includes an array of Braille cells arranged in one or more rows and one or more columns. In some cases, each Braille cell is configured to display any possible Braille character as desired. For instance, a Braille cell may display a first Braille character for a period of time, then display a second different Braille character for a period of time, and then display a third Braille character for a period of time, etc.

In certain embodiments, the Braille display may include an array of Braille elements, each corresponding to a dot in a Braille cell. The Braille elements may be configured to be in a raised position or in a lowered position. For instance, a Braille element in a raised position may be positioned such that the top of the Braille element is extended a distance above the surface of the Braille display. A Braille element is a raised position may be read by a user as a raised dot in a Braille character. A Braille element in a lowered position may be positioned such that the top of the Braille element is not extended above the surface of the Braille display, for instance the top of the Braille element in a lowered position may be substantially flush with the surface of the Braille display. In certain instances, a Braille element includes a ball, bead, bubble, notch, tip, etc. that may be raised and lowered as described above. The Braille display may also include one or more actuators (e.g., lever, solenoid, spring, valve, shape memory material, etc.) configured to raise and lower the Braille elements as described above. For example, each Braille element may have an actuator, such that each Braille element may be individually controlled. In some cases, the array of Braille elements may be attached to a Braille display panel, such as a printed circuit board (PCB). In some instances, the Braille display panel includes a processor configured to analyze data from the health monitor device, such as, but not limited to analyte concentration data, a date, a time, etc., and display the data to the user through the Braille display.

Figure 40A:
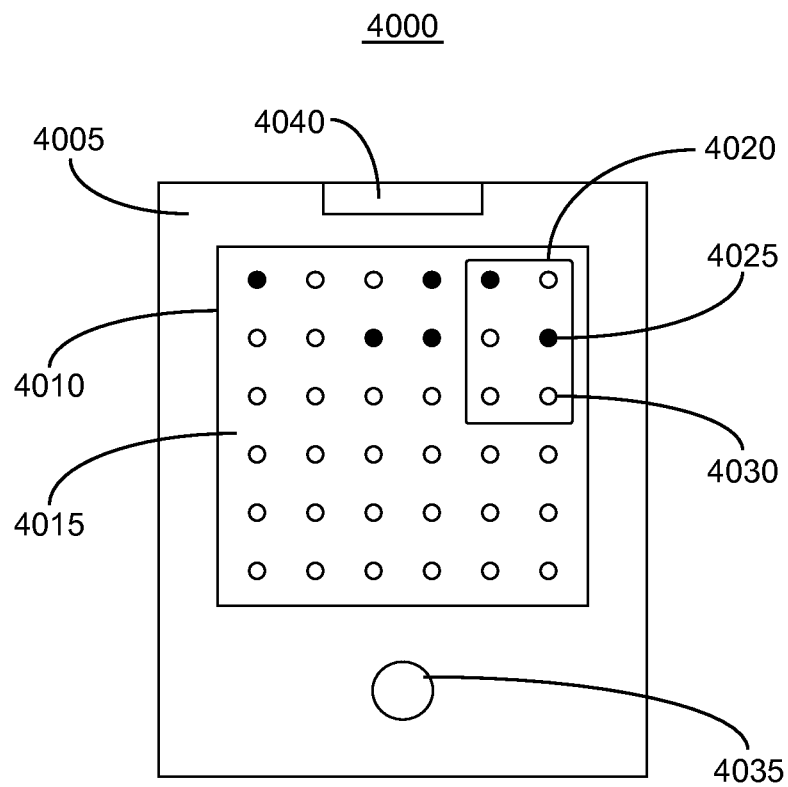
FIG. 40A shows a front view of a health monitor device configured with a Braille display.

FIG. 40A shows a front view of a health monitor device configured with a Braille display. The health monitor device 4000 includes a Braille display 4010 on a front surface 4005 of the health monitor device 4000. The health monitor device may also include a test strip port 4040 and a button 4035. The Braille display 4010 includes an array of Braille elements (e.g., Braille elements 4025 and 4030) arranged in one or more rows and one or more columns of Braille elements. For example, as shown in FIG. 40A, the Braille display 4010 includes an array of Braille elements arranged in 6 rows and 6 columns. The Braille elements are arranged into one or more Braille cells 4020 that can each display a Braille character. Each Braille cell 4020 includes six Braille elements, arranged in a rectangle having two columns of three Braille elements each. Each Braille element is configured to be in either a raised position or in a lowered position. For example, Braille element 4025 is in a raised position (represented as a shaded circle in FIG. 40A) and is positioned such that the top of the Braille element 4025 is extended a distance above the surface of the Braille display 4010. Raised Braille element 4025 may be read by a user as a raised dot in a Braille character. Braille element 4030 is in a lowered position (represented by the open circle in FIG. 40A) and is positioned such that the top of the Braille element 4030 is not extended above the surface of the Braille display 4010. For instance, the top of Braille element 4030 may be substantially flush with the surface of the Braille display. The pattern of raised and lowered Braille elements in each Braille cell may be read by a user as their corresponding letter, numbers, symbols, etc. For example, as shown in FIG. 40A, the top row of Braille cells on the Braille display may be read by a user as the numbers "105". In some instances, the numbers displayed on the Braille display correspond to an analyte concentration of the user, such as a glucose level of the user. The Braille display 4010 may have a flexible cover 4015. The flexible cover 4015 may be provided over the Braille elements. Raising and lowering the Braille elements may produce corresponding raised and lowered portions of the flexible cover 4015 that can be read by the user as Braille characters. The flexible cover 4015 may be a flexible membrane, such as a flexible membrane made of rubber, silicone, polyacrylate, polyester, polyurethane, polyisoprene, nitrile, and the like.

Figure 40B:
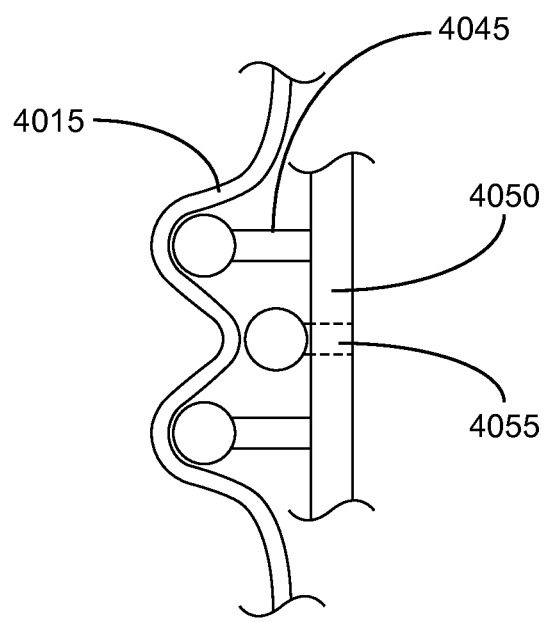
FIG. 40B shows a side view of a cross section of the Braille display according to embodiments of the present disclosure.

FIG. 40B shows a side view of a cross section of the Braille display. The Braille display includes a substrate 4050 with Braille elements (e.g., Braille elements 4045 and 4055) attached to the substrate 4050. The Braille elements are configured to be in either a raised position or a lowered position. For instance, Braille element 4045 is shown in a raised position, and Braille element 4055 is shown in a lowered position. In some cases, the substrate 4050 includes additional components configured to control the positions of the Braille elements. For example, the substrate 4050 may include a printed circuit board (PCB) that includes actuators configured to raise and lower the Braille elements, and a processor configured to control the positions of the Braille elements in the Braille display. As shown in FIG. 40B, the Braille display also includes a flexible cover 4015. As described above, the flexible cover 4015 may be provided over the Braille elements. Raising and lowering the Braille elements may produce corresponding raised and lowered portions of the flexible cover 4015 that can be read by the user as Braille characters.

Expanding Menu Item for Improved Readability

In some embodiments, the display unit includes a graphical user interface including a plurality of menu items, wherein the display unit is configured to provide clarification with respect to the meaning of a menu item based on a user's response speed with respect to a user input for the menu item. The menu item could take any of a variety of forms, e.g., text, icon, object or combination thereof.

In one embodiment, the graphical user interface includes a menu which in turn includes a plurality of selectable menu items. As a user navigates through the menu, e.g., by highlighting or scrolling through individual menu items, a menu item that is either unreadable or incomprehensible to the user could cause the user to pause over a menu item to be selected. In one embodiment, a choice can be presented to the user, e.g., using a dedicated physical button on an input unit, or a soft key on the menu, that offers further explanation of the item to be selected without actually selecting the item. For example, the graphical user interface can be configured such that after a pre-determined period of time a soft key offers an explanation of the menu item to be selected, e.g., by displaying a soft key with the word "MORE", "ADDITIONAL INFORMATION", "EXPAND", "MAGNIFY", "HELP" or a variation thereof displayed thereon.

The pre-determined period of time may be based on a fixed factory preset value, a value set by the user or a health care professional, or through an adaptive mechanism based on an analysis of the user's speed of navigation from past interactions with the graphical user interface. In one embodiment, the pre-determined period of time is from about 5 to about 20 seconds, e.g., from about 10 to about 15 seconds.

If the offer for clarification and/or additional information is selected, e.g., by pressing the softkey, then the menu item to be selected can be displayed in a "high emphasis" mode, e.g., where the item is displayed as if a magnifying lens is held on top of the selected item. In some embodiments, additional emphasis of the menu item to be selected can be provided, e.g., by making the menu item change color, blink, or increase in size to a pre-determined maximum limit.

Alternatively, or in addition to, displaying the menu item in a "high emphasis" mode, a more descriptive explanation of what the menu item is could be provided in response to the selection of the offer for clarification and/or additional information. In some embodiments, the more descriptive explanation may be provided in response to the user pressing the soft key a second or additional time. In one embodiment, a more descriptive explanation of the menu item is provided in the form of scrolling text. Alternatively, or in addition, a pop-up window may be displayed which provides a more detailed explanation and/or animation of the menu item's function.

In another embodiment, pausing on a menu item beyond a pre-determined period of time results in display of a soft key as discussed above. Selection of the soft key by the user results in an audible communication to the user of the menu item's identity, e.g., using a built-in speaker included in the health monitor device. Selection of the soft key a second time results in an audible communication to the user which includes a descriptive explanation of the menu item's function.

In another embodiment, rather than utilizing a dedicated hardware button or a soft key, the graphical user interface can be configured to automatically display a menu item in a "high emphasis" mode and/or display additional information regarding the menu item's function once a user has paused for a pre-determined period of time with respect to a particular menu item. In such embodiments, the health monitor device may include an optional hardware button or soft key which when depressed returns the display to a normal display mode from the "high emphasis" mode.

Modular Meter

In some embodiments, a health monitor device according to the present disclosure is configured as a modular meter or otherwise includes aspects of a modular meter or modular meter system. For example, a health monitor device according to the present disclosure may be configured to accept various hardware modules which may be removably attached to the health monitor device, wherein the various hardware modules are capable of providing various additional functionalities to the health monitor device once attached thereto. In some embodiments, the hardware modules include firmware configured to alter an existing functionality of the health monitor device and/or provide an additional functionality to the health monitor device. Additional disclosure of a modular health monitor device and associated hardware modules is provided in the U.S. Provisional Patent Application No. 61/325,155, filed Apr. 16, 2010, entitled "Modular Analyte Monitoring Device", the disclosure of which is incorporated by reference herein.

Support for On-Demand Analyte Determination Using an Analyte Sensor

In some embodiments, a health monitor device according to the present disclosure is further configured to receive analyte concentration data and/or signals indicative of an analyte concentration from an analyte sensor, e.g., an implanted or partially implanted analyte sensor or a radio-frequency (RF)-powered measurement circuit coupled to an implanted or partially implanted analyte sensor. In some embodiments, the analyte sensor is a self-powered analyte sensor. A health monitor device according to the present disclosure may include software configured to analyze signals received from the analyte sensor. Additional information related to self-powered analyte sensors and methods of communicating therewith are provided in U.S. Patent Application Publication No. 2010/0213057, published Aug. 26, 2010, entitled "Self-Powered Analyte Sensor", the disclosure of which is incorporated by reference herein.

Health Monitor Device Including Pedometer

In some embodiments, a health monitor device as described herein is configured to include an integrated pedometer. The health monitor device may be configured, for example, to physically engage and communicate electronically with a commercially available pedometer device. The pedometer device may be positioned completely within the health monitor device housing. Alternatively, the pedometer device may engage, e.g., via snap-fit engagement, to a portion of the health monitor device housing. The pedometer device may be an electromechanical activity monitor or may utilize global positioning system (GPS) technology. Where the health monitor device is a modular meter as described herein, the pedometer functionality may be provided by a pedometer module configured to engage a base meter.

As an alternative to a physically integrated pedometer, the health monitor device may be configured to communicate with, e.g., via wired or wireless technology, and receive data from an external pedometer device which is not physically integrated with the health monitor device.

Where the health monitor device is physically integrated with or otherwise configured to communicate with a pedometer device, the health monitor device may include software and/or firmware designed to receive, store, analyze, display and/or communicate data received from the pedometer device. In some embodiments, such software and/or firmware may be stored on a pedometer module and configured to be run by a health monitor device control unit or processor in communication with the pedometer module.

Software and/or firmware which may be utilized include software and/or firmware designed to measure and/or display daily activity information for a user of the health monitor device, e.g., miles walked, stairs climbed, etc. Additional software features may include intensity of activity measurement (e.g., corresponding to the rate of user activity); daily, weekly and/or monthly activity targets which may be set by the user or a health care professional; display of current and/or previous activity level with respect to a targeted activity level; historical log of daily activity level (e.g., including trending information); integration with a health management system as described herein; and/or automatic logging of exercise data.

Health Monitor Device with Selectively Activatable Features

Certain features and/or functionalities of a health monitor device may require or benefit from user-training prior to operation or use, e.g., a bolus dosage calculation function. For such features and/or functionalities, it may be desirable to initially provide the health monitor device with these features and/or functionalities in a disabled, but selectively activatable state. The features and/or functionalities may be activated by a user and/or a health care professional. For example, once user-training is verified, e.g., by a health care professional, the features and/or functionalities may be activated. In other words, a health monitor device may be provided with certain features and/or functionalities disabled "out of the box."

In some embodiments, a user interface, e.g., a touchscreen display and/or input unit of the health monitor device provides a mechanism for entry of an activation code, which when entered, enables or "unlocks" one or more of the disabled features and/or functionalities. The activation code may be provided, for example, by a physician via a prescription. A unique activation code may be provided which corresponds to a serial number for a particular health monitor device. In some cases, a single activation code may be provided which is capable of activating features and/or functionalities of multiple health monitor devices. A manufacturer of the health monitor device may provide a service to accept and confirm a prescription of a physician and provide the activation code to a user of the health monitor device.

The activation code may be transmitted and entered into the health monitor device in a number of ways. For example, a manufacturer or a manufacturer's representative may provide the code explicitly, e.g., via telephone or e-mail, to a user who then enters the code into the health monitor device using an input unit of the health monitor device. Tithe activation code may be communicated and entered into the device from a remote location, e.g., using a communication interface of the health monitor device. This may occur, for example, when the health monitor device is in communication with a wireless data network.

In some embodiments, following entry of an activation code, the health monitor device displays available features and/or functionalities in a set-up menu from which a user of the health monitor device can then select particular features and/or functionalities to enable. In some embodiments, this set-up menu can also be utilized by the user to disable particular features and/or functionalities.

The activation of particular features and/or functionalities may also be provided for based on payment of a fee or a paid subscription service. For example, a health monitor device may be provided with a variety of features and/or functionalities disabled, which features and/or functionalities may be enabled upon entry of an activation code, which activation code is provided based on payment an activation or subscription fee.

In certain embodiments, the health monitor device includes a medication dosage calculator in a disabled, but selectively activatable state, as described above. For example, the health monitor device may include an insulin calculator in a disabled, but selectively activatable state. The medication dosage calculator may be activated by a user and/or a health care professional by inputting an activation code into the health monitor device. In some cases, the activation code is an alphanumeric activation code.

Health Monitor Device Incorporated into Protective Skin or Case

In some embodiments, the present disclosure provides a health monitor device, which is incorporated into a protective "skin" or case designed to fit a portable electronic processing device, e.g., a PDA, smart phone, etc. Such devices include for example, BLACKBERRY®, IPHONE®, IPOD®, and ITOUCH® devices as well as a wide variety of other portable electronic processing devices known in the art. Where the protective "skin" or case is designed to fit a portable electronic processing device, the health monitor device itself does not need to physically engage the housing of the portable electronic processing device. Instead, the health monitor device may be positioned in the protective "skin" or case such that when the protective "skin" or case is fit to the portable electronic processing device a convenient portable integrated device combination is provided. In addition, the protective "skin" or case may provide structural support for the integrated device combination.

As used herein the term "skin" refers to a flexible material, e.g., a flexible polymer material, configured to cover at least a portion of a portable electronic processing device. In some embodiments, a skin is sized and shaped to fit one or more external dimensions of a portable electronic processing device, while providing access to one or more features of the portable electronic processing device, e.g., one or more input units, displays, speakers, microphones, headphone jacks, cameras, communication ports, etc. For example, a skin may be configured to cover greater than 40%, e.g., greater than 50%, greater than 60%, greater than 70%, greater than 80% or greater than 90% of the exposed surface of a portable electronic device.

As used herein with reference to a portable electronic processing device, use of the term "case" as opposed to the term skin refers to a relatively rigid covering for a portable electronic processing device. As with the skin, in some embodiments, a case is sized and shaped to fit one or more external dimensions of a portable electronic processing device, while providing access to one or more features of the portable electronic processing device, e.g., one or more input units, displays, speakers, microphones, headphone jacks, cameras, communication ports, etc. For example, a case may be configured to cover greater than 40%, e.g., greater than 50%, greater than 60%, greater than 70%, greater than 80% or greater than 90% of the exposed surface of a portable electronic device.

The health monitor device may be configured as one or more of a discrete analyte measurement device (e.g., a glucose meter configured to receive a glucose test strip), a component of an analyte measurement system including an implanted or partially implanted analyte sensor (e.g., a component of a continuous glucose measurement system), a component of an on-demand analyte measurement system and a component of a medication delivery system (e.g., an insulin delivery system including an insulin pump).

The health monitor device which is incorporated into the protective skin or case is configured for one or two-way communication with a processor and/or control unit of the portable electronic processing device. The communication may be wired or wireless, e.g., using one or more of the wireless communication protocols described herein.

In specific embodiments, communication between processor and/or control unit of the portable electronic processing device and the health monitor device is accomplished using a "wired" connection between a communication interface of the health monitor device and a hard-wired communication port positioned on the portable electronic processing device (e.g., a USB port or a proprietary serial interface such as that found in the IPHONE®). For example, the communication interface of the health monitor device may include a male USB connector while the portable electronic processing device includes a corresponding female USB connector. Connection of the two connectors provides a physical and electrical connection between the health monitor device and the portable electronic processing device.

In some embodiments, where the health monitor device is configured as a discrete analyte measurement device, it may include a test strip port, e.g., a test strip port as described herein. In such embodiments, the discrete analyte measurement device may or may not include a display unit which is separated from a display unit of the portable electronic processing device. Where the discrete analyte measurement device does not include a separate display unit, analyte measurement results obtained using the discrete analyte measurement device may be displayed on the display unit of the portable electronic processing device.

In some embodiments, where the health monitor device is configured as a component of an analyte measurement system including an implanted or partially implanted analyte sensor (e.g., a continuous analyte sensor), the health monitor device in combination with the portable electronic processing device coupled thereto provide a portable hand-held component of the measurement system. In such embodiments, the health monitor device may be configured to include a communication interface which provides for wireless, e.g., RF, communication with an on-body portion of the analyte measurement system, e.g., an implanted or partially implanted analyte sensor or an RF-powered measurement circuit coupled to an implanted or partially implanted analyte sensor.

In some embodiments, where the health monitor device is configured as a component of an on-demand analyte measurement system, the health monitor device in combination with the portable electronic processing device coupled thereto provide a portable hand-held component of the measurement system. In such embodiments, the health monitor device may be configured to include a communication interface which provides for wireless, e.g., RF, communication with an on-body portion of the on-demand analyte measurement system when the portable hand-held component is positioned in proximity to the on-body portion of the on-demand analyte measurement system. In this manner, periodic or intermittent analyte readings may be obtained and communicated to a user. In some embodiments, a button or other input device on the health monitor device may be utilized by a user to initiate the on-demand acquisition of measurement data. Alternatively, the acquisition of measurement data may be initiated using a user interface of the portable electronic processing device.

In some embodiments, where the health monitor device is configured as a component of a medication delivery system, e.g., an insulin delivery system, the health monitor device in combination with the portable electronic processing device coupled thereto provide a portable hand-held component of the medication delivery system. In such embodiments, the health monitor device may be configured to include a communication interface which provides for wireless, e.g., RF, communication with a medication delivery device, e.g., an insulin pump.

In some embodiments, the health monitor device is configured to be powered by a portable electronic processing device to which the health monitor device is coupled, e.g. via a USB connection. Alternatively, or in addition, the health monitor device may include a separate power source, e.g., a disposable or rechargeable battery. Additional information related to the powering of a health monitor device coupled to a portable electronic processing device is provided in U.S. Pat. No. 7,041,468, the disclosure of which is incorporated by reference herein.

The health monitor device may include a memory for storing one or more software applications designed to be uploaded and/or run by a processor or controller unit of a portable electronic processing device to which the health monitor device is coupled.

Health Monitor Device-Associated Software and/or Firmware

The health monitor device disclosed herein may include software and/or firmware configured to be executed by an internal and/or external processing unit. In some embodiments, a health monitor device is configured such that one or more programs are launched automatically, e.g., utilizing a plug and play standard, when the health monitor device is connected to an external processing device, e.g., a computer. The one or more programs may be configured to run on a variety of common hardware platforms (e.g., PC, MAC) and operating systems (e.g., Windows, MAC OS, Linux). The one or more programs may be stored in the health monitor device, e.g., within a machine-readable storage medium (e.g., flash memory or other non-volatile memory) and executed by one or more general-purpose or special-purpose programmable microprocessors and/or microcontrollers. Alternatively, one or more programs may be stored in one or more removable hardware modules as discussed above. Examples of functions which may be implemented by software and/or firmware include, but are not limited to those discussed below and elsewhere herein.

In certain embodiments, the health monitor device-associated software and/or firmware includes programming, such as instructions or routines, which when executed by a processor of a health monitor device, cause the processor to perform various functions associated with determining a patient's medication dosage regimen. In some cases, the health monitor device-associated software and/or firmware includes programming configured to assist a patient in titrating a current dose level of a medication over time until a target threshold range is achieved. For example, the programming may be configured to facilitate the determination of an adjusted dose level for a medication, such as long-acting insulin, as described herein.

To facilitate the determination of an adjusted dose level for a medication, the health monitor device-associated programming may display instructions to a patient, including guided prompts, to assist the patient in gathering the necessary information for determining the adjusted dose level. For instance, to determine an adjusted dose level for long-acting insulin based on fasting blood glucose levels, the programming may direct the patient through a series of actions, including, but not limited to, fasting and blood glucose tests. Based on the data detected and stored, the programming may be configured to determine the adjusted dose level for long-acting insulin, as described above. In certain instances, the programming may direct the patient through additional actions, including, but not limited to, re-testing, insulin injections and food intake. Based on the data detected and stored, the health monitor device may determine additional parameters related to the patient's medication dosage regimen, such as the patient's fasting blood glucose level, an average of the patient's recent fasting blood glucose levels, further adjustments to the dose level for long-acting insulin, and the like.

The programming may direct the patient through a series of actions by displaying guided prompts to the patient through the display unit of the health monitor device. In some cases, the guided prompts include instructions directing the patient to perform an action. The guided prompts may include instructions in one or more forms, such as text, audio, image, video, animation, combinations thereof and the like. In certain instances, the guided prompts are associated with an alert, such as an alarm or reminder. As described herein, the guided prompts and associated alerts can be associated with one or more active scheduling algorithms. For example, to assist a patient in titrating their long-acting insulin dose level, the active scheduling algorithm can provide the patient a recommended time and/or date for detecting a fasting blood glucose sample (e.g., by displaying such information on a display unit of the health monitor device). The active scheduling algorithm may remind the patient to measure a fasting blood glucose sample based on the time of day, the number of previously measured fasting blood glucose samples, the number of fasting blood glucose samples used to determine an adjusted dose level for long-acting insulin, and the like.

As data is collected from the patient through the use of the guided prompts, as described above, the data may be stored in a memory of the health monitor device. The programming may also be configured to retrieve the stored data and determine various settings on the health monitor device based on the stored data. For example, the health monitor device may recommend settings for the determination of an insulin dose level, such as a target fasting blood glucose range, a dose adjustment amount to the insulin dose level, and the like. These settings can be confirmed by the patient or by a health care professional. In addition, the settings recommended by the health monitor device may be customized to meet the needs of the individual patient. For example, the settings on the health monitor device may be modified by the patient or by a health care professional.

Creating an Event Log

Various events (e.g., measurement readings, carbohydrate intake, insulin dosage and times, exercise records, meal-time records, note records, medication-time records, etc.) may be recorded along with date/time tags. Events may be recorded automatically by the health monitor device (e.g., upon measurement reading). Input elements on the health monitor device may also be used by a user to input event data and/or non-event data.

In some embodiments, entry of carbohydrate intake data may be facilitated by providing for the utilization of bar code scanner technology in combination with a database which links product bar codes to carbohydrate information for the product. For example, a health monitor device such as a health monitor device as described herein may include an integrated bar code reader. In addition, the health monitor device may be configured to include, e.g., in a data storage unit, a database which links a product's bar code to its nutritional content (e.g., its carbohydrate content and/or calorie content). Alternatively, such a database could be stored on a remote device and/or system which may be accessed by the health monitor device, e.g., using a communication interface as described herein. In this manner, when a user scans a bar code associated with a food item he or she intends to consume, the nutritional information (e.g., carbohydrate content), can be automatically entered into an event log and/or database for later analysis.

In another embodiment, where a bar code and/or corresponding nutritional information are not available, a user may utilize digital camera technology, e.g., a digital camera incorporated into a health monitor device to capture a digital image of a food item to be consumed. Such digital images may then be compared to images of food items having a known nutritional content, e.g., using image recognition technology. Alternatively, or in addition, such digital images may be utilized, e.g., by a health care professional, in connection with user training designed to assist the user in assessing the carbohydrate content of a food item.

In some embodiments, a health monitor device as described herein and/or a health management software application as described herein may be configured to enable a user to "tag" or link one or more bar code readings or digital images with additional information entered by the user, e.g. information related to a subsequent analyte measurement or measurements.

Visually Representing Data

Collected and/or analyzed data may be represented visually to the user (e.g., on a display unit of the health monitor device and/or a remote device). For example, data from the event log may be presented in various formats and/or further manipulated and presented. Data may be used to generate graphs and reports that help a user such as a diabetic to track glucose and other related information. The test data may be graphed in many ways according to various default or pre-programmed graphs or according to filtering and preferences inputs from a user. The graphs may be generated and displayed on the health monitor device and/or a remote device, e.g., a remote device configured to communicate with the health monitor device.

Remote devices configured to communicate with a health monitor device as disclosed herein may be configured for printing the graphs and/or reports. The remote devices may also be configured to receive data from a storage unit of the health monitor device and enter such data into a database located on the remote device. A remote device could also be utilized for backing-up data and for downloading applications programs to the health monitor device and for communicating with other computers over one or more networks, e.g., for viewing of data by a user, a patient, a physician, and/or a third party.

Trend Calculation

Data from the event log may also be used to perform trending calculations. For example, a health monitor device according to the present disclosure may be capable of displaying a graph of the analyte level over a period of time. Examples of other graphs that may be useful include graphs of the rate of change or acceleration in the rate of change of the analyte level over time (i.e., trending data). Trending data may be used by other applications, e.g., in bolus calculations and/or alerts.

Trending data may also be presented via a display unit on the health monitor device. The display unit may contain symbols, e.g., directional arrows, or other indicators that are activated under certain conditions (e.g., a particular symbol may become visible on the display when a condition, such as hyperglycemia, is indicated by signals from the sensor). Other indicators may be activated in the cases of hypoglycemia, impending hyperglycemia, impending hypoglycemia, etc.

Additional information regarding the use of logs and trending functionalities can be found within U.S. Pat. Nos. 7,041,468, and 6,175,752, disclosures of which are incorporated herein by reference.

In certain embodiments, a health monitor device may be configured to calculate a trend in an analyte level over a period of time. In some cases, the analyte is glucose. In certain instances, the trend is determined from two or more measurements of the analyte level. The two or more measurements of the analyte level may be made over a period of time, such as two or more measurements spaced 5 min apart, or 10 min apart, including 15 min apart, or 20 min apart, for instance, 30 min apart, or 45 min apart, or 60 min apart, or 90 min apart. In some cases, the health monitor device is configured to calculate a trend in an analyte level (e.g., glucose) from two or more analyte level measurements taken 15 minutes apart. Calculation of a trend in an analyte level from analyte level measurements taken 15 min apart may facilitate an optimization in the reliability of the trend. For example, the following table illustrates a rate error grid analysis (R-EGA) of a trend calculated from pairs of glucose measurements using a laboratory-grade glucose analyzer (YSI Life Sciences, Yellow Springs, Ohio). Further information regarding error grid analysis (e.g., the Clarke Error Grid Analysis) is found in Clarke, W. L. et al. "Evaluating Clinical Accuracy of Systems for Self-Monitoring of Blood Glucose" *Diabetes Care*, vol. 10, no. 5, 1987: 622-628.

R-EGA of Trend Calculated from Pairs of Glucose Measurements

|  | % ± 95% confidence interval (C.I.) | | | | |
| --- | --- | --- | --- | --- | --- |
|  | Ar + Br | Ar | Cr | Dr | Er |
| Trend from measurements spaced 15 min apart | 99.0 ± 0.2 | 93.9 ± 0.6 | 0.5 ± 0.1 | 0.4 ± 0.1 | 0.1 ± 0.0 |
| Trend from measurements spaced 30 min apart | 95.0 ± 0.5 | 81.5 ± 1.3 | 1.6 ± 0.2 | 2.2 ± 0.2 | 1.2 ± 0.2 |
| Trend from measurements spaced 45 min apart | 91.8 ± 0.8 | 75.2 ± 1.6 | 2.3 ± 0.3 | 3.8 ± 0.4 | 2.0 ± 0.3 |
| Trend from measurements spaced 60 min apart | 89.9 ± 1.0 | 71.5 ± 1.8 | 2.4 ± 0.3 | 4.7 ± 0.5 | 2.9 ± 0.4 |

Thus, as shown in the table above, a straight line trend calculated from measurements spaced 15 min apart may provide a high correlation to a true glucose trend. In some cases, the accuracy of the glucose trend may depend on two error factors: (1) the correlation between the time spacing and the true trend, where a longer time spacing tend to result in lower correlation; and (2) the measurement error-induced trend error, where a shorter time spacing tends to result in a larger error. In some cases, the first error factor above may be assumed to be patient-independent. In these cases, the optimal time spacing between successive analyte measurements that would minimize the error due to the second error factor above may be calculated based on the analyte level data obtained from the user of the health monitor device. In certain instances, the user's measurement precision may be determined based on previous analyte level measurements from the user and an estimated mean and standard deviation based on population data.

In certain embodiments, for the first error factor above, a priori population data using laboratory glucose measurements may be used to determine what the mean and standard deviation of calculated trend error is in relation to time spacing. For example, given a range of time spacing, T, between successive blood glucose measurements (using an ideal reference glucose measurement device), an estimated mean and standard deviation for the ideal glucose trend error $e_{idealTrend}$ may be calculated. This relationship may be fitted into functions $f_\mu$ and $f_\sigma$:

$$\mu(e_{idealTrend}):=f_\mu(T)$$

$$\sigma(e_{idealTrend}):=f_\sigma(T)$$

In some cases, a binned range of time spacing, T, values and the corresponding mean and standard deviations of ideal glucose trend error may be calculated and stored in a table in a memory of the health monitor device.

In certain embodiments, for the second error factor above, a priori population data using a health monitor device may be used to estimate baseline values for the mean and standard deviations of measurement error-induced trend error $e_{measTrend}$. For example, the mean and standard deviation of measurement error, $\mu(e_{meas})$ and $\sigma(e_{meas})$, may be used to determine the mean and standard deviation of the glucose trend error:

$$v = \frac{g_1 - g_2}{T} = \frac{[g_{1n} + e_1] - [g_{2n} + e_2]}{T} = \frac{g_{1n} - g_{2n}}{T} + \frac{e_1 - e_2}{T} = v_n + e_{measTrend}$$

Where $v_n$ is the measurement error-free glucose trend calculated from two nominal glucose levels $g_{1n}$ and $g_{2n}$ (unknown) from actual glucose measurements $g_1$ and $g_2$. T is assumed to be an error-free measurement on the time interval between the two glucose level measurements. The glucose level measurement in terms $e_1$ and $e_2$ are error distributions with mean $\mu(e_{meas})$ and standard deviation $\sigma(e_{meas})$. The resulting trend error due to glucose measurement term, $e_{measTrend}$ whose mean is equal to $$\frac{2\mu(e_{meas})}{T},$$

and has a standard deviation of $$\frac{\sqrt{2}\,\sigma(e_{meas})}{T}.$$

In some cases, the measurement error-free glucose trend, $v_n$, may still incur ideal trend measurement error, $e_{idealTrend}$, due to the first error factor above. The calculated glucose trend is then represented by the formula:

$$v = v_n + e_{measTrend} = v_{true} + e_{idealTrend} + e_{measTrend}$$

Where:

$$e_{idealTrend} \sim \aleph(f_\mu(T), [f_\sigma(T)]^2)$$

$$e_{idealTrend} \sim \aleph\left(\frac{2\mu(e_{meas})}{T}, \left[\frac{\sqrt{2}\,\sigma(e_{meas})}{T}\right]^2\right)$$

Given fixed ideal trend correlation error parameters $f_\mu$ and $f_\sigma$ (which depend on the time spacing, T, and glucose measurement error parameters $\mu(e_{meas})$ and $\sigma(e_{meas})$ (which also depend on the time spacing, T, and other user-dependent factors), the optimal time spacing, T, in one that minimizes the sum of these two sources of error. When error from the two factors are combined, the glucose trend calculation becomes:

$$v = v_{true} + e_{Trend}$$

Where:

$$e_{Trend} \sim \aleph\left(f_\mu(T) + \frac{2\mu(e_{meas})}{T}, \sqrt{[f_\sigma(T)]^2 + \left[\frac{\sqrt{2}\,\sigma(e_{meas})}{T}\right]^2}\right)$$

In some instances, a true rate distribution is relatively symmetric. In these cases, the composite mean of the trend error, $e_{trend}$, may be assumed to be zero. Thus, only the scatter (parameterized as standard deviation) may be considered. The optimal time spacing, T, for each user varies depending on the relative effect of the user's glucose measurement error consistency, $f_\sigma(T)$, and the effect of time spacing on the true trend correlation, $$\frac{\sqrt{2}\,\sigma(e_{meas})}{T}.$$

Since $\sigma(e_{meas})$ may be user dependent (e.g., some users may perform glucose measurements better than others) and time varying (e.g., a user's method may improve over time or momentarily worsen due to certain conditions), the initial population value-derived may increase over time by observing blood glucose measurements taken close in time to each other.

In certain embodiments of the determination of $\sigma(e_{meas})$, true glucose values spaced within a certain window of time, $T_{corr}$, are correlated and may fit a straight line with minimal error. For example, in one embodiment, $T_{corr}$ may have a value ranging from 0 to 10 minutes. The window of time may be divided into two smaller windows, $T_{corrShort}$ and $T_{corrLong}$, where if repeated glucose measurements are available within a time interval up to $T_{corrShort}$ (e.g., 3 minutes), the true glucose level is assumed to be substantially unchanged, and a straight line with a zero slope over time may be assumed. If repeated glucose measurements are available within a time interval larger than $T_{corrShort}$ but up to $T_{corrLong}$, the true glucose level may be assumed to fit a straight line with an arbitrary slope over time. The glucose measurements may be fitted to a straight line that optimizes fit, either under a zero slope or arbitrary slope assumption, depending on the range of the available glucose measurements over time. An example of a straight line fit optimization is the Least-Squares Error fit criteria. The residual between each glucose measurement in the window of time and the resulting straight line fit may be collected to obtain a revised value for $\sigma(e_{meas})$. The updated $\sigma(e_{meas})$ value may result in an updated optimal time spacing T between two glucose measurements to obtain a glucose trend for that user. As a safety measure, the optimal time spacing T may be bounded below and above by predetermined limits $T_{inf}$ and $T_{sup}$. In certain embodiments, $T_{inf}$ is 7 minutes, and $T_{sup}$ is 35 minutes.

In certain embodiments, the health monitor device includes an alarm configured to alert the user when it is time to take the second glucose measurement. The optimal time to take the second glucose measurement may be determined as discussed above to minimize the error in the calculated glucose trend. Once the second measurement has been taken, the glucose trend may be calculated as described above and displayed to the user.

Alerts, Alarms and/or Reminders

An alert may be activated by the health monitor device and conveyed to the user, e.g., via the display unit. An alarm may be activated if an analyte test strip, for example, indicates a value that is beyond a measurement range of the analyte test strip. An alarm system may also, or alternatively, be activated when the rate of change or acceleration of the rate of change in analyte level increase or decrease reaches or exceeds a threshold rate or acceleration, e.g., to indicate a hyperglycemic or hypoglycemic condition is likely to occur.

An alarm system may be configured to activate when a single data point meets or exceeds a particular threshold value. Alternatively, the alarm may be activated only when a predetermined number of data points spanning a predetermined amount of time meet or exceed the threshold value. As another alternative, the alarm may be activated only when the data points spanning a predetermined amount of time have an average value which meets or exceeds the threshold value.

The alarm system may contain one or more individual alarms. Each of the alarms may be individually activated to indicate one or more conditions of the analyte. The alarms may be, for example, auditory or visual. Other sensory-stimulating alarm systems may be used including alarm systems which heat, cool, vibrate, or produce a mild electrical shock when activated.

Dynamic Scheduling of Therapy Reminders

The present disclosure provides software and/or firmware configured to perform one or more active scheduling algorithms. An active scheduling algorithm can provide a user of the health monitor device a recommended time and/or date for a subsequent therapy administration (e.g., by displaying such information on a display unit of the health monitor device), wherein the recommended time and/or date is determined based on a retrospective analysis of previously administered therapies as compared to a recommended therapy sequence and/or profile. As used herein, the term "therapy" includes analyte measurement as well as the administration of a medication.

The therapy reminders can be determined and configured by a qualified health care professional, such as a physician, clinical specialist or nurse. A health monitor device can then be configured with an appropriate scheduling algorithm directly by the health care professional using an optional input unit incorporated into the health monitor device, via a data management system that interfaces with the health monitor device, and/or via another portable device configured to communicate with the health monitor device. In this manner, a health care professional can update therapy recommendations electronically and communicate the therapy recommendations to an end user.

In one embodiment, a suitable scheduling algorithm provides a reminder to the user based on an analysis of the history of analyte measurements, e.g., blood glucose measurements, made by the user and compared to scheduled analyte measurements yet to be completed. The scheduling algorithm updates the reminder during the course of the day, such that the user is presented with the next scheduled time conforming to the scheduling profile. The dynamic scheduling can continue over multiple days until the user has completed all measurements conforming to the schedule. After the therapies are completed according to the recommended schedule, the scheduling algorithm can be configured to reset and start again, or alternatively a different scheduling algorithm may be activated.

The scheduling algorithm can be configured to provide feedback to the user at any time during the scheduled therapy administration period. For example, the scheduling algorithm can be configured to provide the user with an indication of how much of the schedule has been completed, and/or how many recorded measurement times did not conform to the recommended measurement time profile.

A non-limiting example of a dynamic scheduling procedure according to the present disclosure is as follows: (A) The measurement profile is defined to include the recording of 7 analyte readings before and after lunch, with 30 minute separation, starting at 1 hour prior to lunch (11:00 am). The recommended times are 11:00 am, 11:30 am, 12:00 pm, 12:30 pm, 1:00 pm, 1:30 pm, and 2:00 pm. (B) If the user's first analyte measurement is at 12:00 pm, the algorithm would recommend that the next measurement be performed at 12:30 pm. (C) If the user does not perform an analyte measurement at 12:30 pm, the algorithm would suggest 1:00 pm, and so on. (D) If the user does perform an analyte measurement later in the day, e.g., 8:00 pm, this measurement is not considered as advancing the completion of the measurement profile. (E) If the user on the second day performs an analyte measurement at 12:00 pm, this measurement is also not considered as advancing the completion of the measurement profile, as it was already completed on the previous day. (F) If the user on the second day then samples at 1:00 pm, this measurement is considered to advance the completion of the measurement profile. Based on the above, the health monitor device would display a summary report that 29% (2/7) of the therapy reminders have been completed, and that 2 of the 4 readings did not conform to the scheduled reminders. (G) In addition, the health monitor device would report the outstanding measurement times, e.g., 11:00 am, 11:30 am, 12:30 pm, 1:30 pm and 2:00 pm.

Control of a Drug Administration System

A health monitor device according to the present disclosure may be configured to control a drug administration system based on, for example, measurement readings. The health monitor device may provide (or communicate with a remote device to provide) a drug to counteract the high or low level of the analyte in response to a measurement reading and/or continuous measurement reading (e.g., with an implanted or partially implanted sensor). In one embodiment, the drug administration system includes an insulin pump. See, e.g., FIG. 20.

Implement an Application Programming Interface

A health monitor device according to the present disclosure may be configured to implement an Application Programming Interface (API) to enable interaction with other devices and/or software, e.g., medication delivery pumps.

Displaying Alerts from a Medication Delivery Device

Aspects of the present disclosure include a health monitor device configured to communicate with a medication delivery device, such as an insulin delivery device. Such insulin delivery devices include insulin injectors that inject discrete boluses of insulin and insulin pumps that maintain a basal infusion of insulin and also may infuse boluses of insulin as desired. Insulin delivery devices may be commercially available from a variety of manufacturers, such as Novo Nordisk, Sanofi-Aventis, Eli Lilly and Co., Medtronic, Inc., Roche, Inc., Insulet Corp., Animas Corp., Soil Development Co., and the like.

In accordance with the various embodiments of the present disclosure, provided are health monitor devices that include a communication module coupled to a controller unit, the communication module configured to communicate with and receive alert data from a remote location. In certain cases, the controller unit is configured to output the received alert data through an output unit. Also disclosed are methods of using the health monitor devices for receiving alert data from a remote location, and outputting the received alert data through an output unit.

Aspects of the present disclosure include a health monitor device that includes a communication module coupled to a controller unit. Referring to FIGS. 1 and 2, the communication module or interface 220 in one embodiment of the present disclosure includes a wired communication module. In certain embodiments, the communication module 220 is also configured to include physical ports or interfaces for wired communication, such as a USB port, an RS-232 port, a FIREWIRE® port, or any other suitable electrical connection port to allow data communication between the health monitor device with a medication dose calculation function 100 and other external devices such as a computer terminal (for example, at a physician's office or in hospital environment), an external medical device, such as an infusion device, including an insulin delivery device, or other devices that are configured for similar complementary data communication. In some instances, the communication module 220 is configured to include a wireless communication module configured for bi-directional (e.g., 2-way) communication with other devices to transmit and/or receive data to and from the health monitor device 100. By bi-directional is meant that the communication module 220 is configured to send data to a remote location and configured to receive data from a remote location. In certain embodiments, the wireless communication module can be configured for wireless communication, including, but not limited to, radio frequency (RF) communication (e.g., Radio-Frequency Identification (RFID), ZIGBEE® communication protocols, WIFI®, infrared, wireless Universal Serial Bus (USB), Ultra Wide Band (UWB), BLUETOOTH® communication protocols, and cellular communication, such as code division multiple access (CDMA) or Global System for Mobile communications (GSM).

In certain embodiments, the communication module of the health monitor device is configured to transmit data to and/or receive data from a remote location. The remote location may include, but is not limited to, a medication delivery device, a personal computer, laptop, PDA, cellular phone, smartphone, set-top box, etc. In certain embodiments, the remote location is a medication delivery device. The medication delivery device may include an insulin delivery device, such as, but not limited to an insulin injector (e.g., an insulin pen), an insulin infusion pump, and the like. In some instances, the medication delivery device is configured to deliver a drug (e.g., insulin) to a patient (e.g., a patient with diabetes) based on the analyte (e.g., glucose) level measured by the health monitor device. The medication delivery device may be configured to administer a dose of medication, such as insulin, into a patient based on a prescribed medication dosage, and may be automatically updated with medication dosage information and/or determined analyte concentration received from the analyte monitoring device. In some aspects, the medication dosage of the medication delivery device may include manual entry of dosage changes input into the health monitor device by a user or health care professional. Medication dosage information associated with the medication delivery device may be displayed on a display unit disposed on the health monitor device.

Additional information regarding medication delivery devices or systems, such as, for example, integrated systems, are provided, for example, in U.S. Pat. No. 6,175,752; U.S. Patent Application Publication No. 2006/0224141, published on Oct. 5, 2006, titled "Method and System for Providing Integrated Medication Infusion and Analyte Monitoring System;" and U.S. Patent Application Publication No. 2004/0254434, published on Dec. 16, 2004, titled "Glucose Measuring Module and Insulin Pump Combination," the disclosures of each of which are hereby incorporated by reference in their entirety.

In certain embodiments, the communication module of the health monitor device is configured to receive alert data from a remote location. For instance, the communication module may be configured to receive alert data from a medication delivery device, such as, but not limited to an insulin delivery device. The medication delivery device may be configured to continuously or periodically monitor various aspects related to the function of the medication delivery device. Occasionally, the medication delivery device may detect an issue that requires a user's attention. In some cases, the medication delivery device is configured to generate alert data corresponding to the issue that requires the user's attention. The medication delivery device may be configured to output the alert data through an optional output unit included in the medication delivery device. The medication delivery device may be configured to communicate the alert data to the health monitor device. In some instances, the medication delivery device is configured to automatically communicate the alert data to the health monitor device.

The alert data transmitted by the medication delivery device may be received by the communication module of the health monitor device. Subsequently, the communication module may communicate the received alert data to the controller unit of the health monitor device. In some instances, the controller unit is configured to output the received alert data through an output unit coupled to the controller unit of the health monitor device. The output unit may include various types of output devices, and may be configured to gain the user's attention such that the alert data is communicated to the user. In some aspects, the output unit includes, but is not limited to, a visual display unit, an audible output unit, a vibratory output unit, and the like.

In certain embodiments, the alert data communicated from the medication delivery device to the health monitor device includes, but is not limited to, the following: a low battery alert, which may indicate that the battery life of the medication delivery device is less than or equal to a threshold amount (e.g., 25% or less battery life, 20% or less battery life, 15% or less batter life, 10% or less battery life, 5% or less battery life); a failed battery alert, which may indicate that the voltage of the battery in the medication delivery device is less than or equal to a threshold amount; a battery out alert, which may indicate that the battery has been removed from the medication delivery device for a time equal to or greater than a threshold amount (e.g., 1 min or more, 2 min or more, 5 min or more, 10 min or more, etc.); a low reservoir alert, which may indicate that a medication reservoir of the medication delivery device contains an amount of medication that is less than or equal to a threshold amount (e.g., 20 units of insulin or less, 15 units of insulin or less, 10 units of insulin or less, 5 units of insulin or less); an empty reservoir alert, which may indicate that the medication reservoir does not contain any medication; an incomplete reservoir loading alert, which may indicate that the medication reservoir was not filled property and/or not completely filled; a maximum reservoir fill alert, which may indicate that the medication reservoir has been filled to its maximum capacity; a reservoir out alert, which may indicate that the medication reservoir has not been inserted correctly or that no medication reservoir is detected; an auto off alert, which may indicate that the medication delivery device has or will automatically turn off; a bolus interruption alert, which may indicate that the medication delivery device has not delivered the full amount of a programmed bolus; a basal infusion rate interruption alert, which may indicate that the programmed basal infusion of medication has been cancelled or stopped prematurely; a button error alert, which may indicate an inappropriate or unacceptable button press (e.g., a button has been continually pressed for a time equal to or greater than a threshold amount, such as 2 min, 3 min, 5 min, etc.); a check settings alert, which may indicate to a user that the medication delivery device settings should be checked; a mechanical error alert, which may indicate that a mechanical error has caused medication delivery to stop functioning properly; an electronic error alert, which may indicate that an electronic error has caused medication delivery to stop functioning properly; a maximum bolus alert, which may indicate that the amount of medication delivered or to be delivered is equal to or greater than a threshold amount; a motor error alert, which may indicate that medication delivery has stopped due to a motor or pump error; an infusion set blockage alert, which may indicate that the amount of medication delivered over a certain time is less than a programmed amount, possibly due to an obstruction in the insulin infusion set; a data interruption alert, which may indicate a communication failure between the medication delivery device and another device (e.g., an health monitor device, a PC, laptop, PDA, cellular phone, smartphone, set-top box, etc.); a reset alert, which may indicate that the medication delivery device settings have been or will be cleared; a check time and date alert, which may indicate that the time and date settings have been or will be cleared; an alarm clock alert, which may indicate that an alarm clock reminder was programmed into the medication delivery device; a timer alert, which may indicate that a timer was programmed into the medication delivery device; user customizable alerts; combinations thereof; and the like.

Additional alerts may include reminder alerts. In certain embodiments, reminder alerts are configured to provide an indication to a user of an event that requires the user's attention. For example, a reminder alert may provide an indication, such as an audio, visual or other sensory indication (e.g., vibratory) of a recommended action for the user to perform. In some instances, a reminder alert signals the user to perform actions including, but not limited to, measuring an analyte concentration, administering a medication dose, and the like. For example, the reminder alert may indicate to the user that it is recommended that the user measure their blood glucose concentration. In other cases, the reminder alert may indicate to the user that it is recommended that the user administer an insulin bolus. In certain embodiments, reminder alerts are programmed by the user or health care professional according to a schedule determined by the user or health care professional. In some instances, reminder alerts are programmed to follow a pre-determined scheduling algorithm stored in at least one of the health monitor device and the medication delivery device. The pre-determined scheduling algorithm may be programmed into the health monitor device and/or the medication delivery device by a user or a health care professional using an input unit incorporated into the health monitor device or the medication delivery device, via a data management system that interfaces with the health monitor device or the medication delivery device, and/or via another portable device configured to communicate with the health monitor device or the medication delivery device. In this manner, a health care professional can update therapy recommendations electronically and communicate the therapy recommendations to the user. In certain instances, the pre-determined scheduling algorithm may be modified by the user as desired.

As described above, the communication module of the health monitor device may be configured for bi-directional communication with a remote location, such as a medication delivery device. In certain embodiments, the communication module of the health monitor device is configured to transmit data to a remote location. The types of data that the communication module may transmit to the remote location include, but are not limited to, a determined analyte concentration, a medication dose amount, and the like. For example, the controller unit of the health monitor device may be configured to determine an analyte concentration based on an analyte sample on a received analyte test strip. In some cases, the determined analyte concentration includes a blood glucose concentration. The controller unit may be configured to retrieve stored dose determination information and determine a medication dose amount based on the determined analyte concentration and the retrieved dose determination information. In some cases, the determined medication dose amount includes a bolus insulin dose amount or a basal insulin dose amount.

The communication module of the health monitor device may be configured to communicate one or more of the determined analyte concentration and the medication dose amount to the remote location. For instance, the communication module of the health monitor device may be configured to communicate one or more of the determined analyte concentration and the medication dose amount to a medication delivery device. The medication delivery device may be configured to use the received medication dose amount at least in part to determine an amount of medication to administer to the user. For example, the medication delivery device may receive an insulin dose amount from the health monitor device and use the received insulin dose amount, at least in part, to determine an amount of insulin to administer to the user.

Health Monitor Device Software and/or Firmware for Bolus Dosage Calculation

As discussed previously herein, a health monitor device according to the present disclosure may be configured to determine a dosage, e.g., an insulin bolus dosage, based on one or more signals received from an analyte test strip. Accordingly, in some embodiments, the health monitor device includes a software and/or firmware program which may be implemented by the processing unit to perform one or dosage determination algorithms. In some embodiments, the one or more dosage determination algorithms are modifiable by a user of the health monitor device, e.g., using the optional input unit coupled to the device housing. Alternatively, or in addition, the one or more dosage determination algorithms may be modified via a computer or other suitable device in communication with the health monitor device. In some embodiments, a health monitor device according to the present disclosure is provided with software including a preset dosage determination algorithm which is set prior to providing the health monitor device to an end user. Such a preset dosage determination algorithm may be configured based on information provided by an end user or a health care professional to a provider, e.g., a manufacturer, of the health monitor device.

In some embodiments, a control unit or processor of a health monitor device is configured to prompt a user to enter the delivery time of a medication dosage, e.g., a medication dosage calculated by the processing unit. For example, following a bolus dosage calculation, e.g., an insulin bolus dosage calculation, the control unit or processor may automatically prompt the user, e.g., using the display unit, to enter the time at which the calculated bolus dosage was administered.

In some embodiments, the control unit or processor may be further configured to automatically prompt the user, following entry of the administration time, to enter the time at which a subsequent meal is started. Such information may then be utilized by the control unit or processor to optimize future medication dosage calculations.

In some embodiments, a health monitor device according to the present disclosure is configured to provide the user, e.g., automatically or in response to a user input, information which describes how a particular dosage recommendation was calculated. Such information may include, for example, information relating to the user's target blood glucose level, information relating to carbohydrate intake, and one or more correction factors or amounts. In some embodiments, one or more of the calculation parameters may be adjusted by the user. The user may then request a new recommended dosage recommendation based on the adjusted parameter.

Bolus Calculator Lockout

In some embodiments, a control unit or processor of a health monitor device is configured to provide one or more bolus calculator safety features, such as a bolus calculator lockout. By "lockout" is meant that the bolus calculator is deactivated or partially deactivated for a predetermined period of time. For instance, if the health monitor device displays an option to select the bolus calculator, then the option may be unselectable (e.g., "grayed out") or may not be displayed during the lockout time period.

The health monitor device may include one or more types of bolus calculator lockouts. For example, the health monitor device may include a first type of bolus calculator lockout, where the bolus calculator is deactivated if the most recently measured blood glucose level is a threshold amount or less. In some cases, the bolus calculator may be locked out if the most recently measured blood glucose level is below a threshold amount, such as 80 mg/dL or less, including 70 mg/dL or less, or 60 mg/dL or less, or 50 mg/dL or less. For example, the bolus calculator may be locked out if the most recently measured blood glucose level is below 60 mg/dL. In certain instances, the health monitor device issues a warning indication, such as a visible, audible or tactile alert, to the user if the bolus calculator lockout is activated. The warning indication may include a message displayed to the user to contact a health care professional. The bolus calculator may be locked out for a predetermined time period, such as 1 hour or more, 2 hours or more, 3 hours or more, 4 hours or more, etc. In some instances, the bolus calculator may be locked out until a blood glucose measurement is taken that is above the threshold amount described above.

In some embodiments, the health monitor device may include a second type of bolus calculator lockout, where the bolus calculator is partially deactivated. For example, the bolus calculator may be locked out for a predetermined time period following the logging and/or administration of an insulin dose amount. The bolus calculator may be partially deactivated, such that the bolus calculator is not enabled to calculate an additional correction bolus in addition to the previously administered bolus dosage amount, but is still enabled to calculate a recommended bolus dosage amount to compensate for additional carbohydrates consumed (e.g., a meal bolus). In some cases, the bolus calculator is locked out for a predetermined time period following the administration of an insulin dose amount, such as 1 hour or more, 2 hours or more, 3 hours or more, 4 hours or more, 5 hours or more, or 6 hours or more following the administration of an insulin dose amount.

In certain embodiments, a health monitor device that includes one or more bolus calculator lockouts as described above may facilitate a minimization in the occurrence of insulin stacking and corresponding undesired hypoglycemic events. Other bolus calculator safety features may be provided, as described in more detail below.

Figure 27:
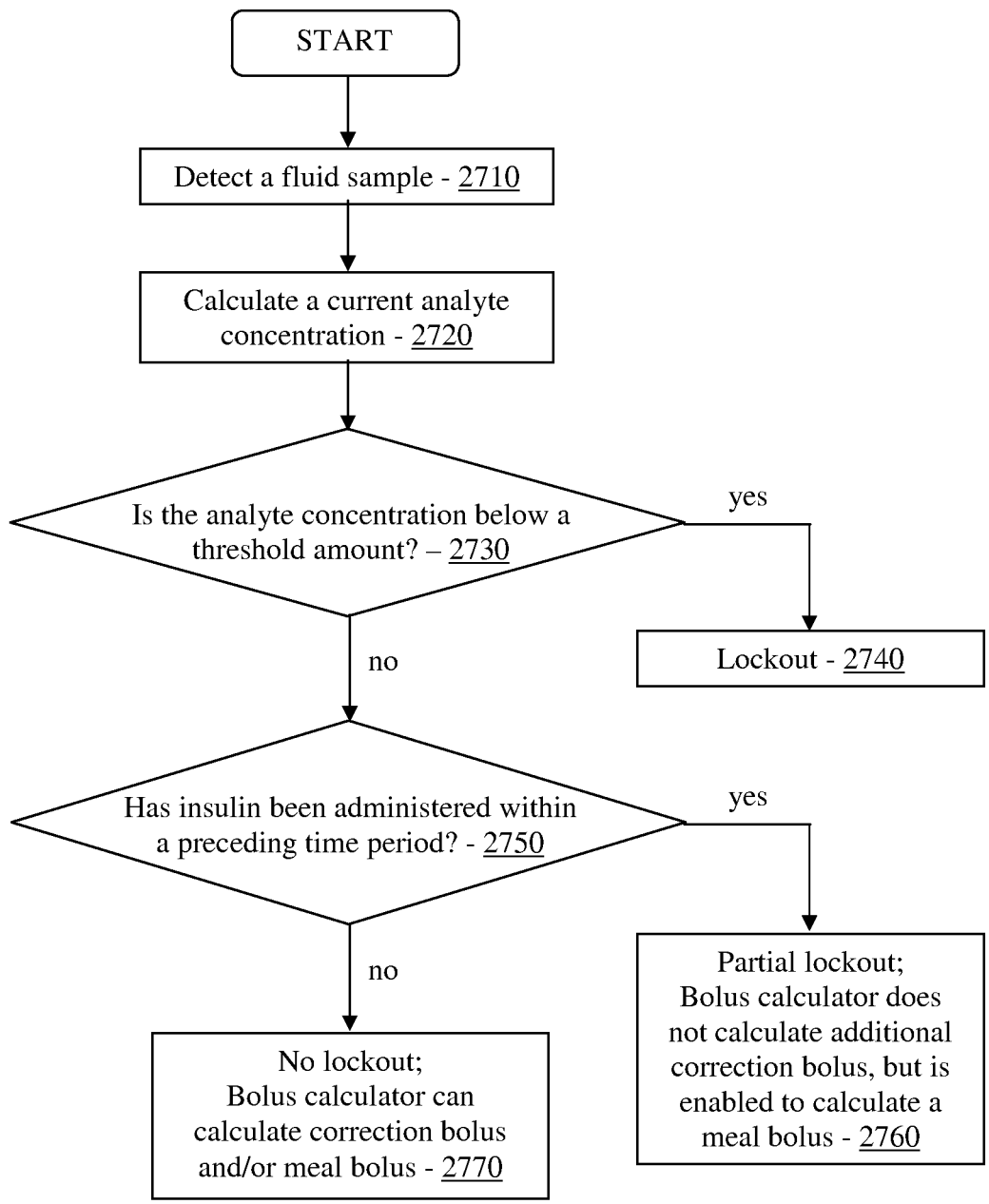
FIG. 27 is a flow chart illustrating a procedure for a bolus calculator lockout according to embodiments of the present disclosure.

FIG. 27 is a flow chart illustrating a procedure for a bolus calculator lockout according to embodiments of the present disclosure. Referring to FIGS. 27 and 6A, a fluid sample is detected (2710), for example, by applying the fluid sample to a test strip 650 and inserting the strip 650 into a strip port 640 of the health monitor device 600. Upon detection of the fluid sample, a current analyte concentration is calculated (2720) based on analysis of the fluid sample. Once the analyte concentration is determined, the value may be compared to a threshold analyte level to determine if the analyte concentration is below a threshold amount (2730). If the analyte concentration is below the threshold analyte level (e.g., 60 mg/dL or less), then the bolus calculator may be locked out (2740). If the analyte concentration is above the threshold analyte concentration, then the health monitor device may determine if an insulin bolus has been administered within a preceding time period (2750). In some instances, the preceding time period may be 1 hour or more, or 2 hours or more, or 3 hours or more, or 4 hours or more, or 5 hours or more, or 6 hours or more, etc. For example, the preceding time period may be 2 hours. If an insulin bolus has been administered within the preceding time period, then the bolus calculator is partially locked out, such that the bolus calculator is disabled from calculating an additional correction bolus, but is enabled to calculate a meal bolus (2760). If the health monitor device determines that no insulin bolus has been administered within the preceding time period, then the bolus calculator is not locked out and may be programmed to calculate a correction bolus and/or a meal bolus (2770).

Bolus Calculator Safety Features

In some embodiments, a control unit or processor of a health monitor device is configured to provide one or more bolus calculator safety features. As discussed herein, a health monitor device according to the present disclosure may be configured to communicate with and receive analyte measurements from an external analyte monitoring device and/or system, e.g., a continuous glucose monitoring (CGM) device and/or system or a "glucose on demand" (GoD) monitoring device and/or system.

Where a health monitor device is configured to communicate with and receive analyte measurements from a CGM device and/or system (e.g., a device and/or system including an implanted or partially implanted analyte sensor configured to automatically measure glucose levels at predetermined intervals), the processor may be configured to automatically (or in response to a user input) initiate a process to specifically monitor a user's glucose response to a bolus dose of insulin. For example, in some embodiments, the control unit or processor is configured to provide an expected glucose profile over a period of time using a physiological model associated with one or more of the user's insulin action time, glucose trajectory, meal input data, insulin input data, exercise data, health data, and time-of-day. The process may provide a "minimum" acceptable profile where the predicted glucose has a minimum value at a predetermined low glucose safety limit. The process may also provide a "maximum" acceptable profile where the predicted glucose has a maximum value at a predetermined high glucose safety limit.

These profiles may be determined in a number of ways. For example, they may be determined by increasing and decreasing carbohydrate intake until the point that the profile limits are reached. Alternatively, meal timing or one or more of the other physiological model parameters may be varied.

The control unit or processor may then monitor using the CGM device and/or system received real-time data to determine if it falls within the minimum and maximum profiles indicated at that point in time. If a predetermined number of glucose readings (e.g., one or more) fall outside the profile range, then the processor can be configured to communicate an alarm and/or alert to the user and indicated that the glucose reading was lower or higher than expected. In some embodiments, the processing device may then communicate to the user a recommended course of action.

Additional description of glucose-on-demand devices and/or systems can be found in U.S. Patent Application Publication Nos. 2008/0319296, 2009/0054749, 2009/0294277, 2008/0319295; in U.S. Patent Application Publication No. 2010/0213057, published Aug. 26, 2010, entitled "Self-Powered Analyte Sensor"; and U.S. Patent Application Publication No. 2010/0152561, published Jun. 17, 2010, entitled "RF Tag on Test Strips, Test Strip Vials and Boxes"; and in U.S. Provisional Patent Application Nos. 61/247,519, filed Sep. 30, 2009, and entitled "Electromagnetically-Coupled On-Body Analyte Sensor and System"; U.S. Application Publication No. 2010/0230285, published Sep. 16, 2010, entitled "Analyte Sensors and Methods of Making and Using the Same"; 61/238,581, filed on Aug. 31, 2009, and entitled "Analyte Monitoring System with Electrochemical Sensor"; 61/163,006, filed on Mar. 24, 2009, and entitled "Methods Of Treatment And Monitoring Systems For Same"; 61/247,508, filed on Sep. 30, 2009, and entitled "Methods and Systems for Calibrating On-Demand Analyte Measurement Device"; U.S. Patent Application Publication No. 2010/0198034 published Aug. 5, 2010 titled "Compact On-Body Physiological Monitoring Devices and Methods Thereof"; U.S. Patent Application Publication No. 2010/0324392 published Dec. 23, 2010 titled "Analyte Sensor and Apparatus for Insertion of the Sensor"; and 61/291,326, filed on Dec. 30, 2009, and entitled "Ultra High Frequency (UHF) Loop Antenna for Passive Glucose Sensor and Reader"; the disclosures of each which are incorporated by reference herein.

Where a health monitor device is configured to communicate with and receive analyte measurements from a GoD device and/or system (e.g., a glucose monitoring device and/or system including an implanted or partially implanted analyte sensor and requiring user initiation to receive a glucose reading), the processor may be configured to prompt the user to obtain a glucose measurement from the GoD device and/or system at predetermined time points relative to a bolus administration, e.g., at 20 min and 45 min following the bolus administration. These measurements may then be compared to a predetermined glucose profile or profiles. If a predetermined number of glucose readings (e.g., one or more) fall outside the profile range, then the processor can be configured to communicate an alarm and/or alert to the user and indicated that the glucose reading was lower or higher than expected. In some embodiments, the control unit or processor may then communicate to the user a recommended course of action.

Bolus calculator safety features may also be incorporated into health monitor devices which are not in communication with external analyte monitoring devices and/or systems, but which are instead configured for self-monitoring of blood glucose (SMBG). For example, such a health monitor device may include a control unit or processor configured to issue an alarm, alert or reminder to a user to perform an additional glucose reading at a predetermined time, e.g. 5 min, following an initial glucose reading and an associated bolus calculation. This allows the control unit or processor to determine a rate factor based on the two glucose values separated in time. This rate factor may then be taken into account by the control unit or processor in performing a new bolus calculation or providing an adjustment to a previous bolus calculation. In some embodiments, the control unit or processor may determine that an initial bolus which was fully delivered was too high and that corrective action, e.g., ingestion of carbohydrate, should be taken to avoid overdelivery.

In some embodiments, a portion (e.g., 70%) of the calculated bolus dose is delivered or recommended for delivery based on an initial glucose reading. Subsequently, some, all or none of the remaining portion of the calculated bolus may be delivered or recommended for delivery based on a second calculated bolus taking into account the glucose rate determined following the second glucose reading.

Analytes

A variety of analytes can be detected and quantified using the disclosed health monitor device. Analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Assays suitable for determining the concentration of DNA and/or RNA are disclosed in U.S. Pat. Nos. 6,281,006 and 6,638,716, the disclosures of each of which are incorporated by reference herein.

Health Management System

A health monitor device according to the present disclosure can be configured to operate as one component of a health management system. For example, in one embodiment a health monitor device as described herein is configured to communicate, e.g., via a communication interface as described herein, with a central data repository which is in turn configured to analyze and store user-specific data in a user-specific therapy management database. The communication between the health monitor device and the central data repository may be initiated by the user or may occur automatically, e.g., when the health monitor device is in range of a wireless network.

In one embodiment, a health monitor device as described herein is one of multiple devices utilized by the user and configured to communicate with the central data repository. In such an embodiment, the central data repository can be configured to integrate incoming data from multiple devices. For example, the central data repository can be configured to integrate data received from one or more Personal Digital Assistants (PDAs), mobile phones, (e.g., iPhone® or BlackBerry® devices), etc. The central data repository may be located on a server and/or computer network and may include a variety of software and/or hardware components as appropriate.

The data may be transmitted from the multiple devices in a variety of ways, e.g., via text messaging, e-mail, microblogging services (e.g., Twitter™), voicemail, or any other suitable messaging format. Depending on the transmission form, data may be sent by a user to, e.g., a phone number, text number, e-mail address, Twitter™ account, etc. The received data can include a variety of health related information depending on the health condition being managed. For example, in the context of diabetes, the data received by the central data repository can include, e.g., meal data, exercise data, insulin administration data, blood glucose data, blood ketone data, etc.

User-specific data received from one or more of these devices can be merged with data received from a health monitor device as described herein. Once the data is received, the central data repository interprets the message as containing, e.g., meal data exercise data, insulin administration data, blood glucose data, blood ketone data, etc., and populates the user-specific therapy management database accordingly.

The user-specific therapy management database can be configured such that it is accessible by the user, health care professional, or other suitable party, for viewing and/or editing. For example, access to the user-specific therapy management database may be provided via a website, e.g., a secure website. In one embodiment, the user-specific therapy management database is hosted on a server and the system is configured such that a health care professional can access the user-specific therapy management database from a computer via a wired or wireless IP connection to the server hosting the user-specific therapy management database.

Health Management System-Associated Software and/or Firmware

In one embodiment, the present disclosure provides one or more software applications which facilitate specific functionalities of a health management system, e.g. a diabetes management system. Such software applications may reside, for example, in the memory of a health monitor device as described herein. Alternatively, or in addition, such software may be located on a computer, server, and/or network located external to a health monitor device as described herein.

In one embodiment, such software resides in the memory of a health monitor device as described herein and is configured to launch automatically, e.g., via a "Plug and Play" standard, on an external processing device such as a desktop computer or laptop computer when the health monitor device is connected to the external processing device, e.g. via a USB connection.

In another embodiment, such software resides in memory of an external processing device such as a desktop computer or laptop computer and is configured to launch automatically on the external processing device when a health monitor device as described herein is connected to the external processing device, e.g. via a USB connection.

In another embodiment, such software resides in memory of a health monitor device as described herein and is configured to run on the health monitor device itself.

In another embodiment, such software resides in memory of a processing device other than a health monitor device according to the present disclosure and is configured to run on the processing device itself.

The health management system-associated software and/or firmware may include programming, such as instructions or routines, which when executed by a processor of a health management system, cause the processor to perform various functions associated with determining a patient's medication dosage regimen. In some cases, the health management system-associated software and/or firmware includes programming configured to assist a patient in titrating a current dose level of a medication over time until a target threshold range is achieved. For example, the programming may be configured to facilitate the determination of an adjusted dose level for a medication, such as long-acting insulin, as described above.

The health management system software may be loaded and saved in a memory of an external processing device such as a desktop computer or laptop computer, as described above. The patient or a health care professional may create a profile for storing and retrieving patient data, the patient's health monitor device settings, and the like. For instance, a patient profile may include patient profile data used for determining a patient's medication dosage regimen, such as a long-acting insulin dose level. The patient profile data may include, but is not limited to, a current dose level (e.g., a current long-acting insulin dose level), a threshold range for an analyte concentration (e.g., a fasting blood glucose threshold range), a predetermined dose adjustment amount (e.g., a number of units to adjust the current dose level if the analyte concentration is outside the threshold range), and a predetermined schedule (e.g., how frequently the adjusted dose level is determined. One or more patient profiles may be created and each profile may include individualized settings for a particular patient. For example, a first profile may include conservative settings such as a fasting blood glucose target range of 100-120 mg/dL, a current long-acting insulin dose level of 15 units and a maximum long-acting insulin dose of 25 units. A second profile may include standard settings such as a fasting blood glucose target range of 70-110 mg/dL, a current long-acting insulin dose level of 15 units and a maximum long-acting insulin dose of 30 units. A third profile may include pediatric settings such as a fasting blood glucose target range of 70-110 mg/dL, a current long-acting insulin dose level of 5 units and a maximum long-acting insulin dose of 10 units. Other settings may be used as desired and may be customized by the patient and/or the health care professional depending on the individual needs of the patient.

A patient and/or a health care professional may input the initial values for the patient profile data. The initial values for the patient profile data may be transmitted to the patient's health monitor device by, for example, connecting the patient's health monitor device to the health management system via a wired or a wireless connection. In certain embodiments, the patient and/or the health care professional can modify the patient profile data as desired. Once the initial values for the patient profile data are transferred to the patient's health monitor device, the patient may begin titrating their current dose level until the adjusted dose level is within a threshold range. The patient may follow guided prompts on the health monitor device to gather the necessary data (e.g., fasting blood glucose levels) for determining the adjusted dose level, as described above.

Instant Messaging

In one embodiment, a software application which facilitates specific functionalities of a health management system is one which in addition to providing data display and analysis tools for health management also provides Instant Messaging (IM) functionality.

For example, in one embodiment health management software, e.g., diabetes management software, is provided which allows a health care professional using the health management software to review data related to a user's health, e.g., diabetes related data, and send comments, therapy recommendations, and/or scheduling information via IM to an interface accessible by the user. The interface could be, e.g., a user's personal computer, a portable electronic device, or a health monitor device with communication functionality as described herein.

In one embodiment, health management software, e.g., diabetes management software, is provided which allows an end user to utilize the health management software to review data related to the end user's health, e.g., diabetes related data, and send comments, questions, and/or analyte measurement results via IM to an interface accessible by a health care professional.

The above functionalities may be combined in a single software application such that the health care professional and the end user are capable of reviewing data related to the end user's health and communicating with each other via IM functionality built in to the software application. In certain embodiments, the IM functionalities used to communicate the user's health data may be provided by a third-party application, such as, but not limited to, IM or social networking software, web or mobile device applications by YAHOO!®, GOOGLE®, FACEBOOK®, TWITTER®, MYSPACE®, FRIENDSTER®, and the like.

Health management software having integrated, i.e., "built in", IM functionality can also be utilized to allow communication between an end user and a customer support representative in order to provide the end user with product support information, e.g. for the software itself, a health monitor device or other product utilized in connection with the health management system.

In one embodiment, the health management software is configured to prompt the end user to select an IM recipient among, e.g., product support specialists; health management specialists; e.g., diabetes management specialists; and product sales specialists.

The mode of communication utilized by the IM feature of the health management software may be text-based, image-based, animation-based, voice-based and/or video-based. It should be noted that responses to the IM communications need not be in real-time.

A software application configured to provide IM functionality may be stored in and/or run from a health monitor device as described herein. Alternatively, the software application may be stored in and/or run from a processing device such as a smart phone device, PDA, server device, laptop or desktop computer.

Report Plug-in for Health-Management Software

In one embodiment, the present disclosure provides a stand-alone health management software application capable of incorporating a report plug-in application which provides for full integration of new reports into the stand-alone health management software application. Such a health management software application may be stored in and/or run from a health monitor device as described herein. Alternatively, the software application may be stored in and/or run from a processing device such as a smart phone device, PDA, server device, laptop or desktop computer.

The report plug-in application can be made available to a user at start-up of the stand-alone health management software application and/or via a menu action. For example, in one embodiment, a health management software application is provided to a user with certain reports "built-in." At a later time point, the set of built-in reports can be augmented with one or more newly published reports. The user can be made aware of the additional reports by, e.g., a message displayed upon start-up of the health management software application.

In one embodiment, when the new report is accepted by the user, the new report is fully integrated into the stand-alone health management software application, i.e., the new report includes all of the functionalities that are common to the existing set of reports. Such functionalities may include, e.g.: (A) inclusion of reports in existing or new dashboards, (B) relaying user event data to other application components, e.g., other reports displayed on the dashboard, (C) receiving user event data from other application components, e.g., other reports displayed on the dashboard, (D) printing of a report using the application print engine, (E) the report can be uninstalled by the user, and (F) multiple versions of the same report are supported by implementing a versioning scheme.

As used herein, the term "dashboard" is used to refer to a visualization component of a health management software application which includes multiple component reports. The health management software application may be configured to provide multiple dashboards having different combinations and or arrangement of displayed reports.

Health-management software is well known in the art and includes, e.g., the COPILOT™ Health Management System and the PRECISIONWEB™ Point-of-Care Data Management System available through Abbot Diabetes Care Inc., Alameda, Calif.

In one embodiment, the health management software application provided by the present disclosure is a diabetes management software application. Such an application may be configured to run one or more reports relevant to diabetes management, e.g., a diary list report, glucose modal day report, glucose line report, glucose average report, glucose histogram report, glucose pie chart report, logbook report, lab and exam record report, statistics report, daily combination view report, weekly pump review report, and an HCP group analysis report. See, e.g., the COPILOT™ Health Management system Version 4.0 User's Guide, available online at the web address located by placing "www." immediately preceding "abbottdiabetescare.com/static/cms_workspace/document/ART12542_Rev-A_US_English-.pdf", the disclosure of which is incorporated by reference herein. Embodiments of health management system-associated software and a host-client architecture for communicating, managing and analyzing health management data and for generating versatile reports are described in U.S. Application Publication No. 2006/0010098, published Jan. 12, 2006, titled "Diabetes Care lost-Client Architecture and Data Management System", the disclosure of which is incorporated by reference herein in its entirety.

Customizable Dashboards for Health Management Software

In one embodiment, the present disclosure provides a stand-alone health management software application including customizable dashboards for the management of a health condition, e.g., diabetes. Such a health management software application may be stored in and/or run from a health monitor device as described herein. Alternatively, the software application may be stored in and/or run from a processing device such as a smart phone device, PDA, server device, laptop or desktop computer.

The health management software can be configured such that an end user can create a new dashboard, e.g., using a "Create Dashboard Wizard" functionality which presents dashboard options to a user for selection, and/or modify an existing dashboard of the health management software. In one embodiment, the health management software is configured to allow an end user or health care provide to name or rename a dashboard so that it may be readily identifiable.

In another embodiment, the health management software is configured such that reports contained within a particular dashboard, e.g., a user configured dashboard, are dynamically refreshed in concert, as a result of a user changing the view on any individual report contained within the dashboard. For example, if the user changes a view period for a glucose modal day report included in a dashboard, the health management software can be configured such that each of one or more additional reports included in the dashboard are refreshed using the same time period as that selected for the glucose modal day report.

Reports within a dashboard can be refreshed with the same time period (exact time alignment) or each additional report may represent a previous or subsequent time period (sequential time alignment). Additional alignment relationships are also possible.

In another embodiment, the health management software is configured to allow a user to publish and/or distribute a dashboard to other users of the health management software and/or a health care professional, e.g., via an internet connection. Similarly, a health care professional could develop a dashboard and distribute the dashboard to one or more users (e.g., a primary care giver distributing a dashboard to his/her patients).

In one embodiment, the health management software is configured to automatically check for updates upon launch of the application. Alternatively, or in addition, such a check may be initiated by the user. Updates can include, e.g., new dashboards developed by the manufacturer of the health management software, its business partners, or a health care professional.

Meal Intake Reminder for Diabetes Management Devices and Application Software

In one embodiment, the present disclosure provides a diabetes management software application which includes a reminder algorithm for meal intake data entry. In one such embodiment, the algorithm results in presentation to the user of a reminder to enter meal intake data on, e.g., a health monitor device as described herein, a portable processing device (e.g., a smart phone (e.g., IPHONE® or BLACKBERRY®) laptop or PDA), and/or computer. Meal intake data can include, e.g., time of meal intake, meal composition, and meal-component quantification (e.g., carbohydrates in grams, servings, or bread units).

The algorithm may present the reminder based on one or more of (a) a "reminder profile" including frequency of data entry and meal content established by the user and/or by a health care professional (HCP), (b) the number of data entries, and meal composition for each entry, that have already been entered within the day and within a time period, (c) a recommendation on the type of meal(s) to be consumed for the remainder of the day or time period.

In one embodiment, the reminder algorithm is configured to provide a reminder to the user based on an analysis of the history of meal-intake data entries made by the user and compared to a reminder profile configured by the user or HCP.

The algorithm may generate summary results from the data entries made by the user that indicate how many days have a full set of data, how many days have partial or incomplete data, and how many days have no data at all. In addition, the algorithm may generate data associated with meal composition for each day, and generate cumulative summaries for defined time intervals (e.g., each week in the current month).

The reminder profile may be configured by the user or by a qualified health care professional, such as a physician, clinical specialist or nurse.

In one embodiment, where the algorithm is configured to be run on an a health monitor device as described herein, e.g., a glucose meter, the health monitor device may be configured with the reminder profile either (a) directly by the health care professional using the health monitor device's user interface, (b) via a data management system that interfaces with the health monitor device, or (c) via another portable processing device.

The reminder algorithm may be configured to provide feedback to the user at any time regarding how many meal-intake entries have been made and how much of the schedule or reminder profile has been completed.

It should be noted that while the above reminder algorithm is discussed in the context of a meal-intake data entry reminder, additional algorithms and associated reminders may be configured for use with the health monitor devices and/or health management systems described herein, e.g., analyte measurement reminders or other therapy reminders.

Recommendation for Health Monitor Type Based on Simulations

In some embodiments, the present disclosure provides methods for selecting for a user a health monitor device and/or system among multiple health monitor devices and/or systems based on simulation data. CGM, GoD and SMBG analyte monitoring devices and/or systems are discussed previously herein and in the materials incorporated by reference herein. In one embodiment, the present disclosure provides a method for selecting a glucose monitoring device and/or system from among a CGM device and/or system, a GoD device and/or system and a SMBG device and/or system. The method includes running a simulation for each device and/or system, taking into account multiple meal and/or correction events that have been recorded for a particular user. The method utilizes glucose history, meal information and insulin delivery information in connection with these events as available for a particular device and/or system to calculate the optimal parameters specific to the user for the particular device and/or system.

For example, in one embodiment, a simulation for a SMBG device and/or system assumes that for each meal bolus event, the bolus is based on the meal information and the glucose level, but not on glucose trending information.

In one embodiment, a simulation for a GoD device and/or system includes information similar to that for the SMBG device and/or system except that trending information is also taken into account for the bolus calculation. In one embodiment, a simulation for a CGM device and/or system assumes that whenever the glucose measurement exceeds a high or low threshold, that a correction bolus occurs based on glucose level and trending information.

Alternatively, or in addition, the CGM simulation may take into account that a correction is triggered based on projected high or low thresholds. Metrics based on the simulation results may be used to provide an indication of acceptable glucose control. The method may be utilized by a health care professional in order to determine the appropriate health monitor device and/or system for a particular patient and/or user.

Insulin on Board

In certain instances, an entire bolus of insulin administered to a patient does not have an immediate effect, and may take several hours for its full blood glucose-lowering effects to occur. For instance, the duration of insulin action (DIA) time may be 1 hour or more, such as 2 hours of more, or 3 hours or more, or 4 hours or more, or 5 hours or more, or 6 hours or more, or 7 hours or more, or 8 hours or more. Thus, the amount of insulin remaining in a patient's bloodstream, or "insulin on board" (i.e., "bolus on board" or "BOB"), may slowly decrease over time from when the dose of insulin was first administered. In some cases, the duration of action time of insulin may lead to the occurrence of "insulin stacking", where a patient administers multiple doses of insulin without taking into account the amount of insulin remaining in their bloodstream from a previously administered dose of insulin (e.g., the patient's insulin on board (IOB)). For example, a patient may administer an appropriate bolus dosage of insulin to correct for an amount of carbohydrates consumed at a meal. If the patient measures their blood glucose value at a time point less than their duration of insulin action, then the patient may observe a blood glucose value that is higher than the patient's blood glucose target range because the full effects of the administered insulin bolus have not had sufficient time to occur. The patient may then attempt to correct for this observed high blood glucose value by administering a correction dose of insulin. Insulin stacking, and an unintended hypoglycemic event due to the administration of too much insulin, may result if the patient administers a second insulin bolus in an attempt to correct the observed high blood glucose value without taking into account the patient's insulin on board.

Figure 28:
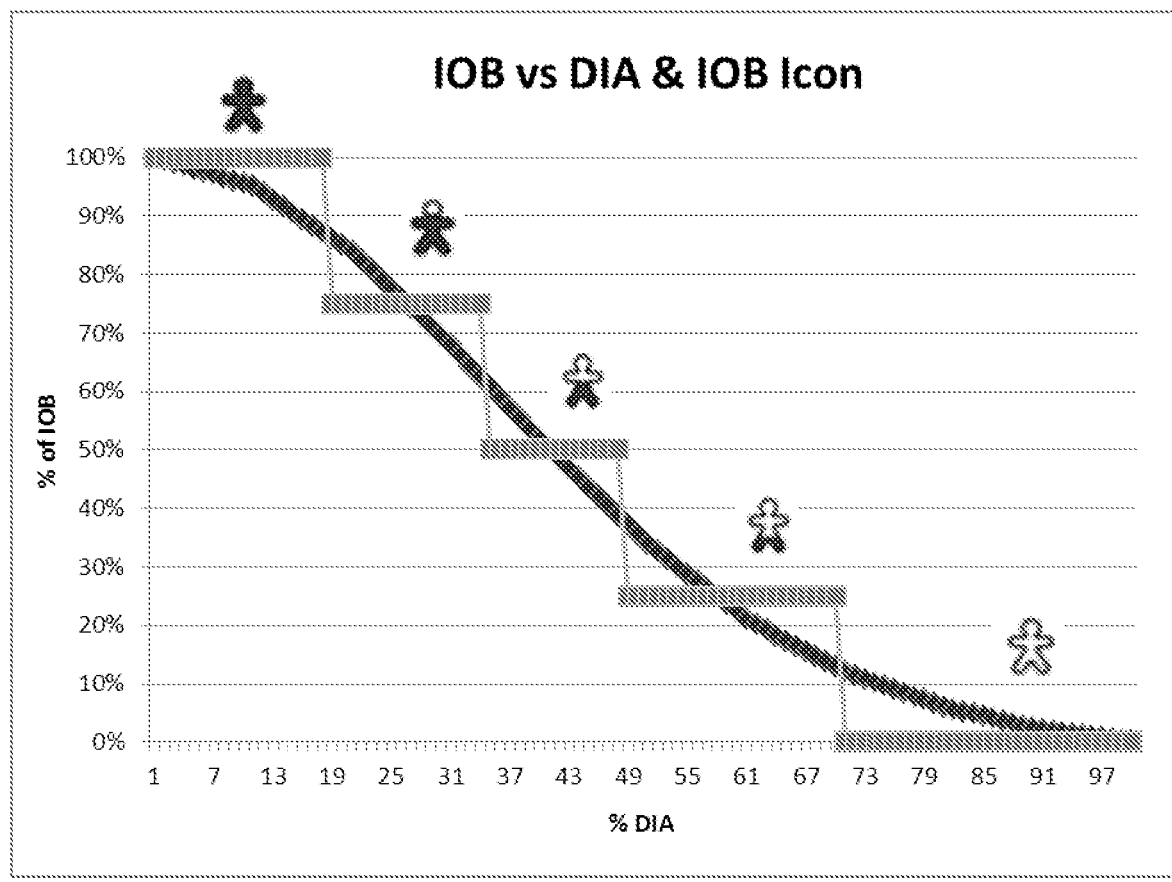
FIG. 28 shows a graph of a curvilinear duration of insulin action (dark shaded line), and a graph of how an insulin on board icon can be correlated to the amount of a patient's insulin on board and duration of insulin action (light shaded line), according to embodiments of the present disclosure.

In some cases, the duration of insulin action (DIA) time can be represented by a graph, where the insulin on board decreases over time. For instance, the DIA time can be represented by a graph, where the percent insulin on board remaining decreases over time. In certain instances, the DIA time can be represented by a graph, where the percent insulin on board remaining decreases as the percent of the DIA time increases. The duration of insulin action time may be represented by a linear graph, and in some cases, may be represented by a curvilinear graph. FIG. 28 shows a graph of a curvilinear DIA time (dark shaded line), where the percent insulin on board remaining decreases as the percent of the duration of insulin action time increases. An example of values showing how the percent IOB remaining decreases as the percent of the DIA time increases is shown in the table below.

| Table of % IOB vs. % DIA Time | |
|---|---|
| % IOB | % DIA Time |
| 100 | 0 |
| 95 | 10 |
| 84 | 20 |
| 68 | 30 |
| 50 | 40 |
| 34 | 50 |
| 21 | 60 |
| 12 | 70 |
| 6 | 80 |
| 2 | 90 |
| 0 | 100 |

Aspects of certain embodiments of the health monitor device include programming configured to facilitate a minimization in the occurrence of insulin stacking. In certain embodiments, a patient's insulin on board is taken into account by the health monitor device when determining a recommended bolus dosage amount. For example, a patient may attempt to calculate a recommended bolus dosage of insulin after previously administering a dose of insulin. If the patient attempts to calculate a recommended bolus dosage of insulin in a time period after the previously administered bolus that is less than the patient's duration of insulin action, then the patient is likely to have an amount of active insulin in their bloodstream (e.g., insulin on board or IOB). To take the patient's IOB into account, the health monitor device may be programmed to recommend a current dose level based on a determined analyte concentration and dose determination information. In some cases, the dose determination information includes, but is not limited to, insulin on board information, such as a previously administered medication dose amount, a previously administered medication dose time, administered dose frequency information over a predetermined time period, and the like. For example, the health monitor device may be programmed to recommend a current dose level based on a blood glucose concentration and a patient's insulin on board information. In some instances, the health monitor device may be programmed to subtract the patient's IOB from the dose level based on the patient's current blood glucose measurement. Subtracting the patient's IOB from the bolus dosage amount may facilitate a minimization in the occurrence of insulin stacking.

Figure 29:
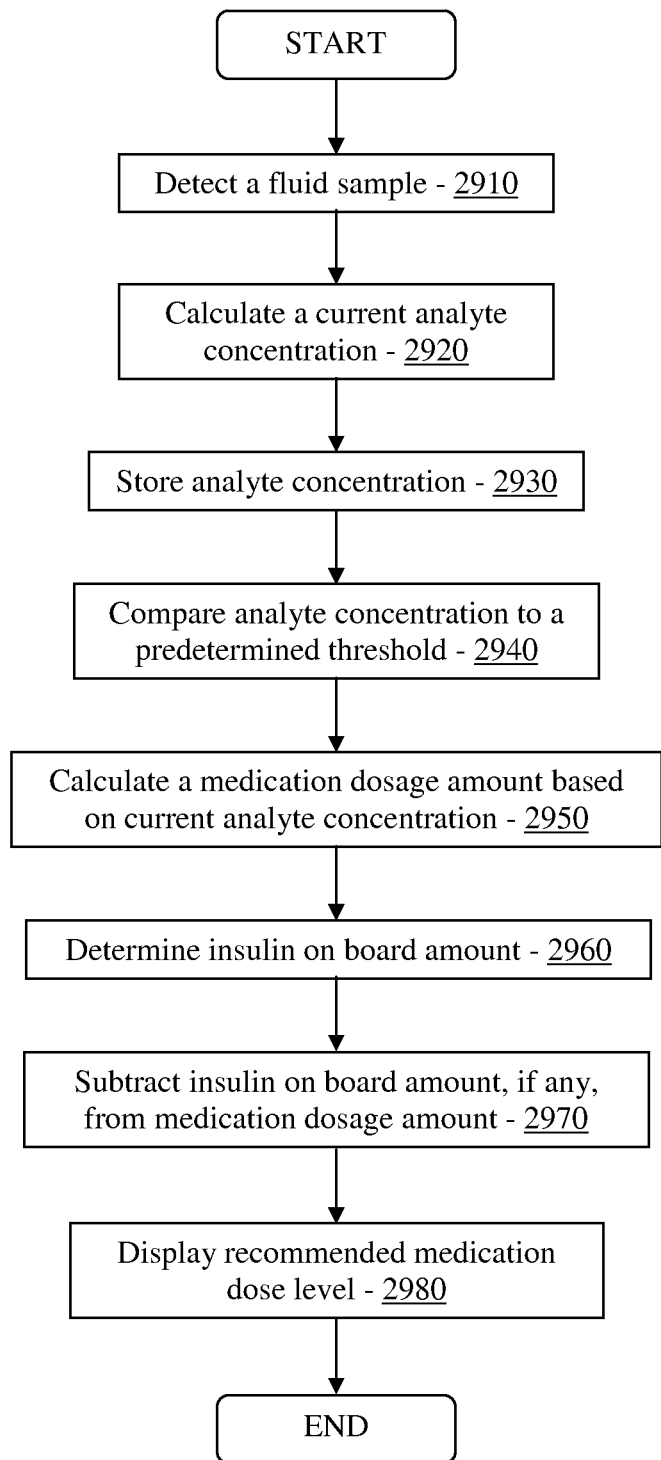
FIG. 29 is a flow chart illustrating a procedure for determining a recommended medication dose level taking into account insulin on board, if any, according to embodiments of the present disclosure.

FIG. 29 is a flow chart illustrating a procedure for determining a current dose level of a medication in one embodiment of the present disclosure. Referring to FIGS. 29 and 6A, a fluid sample is detected (2910), for example, by applying the fluid sample to a test strip 650 and inserting the strip 650 into a strip port 640 of the health monitor device 600. Upon detection of the fluid sample, a current analyte concentration is calculated (2920) based on analysis of the fluid sample. Once the analyte concentration is determined, the value may be stored (2930) in a memory 670 of the health monitor device 600. Alternatively, the value may be transmitted for storage in a memory of a secondary device or computer. In some embodiments, the stored analyte concentration data is time and/or date stamped. For example, a time and/or date associated with the determined analyte concentration (e.g., the determined fasting blood glucose level) may be stored in a memory 670 of the health monitor device 600, or alternatively, may be transmitted for storage in a memory of a secondary device or computer. The analyte concentration is compared to a predetermined threshold analyte level (2940). For example, if the analyte is glucose and the analyte level is a blood glucose level of a patient, the threshold blood glucose level may be between 80 mg/dL and 120 mg/dL, or a tailored threshold determined by the patient or a health care professional. If the current analyte concentration level is above the predetermined threshold, the health monitor device may proceed with calculating a recommended bolus dosage amount to bring the current analyte concentration within the patient's threshold blood glucose range. The health monitor device 600 determines a medication dosage based upon the current analyte concentration level (2950). In certain instances, the health monitor device 600 determines if the patient has any insulin on board based on dose determination information, such as a previously administered medication dose amount, a previously administered medication dose time, and an administered dose frequency information over a predetermined time period (2960). If the health monitor device 600 determines that the patient has insulin on board, then the health monitor device 600 subtracts the insulin on board amount from the determined medication dosage above to determine a current medication dose level (e.g., a recommended insulin dose amount) (2970). The health monitor device 600 may display the result to the user (2980).

In certain embodiments, a patient's insulin on board may be displayed on a display unit of the health monitor device. The patient's insulin on board may be displayed numerically and/or graphically. For example, the patient's insulin on board may be displayed as an IOB icon. The icon may be a shaded icon, where the amount of shading of the icon represents the amount of the patient's insulin on board. In some cases, the shading of the icon is full when the patient's insulin on board is at a maximum, and the amount of shading of the icon decreases over time as the patient's insulin on board decreases over time. FIG. 28 shows a graph of how an insulin on board icon can be correlated to the amount of a patient's insulin on board and duration of inulin action time (light shaded line). For example, the IOB icon may be fully shaded (e.g., 100% full) when the patient's % DIA time ranges from 0% to 20% of the total DIA time, which according to the table above may correspond to a % IOB remaining ranging from 100% to 84%. The IOB icon may be more than half shaded (e.g., 75% full) when the patient's % DIA time ranges from 20% to 35% of the total DIA time, which according to the table above may correspond to a % IOB remaining ranging from 84% to 60%. The IOB icon may be half shaded (e.g., 50% full) when the patient's % DIA time ranges from 35% to 50% of the total DIA time, which according to the table above may correspond to a % IOB remaining ranging from 60% to 34%. The IOB icon may be less than half shaded (e.g., 25% full) when the patient's % DIA time ranges from 50% to 70% of the total DIA time, which according to the table above may correspond to a % IOB remaining ranging from 34% to 12%. The IOB icon may be un-shaded (e.g., 0% full) when the patient's % DIA time ranges from 70% to 100% of the total DIA time, which according to the table above may correspond to a % IOB remaining ranging from 12% to 0%.

Other values correlating a patient's % IOB remaining to the % DIA time and amount of shading of the IOB icon may be used as desired. For example, the IOB icon may be fully shaded (e.g., 100% full) when the patient's % IOB remaining ranges from 100% to 87%. The IOB icon may be more than half shaded (e.g., 75% full) when the patient's % IOB remaining ranges from 86% to 62%. The IOB icon may be half shaded (e.g., 50% full) when the patient's % IOB remaining ranges from 61% to 37%. The IOB icon may be less than half shaded (e.g., 25% full) when the patient's % IOB remaining ranges from 36% to 12%. The IOB icon may be un-shaded (e.g., 0% full) when the patient's % IOB remaining ranges from 12% to 1%. No IOB icon may be displayed when the patient's % IOB remaining is 0%.

In certain embodiments, a patient's insulin on board (IOB) information is used in the calculation of a recommended bolus dosage amount if the patient's most recent insulin dose was administered within a certain time period. For example, as described above regarding a bolus calculator lockout, the bolus calculator may be partially locked out if the difference between the current time and the time the most recent insulin bolus was administered is less than a lock out time period (e.g., the most recent insulin dose was administered within a preceding lockout time period, such as within the past 2 hours). During the lockout time period, the insulin calculator may be programmed to only calculate a meal bolus and may not calculate an additional correction bolus. During the lockout time period, the insulin calculator may not include insulin on board into the calculation of a meal bolus.

If the difference between the current time and the time the most recent insulin bolus was administered is greater than a threshold time period (e.g., the lockout time period) and less than the duration of insulin action, then the bolus calculator may be programmed to include the patient's IOB into the calculation of the recommended bolus dosage amount. In the time period between the end of the lockout time period and the end of the patient's duration of insulin action, the bolus calculator may be programmed to determine the recommended medication dosage amount based on the determined analyte concentration and the insulin on board information. For instance, in the time period between the end of the lockout time period and the end of the patient's duration of insulin action, the bolus calculator may be programmed to subtract the patient's IOB from the medication dosage based upon the current analyte concentration level to determine the recommended bolus dosage amount.

In certain instances, if the difference between the current time and the time the most recent insulin bolus was administered is greater than the patient's duration of insulin action, then the bolus calculator will not include insulin on board into the calculation of a recommended bolus dosage amount. In the time period after the patient's duration of insulin action has expired (and before the next dose of insulin is administered), the insulin calculator may assume the patient's insulin on board is zero. In the time period after the patient's duration of insulin action has expired (and before the next dose of insulin is administered), the insulin calculator may be programmed to determine the medication dosage amount based on the determined analyte concentration (without including the insulin on board information).

Figure 30:
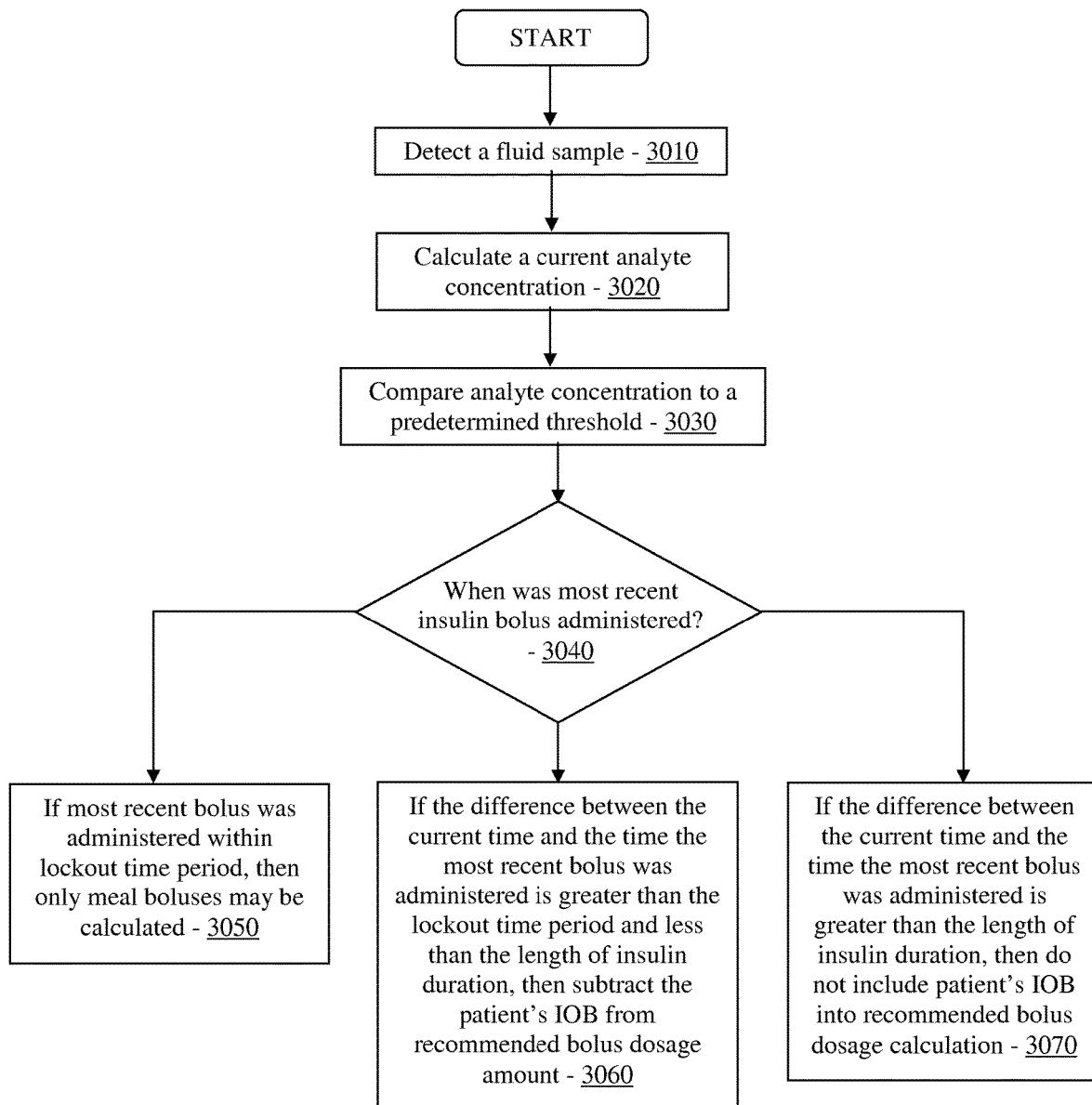
FIG. 30 is a flow chart illustrating a procedure for determining when to subtract a patient's insulin on board when calculating a recommended medication dosage amount according to embodiments of the present disclosure.

FIG. 30 is a flow chart illustrating a procedure for determining when to subtract a patient's insulin on board when calculating a recommended medication dosage amount according to an embodiment of the present disclosure. Referring to FIGS. 30 and 6A, a fluid sample is detected (3010), for example, by applying the fluid sample to a test strip 650 and inserting the strip 650 into a strip port 640 of the health monitor device 600. Upon detection of the fluid sample, a current analyte concentration is calculated (3020) based on analysis of the fluid sample. The analyte concentration is compared to a predetermined threshold analyte level (3030). For example, if the analyte is glucose and the analyte level is a blood glucose level of a patient, the threshold blood glucose level may be between 80 mg/dL and 120 mg/dL, or a tailored threshold determined by the patient or a health care professional. If the current analyte concentration level is above the predetermined threshold, the health monitor device may proceed with calculating a recommended bolus dosage amount to bring the current analyte concentration within the patient's threshold blood glucose range. In certain instances, the health monitor device 600 determines when the most recent insulin bolus was administered (3040). If the most recent insulin bolus was administered within the lockout time period (e.g., if the most recent bolus was administered 2 hours or less ago), then only meal boluses may be calculated (3050). If the most recent insulin bolus was administered between the lockout time period ago and the patient's length of insulin duration, then the patient's IOB is subtracted from the recommended bolus dosage amount (3060). If the most recent insulin bolus was administered longer ago than length of the patient's insulin duration, then the patient's IOB is substantially zero and is not included into the calculation of the recommended bolus dosage amount (3070).

Historical Data Analysis

Aspects of certain embodiments of the health monitor device include a processor configured to analyze historical data stored in a memory of the health monitor device. By "historical data" is meant data that has been stored in a memory of the health monitor device. For example, previously obtained data may be stored in the memory of a health monitor device and may include blood glucose values, an amount of carbohydrates consumed, a time and date, and the like. The data may have been obtained over a preceding time period, such as the previous 2 hours or more, 4 hours or more, 8 hours or more, 12 hours or more, 24 hours or more, 2 days or more, 3 days or more, 4 days or more, 5 days or more, 6 days or more, 7 days or more, 2 weeks or more, 3 weeks or more, 1 month or more, 2 months or more, 3 months or more, 6 months or more, 9 months or more, or 1 year or more, and stored in a memory of the health monitor device.

In certain embodiments, the health monitor device may store an event log that includes one or more of the following events: analyte measurement readings (e.g., blood glucose readings); amount of carbohydrate intake; type of carbohydrate intake; insulin dosage and times; exercise records; meal-time records; note records; medication time and/or dose records; and the like. Additional information may also be stored in the memory of the health monitor device, such as, but not limited to, information relating to the user's target blood glucose level, carbohydrate ratio, insulin sensitivity (e.g., correction factor), duration of insulin action, and the like. Events and the additional information may be recorded automatically by the health monitor device (e.g., upon measurement reading), or may be input into the health monitor device by a patient or by a health care professional.

In certain instances, the health monitor device may include a bolus calculation function as described herein, where a recommended medication dosage amount is calculated based on information, such as the patient's insulin sensitivity, the amount of carbohydrates consumed, and the like. The health monitor device may include programming configured to analyze the events and/or additional information stored in the memory of the health monitor device. For example, the health monitor device may include programming configured to analyze previously stored data (e.g., events and information as described above) and find one or more historical medication dosages (e.g., previously administered medication dosages) that are substantially similar to the current recommended medication dosage. By "substantially similar" is meant that one or more parameters associated with the historical medication dosage amount are substantially the same as the corresponding parameters associated with the current recommended medication dosage. For instance, the health monitor device may analyze parameters such as, but not limited to, the type of meal, the time of day, the amount of carbohydrates consumed, the current analyte measurement value (e.g., the current blood glucose value), the pre-meal analyte measurement value (e.g., the pre-meal blood glucose value), the post-meal analyte measurement value (e.g., the post-meal blood glucose value), the carbohydrate to insulin ratio (e.g., insulin to carbohydrate ratio), the insulin sensitivity (e.g., correction factor), the duration of insulin action, and the like.

If the health monitor device finds a historical medication dosage amount that is substantially similar to the current recommended medication dosage amount, then the health monitor device may display the substantially similar historical medication dosage amount to the user. For example, if the health monitor device determines that a historical insulin bolus dosage is substantially similar to the current recommended insulin bolus dosage (e.g., based on one or more of: the type of meal, the amount of carbohydrate consumed, the current blood glucose value, the insulin sensitivity (e.g., the correction factor), or other parameters discussed above), then the health monitor device may display the historical insulin bolus dosage to the user. Additional historical information may also be displayed to the user, such as, but not limited to an analyte measurement value at a point in time after the historical insulin bolus dosage was administered to the user. For instance, the health monitor device may display the substantially similar historical insulin bolus dosage to the user and also one or more historical blood glucose values at a point in time, such as 1 hour, 2 hours, 3 hours, 4 hours, 5 hours, 6 hours, 7 hours, or 8 hours or more after the historical insulin bolus dosage was administered to the user.

Displaying substantially similar historical medication dosage amounts and associated historical analyte measurement values to the user may facilitate the determination of a correction to the current recommended medication dosage amount. For example, the health monitor device may display a historical insulin bolus dosage that was administered to the user and the associated blood glucose value at a time point (e.g., 2-4 hours) after the insulin bolus dosage was administered to the user. If the associated historical blood glucose value was higher than the user's blood glucose target range, then the user may determine that the current recommended insulin bolus dosage may be increased by a desired correction amount. Alternatively, if the associated historical blood glucose value was lower than the user's blood glucose target range, then the user may determine that the current recommended insulin bolus dosage may be decreased by a desired correction amount. If the associated historical blood glucose value was within the user's blood glucose target range, then the user may determine that no change is desired for the current recommended insulin bolus dosage. In certain embodiments, the health monitor device displays the substantially similar historical medication dosage amounts and associated historical analyte measurement values to the user before the user administers the current recommended medication dosage so that the user may determine whether any correction to the current recommended medication dosage amount is desired before administering the medication dosage amount.

Figure 31:
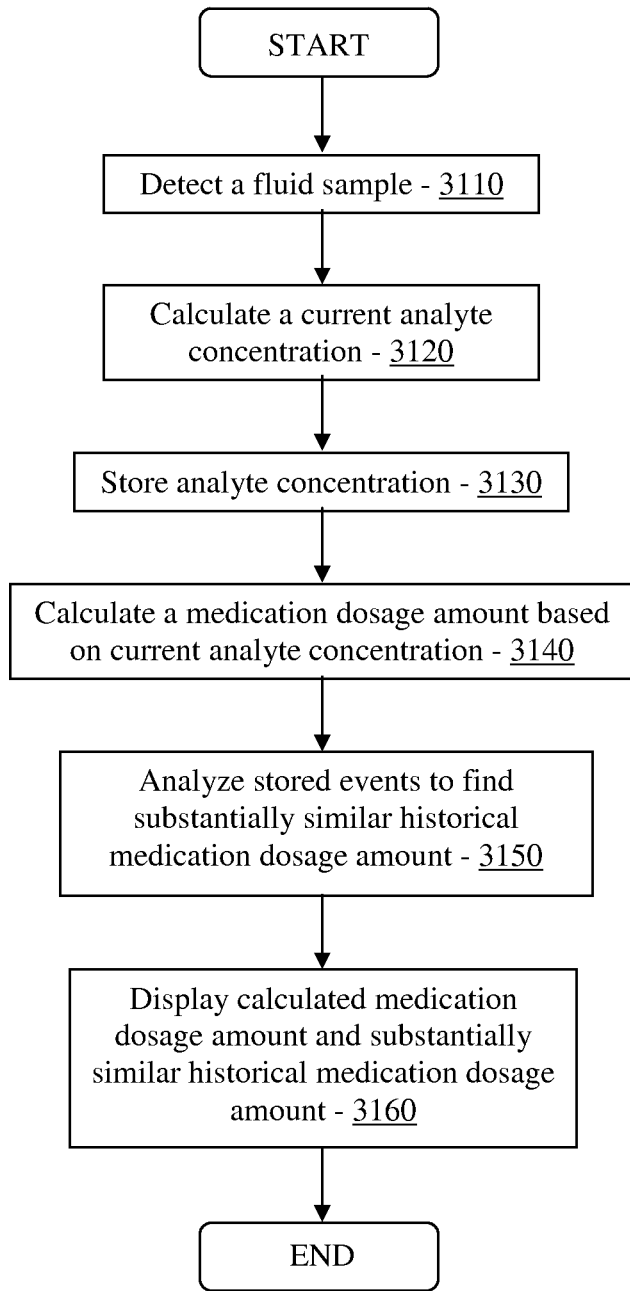
FIG. 31 is a flow chart illustrating a procedure for displaying a historical medication dosage amount to a user according to embodiments of the present disclosure.

FIG. 31 is a flow chart illustrating a procedure for displaying a historical medication dosage amount to a user according to an embodiment of the present disclosure. Referring to FIGS. 31 and 6A, a fluid sample is detected (3110), for example, by applying the fluid sample to a test strip 650 and inserting the strip 650 into a strip port 640 of the health monitor device 600. Upon detection of the fluid sample, a current analyte concentration is calculated (3120) based on analysis of the fluid sample. Once the analyte concentration is determined, the value may be stored (3130) in a memory 670 of the health monitor device 600. Alternatively, the value may be transmitted for storage in a memory of a secondary device or computer. Based on the current analyte concentration, the health monitor device 600 may calculate a recommended medication dosage amount to bring the current analyte concentration within the patient's threshold analyte concentration range (3140). In certain instances, the health monitor device 600 analyzes events and/or additional information stored in the memory of the health monitor device to determine if there is a historical medication dosage amount that is substantially similar to the current recommended medication dosage amount (3150). If the health monitor device finds a substantially similar historical medication dosage amount, then the health monitor device may display the substantially similar historical medication dosage amount to the user (3160).

Projected Analyte Values

In some embodiments, the health monitor device includes a processor configured to analyze patient data and determine a projected analyte offset (e.g., a projected blood glucose offset). By "projected analyte offset" is meant an estimated change in a patient's analyte value (e.g., blood glucose value) associated with the patient's insulin on board. In certain embodiments, the health monitor device includes a processor configured to analyze patient data and determine a projected analyte value (e.g., a projected blood glucose value). By "projected analyte value" is meant an estimated analyte value at a future time point or interval. The projected analyte value may be the current analyte value minus the projected analyte offset. For example, the health monitor device may include programming configured to determine a projected analyte value at a time 1 hour or more, such as 2 hours or more, or 3 hours or more, or 4 hours or more, or 5 hours or more, or 6 hours or more, or 7 hours or more, or 8 hours or more in the future.

In certain embodiments, the health monitor device analyzes patient data, such as, but not limited to, the current blood glucose value, the patient's insulin sensitivity or correction factor (e.g., the reduction in blood glucose per unit of insulin administered), the insulin on board, the duration of insulin action, the amount of carbohydrates consumed, the patient's carbohydrate ratio, the amount of exercise, the current blood glucose trend, and the like, to determine a projected analyte offset (e.g., a projected blood glucose offset) and/or a projected analyte value (e.g., a projected analyte value). For example, the health monitor device may analyze patient data including the amount and time of a preceding insulin bolus administered to the patient, the duration of insulin action, the insulin on board, and the patient's insulin sensitivity (e.g., correction factor) to determine a projected analyte offset (e.g., a projected blood glucose offset). In some cases, the projected analyte offset represents the change in a patient's analyte value (e.g., blood glucose value) that can be expected due to the amount of insulin remaining in the patient's bloodstream (e.g., the patient's insulin on board).

In certain instances, the health monitor device analyzes patient data, as described above, to determine a projected analyte value, such as a projected blood glucose value. For example, the health monitor device may analyze patient data including the amount and time of a preceding insulin bolus administered to the patient, the duration of insulin action, the insulin on board, the patient's insulin sensitivity (e.g., correction factor), and the current analyte value (e.g., the current blood glucose value) to determine a projected analyte value. In some cases, the health monitor device determines the projected analyte offset (e.g., the projected blood glucose offset) and subtracts the projected analyte offset from the current analyte value (e.g., the current blood glucose value) to determine the projected analyte value (e.g., the projected blood glucose value). The projected analyte value may represent the estimated analyte value (e.g., blood glucose value) that can be expected after the amount of insulin remaining in the patient's bloodstream (e.g., the insulin on board) has had time to act.

The projected blood glucose offset and/or the projected blood glucose value may be displayed on the health monitor device to a user. The projected blood glucose offset and/or the projected blood glucose value may be displayed numerically and/or graphically to the user. In some instances, the projected blood glucose offset and/or the projected blood glucose value is displayed to the user along with the currently measured blood glucose value. Displaying the projected blood glucose offset and/or the projected blood glucose value to the user may facilitate a minimization in the occurrence of insulin stacking because, although the current blood glucose value may be outside the user's target range, the user is able to see the projected blood glucose offset and/or the projected blood glucose value before administering any subsequent doses of insulin.

Figure 32:
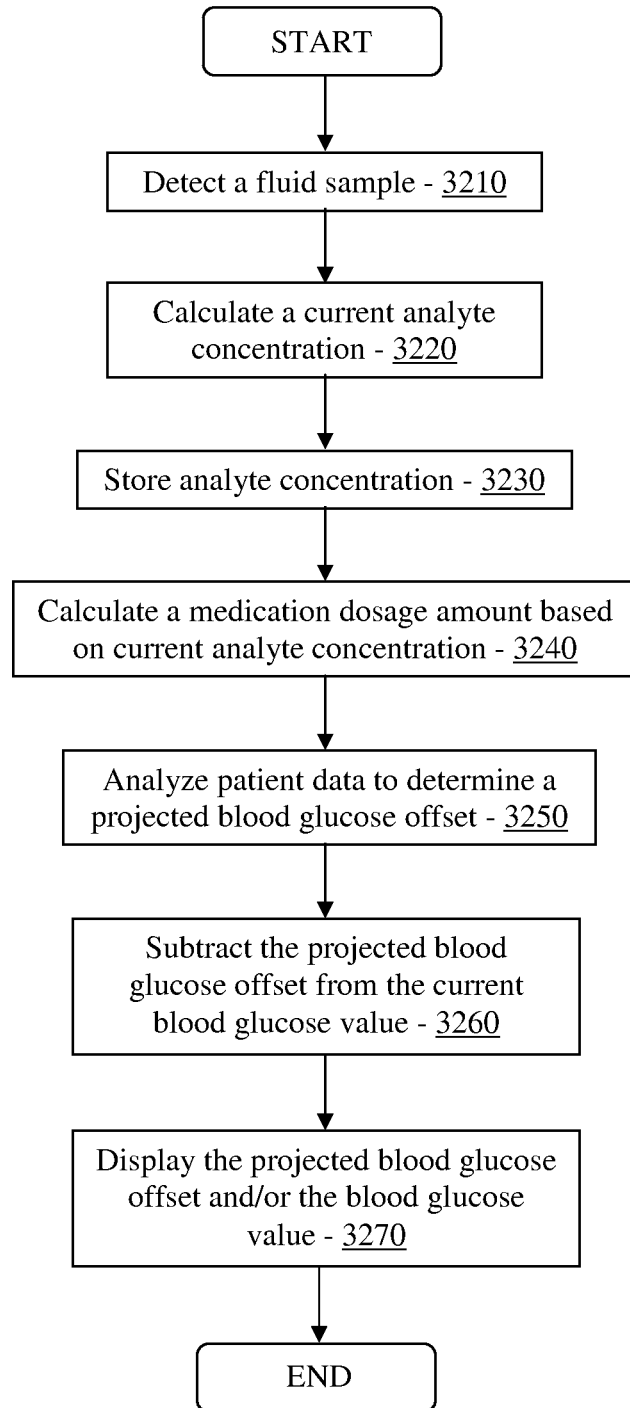
FIG. 32 is a flow chart illustrating a procedure for determining a projected analyte value according to embodiments of the present disclosure.

FIG. 32 is a flow chart illustrating a procedure for determining a projected analyte value according to an embodiment of the present disclosure. Referring to FIGS. 32 and 6A, a fluid sample is detected (3210), for example, by applying the fluid sample to a test strip 650 and inserting the strip 650 into a strip port 640 of the health monitor device 600. Upon detection of the fluid sample, a current analyte concentration is calculated (3220) based on analysis of the fluid sample. Once the analyte concentration is determined, the value may be stored (3230) in a memory 670 of the health monitor device 600 or the value may be transmitted for storage in a memory of a secondary device or computer. Based on the current analyte concentration, the health monitor device 600 may calculate a recommended medication dosage amount to bring the current analyte concentration within the patient's threshold analyte concentration range (3240). In certain instances, the health monitor device 600 analyzes patient data including the amount and time of a preceding insulin bolus administered to the patient, the duration of insulin action, the insulin on board, and the patient's insulin sensitivity (e.g., correction factor) to determine a projected analyte concentration offset (e.g., a projected blood glucose offset) (3250). In some cases, the health monitor device 600 subtracts the projected analyte concentration offset from the current analyte value to determine the projected analyte value (e.g., the projected blood glucose value) (3260). The projected analyte offset (e.g., the projected blood glucose offset) and/or the projected analyte value (e.g., the projected blood glucose value) may be displayed to the user (3270).

Determination of Medication Dosage Calculator Settings

In certain embodiments, the health monitor device may include programming configured to facilitate the determination of one or more settings for a medication dosage calculator (e.g., an insulin bolus calculator). In some instances, the health monitor device-associated programming may be configured to display instructions to a patient, including guided prompts, to assist the patient in gathering the necessary information for determining one or more settings for a medication dosage calculator. For example, the health monitor device may include programming configured to assist the patient in determining insulin bolus calculator settings, such as, but not limited to the patient's insulin sensitivity, the patient's carbohydrate ratio, the patient's duration of insulin action (DIA), and the like.

The programming may direct the patient through a series of actions by displaying guided prompts to the patient through the display unit of the health monitor device. In some cases, the guided prompts include instructions directing the patient to perform an action. The guided prompts may include instructions in one or more forms, such as text, audio, image, video, animation, combinations thereof and the like. In certain instances, the guided prompts are associated with an alert, such as an alarm or reminder. As described herein, the guided prompts and associated alerts can be associated with one or more active scheduling algorithms. For example, to assist a patient in determining one or more settings for their medication dosage calculator (e.g., insulin bolus calculator), the active scheduling algorithm can provide the patient with instructions for performing one or more of the following actions: fasting, measuring a fasting blood glucose level, administering a bolus of insulin, measuring a blood glucose level, consuming an amount of carbohydrates, and the like. The health monitor device may also instruct the patient by displaying a recommended time and/or date for performing one or more of the actions described above (e.g., by displaying such information on a display unit of the health monitor device). The active scheduling algorithm may remind the patient to perform an action described above, or perform a series of actions needed to gathering the necessary information for determining one or more settings for a medication dosage calculator. In certain instances, the active scheduling algorithm may be modified as desired by the patient or by a health care professional.

As data is collected from the patient through the use of the guided prompts, as described above, the data may be stored in a memory of the health monitor device. The programming may also be configured to retrieve the stored data and determine one or more settings for the medication dosage calculator (e.g., insulin bolus calculator) based on the stored data. In some cases, the health monitor device may recommend settings for the bolus calculator such as, but not limited to, the patient's insulin sensitivity, the patient's carbohydrate ratio, the patient's duration of insulin action (DIA) time, and the like.

For example, the health monitor device may determine a patient's insulin sensitivity based on the patient's fasting blood glucose level and the fasting insulin level. In some instances, the health monitor device may determine a patient's carbohydrate ratio based on the type of insulin and the total daily insulin dosage amount. In certain cases, the health monitor device may determine a patient's duration of insulin action based on an initial blood glucose measurement (e.g., a pre-meal blood glucose measurement), an insulin bolus dosage amount, and the length of time it takes the patient's blood glucose value to return to a threshold level. In certain embodiments, the algorithm used by the health monitor device to determine the recommended bolus calculator settings may be modified as desired by the patient or by a health care professional.

Once the health monitor device determines the recommended settings for the medication dosage calculator, the health monitor device may display the recommended settings to the user. In some instances, the recommended settings may be transmitted to a health care professional, such as to a health care professional's computer. The settings can be confirmed by the patient or by a health care professional. In addition, the bolus calculator settings recommended by the health monitor device may be customized as desired. For example, the recommended bolus calculator settings may be modified by the patient or by a health care professional to meet the needs of the individual patient. In some instances, the recommended bolus calculator settings may be set and modified only by a health care professional.

Figure 33:
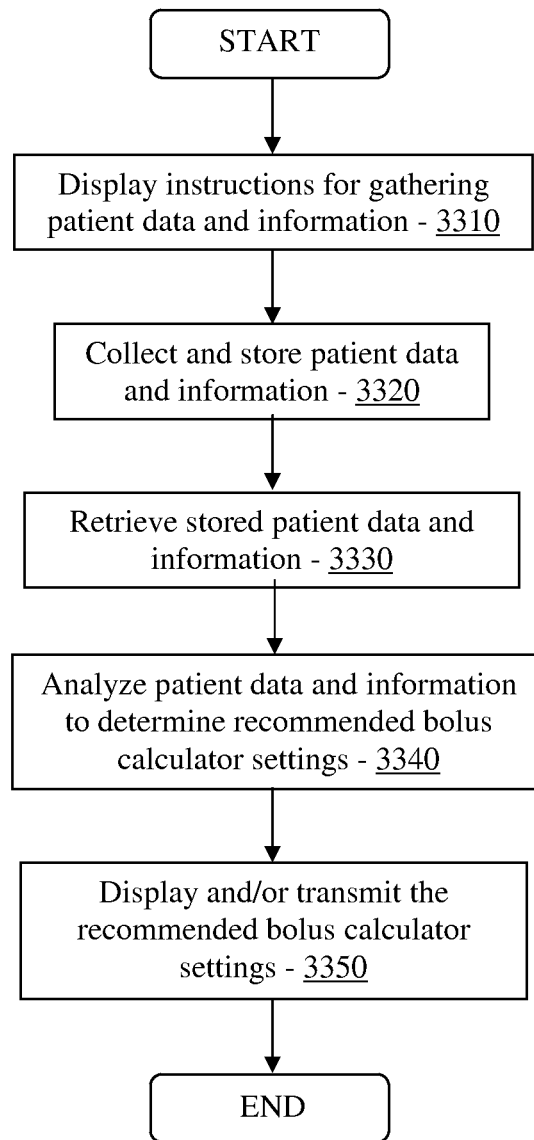
FIG. 33 is a flow chart illustrating a procedure for determining bolus calculator settings according to embodiments of the present disclosure.

FIG. 33 is a flow chart illustrating a procedure for determining bolus calculator settings according to an embodiment of the present disclosure. The health monitor device may display instructions to a patient, including guided prompts, to assist the patient in gathering the necessary data and information for determining one or more settings for a bolus calculator (3310). The data and information is collected from the patient through the use of the guided prompts and stored in a memory of the health monitor device (3320). The stored patient data and information is retrieved from the memory of the health monitor device (3330). The stored patient data and information is analyzed by the health monitor device to determine one or more recommended settings for the bolus calculator (3340). The health monitor device may display the recommended settings to the user and/or transmit the recommended settings to a health care professional (3350).

In certain instances, rather than guide the patient through a series of actions to gather the data and/or information necessary to determine the recommended settings for the bolus calculator, the health monitor device may include programming that analyzes data previously stored in the memory of the health monitor device to determine the recommended settings for the bolus calculator. In some cases, the health monitor device may analyze previously stored data to determine whether additional data is needed to determine the recommended settings for the bolus calculator. In these cases, if the health monitor device determines that additional data is needed, then the health monitor device may direct the patient through a series of actions as described above to generate the necessary additional data.

Types of Medication Dosage Calculators

Aspects of embodiments of the health monitor device include a health monitor device that has programming for one or more types of medication dosage calculators (e.g., bolus calculator, such as insulin dosage calculator). For example, the health monitor device may include programming for one type of medication dosage calculator. In some cases, the health monitor device may include programming for two or more types of medication dosage calculator. During setup of the health monitor device, the health monitor device may prompt the user and/or the health care professional to select a type of medication dosage calculator (e.g., insulin bolus calculator). The initial selection of the type of medication dosage calculator may be changed as desired by the user or the health care professional. In certain embodiments, the two or more types of medication dosage calculators include two types of bolus calculators. For instance, the two types of bolus calculators can include an easy bolus calculator and an advanced bolus calculator.

By "easy bolus calculator", "simple bolus calculator", "easy insulin calculator" or "simple insulin calculator" is meant a bolus calculator that includes basic features for determining a recommended medication dosage amount, such as a recommended insulin dosage amount. For example, an easy bolus calculator may include algorithms configured to determine a recommended medication dosage amount based on a fixed medication dosage amount. In these instances, the easy bolus calculator may be appropriate for a user that administers a fixed medication dosage amount (e.g., a fixed insulin dosage amount) for each meal. In some embodiments, the easy bolus calculator only takes into account the fixed medication dosage amount when recommending the medication dosage amount to the user, and thus functions as a reminder and/or log for the fixed medication dosage amount.

In certain embodiments, the easy bolus calculator may determine a recommended medication dosage amount (e.g., a recommended insulin dosage amount) based on additional information, such as, but not limited to, the patient's the current blood glucose level, fixed medication dosage amount, target blood glucose range, and insulin sensitivity (e.g., correction factor). In some instances, the easy bolus calculator may also include information, such as the patient's insulin on board, in the determination of a recommended medication dosage amount.

In certain embodiments, the easy bolus calculator includes algorithms configured to determine a recommended medication dosage amount (e.g., a recommended insulin dosage amount) based on a fixed medication dosage amount (e.g., a fixed insulin dosage amount) and a medication dosage (e.g., insulin dosage) to correct the patient's current blood glucose level to the target analyte concentration (e.g., a target blood glucose range). For example, the easy bolus calculator may include an algorithm configured to determine a recommended insulin dosage amount based on the sum of the fixed insulin dosage amount and the insulin dosage amount to correct the patient's current blood glucose level to the target blood glucose range.

By "advanced bolus calculator" or "advanced insulin calculator" is meant a bolus calculator that includes additional information, such as, but not limited to, the amount of carbohydrates consumed, in determining a recommended medication dosage amount (e.g., a recommended insulin dosage amount). For example, rather than using a fixed medication dosage amount for each meal, the advanced bolus calculator may use dose determination information entered by the user, such as the amount of carbohydrates consumed, to determine a recommended medication dosage amount. The advanced bolus calculator may also include additional dose determination information into the determination of the recommended medication dosage amount, such as but not limited to, a patient's the current blood glucose level, an amount of exercise, a target analyte concentration (e.g., a target blood glucose range), an insulin sensitivity (e.g., correction factor), a duration of insulin action, a carbohydrate ratio, and insulin on board information, such as an administered medication dose time information, an administered dose frequency information over a predetermined time period, and an administered medication dose amount.

In certain embodiments, the advanced bolus calculator may include additional settings that may be set and/or customized by the patient and/or a health care professional. For example, the advanced bolus calculator may include settings for a target analyte range, such as a target range for a blood glucose level. The advanced bolus calculator may include one target analyte range that can be used at any time. In other instances, the advanced bolus calculator includes two or more target analyte ranges that can be used at different times. For example, the advanced bolus calculator may include different target analyte ranges (e.g., target blood glucose ranges) for pre-meal and post-meal time periods. In some instances, the pre-meal target analyte range (e.g., target blood glucose range) is less than the post-meal target analyte range.

In certain embodiments, the advanced bolus calculator includes settings for a patient's insulin sensitivity (e.g., correction factor). The advanced bolus calculator may include one setting for the patient's insulin sensitivity that can be used at any time. In other instances, the advanced bolus calculator includes two or more settings for a patient's insulin sensitivity that can be used at different times. For example, the advanced bolus calculator may include different insulin sensitivities at morning, midday, evening and night time periods.

Medication Dosage Calculator Units and Rounding of Units

Aspects of embodiments of the health monitor device include a medication dosage calculator (e.g., bolus calculator, such as an insulin dosage calculator) that includes programming configured to determine a recommended medication dosage amount and display the recommended medication dosage amount. In certain embodiments, the medication dosage calculator displays the recommended medication dosage amount (e.g., insulin dosage amount) in whole unit increments, such as in whole units of insulin. In some instances, the medication dosage calculator displays the recommended medication dosage amount (e.g., insulin dosage amount) in half unit increments, such as in half units of insulin. The user and/or health care professional may change the settings of the medication dosage calculator, such that the medication dosage calculator displays the recommended medication dosage amount in whole units or in half units. For example, the option to change the units displayed (e.g., whole units or half units) may be included as a user-selectable setting in the software or firmware associated with the health monitor device. In certain cases, the option to change the units displayed (e.g., whole units or half units) may be included as a user-selectable setting in the software or firmware associated with a health management system. In some instances, the option to change the units displayed is included in both the health monitor device and the health management system, whereas in other instances, the option to change the units displayed in only included in either the health monitor device or the health management system.

In certain embodiments, the health monitor device includes programming configured to perform a rounding and/or a truncation function on the recommended medication dosage amount. For example, the medication dosage calculator of the health monitor device may be programmed to round off the recommended medication dosage amount. If the medication dosage calculator is set to display whole units as described above, and the recommended medication dosage amount is less than 0.5 units above the nearest lower integer, then the bolus calculator may be programmed to round the recommended medication dosage amount down to the nearest lower whole unit. If the recommended medication dosage amount is 0.5 units or more above the nearest lower integer, then the medication dosage calculator may be programmed to round the recommended medication dosage up to the nearest greater whole unit.

In certain instances, the medication dosage calculator is programmed to truncate the recommended medication dosage amount if the medication dosage calculator determines that rounding the recommended medication dosage up to the nearest greater whole unit may result in a blood glucose level that is below the target blood glucose level. For instance, if the recommended medication dosage amount is 2.5 units of insulin, the medication dosage calculator may normally round the recommended medication dosage amount up to 3 units of insulin. However, if the medication dosage calculator determines that a medication dosage of 3 units of insulin may result in a projected blood glucose value that is below the target blood glucose range, then the medication dosage calculator will not round the recommended medication dosage amount up to 3 units of insulin, and instead will truncate the recommended medication dosage amount to 2 units of insulin. Truncation (rather than rounding up) of recommended medication dosage amounts that may result in projected blood glucose levels that are below the target blood glucose range may facilitate a reduction in the occurrence of undesired hypoglycemic events.

Figure 34:
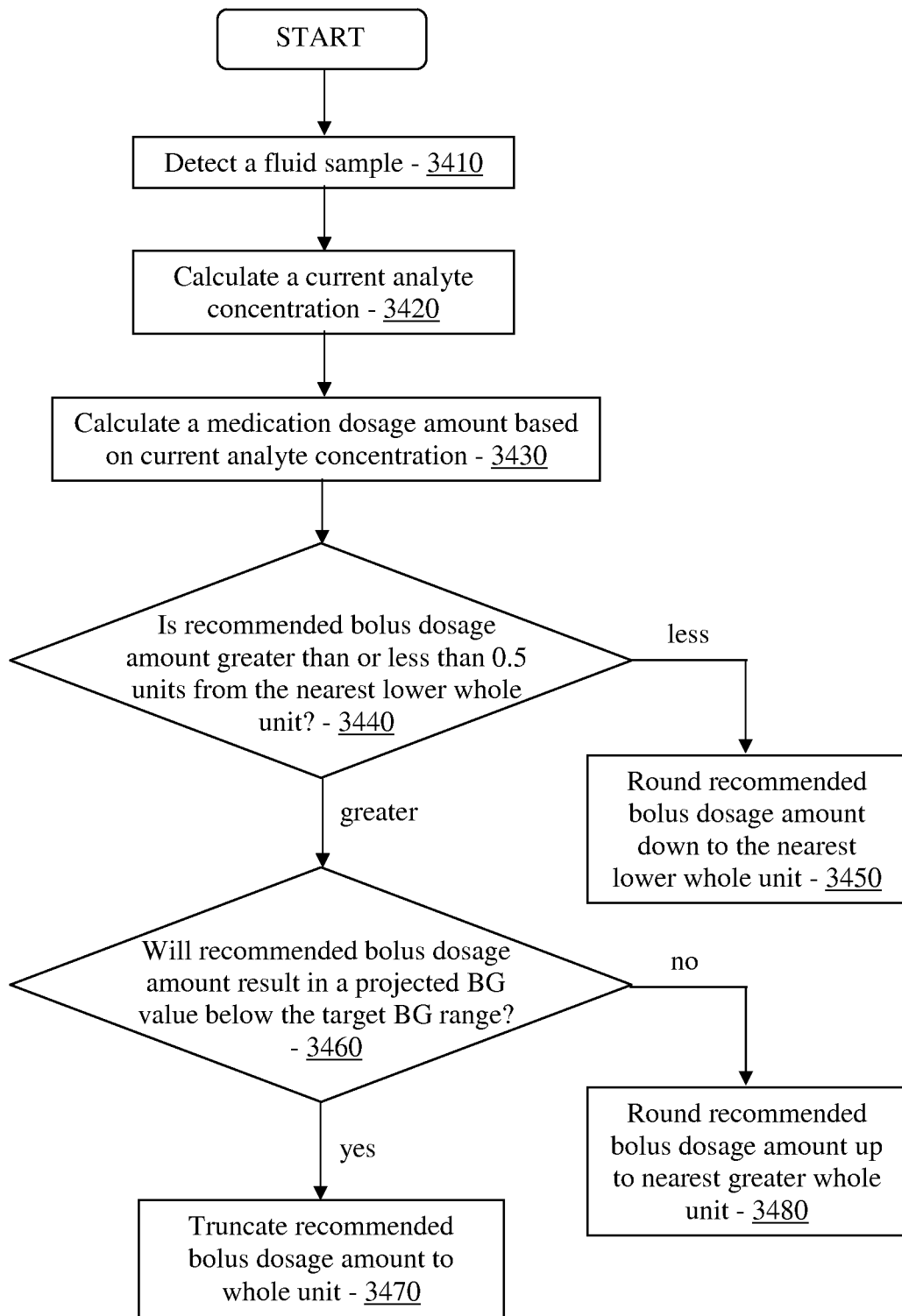
FIG. 34 is a flow chart illustrating a procedure for rounding and/or truncating a recommended bolus dosage amount according to embodiments of the present disclosure.

FIG. 34 is a flow chart illustrating a procedure for rounding and/or truncating a recommended medication dosage amount according to an embodiment of the present disclosure. Referring to FIGS. 34 and 6A, a fluid sample is detected (3410), for example, by applying the fluid sample to a test strip 650 and inserting the strip 650 into a strip port 640 of the health monitor device 600. Upon detection of the fluid sample, a current analyte concentration is calculated (3420) based on analysis of the fluid sample. Based on the current analyte concentration, the health monitor device 600 may calculate a recommended medication dosage amount to bring the current analyte concentration within the patient's threshold analyte concentration range (3430). In certain embodiments, the bolus calculator displays the recommended medication dosage amount (e.g., insulin dosage amount) in the nearest whole unit increment, such as whole units of insulin. In these embodiments, the medication dosage calculator determines if the recommended medication dosage amount is greater than or less than 0.5 units from the nearest lower whole unit (3440). If the recommended medication dosage amount is less than 0.5 units from the nearest lower whole unit, then the recommended medication dosage amount is rounded down to the nearest lower whole unit (3450). If the recommended medication dosage amount is greater than 0.5 units from the nearest lower whole unit, then the medication dosage calculator may be programmed to round the recommended medication dosage amount up to the nearest greater whole unit (3480). In some instances, before rounding the recommended medication dosage amount up to the nearest greater whole unit, the medication dosage calculator determines if administration of the nearest greater whole unit of medication (e.g., insulin) would result in a projected blood glucose value that is below the target blood glucose range (3460). If administration of the nearest greater whole unit of medication (e.g., insulin) would result in a projected blood glucose value that is below the target blood glucose range, then the medication dosage calculator may truncate the recommended medication dosage amount to a whole unit, rather than performing any rounding (3470). If administration of the nearest greater whole unit of medication (e.g., insulin) would not result in a projected blood glucose value that is below the target blood glucose range, then the medication dosage calculator may round the recommended medication dosage amount up to the nearest greater whole unit, as described above (3480).

As described above, the medication dosage calculator may be configured to display the recommended medication dosage amount in half unit increments. Similar to the rounding of recommended medication dosage amounts to the nearest whole unit, the medication dosage calculator may be configured to round off the recommended medication dosage amount to the nearest half unit. For example, if the recommended medication dosage amount is less than 0.25 units above the nearest lower half unit, then the medication dosage calculator may be programmed to round the recommended medication dosage amount down to the nearest lower half unit. If the recommended medication dosage amount is 0.25 units or more above the nearest lower half unit, then the medication dosage calculator may be programmed to round the recommended medication dosage up to the nearest greater half unit.

Messages

In certain embodiments, the health monitor device includes programming configured to display one or more messages to the user. The messages may include guided interpretation notes, such as a summary of user data and/or information stored over a preceding time period. The messages may be displayed to the user on the display of the health monitor device. In some instances, one or more messages are displayed to the user as part of a health management software application that can be stored and/or run from a processing device such as a smart phone device, PDA, server device, laptop or desktop computer. The messages may be presented to the user as part of a report.

In some embodiments, the messages include a summary of user data and/or information stored over a preceding time period. For instance, the messages may include a summary of user data and/or information over the preceding day, or 2 days, or 3 days, or 4 days, or 5 days, or 6 days, or over the preceding week, or 2 weeks, or 3 weeks, or over the preceding month, or 2 months, or 3 months, etc. The summary of user data and/or information may include, but is not limited to, the number of hypoglycemic events that occurred in a preceding time period, the number of pre-meal blood glucose values that were within the target blood glucose range, the number of post-meal blood glucose values that were within the blood glucose target range, the number of blood glucose values that were above the target range in a preceding time period, the ratio of the average correction insulin dose to the average total daily insulin dose, the number of times the user changed the recommended insulin dose, the average number of analyte measurements per day, and the like.

In some cases, the messages include warning messages or notifications to the user that, based on user data and/or information stored over a preceding time period, certain events have occurred in the preceding time period. For example, the messages may include, but are not limited to, an indication that the average blood glucose level is outside a target range, an indication that the number of blood glucose measurements in the preceding time period was a threshold amount or fewer, an indication that the standard deviation of the blood glucose measurements was a target value or greater for a preceding time period, an indication of the number of days in the preceding time period that did not have any insulin doses logged, a prompt for whether the user has made any changes in medication, lifestyle, or health status in the preceding time period, an indication of the percentage the average number of blood glucose measurements increased or decreased in the preceding time period from a previously reported time period, and the like.

In certain embodiments, a message is only displayed to the user if, based on user data and/or information stored over a preceding time period, certain criteria are met. For example, the number of hypoglycemic events that occurred in a preceding time period may be displayed if the number of hypoglycemic events was above a threshold number, such as 1 or more, 2 or more, 3 or more, 4 or more, 5 or more, etc. during the preceding time period. In some cases, the number of pre-meal blood glucose values that were within the target blood glucose range, and the number of post-meal blood glucose values that were within the blood glucose target range may be displayed if pre- and post-meal blood glucose measurements were made during the preceding time period. In certain instances, the number of blood glucose values that were above the target range in a preceding time period may be displayed if the blood glucose values were greater than a threshold amount above the target range, such as 10% or more, 20% or more, 30% or more, 40% or more, 50% or more, etc. above the target range. In some embodiments, the ratio of the average correction insulin dose to the average total daily insulin dose may be displayed if the average daily correction insulin dose is greater than a threshold amount of the total daily insulin dose, such as 5% or more, 10% or more, 15% or more, 20% or more, 25% or more, or 30% or more, etc. of the total daily insulin dose. In some cases, the number of times the user changed the recommended insulin dose may be displayed if the number of times the user changed the recommended insulin dose is greater than a threshold number over the preceding time period, such as 1 time or more, 2 times or more, 3 times or more, 4 times or more, or 5 times or more, etc. over the preceding time period.

In certain embodiments, the indication that the average blood glucose level is outside a target range may be displayed if the average blood glucose level over the preceding time period is greater than an upper threshold amount of the target range or below a lower threshold amount of the target range, such as if the average blood glucose level is 150 mg/dL or more, or 160 mg/dL or more, or 170 mg/dL or more, or 180 mg/dL or more, or 190 mg/dL or more, or 200 mg/dL or more, etc., or if the average blood glucose level is 120 mg/dL or less, or 110 mg/dL or less, or 100 mg/dL or less, or 90 mg/dL or less, or 80 mg/dL or less, or 70 mg/dL or less, etc. In some instances, the indication that there were less than a threshold number of blood glucose measurements in the preceding time period may be displayed if the number of blood glucose measurements in the preceding time period was less than a threshold amount, such 10 measurements or less, 7 measurements or less, 5 measurements or less, 3 measurements or less, 2 measurements or less, or 1 measurements or less, etc. In certain cases, the indication that the standard deviation of the blood glucose measurements was above a target value for a preceding time period may be displayed if the standard deviation of the blood glucose measurements for a preceding time period is greater than half the average of the blood glucose measurements over the preceding time period. In some embodiments, the indication of the number of days in the preceding time period that did not have any insulin doses logged is displayed if no insulin doses were logged for 1 day or more, or 2 days or more, or 3 days or more, or 4 days or more, or 5 days or more, etc. in the preceding time period. In some instances, the prompt for whether the user has made any changes in medication, lifestyle, or health status in the preceding time period may be displayed if any other message as described herein is displayed to the user. In certain instances, the indication of the percentage the average number of blood glucose measurements increased or decreased in the preceding time period from a previously reported time period is displayed if percent change in the average number of blood glucose measurements in the preceding time period as compared to a previously reported time period was greater than a threshold amount, such as 5% or more, or 10% or more, or 15% or more, or 20% or more, or 25% or more, etc.

Examples of messages and the corresponding criteria for displaying each message are shown in the table below. The information contained in brackets in the messages below may be replaced with data. In some cases, the data is based on a patient's data as determined by the health monitor device and/or input into the health monitor device by the patient and/or a health care professional.

| Message | Criteria |
| --- | --- |
| [#] of hypoglycemic events (below [HYPOGLYCEMIC THRESHOLD]) in [TIME PERIOD]. | Number of Hypoglycemic Events is ≥2 per week/period. If more than one time period falls in this threshold, then repeat the message for all applicable time periods. |
| Pre-meal BG's are within target [%] of time ([#pre-meal tests in target] out of [total # pre-meal tests]). | Average Meal Report is populated with data. |
| Post-meal BG's are within target [%] of time ([# post-meal tests in target] out of [total # post-meal tests]). | Average Meal Report is populated with data. |
| BG average is outside the range of 110-180. | BG average <110 mg/dl or >180 mg/dl. |
| There is less than 5 BG values in this reporting period. | Total number of tests in reporting period is <5. |
| BG standard deviation is above target in [TIME PERIOD]. This may be an indication of high variability in glucose values. | BG Standard Deviation is > Target (e.g., BG Average/2). This message may be displayed by time period and may include all time periods that fall within the criteria. |
| [%] BG values above target range ([TARGET RANGE]) in [TIME PERIOD]. | BG values are >50% above target range. This message may be repeated for all applicable time periods. |
| Gaps found in the insulin data. [# DAYS WITHOUT INSULIN EVENTS] days in this reporting period have no recorded insulin events. | Insulin calculator enabled and there is a 24 hour period without recorded insulin events. |
| Ratio of average correction insulin is [%] of average total daily insulin dose. | Insulin calculator enabled and the average daily correction insulin dose is >20% of average total daily insulin dose. |
| [#] overrides of the suggested insulin dose were given over the reporting period. | Insulin calculator enabled and the total number of overrides >0 throughout the reporting period. |
| Has there been a change in medication, lifestyle, or health status? | Display if any other message is displayed. |
| Average number of tests per day [INCREASED or DECREASED] [X %] from previous reporting period. | If average number of tests per day is >10% from previous reporting period, then display "increased" in message and display percent change. Or if average number of tests per day is <10% from previous reporting period, then display "decreased" in message and display percent change. |

The messages may be displayed to the user according to a predetermined schedule. For example, the messages may be displayed to the user daily, or weekly, or monthly, etc. In some cases, the user my input a request for the messages to be displayed by the health monitor device. In response to the request for the messages, the health monitor device may display one or more messages as described above to the user.

Light Sensor

In certain embodiments, the health monitor device includes a light sensor. The light sensor may be configured to detect the amount of light in the area surrounding the health monitor device. For example, the light sensor may detect the ambient light level in the area where the health monitor device is being used. In some cases, the light sensor is configured to detect the ambient light level and transmit a signal to a processor of the health monitor device, where the signal is an indication of the ambient light level. The processor may analyze the signal indicating the ambient light level and compare the signal to a threshold value. In some cases, the health monitor device may be configured to perform a function if the signal indicates that the ambient light is above or below a threshold value. For example, if the signal is below a threshold value, which may correspond to an indication that the ambient light level is below a certain level, then the health monitor device may be configured to perform a function. In some instances, the function may include, but is not limited to, activating a light on the device, activating a backlight for a display on the device, activating a strip port light, and the like. Activating a light on the device if the ambient light level is below a threshold amount may assist a user in seeing the display on the device, inserting a test strip into the device, using a test strip inserted into the device, etc. In certain instances, if the signal is above a threshold value, which may correspond to an indication that the ambient light level is above a certain level, then the health monitor device may be configured to not perform a function. For instance, if the ambient light level is above a threshold amount, then the device may be configured to not activate a light on the device, activate a backlight for a display on the device, activate a strip port light, and the like.

In certain embodiments, the light sensor is activated automatically such that an input from the user is not required for the light sensor to function. In other cases, the light sensor is configured to activate in response to an input from the user, such as if the user presses a button on the health monitor device, inserts a strip into a strip port on the device, touches a touch screen display on the device, and the like. Any type of light sensor may be used, such as, but not limited to, a photocell, a photodiode, a photoresistor, and the like.

Various other modifications and alternations in the structure and method of operation of the present disclosure will be apparent to those skilled in the art without departing from the scope and spirit of the present disclosure. Although the present disclosure has been described in connection with specific preferred embodiments, it should be understood that the present disclosure as claimed should not be unduly limited to such specific embodiments.

The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Methods of setting up and using the easy and advanced insulin calculator according to embodiments of the present disclosure are described in detail below.

Setup for Easy Insulin Calculator

Figure 35:
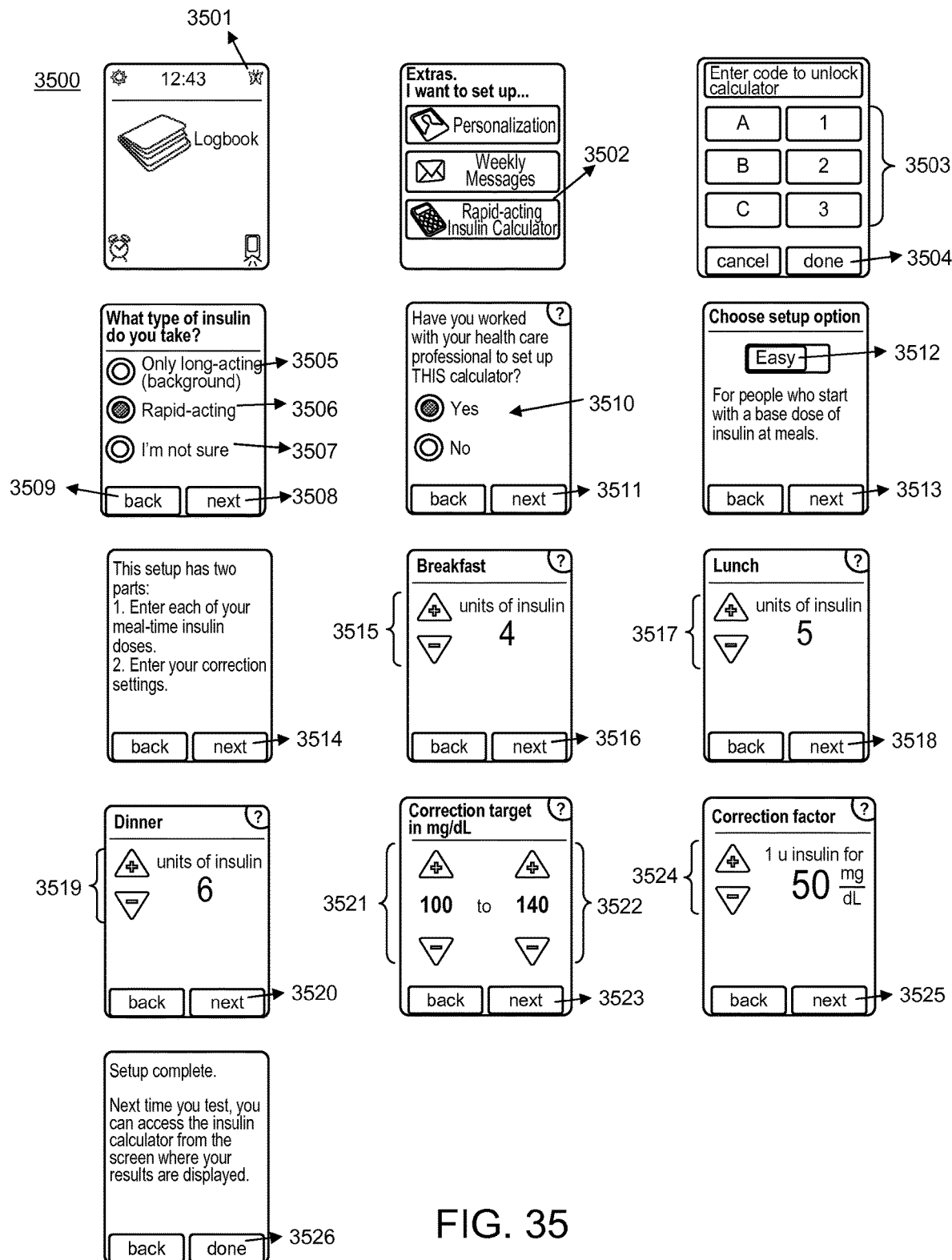
FIG. 35 shows a method of setting up an easy insulin calculator according to embodiments of the present disclosure.

With reference to FIG. 35, a method of setting up the easy insulin calculator is described below. From the home screen (3500) of the health monitor device (e.g., blood glucose meter), a user has several options available. In the upper right corner, for instance, is an icon (3501) for the Extras menu, where the user may set up various settings on the health monitor device, such as, but not limited to, personalization settings, weekly messages, and the rapid-acting insulin calculator settings. For touch screen health monitor devices, by pressing the Extras menu icon (3501) on the home screen (3500) the user may access the Extras menu. To setup the rapid-acting insulin calculator, the user presses the touch screen button (3502) to access the settings for the insulin calculator. By "touch screen button" or "soft button" is meant an area on the touch screen that is configured to detect a press or touch from the user. A "touch screen button" or "soft button" may not be a physical button, but rather an area on the touch screen that has a graphical representation of a button or icon and is configured to detect a press or touch from the user. After pressing the rapid-acting insulin calculator button (3502) the user is presented with the next screen, which may be a screen requesting that the user enter a code or password to proceed with setting up the insulin calculator (3503). In some cases, a health care professional is the user who sets up the insulin calculator for a patient. In some instances, the user may be the patient who sets up the insulin calculator under the direction of a health care professional. To proceed to the next setup screen, the user enters the code by pressing the corresponding buttons (3503) on the screen and then pressing the "done" button (3504). On the next screen, the health monitor device presents the user with a question asking, for example, "what type of insulin do you take?" and presenting the user with 3 choices: only long-acting (e.g., background or basal) insulin (3505); rapid-acting insulin (3506); or an indication that the user is not sure what type of insulin they take (3507). The user enters their choice by pressing the radio button to the left of their choice and then pressing the "next" button (3508). At any time, if the user wants to return to the previous screen, the user may press the "back" button (3509). If the user selects the choice indicating that the user does not know what type of insulin they take, then the user may be presented with a screen instructing the user to consult with their doctor or a health care professional (not shown). If the user indicates that they take rapid-acting insulin, then on the next screen the user is presented with a question asking whether the user is or has worked with their health care professional to determine the appropriate settings for their insulin calculator (3510). The user may select "yes" or "no" by pressing the radio button to the left of their choice and then pressing the "next" button (3511). If the user indicates that they have not consulted their health care professional to determine the appropriate settings for the insulin calculator, then the user may be presented with a screen instructing the user to consult with their doctor or health care professional. If the user indicates that they have worked with their healthcare professional to determine the appropriate settings for their insulin calculator, then the user is presented with the next screen. The user is presented with a toggle button (3512) with which the user may select to setup the easy or the advanced insulin calculator. The user may select the easy insulin calculator option and press the "next" button (3513) to proceed. On the next screen, the user is presented with brief instructions on the setup process. The user may advance to the next screen by pressing the "next" button (3514). On the next screen, the user may enter the number of units of insulin the user takes with breakfast, as advised by their healthcare professional. The user may increase or decrease the number of units by pressing the "+" or "−" buttons (3515). After selecting the number of units of insulin the user takes with breakfast, the user may advance to the next screen by pressing the "next" button (3516). On the next screen, the user may enter the number of units of insulin the user takes with lunch, as advised by their healthcare professional. The user may increase or decrease the number of units by pressing the "+" or "−" buttons (3517). After selecting the number of units of insulin the user takes with lunch, the user may advance to the next screen by pressing the "next" button (3518). On the next screen, the user may enter the number of units of insulin the user takes with dinner, as advised by their healthcare professional. The user may increase or decrease the number of units by pressing the "+" or "−" buttons (3519). After selecting the number of units of insulin the user takes with breakfast, the user may advance to the next screen by pressing the "next" button (3520). On the next screen, the user may enter their blood glucose target range or value. The user may select the lower threshold and the upper threshold for their target blood glucose range by pressing the "+" or "−" buttons for the lower threshold (3521) and the "+" or "−" buttons for the upper threshold (3522). To enter a single blood glucose target value, rather than a range, the user may set the lower and upper threshold values to the same value. After selecting the target blood glucose range or value, the use may advance to the next screen by pressing the "next" button (3523). On the next screen, the user may enter their correction factor (e.g., the amount the user's blood glucose will decrease from 1 unit of insulin), as advised by their healthcare professional. The user may increase or decrease the value for their correction factor by pressing the "+" or "−" buttons (3524). The user may select no correction insulin (e.g., a correction factor of 0 mg/dL) by pressing the "−" button past the setting of 1 mg/dL. The user may advance to the next screen by pressing the "next" button (3525). On the next screen, the user is presented with a screen informing the user that setup is complete, and the user may confirm and save the settings by pressing the "done" button (3526).

Easy Insulin Calculator Use

Figure 36:
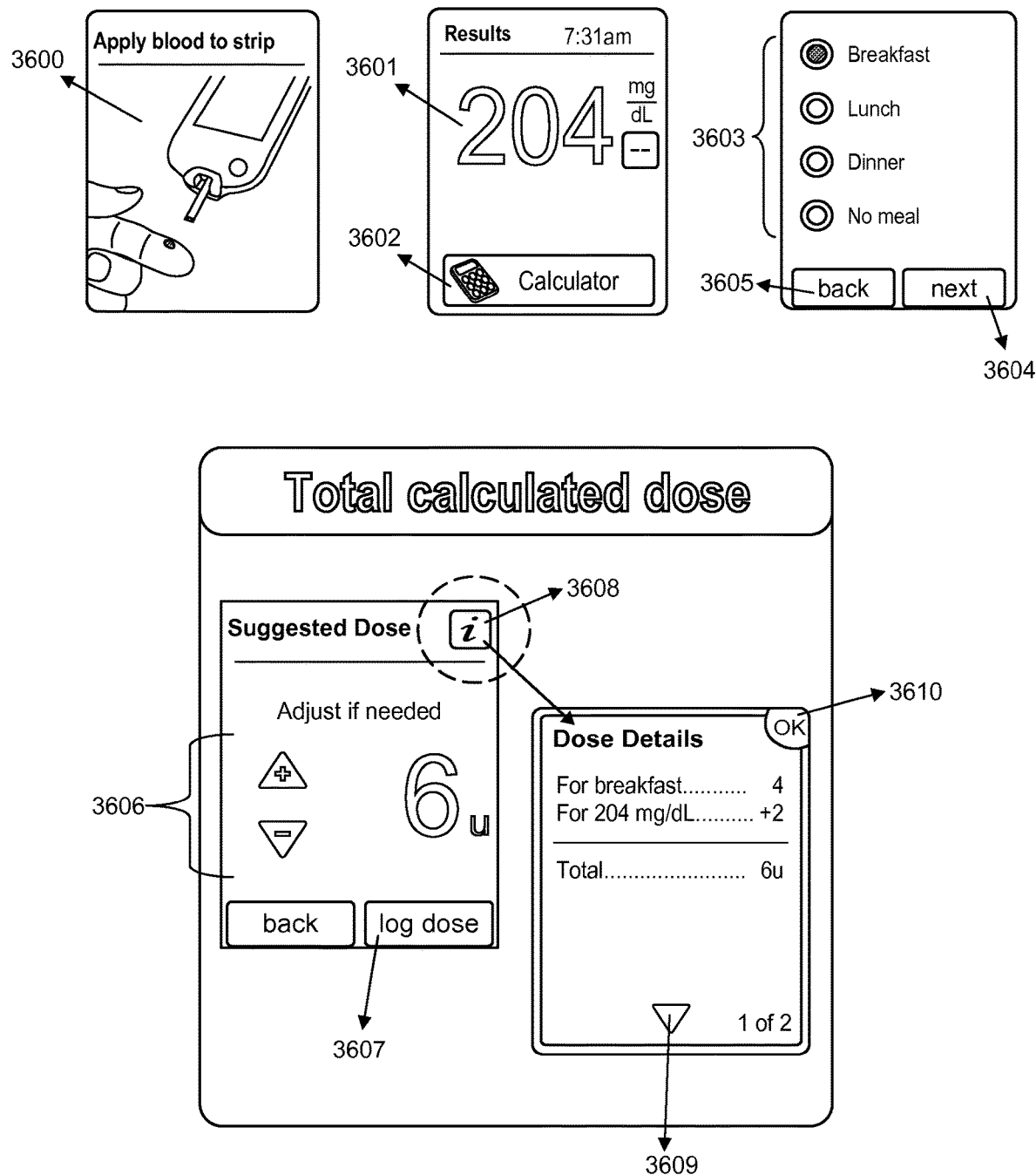
FIG. 36 shows a method of using an easy insulin calculator according to embodiments of the present disclosure.
Figure 36:
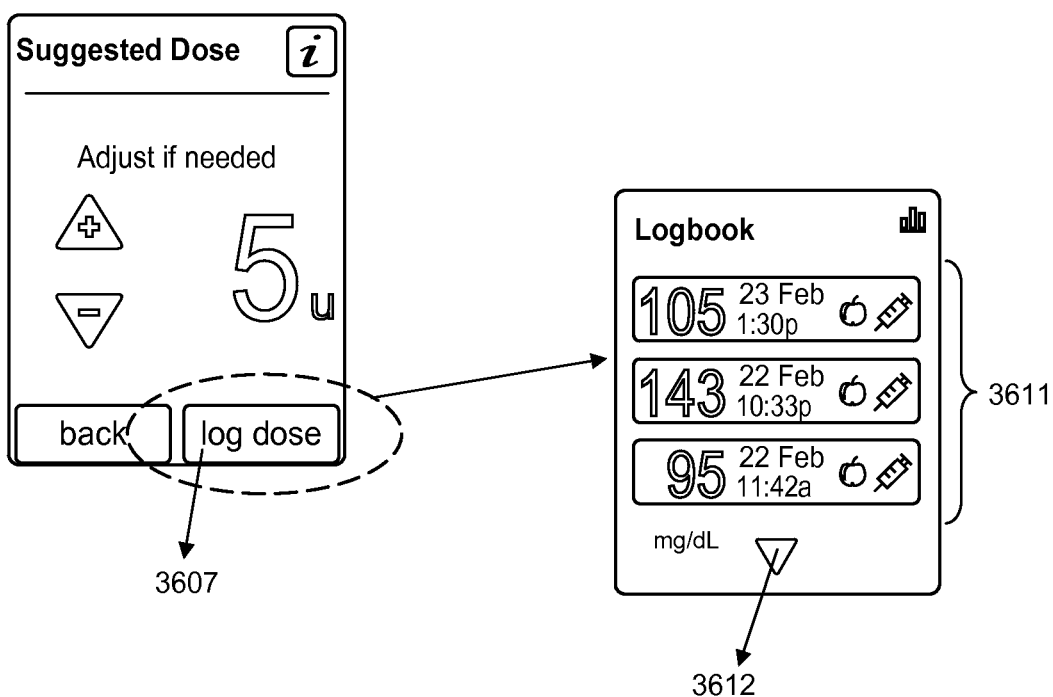

With reference to FIG. 36, a method of using the easy insulin calculator according to embodiments of the present disclosure is described in detail below. To begin a blood glucose measurement, a user inserts a test strip into the test strip port of the health monitor device (e.g., blood glucose meter). After inserting the test strip, the user is presented with a screen (3600) instructing the user to apply blood to the test strip. The screen (3600) may have instructions to apply blood to the test strip in text form and/or in an optional graphical form (e.g., a picture, an icon, a drawing, a schematic, etc.). After applying blood to the test strip, the health monitor device will determine the blood glucose level in the blood sample applied to the test strip and display the result on the screen (3601). The user may select to use the insulin calculator option by pressing the "calculator" button (3602) on the screen. On the next screen, the user is presented with options to select which meal or no meal the user is performing the blood glucose measurement for. For instance, the user may select breakfast, lunch, dinner or no meal by pressing the radio button (3603) corresponding to their choice. The user may advance to the next screen by pressing the "next" button (3604), or may go back to the previous screen by pressing the "back" button (3605). After selecting which meal or no meal and pressing the "next" button (3604), the user is presented with a suggested dose of insulin. The user may adjust the dose as desired by pressing the "+" or "−" buttons (3606), or the user may use the dose suggested by the health monitor device. The user may view further information about the suggested dose by pressing the "i" button (3608). If the user presses the "i" button (3608), the user is presented with one or more screens that present further details about the suggested dose of insulin. For instance, the health monitor device may display the suggested number of units of insulin to cover the meal (e.g., breakfast, lunch or dinner). In addition, the health monitor device may display the suggested number of units of insulin the user should take to correct for a high blood glucose level based on the prior blood glucose measurement, blood glucose target, and correction factor. If the additional insulin dose details span more than one screen, the user may advance to the next screen by pressing the down arrow icon (3609). If the user wants to return to the suggested dose screen, the user may press the "ok" button (3610). To confirm that the user has or will shortly take the suggested dose of insulin, the user may press the "log dose" button (3607) on the suggested dose screen. If the user logs the suggested dose of insulin by pressing the "log dose" button (3607), the user is then presented with the logbook screen (3611). The logbook screen may include information, such as the previous blood glucose measurements, the time and date associated with the previous blood glucose measurements, a pre-meal/post-meal icon, an icon indicating whether insulin was logged, and the like. The user may advance to the next logbook screen by pressing the down arrow button (3612).

Setup for Advanced Insulin Calculator

Figure 37:
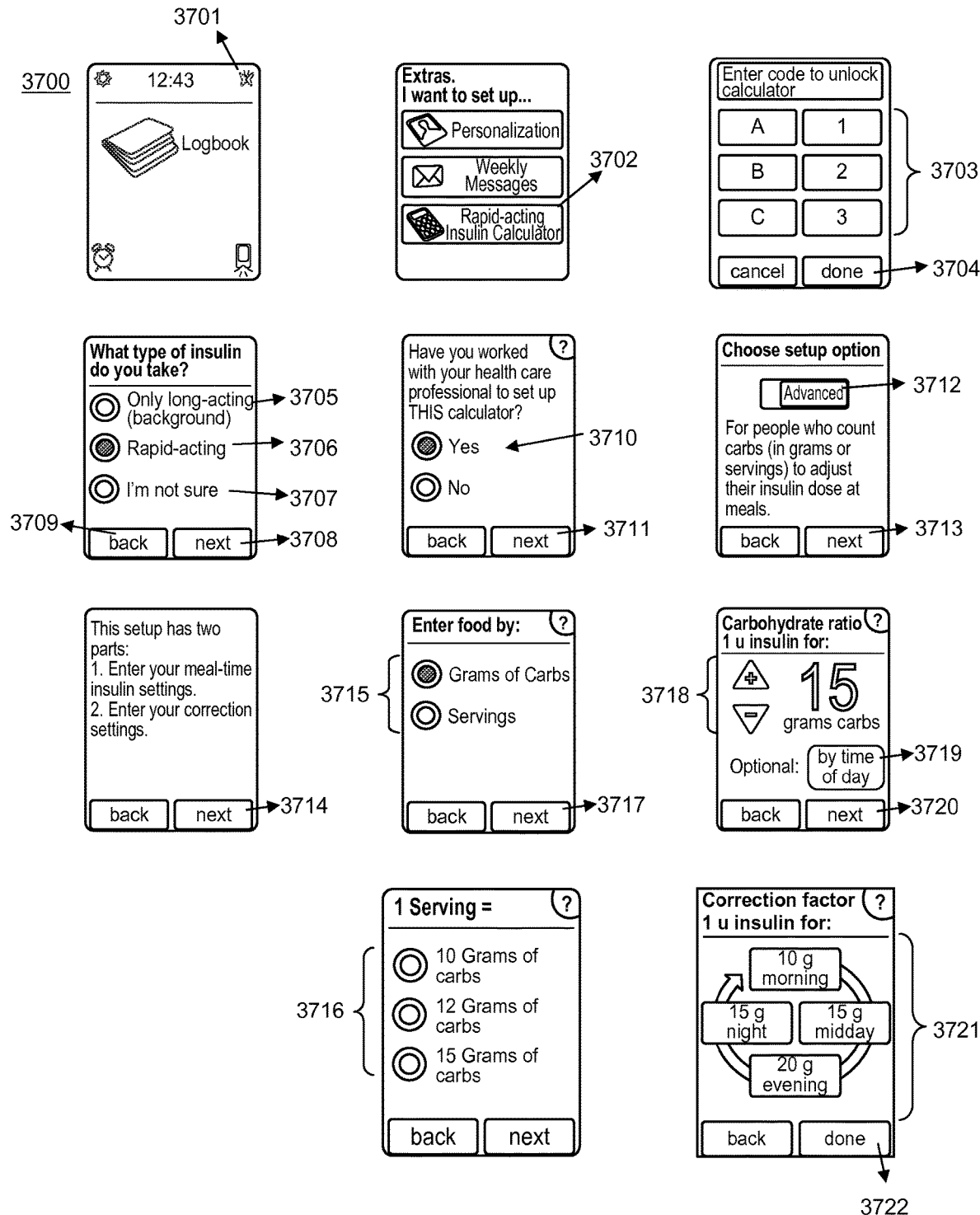
FIG. 37 shows a method of setting up an advanced insulin calculator according to embodiments of the present disclosure.
Figure 37:
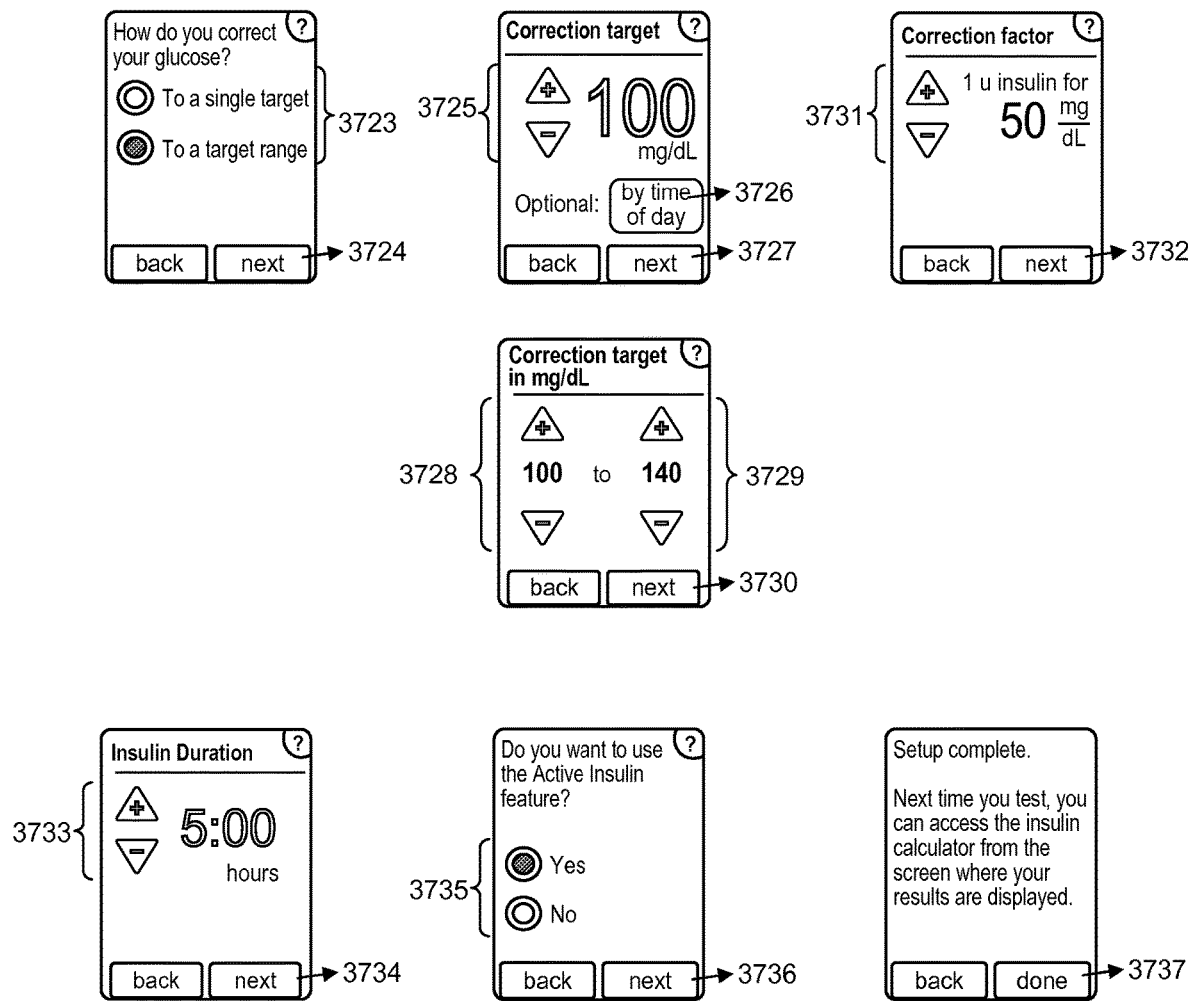

With reference to FIG. 37, a method of setting up the advanced insulin calculator is described below. From the home screen (3700) of the health monitor device (e.g., blood glucose meter), a user has several options available. In the upper right corner, for instance, is an icon (3701) for the Extras menu, where the user may set up various settings on the health monitor device, such as, but not limited to, personalization settings, weekly messages, and the rapid-acting insulin calculator settings. For touch screen health monitor devices, by pressing the Extras menu icon (3701) on the home screen (3700) the user may access the Extras menu. To setup the rapid-acting insulin calculator, the user presses the touch screen button (3702) to access the settings for the insulin calculator. After pressing the rapid-acting insulin calculator button (3702) the user is presented with the next screen, which may be a screen requesting that the user enter a code or password to proceed with setting up the insulin calculator (3703). In some cases, a health care professional is the user who sets up the insulin calculator for a patient. In some instances, the user may be the patient who sets up the insulin calculator under the direction of a health care professional. To proceed to the next setup screen, the user enters the code by pressing the corresponding buttons (3703) on the screen and then pressing the "done" button (3704). On the next screen, the health monitor device presents the user with a question asking, for example, "what type of insulin do you take?" and presenting the user with 3 choices: only long-acting (e.g., background or basal) insulin (3705); rapid-acting insulin (3706); or an indication that the user is not sure what type of insulin they take (3707). The user enters their choice by pressing the radio button to the left of their choice and then pressing the "next" button (3708). At any time, if the user wants to return to the previous screen, the user may press the "back" button (3709). If the user selects the choice indicating that the user does not know what type of insulin they take, then the user may be presented with a screen instructing the user to consult with their doctor or a health care professional (not shown). If the user indicates that they take rapid-acting insulin, then on the next screen the user is presented with a question asking whether the user is or has worked with their health care professional to determine the appropriate settings for their insulin calculator (3710). The user may select "yes" or "no" by pressing the radio button to the left of their choice and then pressing the "next" button (3711). If the user indicates that they have not consulted their health care professional to determine the appropriate settings for the insulin calculator, then the user may be presented with a screen instructing the user to consult with their doctor or health care professional. If the user indicates that they have worked with their healthcare professional to determine the appropriate settings for their insulin calculator, then the user is presented with the next screen. The user is presented with a toggle button (3712) with which the user may select to setup the easy or the advanced insulin calculator. The user may select the advanced insulin calculator option and press the "next" button (3713) to proceed. On the next screen, the user is presented with brief instructions on the setup process. The user may advance to the next screen by pressing the "next" button (3714). On the next screen, the user may select whether they count carbohydrates by grams or by servings by pressing the corresponding radio button (3715) next to their selection and pressing the "next" button (3717). If the user selects that they enter the amount of carbohydrates consumed by servings, the user is presented with options for how many grams of carbohydrates corresponds to one serving (e.g., 10 grams of carbohydrates/serving, or 12 grams of carbohydrates/serving, 12.5 grams of carbohydrates/serving, or 15 grams of carbohydrates/serving). In some instances, more or fewer values may be available to the user for how many grams of carbohydrates corresponds to one serving. In certain cases, the option for the user to select whether they count carbohydrates by grams or by servings is not available, and the user is only able to count carbohydrate by either grams or servings. The user may select the appropriate number of grams of carbohydrates per serving by pressing the radio button (3716) next to their selection. After selecting whether they enter carbohydrates by grams or servings, the user may set their carbohydrate to insulin ratio. The user may enter the number of grams of carbohydrates (or number of servings of carbohydrates if the user had selected that they enter carbohydrates by servings above) covered by one unit of insulin. The user may increase or decrease the number of grams of carbohydrates per one unit of insulin by pressing the "+" or "−" buttons (3718). Optionally, the user may set up their carbohydrate ratio by time of day by pressing the "by time of day" button (3719). On the time of day screen, the user may enter different (or the same) carbohydrate ratio for various times of day (e.g., morning, midday, evening and night) (3721). For instance, the morning time period may range from 6:00 am to 9:59 am; the midday time period may range from 10:00 am to 3:59 pm; the evening time period may range from 4:00 pm to 9:59 pm; and the night time period may range from 10:00 pm to 5:59 am. After the user enters their carbohydrate ratio(s) by time of day, the user may return to the carbohydrate ratio screen by pressing the "done" button (3722). After entering their carbohydrate ratio (either a single ratio or by time of day) the user may advance to the next screen by pressing the "next" button (3720). On the next screen, the user may select whether they correct their blood glucose level to a single target or to a target range by pressing the corresponding radio button (3723) next to their selection and pressing the "next" button (3724). If the user selects that they correct their blood glucose level to a single target, the user may select that target value on the next screen by pressing the "+" or "−" buttons (3725). Optionally, the user may select their blood glucose target by time of day by pressing the "by time of day" button (3726). The user may confirm their blood glucose target value and advance to the next screen by pressing the "next" button (3727). If the user selects that they correct their blood glucose level to a target range, the user is instead presented with a screen to enter their blood glucose target range. The user may select the lower threshold and the upper threshold for their target blood glucose range by pressing the "+" or "−" buttons for the lower threshold (3728) and the "+" or "−" buttons for the upper threshold (3729). After selecting the target blood glucose range, the use may advance to the next screen by pressing the "next" button (3730). On the next screen, the user may enter their correction factor (e.g., the amount the user's blood glucose will decrease from 1 unit of insulin), as advised by their healthcare professional. The user may increase or decrease the value for their correction factor by pressing the "+" or "−" buttons (3731). The user may advance to the next screen by pressing the "next" button (3732). On the next screen, the user may enter their duration of insulin action time. The user may increase or decrease the time by pressing the "+" or "−" buttons (3733). After selecting their duration of insulin action time, the user may advance to the next screen by pressing the "next" button (3734). On the next screen, the user may select whether they want to use the active insulin feature (e.g., insulin on board) by pressing the radio button (3735) next to either "yes" or "no". The user may advance to the next screen by pressing the "next" button (3736). On the next screen, the user is presented with a screen informing the user that setup is complete, and the user may confirm and save the settings by pressing the "done" button (3737).

Advanced Insulin Calculator Use

Figure 38:
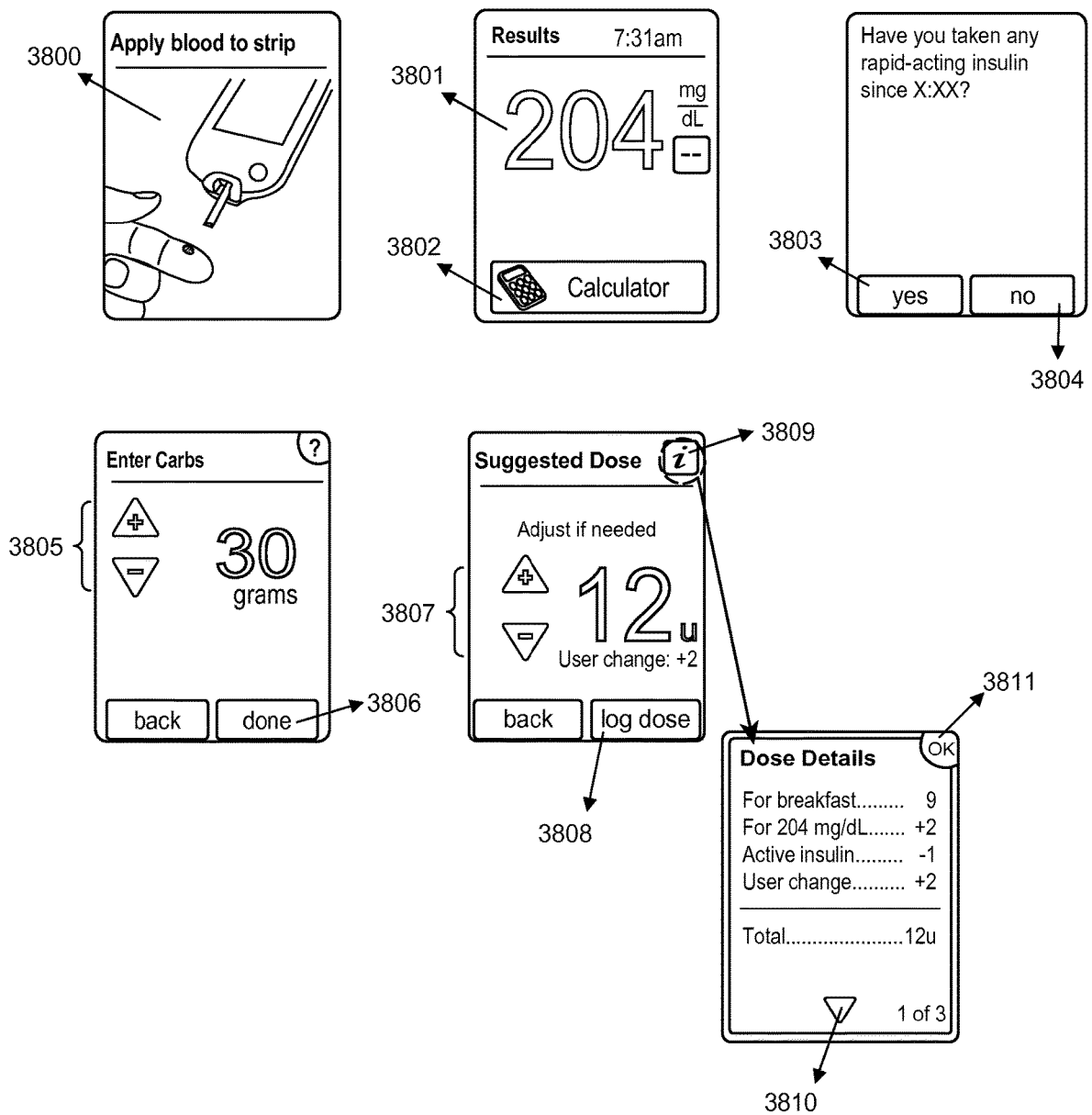
FIG. 38 shows a method of using an advanced insulin calculator according to embodiments of the present disclosure.
Figure 38:
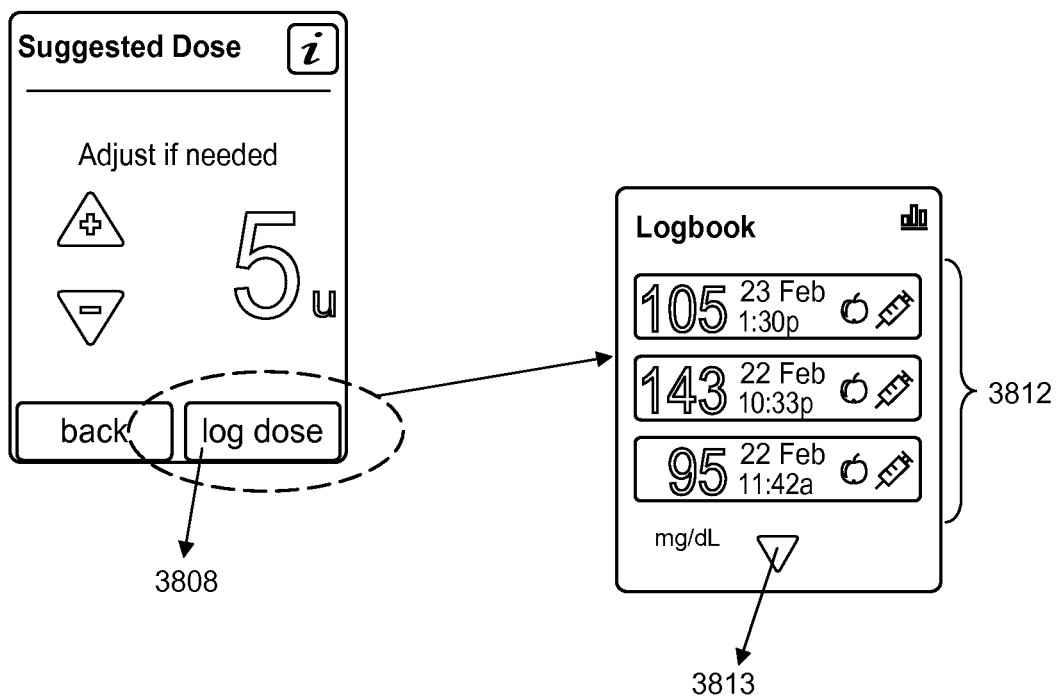

With reference to FIG. 38, a method of using the advanced insulin calculator according to embodiments of the present disclosure is described in detail below. To begin a blood glucose measurement, a user inserts a test strip into the test strip port of the health monitor device (e.g., blood glucose meter). After inserting the test strip, the user is presented with a screen (3800) instructing the user to apply blood to the test strip. The screen (3800) may have instructions to apply blood to the test strip in text form and/or in graphical form (e.g., a picture, drawing, schematic, etc.) After applying blood to the test strip, the health monitor device will determine the blood glucose level in the blood sample applied to the test strip and display the result on the screen (3801). The user may select to use the insulin calculator option by pressing the "calculator" button (3802) on the screen. On the next screen, to account for insulin on board, if any, the user is asked whether they have taken any additional rapid-acting insulin since the previous dose that was logged. The user may select yes or no by pressing the "yes" button (3803) or the "no" button (3804). On the next screen, the user enters the amount of carbohydrates they are about to consume. The user may increase or decrease the amount of carbohydrates by pressing the "+" or "−" buttons (3805). After entering the amount of carbohydrates, the user may advance to the next screen by pressing the "done" button (3806). On the next screen, the user is presented with a suggested dose of insulin. The user may adjust the dose as desired by pressing the "+" or "−" buttons (3807), or the user may use the dose suggested by the health monitor device. The user may view further information about the suggested dose by pressing the "i" button (3809). If the user presses the "i" button (3809), the user is presented with one or more screens that present further details about the suggested dose of insulin. For instance, the health monitor device may display the suggested number of units of insulin to cover the meal (e.g., breakfast, lunch or dinner). In addition, the health monitor device may display the suggested number of units of insulin the user should take to correct for a high blood glucose level based on the prior blood glucose measurement, blood glucose target, and correction factor. The user may also be presented with information regarding the amount of insulin on board that is remaining in their body based on a previously logged dose of insulin. The user may also be presented with information regarding the amount that the user adjusted the suggested dose of insulin. If the additional insulin dose details span more than one screen, the user may advance to the next screen by pressing the down arrow icon (3810). If the user wants to return to the suggested dose screen, the user may press the "ok" button (3811). To confirm that the user has or will shortly take the suggested dose of insulin, the user may press the "log dose" button (3808) on the suggested dose screen. If the user logs the suggested dose of insulin by pressing the "log dose" button (3808), the user is then presented with the logbook screen (3812). The logbook screen may include information, such as the previous blood glucose measurements, the time and date associated with the previous blood glucose measurements, a pre-meal/post-meal icon, an icon indicating whether insulin was logged, and the like. The user may advance to the next logbook screen by pressing the down arrow button (3813).

Insulin Dose Titration

Figure 39:
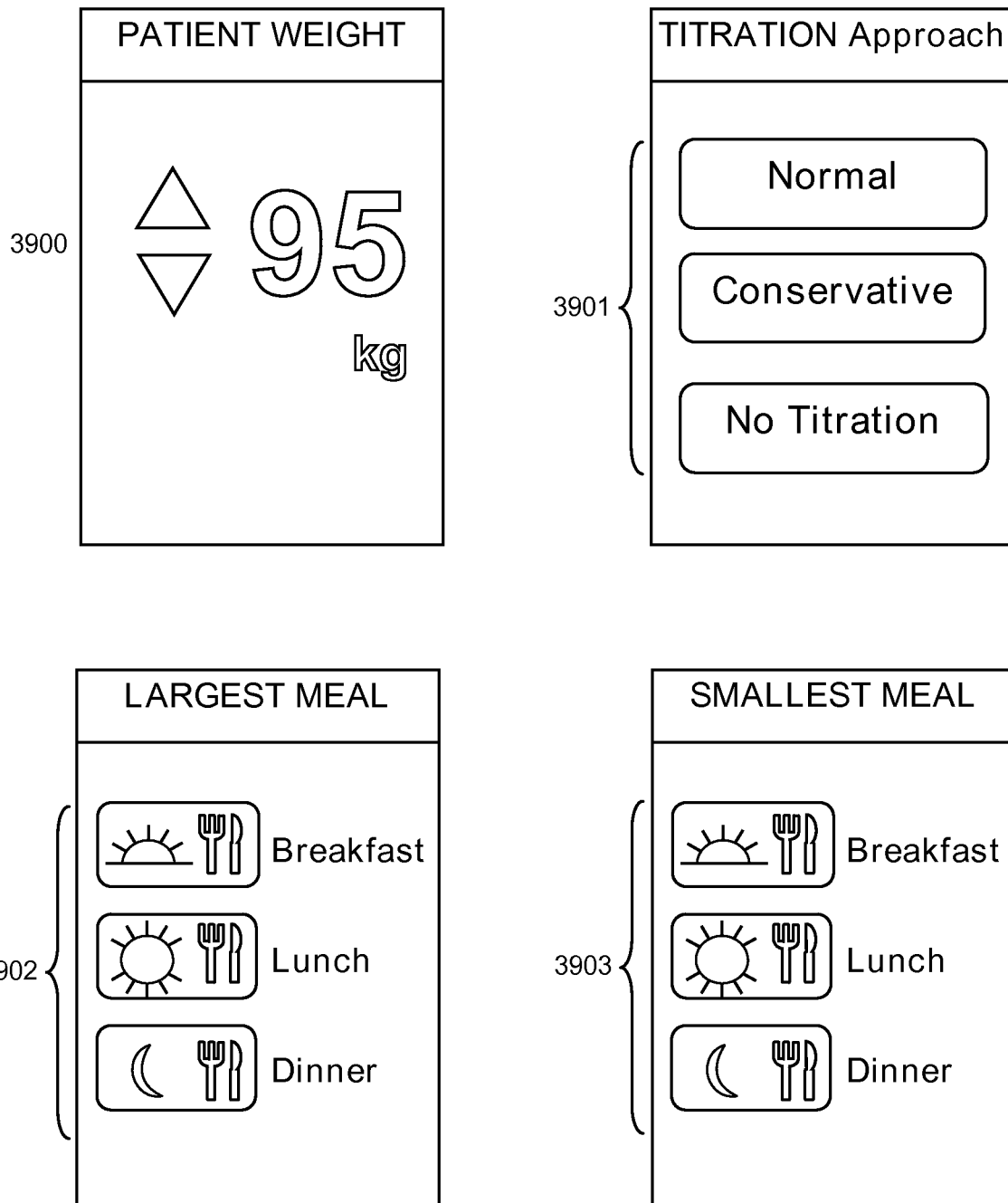
FIG. 39 shows a method of setting up and using an insulin titration feature of a health monitor device according to embodiments of the present disclosure.
Figure 39:
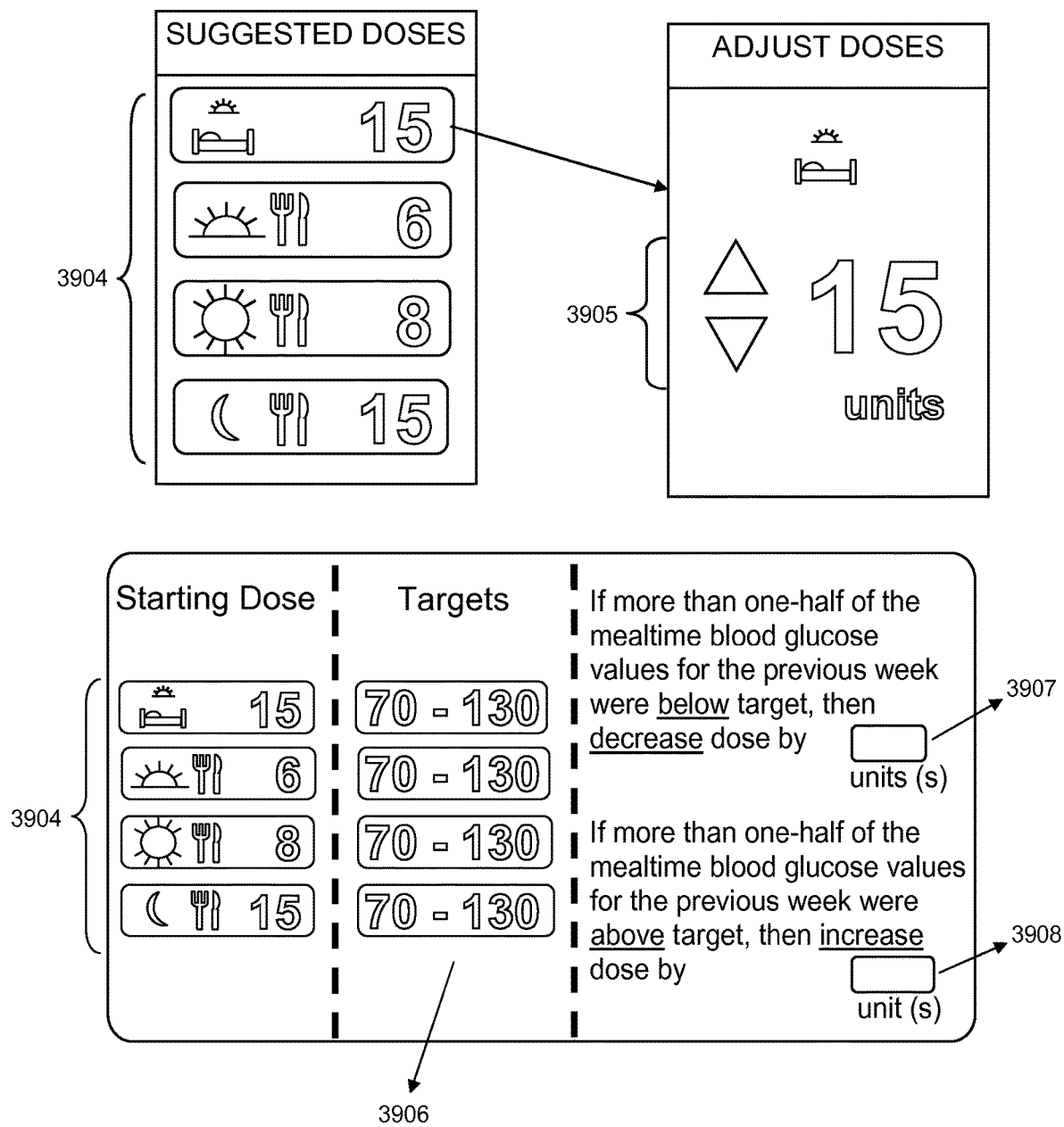
Figure 39:
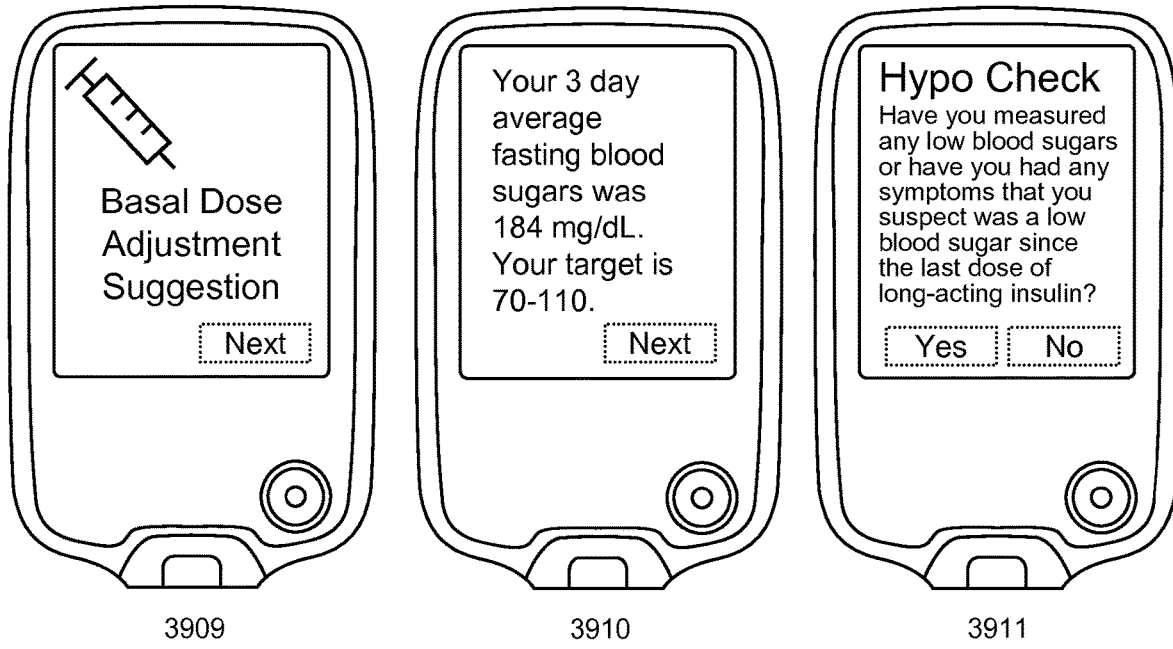
Figure 39:
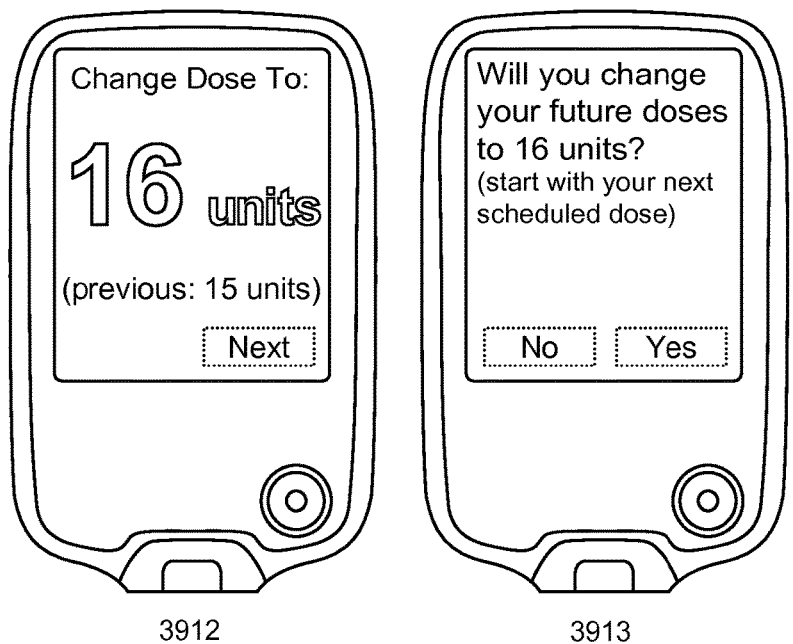

With reference to FIG. 39, a method of using the insulin dose titration feature of a health monitor device (e.g., blood glucose monitor) according to embodiments of the present disclosure is described in detail below. To set up the insulin dose titration feature of the health monitor device a user, a health care professional, or a user under the direction of a health care professional may begin by entering the user's weight. The user may adjust the weight up or down by pressing the up arrow and/or down arrow buttons (3900). The user may then select what type of titration algorithm they want to use (e.g., normal, conservative or no titration) (3901). Next, the user may select which meal is typically the largest meal they consume per day (e.g., breakfast, lunch or dinner) by pressing the corresponding button (3902). The user may then select which meal is typically the smallest meal they consume per day (e.g., breakfast, lunch or dinner) by pressing the corresponding button (3903). Based on the information the user entered, the health monitor device determines suggested initial insulin doses for the user for various times of day (e.g., morning, breakfast, lunch and dinner) (3904). The user may adjust the suggested initial insulin doses by pressing the dose they want to adjust. After pressing the dose they want to adjust, the health monitor device will display a screen showing the suggested dose, and the user may increase or decrease the suggested dose by pressing the up or down arrow buttons (3905). The user may also adjust the target blood glucose level for each of the various times of day (3906). In addition, the user may set the number of units the health monitor device will suggest that the user decrease the initial insulin dose by if the user's blood glucose measurements are below their target blood glucose level (3907). For instance, the health monitor device may suggest that the user decrease their dose of insulin if more than one-half of the mealtime blood glucose measurements for the previous week were below their target blood glucose level. In addition, the user may set the number of units the health monitor device will suggest that the user increase the initial insulin dose by if the user's blood glucose measurements are above their target blood glucose level (3908). For instance, the health monitor device may suggest that the user increase their dose of insulin if more than one-half of the mealtime blood glucose measurements for the previous week were above their target blood glucose level.

After setting up the insulin titration settings, the user may titrate their suggested doses of insulin as described in the present disclosure. For example, the user may titrate their basal insulin dosage amount by pressing the "next" button (3909) on the basal dose adjustment suggestion screen. The user may then be presented with information about their basal dose titration. For example, the health monitor device may display the average of the user's fasting blood glucose values over a preceding time period and the user's target blood glucose range (3910). The user may advance to the next screen by pressing the "next" button. The health monitor device may then prompt the user to indicate whether the user experienced any low blood sugar (e.g., hypoglycemic) events over a preceding time period (3911). For example, the health monitor device may ask whether the user measured any low blood sugar levels or had symptoms indicative of low blood sugar since the user's last dose of long-acting insulin. The user may enter their selection by pressing the yes or the no button. Next, the health monitor device may display the suggested new dose of basal insulin for the user (3912). The health monitor device may also display the previous basal insulin dosage amount. The user may then confirm whether the user wants to use the suggested basal insulin dosage amount as the user's new basal insulin dosage amount by pressing the yes or the no button (3913).

The invention claimed is:

1. A device, comprising:
a housing;
a processor coupled to the housing;
a display unit coupled to the processor;
an input unit coupled to the processor; and
a memory device coupled to the housing and the processor, wherein the memory device comprises programming which, when executed by the processor, causes the processor to:
store an analyte concentration and a time associated with the analyte concentration;
determine a medication dosage amount based at least in part on the analyte concentration;
display, using the display unit, one or more instructions to a user for generating user information for determining one or more settings for a medication dosage calculator;
store the user information for determining the one or more settings for the medication dosage calculator;
determine the one or more settings for the medication dosage calculator based on the stored user information;
output, using the display unit, the one or more settings for the medication dosage calculator; and
detect, using the input unit, one or more input commands, wherein the one or more input commands comprise a request to recalculate the one or more settings for the medication dosage calculator.

2. The device of claim 1, wherein the medication dosage calculator is an insulin bolus calculator.

3. The device of claim 1, wherein the medication dosage amount comprises one or more of a long acting insulin dose amount and a rapid acting insulin dose amount.

4. The device of claim 1, wherein the analyte concentration is associated with a glucose concentration.

5. The device of claim 1, wherein the user information comprises one or more of a fasting glucose level, a fasting insulin level, a type of insulin, a total daily insulin dosage amount, an insulin bolus dosage amount, and length of time it takes a glucose value to return to a threshold level.

6. The device of claim 1, wherein the memory device comprises programming which, when executed by the processor, causes the processor to determine an insulin sensitivity based on the user information of a fasting glucose level and a fasting insulin level.

7. The device of claim 1, wherein the memory device comprises programming which, when executed by the processor, causes the processor to determine a carbohydrate ratio based on the user information of a type of insulin and a total daily insulin dosage amount.

8. The device of claim 1, wherein the memory device comprises programming which, when executed by the processor, causes the processor to determine a duration of insulin action based on the user information of a fasting glucose level, an insulin bolus dosage amount, and a length of time it takes a glucose value to return to a threshold level.

9. The device of claim 1, wherein the output using the display unit is in the form of one or more of a visual output, an audible output, and a vibratory output.

10. The device of claim 1, wherein the display unit comprises a touch-screen display.

11. The device of claim 1, wherein the one or more input commands comprise an acknowledgement confirmation of the one or more settings for the medication dosage calculator.

12. The device of claim 1, wherein the one or more input commands comprises a rejection of the one or more settings for the medication dosage calculator.

13. The device of claim 1, wherein the one or more input commands comprises a calibration code used to calibrate the device.

14. The device of claim 1, further comprising a communication module operatively coupled to the processor, wherein the communication module is configured to transmit one or more of the analyte concentration, the determined medication dosage amount, and the one or more settings for the medication dosage calculator to a remote location.

15. The device of claim 14, wherein the communication module comprises one or more of an RF transmitter, an RF transceiver, a wireless communication module, an infrared communication module, and a wired communication module.

16. The device of claim 1, wherein the analyte concentration is determined based on an analyte sample detected by an in vivo analyte sensor.

17. The device of claim 1, wherein the analyte concentration is determined based on an analyte sample detected by an in vivo continuous analyte sensor.

18. A method comprising:
storing, with a processor of a device, an analyte concentration and a time associated with the analyte concentration;
determining, with the processor, a medication dosage amount based at least in part on the analyte concentration;
displaying, using a display unit coupled to the processor, one or more instructions to a user for generating user information for determining one or more settings for a medication dosage calculator;

storing, with the processor, the user information for determining the one or more settings for the medication dosage calculator;

determining, with the processor, the one or more settings for the medication dosage calculator based on the stored user information;

outputting, using the display unit coupled to the processor, the one or more settings for the medication dosage calculator; and detecting, using an input unit coupled to the processor, one or more input commands, wherein the one or more input commands comprise a request to recalculate the one or more settings for the medication dosage calculator.

19. The method of claim 18, wherein the analyte concentration is associated with a blood glucose concentration.

20. The method of claim 18, wherein the user information comprises one or more of a fasting glucose level, a fasting insulin level, a type of insulin, a total daily insulin dosage amount, an insulin bolus dosage amount, and length of time it takes a glucose value to return to a threshold level.

* * * * *